United States Patent
Clement et al.

(10) Patent No.: US 11,834,718 B2
(45) Date of Patent: Dec. 5, 2023

(54) COMPOSITIONS AND METHODS FOR DIAGNOSING, EVALUATING AND TREATING CANCER BY MEANS OF THE DNA METHYLATION STATUS

(71) Applicants: The Broad Institute, Inc., Cambridge, MA (US); Dana-Farber Cancer Institute, Inc., Boston, MA (US); The General Hospital Corporation, Boston, MA (US); President and Fellows of Harvard College, Cambridge, MA (US)

(72) Inventors: Mark Kendell Clement, Cambridge, MA (US); Gad Getz, Cambridge, MA (US); Dan-Avi Landau, Cambridge, MA (US); Alexander Meissner, Brookline, MA (US); Catherine Ju-Ying Wu, Brookline, MA (US)

(73) Assignees: The Broad Institute, Inc., Cambridge, MA (US); Dana-Farber Cancer Institute, Inc., Boston, MA (US); The General Hospital Corporation, Boston, MA (US); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 17/017,045

(22) Filed: Sep. 10, 2020

(65) Prior Publication Data
US 2020/0407804 A1 Dec. 31, 2020

Related U.S. Application Data

(62) Division of application No. 15/038,504, filed as application No. PCT/US2014/067146 on Nov. 24, 2014, now Pat. No. 10,801,070.

(60) Provisional application No. 61/908,316, filed on Nov. 25, 2013.

(51) Int. Cl.
  *C12Q 1/6886* (2018.01)
  *C12Q 1/6869* (2018.01)
  *G16B 30/00* (2019.01)
  *G16B 30/10* (2019.01)

(52) U.S. Cl.
  CPC ......... *C12Q 1/6886* (2013.01); *C12Q 1/6869* (2013.01); *G16B 30/00* (2019.02); *G16B 30/10* (2019.02); *C12Q 2600/106* (2013.01); *C12Q 2600/118* (2013.01); *C12Q 2600/154* (2013.01); *C12Q 2600/156* (2013.01)

(58) Field of Classification Search
  CPC ............ C12Q 1/6869; C12Q 2600/154; C12Q 2523/125
  See application file for complete search history.

(56) References Cited

U.S. PATENT DOCUMENTS

| | | |
|---|---|---|
| 3,854,480 A | 12/1974 | Zaffaroni |
| 3,870,790 A | 3/1975 | Lowey et al. |
| 4,210,644 A | 7/1980 | Ewing et al. |
| 4,226,859 A | 10/1980 | Stach |
| 4,369,172 A | 1/1983 | Schor et al. |
| 4,379,454 A | 4/1983 | Campbell et al. |
| 4,452,775 A | 6/1984 | Kent |
| 4,554,101 A | 11/1985 | Hopp |
| 4,588,585 A | 5/1986 | Mark et al. |
| 4,603,112 A | 7/1986 | Paoletti et al. |
| 4,656,127 A | 4/1987 | Mundy |
| 4,675,189 A | 6/1987 | Kent et al. |
| 4,683,195 A | 7/1987 | Mullis et al. |
| 4,683,202 A | 7/1987 | Mullis |
| 4,690,915 A | 9/1987 | Rosenberg |
| 4,722,848 A | 2/1988 | Paoletti et al. |
| 4,743,249 A | 5/1988 | Loveland |
| 4,751,180 A | 6/1988 | Cousens et al. |
| 4,769,330 A | 9/1988 | Paoletti et al. |
| 4,816,540 A | 3/1989 | Onishi |
| 4,842,866 A | 6/1989 | Horder et al. |
| 4,844,893 A | 7/1989 | Honsik et al. |
| 4,906,169 A | 3/1990 | Chien et al. |
| 4,935,233 A | 6/1990 | Bell et al. |
| 4,973,468 A | 11/1990 | Chiang et al. |
| 5,023,084 A | 6/1991 | Chien et al. |
| 5,035,891 A | 7/1991 | Runkel et al. |
| 5,110,587 A | 5/1992 | Paoletti et al. |

(Continued)

FOREIGN PATENT DOCUMENTS

| CN | 103180730 A | 6/2013 |
|---|---|---|
| EP | 1486567 A1 | 12/2004 |

(Continued)

OTHER PUBLICATIONS

Wu et al. Clin Cancer Res. 2008. 14(7):1938-1946. (Year: 2008).*
Fackler et al. Cancer Research. 2004. 64:4442-4452. (Year: 2004).*
Sigalotti et al. Cancer Research. 2004. 64:9167-9171. (Year: 2004).*
"A Phase 1 Study of Nivolumab (BMS-936558) in Subjects With Advanced or Recurrent Malignancies (MDX1106-03)," National Library of Medicine, First posted: Aug. 8, 2008 and last updated Mar. 24, 2020. https://clinicaltrials.gov/ct2/show/NCT00730639, Clinical Trials Identifier NCT00730639.
"CT-011 and p53 Genetic Vaccine for Advance Solid Tumor," National Library of Medicine, updated: Jun. 30, 2011, XP002738554, https://clinicaltrials.gov/archive/NCT01386502/2011_06_30, Clinical Trials Identifier NCT01386502.

(Continued)

*Primary Examiner* — Joseph G. Dauner
(74) *Attorney, Agent, or Firm* — Foley Hoag LLP; DeAnn F. Smith; Thi K. Dio

(57) ABSTRACT

The present invention relates to methods of determining a cancer treatment prognosis for a subject in need thereof by evaluating epigenetic and genetic changes within a tumor sample from the subject. The present invention further provides methods of treating cancer in a subject by evaluating epigenetic and genetic changes within a tumor sample from the subject. In addition, the present invention provides methods of screening test agents to identify agents that decrease tumor cell plasticity.

10 Claims, 24 Drawing Sheets

(56) References Cited

U.S. PATENT DOCUMENTS

| | | |
|---|---|---|
| 5,133,974 A | 7/1992 | Paradissis et al. |
| 5,174,993 A | 12/1992 | Paoletti |
| 5,185,146 A | 2/1993 | Altenburger |
| 5,198,223 A | 3/1993 | Gale et al. |
| 5,204,253 A | 4/1993 | Sanford et al. |
| 5,217,720 A | 6/1993 | Sekigawa et al. |
| 5,279,833 A | 1/1994 | Rose |
| 5,364,773 A | 11/1994 | Paoletti et al. |
| 5,407,686 A | 4/1995 | Patel et al. |
| 5,422,119 A | 6/1995 | Casper |
| 5,494,807 A | 2/1996 | Paoletti et al. |
| 5,541,171 A | 7/1996 | Rhodes et al. |
| 5,580,859 A | 12/1996 | Felgner et al. |
| 5,589,466 A | 12/1996 | Felgner et al. |
| 5,658,785 A | 8/1997 | Johnson |
| 5,686,281 A | 11/1997 | Roberts |
| 5,705,190 A | 1/1998 | Broad et al. |
| 5,736,152 A | 4/1998 | Dunn |
| 5,756,101 A | 5/1998 | Paoletti et al. |
| 5,762,938 A | 6/1998 | Paoletti et al. |
| 5,766,597 A | 6/1998 | Paoletti et al. |
| 5,766,882 A | 6/1998 | Falkner et al. |
| 5,770,212 A | 6/1998 | Falkner et al. |
| 5,811,104 A | 9/1998 | Dale et al. |
| 5,833,975 A | 11/1998 | Paoletti et al. |
| 5,843,728 A | 12/1998 | Seed et al. |
| 5,849,303 A | 12/1998 | Wasmoen et al. |
| 5,849,589 A | 12/1998 | Tedder et al. |
| 5,851,828 A | 12/1998 | Seed et al. |
| 5,858,358 A | 1/1999 | June et al. |
| 5,883,223 A | 3/1999 | Gray |
| 5,906,936 A | 5/1999 | Eshhar et al. |
| 5,912,170 A | 6/1999 | Seed et al. |
| 5,912,172 A | 6/1999 | Eshhar et al. |
| 5,942,235 A | 8/1999 | Paoletti |
| 5,989,562 A | 11/1999 | Wasmoen et al. |
| 5,990,091 A | 11/1999 | Tartaglia et al. |
| 5,994,136 A | 11/1999 | Naldini et al. |
| 6,004,777 A | 12/1999 | Tartaglia et al. |
| 6,004,811 A | 12/1999 | Seed et al. |
| 6,013,516 A | 1/2000 | Verma et al. |
| 6,090,393 A | 7/2000 | Fischer |
| 6,130,066 A | 10/2000 | Tartaglia et al. |
| 6,156,567 A | 12/2000 | Fischer |
| 6,159,477 A | 12/2000 | Audonnet et al. |
| 6,165,782 A | 12/2000 | Naldini et al. |
| 6,214,353 B1 | 4/2001 | Paoletti et al. |
| 6,228,846 B1 | 5/2001 | Audonnet et al. |
| 6,258,595 B1 | 7/2001 | Gao et al. |
| 6,265,189 B1 | 7/2001 | Paoletti et al. |
| 6,277,558 B1 | 8/2001 | Hudson |
| 6,284,240 B1 | 9/2001 | Seed et al. |
| 6,309,647 B1 | 10/2001 | Paoletti et al. |
| 6,312,682 B1 | 11/2001 | Kingsman et al. |
| 6,352,694 B1 | 3/2002 | June et al. |
| 6,392,013 B1 | 5/2002 | Seed et al. |
| 6,406,705 B1 | 6/2002 | Davis et al. |
| 6,410,014 B1 | 6/2002 | Seed et al. |
| 6,428,953 B1 | 8/2002 | Naldini et al. |
| 6,475,769 B1 | 11/2002 | Wilson et al. |
| 6,489,458 B2 | 12/2002 | Hackett et al. |
| 6,534,055 B1 | 3/2003 | June et al. |
| 6,537,540 B1 | 3/2003 | Burstein et al. |
| 6,537,594 B1 | 3/2003 | Paoletti et al. |
| 6,569,457 B2 | 5/2003 | Ullah et al. |
| 6,638,534 B1 | 10/2003 | Ishibashi et al. |
| 6,682,743 B2 | 1/2004 | Mayr |
| 6,713,068 B1 | 3/2004 | Audonnet et al. |
| 6,753,162 B1 | 6/2004 | Seed et al. |
| 6,761,893 B2 | 7/2004 | Chaplin et al. |
| 6,780,407 B1 | 8/2004 | Paoletti et al. |
| 6,780,417 B2 | 8/2004 | Kaslow et al. |
| 6,793,926 B1 | 9/2004 | Rasty et al. |
| 6,797,514 B2 | 9/2004 | Berenson et al. |
| 6,821,515 B1 | 11/2004 | Cleland et al. |
| 6,867,041 B2 | 3/2005 | Berenson et al. |
| 6,869,794 B2 | 3/2005 | Vogels et al. |
| 6,887,466 B2 | 5/2005 | June et al. |
| 6,893,865 B1 | 5/2005 | Lockert et al. |
| 6,905,680 B2 | 6/2005 | June et al. |
| 6,905,681 B1 | 6/2005 | June et al. |
| 6,905,874 B2 | 6/2005 | Berenson et al. |
| 6,913,752 B2 | 7/2005 | Chaplin et al. |
| 6,913,922 B1 | 7/2005 | Bout et al. |
| 6,923,973 B1 | 8/2005 | Cox et al. |
| 6,924,128 B2 | 8/2005 | Allen |
| 6,936,466 B2 | 8/2005 | Feldhaus |
| 6,943,019 B2 | 9/2005 | Wilson et al. |
| 6,953,690 B1 | 10/2005 | Gao et al. |
| 6,955,808 B2 | 10/2005 | Curiel |
| 6,974,695 B2 | 12/2005 | Vogels et al. |
| 6,991,797 B2 | 1/2006 | Andersen et al. |
| 7,029,848 B2 | 4/2006 | Vogels et al. |
| 7,045,313 B1 | 5/2006 | Moss et al. |
| 7,097,842 B2 | 8/2006 | Suter et al. |
| 7,115,391 B1 | 10/2006 | Chen et al. |
| 7,144,575 B2 | 12/2006 | June et al. |
| 7,148,203 B2 | 12/2006 | Hackett et al. |
| 7,160,682 B2 | 1/2007 | Hackett et al. |
| 7,172,893 B2 | 2/2007 | Rabinowitz et al. |
| 7,175,843 B2 | 2/2007 | June et al. |
| 7,189,536 B2 | 3/2007 | Chaplin et al. |
| 7,198,784 B2 | 4/2007 | Kingsman et al. |
| 7,232,566 B2 | 6/2007 | June et al. |
| 7,255,862 B1 | 8/2007 | Tartaglia et al. |
| 7,259,015 B2 | 8/2007 | Kingsman et al. |
| 7,283,337 B2 | 10/2007 | Sakai et al. |
| 7,303,910 B2 | 12/2007 | Bebbington et al. |
| 7,335,364 B2 | 2/2008 | Chaplin et al. |
| 7,351,585 B2 | 4/2008 | Mitrophanous et al. |
| 7,384,644 B2 | 6/2008 | Chaplin et al. |
| 7,445,924 B2 | 11/2008 | Chaplin et al. |
| 7,459,270 B2 | 12/2008 | Chaplin et al. |
| 7,572,631 B2 | 8/2009 | Berenson et al. |
| 7,572,821 B2 | 8/2009 | Sun et al. |
| 7,608,279 B2 | 10/2009 | Parisot et al. |
| 7,628,980 B2 | 12/2009 | Suter et al. |
| 7,705,120 B2 | 4/2010 | Lillie et al. |
| 7,708,949 B2 | 5/2010 | Stone et al. |
| 7,741,465 B1 | 6/2010 | Eshhar et al. |
| 7,767,449 B1 | 8/2010 | Paoletti |
| 7,892,533 B2 | 2/2011 | Suter et al. |
| 7,897,156 B2 | 3/2011 | Ackermann et al. |
| 7,923,017 B2 | 4/2011 | Chaplin et al. |
| 7,939,086 B2 | 5/2011 | Chaplin et al. |
| 7,964,395 B2 | 6/2011 | Chaplin et al. |
| 7,964,396 B2 | 6/2011 | Chaplin et al. |
| 7,964,398 B2 | 6/2011 | Chaplin et al. |
| 7,985,739 B2 | 7/2011 | Kay et al. |
| 8,034,334 B2 | 10/2011 | Dudley et al. |
| 8,088,379 B2 | 1/2012 | Robbins et al. |
| 8,163,293 B2 | 4/2012 | Chaplin |
| 8,211,422 B2 | 7/2012 | Eshhar et al. |
| 8,227,432 B2 | 7/2012 | Hackett et al. |
| 8,236,560 B2 | 8/2012 | Chaplin et al. |
| 8,268,325 B2 | 9/2012 | Chaplin et al. |
| 8,268,329 B2 | 9/2012 | Chaplin et al. |
| 8,278,036 B2 | 10/2012 | Kariko et al. |
| 8,309,098 B2 | 11/2012 | Howley et al. |
| 8,372,622 B2 | 2/2013 | Suter et al. |
| 8,399,645 B2 | 3/2013 | Campana et al. |
| 8,404,658 B2 | 3/2013 | Hajjar et al. |
| 8,454,972 B2 | 6/2013 | Nabel et al. |
| 8,470,598 B2 | 6/2013 | Chaplin et al. |
| 8,557,779 B2 | 10/2013 | Sugiyama |
| 8,648,104 B2 | 2/2014 | Du et al. |
| 8,697,854 B2 | 4/2014 | Schendel et al. |
| 8,796,414 B2 | 8/2014 | Johnston |
| 8,906,682 B2 | 12/2014 | June et al. |
| 8,911,993 B2 | 12/2014 | June et al. |
| 8,916,381 B1 | 12/2014 | June et al. |
| 8,975,071 B1 | 3/2015 | June et al. |
| 9,101,584 B2 | 8/2015 | June et al. |
| 9,102,760 B2 | 8/2015 | June et al. |

(56) References Cited

U.S. PATENT DOCUMENTS

| | | |
|---|---|---|
| 9,102,761 B2 | 8/2015 | June et al. |
| 9,115,402 B2 | 8/2015 | Hacohen et al. |
| 9,556,237 B2 | 1/2017 | Schmaljohn et al. |
| 9,909,159 B2 | 3/2018 | Marras et al. |
| 9,962,453 B2 | 5/2018 | Georges |
| 10,202,640 B2 | 2/2019 | Davis et al. |
| 10,426,824 B1 | 10/2019 | Hacohen et al. |
| 10,801,070 B2 | 10/2020 | Clement et al. |
| 10,835,585 B2 | 11/2020 | Fritsch et al. |
| 10,975,442 B2 | 4/2021 | Hacohen et al. |
| 10,993,997 B2 | 5/2021 | Hacohen et al. |
| 11,452,768 B2 | 9/2022 | Hacohen et al. |
| 2003/0104008 A1 | 6/2003 | Loosmore et al. |
| 2004/0013648 A1 | 1/2004 | Kingsman et al. |
| 2004/0018971 A1 | 1/2004 | Fikes et al. |
| 2004/0053304 A1 | 3/2004 | Markowitz |
| 2006/0008468 A1 | 1/2006 | Chiang et al. |
| 2006/0163385 A1 | 7/2006 | Link et al. |
| 2006/0252077 A1 | 11/2006 | Buzby |
| 2006/0258607 A1 | 11/2006 | Jarosch et al. |
| 2007/0003442 A1 | 1/2007 | Link et al. |
| 2007/0025970 A1 | 2/2007 | Kingsman et al. |
| 2007/0055049 A1 | 3/2007 | Grey et al. |
| 2007/0083334 A1 | 4/2007 | Mintz et al. |
| 2007/0134197 A1 | 6/2007 | Eichner et al. |
| 2007/0184489 A1 | 8/2007 | Griffiths et al. |
| 2007/0195127 A1 | 8/2007 | Ahn et al. |
| 2008/0003142 A1 | 1/2008 | Link et al. |
| 2008/0014222 A1 | 1/2008 | Simmons et al. |
| 2008/0014589 A1 | 1/2008 | Link et al. |
| 2008/0071706 A1 | 3/2008 | Honda et al. |
| 2008/0254008 A1 | 10/2008 | Dropulic et al. |
| 2009/0005254 A1 | 1/2009 | Griffiths et al. |
| 2009/0026082 A1 | 1/2009 | Rothberg et al. |
| 2009/0028888 A1 | 1/2009 | Bergeron et al. |
| 2009/0055944 A1 | 2/2009 | Korman et al. |
| 2009/0111106 A1 | 4/2009 | Mitrophanous et al. |
| 2009/0131543 A1 | 5/2009 | Weitz et al. |
| 2009/0136494 A1 | 5/2009 | Ponath et al. |
| 2009/0186042 A1 | 7/2009 | Johnston et al. |
| 2009/0220980 A1 | 9/2009 | Hoon et al. |
| 2009/0304711 A1 | 12/2009 | Pardoll et al. |
| 2010/0137143 A1 | 6/2010 | Rothberg et al. |
| 2010/0137163 A1 | 6/2010 | Link et al. |
| 2010/0158951 A1 | 6/2010 | Randolph et al. |
| 2010/0203531 A1 | 8/2010 | Sarkaria et al. |
| 2010/0210529 A1 | 8/2010 | van der Burg et al. |
| 2010/0282617 A1 | 11/2010 | Rothberg et al. |
| 2010/0286057 A1 | 11/2010 | Walensky et al. |
| 2010/0297071 A1 | 11/2010 | Ishibashi et al. |
| 2010/0304989 A1 | 12/2010 | Von Hoff et al. |
| 2011/0097312 A1 | 4/2011 | Molldrem |
| 2011/0223149 A1 | 9/2011 | Nash et al. |
| 2011/0257890 A1 | 10/2011 | Weinschenk et al. |
| 2011/0293571 A1 | 12/2011 | Widdowson et al. |
| 2011/0293637 A1 | 12/2011 | Hacohen et al. |
| 2012/0082691 A1 | 4/2012 | Rammensee et al. |
| 2012/0219947 A1 | 8/2012 | Yurkovetsky et al. |
| 2012/0244133 A1 | 9/2012 | Rosenberg et al. |
| 2012/0288539 A1 | 11/2012 | Eber |
| 2012/0295960 A1 | 11/2012 | Palfi et al. |
| 2013/0071414 A1 | 3/2013 | Dotti et al. |
| 2013/0210014 A1 | 8/2013 | Sharman |
| 2013/0295110 A1 | 11/2013 | Binder et al. |
| 2014/0056986 A1 | 2/2014 | Desai et al. |
| 2014/0178438 A1 | 6/2014 | Sahin et al. |
| 2014/0256595 A1 | 9/2014 | Link et al. |
| 2014/0322716 A1 | 10/2014 | Robins |
| 2015/0079119 A1 | 3/2015 | Johnston |
| 2015/0125463 A1 | 5/2015 | Cogswell et al. |
| 2015/0140041 A1 | 5/2015 | Vitiello |
| 2015/0224182 A1 | 8/2015 | Hunt et al. |
| 2015/0278441 A1 | 10/2015 | Min et al. |
| 2016/0008447 A1 | 1/2016 | Hacohen et al. |
| 2016/0101170 A1 | 4/2016 | Hacohen et al. |
| 2016/0130641 A1 | 5/2016 | Wang et al. |
| 2016/0213771 A1 | 7/2016 | Sampson et al. |
| 2016/0310584 A1 | 10/2016 | Fritsch et al. |
| 2016/0326593 A1 | 11/2016 | Clement et al. |
| 2016/0331822 A1 | 11/2016 | Hacohen et al. |
| 2016/0339090 A1 | 11/2016 | Hacohen et al. |
| 2017/0022251 A1 | 1/2017 | Rammensee et al. |
| 2017/0067090 A1 | 3/2017 | Zhang et al. |
| 2017/0160269 A1 | 6/2017 | Linnemann et al. |
| 2017/0199961 A1 | 7/2017 | Yelensky et al. |
| 2017/0233821 A1 | 8/2017 | Lianidou et al. |
| 2017/0298441 A1 | 10/2017 | Wu et al. |
| 2018/0000913 A1 | 1/2018 | Hacohen et al. |
| 2018/0055922 A1 | 3/2018 | Hacohen et al. |
| 2018/0127803 A1 | 5/2018 | Lei et al. |
| 2018/0153975 A1 | 6/2018 | Fritsch et al. |
| 2019/0060428 A1 | 2/2019 | Fritsch |
| 2019/0060432 A1 | 2/2019 | Hacohen et al. |
| 2019/0099475 A1 | 4/2019 | Benz et al. |
| 2019/0376147 A1 | 12/2019 | Fritsch |
| 2020/0016251 A1 | 1/2020 | Hacohen et al. |
| 2020/0069783 A1 | 3/2020 | Hacohen et al. |
| 2020/0101147 A1 | 4/2020 | Zeng |
| 2020/0330571 A1 | 10/2020 | Fritsch et al. |
| 2020/0368337 A1 | 11/2020 | Fritsch et al. |
| 2020/0407804 A1 | 12/2020 | Clement et al. |
| 2021/0220455 A1 | 7/2021 | Hacohen et al. |
| 2021/0262039 A1 | 8/2021 | Hacohen et al. |
| 2021/0379168 A1 | 12/2021 | Hacohen et al. |

FOREIGN PATENT DOCUMENTS

| | | |
|---|---|---|
| EP | 1680681 B1 | 11/2011 |
| EP | 2390363 A1 | 11/2011 |
| EP | 2569633 A2 | 3/2013 |
| EP | 2574346 A1 | 4/2013 |
| JP | 2003/517274 A | 5/2003 |
| JP | 2003/523365 A | 8/2003 |
| JP | 2003/535024 A | 11/2003 |
| JP | 2005/505271 A | 2/2005 |
| JP | 2005/529187 A | 9/2005 |
| JP | 2006/526628 A | 11/2006 |
| JP | 2009/532664 A | 9/2009 |
| JP | 2009532350 A | 9/2009 |
| JP | 2010533184 A | 10/2010 |
| JP | 2012/522500 A | 9/2012 |
| JP | 2013/530943 A | 8/2013 |
| WO | WO-91/02087 A1 | 2/1991 |
| WO | WO-91/06309 A1 | 5/1991 |
| WO | WO-92/15322 A1 | 9/1992 |
| WO | WO-92/15672 A1 | 9/1992 |
| WO | WO-92/15712 A1 | 9/1992 |
| WO | WO-93/24640 A2 | 12/1993 |
| WO | WO-95/27780 A1 | 10/1995 |
| WO | WO-95/30018 A2 | 11/1995 |
| WO | WO-96/18372 A2 | 6/1996 |
| WO | WO-00/20587 A2 | 4/2000 |
| WO | WO-00/66153 A1 | 11/2000 |
| WO | WO-2001/89788 A2 | 11/2001 |
| WO | WO-2003/020763 A2 | 3/2003 |
| WO | WO-2003/057171 A2 | 7/2003 |
| WO | WO-2003/086459 A1 | 10/2003 |
| WO | WO-2003/106692 A2 | 12/2003 |
| WO | WO-2004/002627 A2 | 1/2004 |
| WO | WO-2004/026897 A1 | 4/2004 |
| WO | WO-2004/030615 A2 | 4/2004 |
| WO | WO-2004/033685 A1 | 4/2004 |
| WO | WO-2004/044004 A2 | 5/2004 |
| WO | WO-2004/058801 A2 | 7/2004 |
| WO | WO-2004/074322 A1 | 9/2004 |
| WO | WO-2004/091763 A2 | 10/2004 |
| WO | WO-2005/021151 A1 | 3/2005 |
| WO | WO-2005/087261 A2 | 9/2005 |
| WO | WO-2005/113595 A2 | 12/2005 |
| WO | WO-2005/114215 A2 | 12/2005 |
| WO | WO-2006/000830 A2 | 1/2006 |
| WO | WO-2006/040551 A2 | 4/2006 |
| WO | WO-2006/040554 A1 | 4/2006 |
| WO | WO-2006/096571 A2 | 9/2006 |

(56) References Cited

FOREIGN PATENT DOCUMENTS

| | | |
|---|---|---|
| WO | WO-2006/121168 A1 | 11/2006 |
| WO | WO-2006/125962 A2 | 11/2006 |
| WO | WO-2007/015540 A1 | 2/2007 |
| WO | WO-2007/059033 A1 | 5/2007 |
| WO | WO-2007/089541 A2 | 8/2007 |
| WO | WO-2007/095033 A2 | 8/2007 |
| WO | WO-2007/101227 A2 | 9/2007 |
| WO | WO-2007/124090 A2 | 11/2007 |
| WO | WO-2007/133710 A2 | 11/2007 |
| WO | WO-2008/011344 A2 | 1/2008 |
| WO | WO-2008/038002 A2 | 4/2008 |
| WO | WO-2008/039818 A2 | 4/2008 |
| WO | WO-2008/063227 A2 | 5/2008 |
| WO | WO-2008/096831 A1 | 8/2008 |
| WO | WO-2008/109075 A2 | 9/2008 |
| WO | WO-2009/014708 A2 | 1/2009 |
| WO | WO-2009/025117 A1 | 2/2009 |
| WO | WO-2009/032477 A2 | 3/2009 |
| WO | WO-2009/043520 A1 | 4/2009 |
| WO | WO-2009/126306 A2 | 10/2009 |
| WO | WO-2010/033949 A1 | 3/2010 |
| WO | WO-2010/045345 A2 | 4/2010 |
| WO | WO-2010/093784 A2 | 8/2010 |
| WO | WO-2011/051489 A2 | 5/2011 |
| WO | WO-2011/079176 A2 | 6/2011 |
| WO | WO-2011/134944 A2 | 11/2011 |
| WO | WO-2011/143656 A2 | 11/2011 |
| WO | WO-2011/146862 A1 | 11/2011 |
| WO | WO-2012/027379 A2 | 3/2012 |
| WO | WO-2012079000 A1 | 6/2012 |
| WO | WO-2012/095639 A2 | 7/2012 |
| WO | WO-2012/101112 A1 | 8/2012 |
| WO | WO-2012/159643 A1 | 11/2012 |
| WO | WO-2012/159754 A2 | 11/2012 |
| WO | WO-2013/026027 A1 | 2/2013 |
| WO | WO-2013/036201 A1 | 3/2013 |
| WO | WO-2013/039889 A1 | 3/2013 |
| WO | WO-2013/040371 A2 | 3/2013 |
| WO | WO-2013/086464 A1 | 6/2013 |
| WO | WO-2013/123031 A2 | 8/2013 |
| WO | WO-2013/133405 A1 | 9/2013 |
| WO | WO-2013/166321 A1 | 11/2013 |
| WO | WO-2013/173223 A1 | 11/2013 |
| WO | WO-2013/176915 A1 | 11/2013 |
| WO | WO-2013164754 A2 | 11/2013 |
| WO | WO-2014/009535 A2 | 1/2014 |
| WO | WO-2014/011987 A1 | 1/2014 |
| WO | WO-2014/012051 A1 | 1/2014 |
| WO | WO-2014/018863 A1 | 1/2014 |
| WO | WO-2014/047561 A1 | 3/2014 |
| WO | WO-2014/056986 A1 | 4/2014 |
| WO | WO-2014/059173 A2 | 4/2014 |
| WO | WO-2014/083173 A1 | 6/2014 |
| WO | WO-2014/085802 A1 | 6/2014 |
| WO | WO-2014/133567 A1 | 9/2014 |
| WO | WO-2014/133568 A1 | 9/2014 |
| WO | WO-2014/134165 A1 | 9/2014 |
| WO | WO-2014/150924 A2 | 9/2014 |
| WO | WO-2014/168874 A2 | 10/2014 |
| WO | WO-2014/172606 A1 | 10/2014 |
| WO | WO-2014/183649 A1 | 11/2014 |
| WO | WO-2014/184744 A1 | 11/2014 |
| WO | WO-2014/191128 A1 | 12/2014 |
| WO | WO-2014/197369 A1 | 12/2014 |
| WO | WO-2015/085233 A1 | 6/2015 |
| WO | WO-2015/094995 A2 | 6/2015 |
| WO | WO-2015/095811 A2 | 6/2015 |
| WO | WO-2016/020710 A1 | 2/2016 |
| WO | WO-2016/100975 A1 | 6/2016 |
| WO | WO-2016/164833 A3 | 10/2016 |
| WO | WO-2016/187508 A2 | 11/2016 |
| WO | WO-2016/201049 A2 | 12/2016 |
| WO | WO-2017/173321 A1 | 10/2017 |
| WO | WO-2017/184590 A1 | 10/2017 |
| WO | WO-2018/140391 A1 | 8/2018 |

OTHER PUBLICATIONS

"Dose-escalation Study of Combination BMS-936558 (MDX-1106) and Ipilimumab in Subjects With Unresectable Stage III or Stage IV Malignant Melanoma," National Library of Medicine, First posted: Dec. 2, 2009 and last updated Mar. 22, 2021. https://www.clinicaltrials.gov/ct2/show/NCT01024231, Clinical Trials Identifier NCT01024231.

"Monoclonal Antibody Therapy and Vaccine Therapy in Treating Patients with Stage IV Melanoma That Has Been Removed By Surgery," National Library of Medicine, 2010, XP002738553, https:clinicaltrials.gov/archive/NCT01176474/2010_08_05.

"Neon Therapeutics' Personal Neoantigen Vaccine Study Demonstrates Prolonged Progression-Free Survival in Advanced or Metastatic Melanoma, Non-Small Cell Lung and Bladder Cancers," published by Globe Newswire on Jul. 15, 2019 ("Neon Press Release 2019").

"Single-cell sequencing: A brief overview of how to derive a genome or transcriptome from a single cell," Nature Methods, 18(11) (2014).

"Study of Pembrolizumab (MK-3475) in Participants With Progressive Locally Advanced or Metastatic Carcinoma, Melanoma, or Non-small Cell Lung Carcinoma (P07990/MK-3475-001/KEYNOTE-001) (KEYNOTE-001)," National Library of Medicine, First posted: Feb. 15, 2011 and last updated Dec. 13, 2019 https://clinicaltrials.gov/ct2/show/NCT01295827, Clinical Trials Identifier NCT01295827.

Acevedo et al., "Analysis of the mechanisms mediating tumor-specific changes in gene expression in human liver tumors," Cancer Res, 68(8):2641-2651 (2008).

Acknowledgment of Receipt dated Jun. 28, 2017 for Response to Notices of Opposition of EP2569633.

Adam Piore., "Custom Cancer Vaccines," Feb. 27, 2019 edition of MIT Technology Review.

Adams, "Toll-like receptor agonists in cancer therapy," Immunotherapy, 1(6):949-964 (2009).

Akinleye et al., "Ibrutinib and novel BTK inhibitors in clinical development," Journal of Hematology & Oncology, 6(59): 1-9 (2013).

Akiyama et al., "GATA-4 and GATA-5 transcription factor genes and potential downstream antitumor target genes are epigenetically silenced in colorectal and gastric cancer," Mol Cell Biol, 23:8429-8439 (2003).

Alarcon et al., "DNA vaccines: technology and application as anti-parasite and anti-microbial agents," Advances in Parasitology, 42:343-410 (1999).

Albert et al., "Direct Selection of Human Genomic Loci by Microarray Hybridization," Nat Methods, 4(11): 903-905 (2007).

Alderton G. "Research Highlights" from vol. 13 of *Nature Reviews, Cancer* (Apr. 2013).

Ali et al., "In situ regulation of DC subsets and T cells mediates tumor regression in mice," Cancer Immunotherapy, 1(8):1-10 (2009).

Ali et al., "Infection-mimicking materials to program dendritic cells in situ," Nat Mater, 8:151-8 (2009).

Allison, "The Mode of Action of Immunological Adjuvants," Dev Biol Stand, 92: 3-11 (1998).

Allocca et al., "Novel adeno-associated virus serotypes efficiently transduce murine Photoreceptors," Journal of Virology, 81 (20): 11372-11380 (2007).

Almeida et al., "CTdatabase: a knowledge-base of high-throughput and curated data on cancer-testis antigens," Nucleic acids research, 37:D816-819 (2008).

Altman et al., "Phenotypic analysis of antigen-specific T lymphocytes," Science, 274(5284):94-6 (1996).

Alvarez, "Present and future evolution of advanced breast cancer therapy," Breast Cancer Research, 12(Suppl 2):S1 (2010).

Alyea et al., "Toxicity and Efficacy of Defined Doses of CD4+ Donor Lymphocytes for Treatment of Relapse After Allogeneic Bone Marrow Transplant," Blood, 91(10):3671-3680 (1998).

Amara et al., "Control of a mucosal challenge and prevention of AIDS by a multiprotein DNA/MVA vaccine," Science, 292(5514):69-74 (2001).

(56) References Cited

OTHER PUBLICATIONS

Amato et al., "Vaccination of metastatic renal cancer patients with MVA-5T4: a randomized, double-blind, placebo-controlled phase III study," Clin Can Res, 16(22):5539-47 (2010).
Amato et al., "Vaccination of renal cell cancer patients with modified vaccinia ankara delivering tumor antigen 5T4 (TroVax) administered with interleukin 2: a phase II trial," Clin Cancer Res, 14(22):7504-10 (2008).
Anders et al., "HTSeq-A Python framework to work with high-throughput sequencing data," Bioinformatics, 31(2):166-169 (2015).
Andersen et al., "Parallel detection of antigen-specific T cell responses by combinatorial encoding of MHC multimers," Nature protocols, 7(5):891-902 (2012).
Anderson et al., "Next Generation DNA Sequencing and the Future of Genomic Medicine," Genes, 1: 38-69 (2010).
Andreatta et al., "Gapped sequence alignment using artificial neural networks: application to the MHC class I system," Bioinformatics 32(4):511-517 (2016).
Annunziata et al., "Frequent Engagement of the Classical and Alternative NF-KB Pathways by Diverse Genetic Abnormalities in Multiple Myeloma," Cancer Cell, 12(2):115-130 (2007).
Antoine et al., "The complete genomic sequence of the modified vaccinia Ankara strain: comparison with other orthopoxviruses," Virology, 244(2):365-96 (1998).
Antonis et al., "Vaccination with recombinant modified vaccinia virus Ankara expressing bovine respiratory syncytial virus (bRSV) proteins protects calves against RSV challenge," Vaccine, 25(25):4818-4827 (2007).
Applicant's Authorization and Release Form of the Massachusetts General Hospital, Aug. 12, 2008; and Supplemental Release to Applicant of the Partners Healthcare System, Aug. 13, 2008.
Aranda et al. "Motely Malignancies" p. 1565 from vol. 19, No. 12 of *Nature Medicine* (Dec. 2013), entitled "Notable advances 2013".
Attia et al., "Autoimmunity Correlates With Tumor Regression in Patients With Metastatic Melanoma Treated with Anti-Cytotoxic T-Lymphocyte Antigen-4," J Clin Oncol, 23.(25): 6043-6053 (2005).
Aucouturier et al., "Adjuvants designed for veterinary and human vaccines," Vaccine, 19(17-19):2666-2672 (2001).
Austen et al., "Mutations in the ATM Gene Lead to Impaired Overall and Treatment-Free Survival that is Independent of IGVH Mutation Status in Patients with B-CLL," Blood, 106(9): 3175-3182 (2005).
Ausubel, "A botanical macroscope," Proceedings of the National Academy of Sciences, 106(31):12569-12570 (2009).
Avogadri et al. "Modulation of CTLA-4 and GITR for Cancer Immunotherapy," Curr Top Microbiol Immunol, 344:211 (2011).
Azvolinsky et al., "PD-1 Inhibitor MK-3475 Again Shows Promise in Advanced Melanoma," Cancer Network, 2013. [Retrieved online] http://www.cancernetwork.com/melanoma/pd-1-inhibitor-mk-3475-again-shows-promise-advanced-melanoma.
Bachem et al., "Superior antigen cross-presentation and XCR1 expression define human CD11c+ CD141+ cells as homologues of mouse CD8+ dendritic cells," Journal of Experimental Medicine, 207(6):1273-1281 (2010).
Bachireddy et al., "Reversal of in situ T cell exhaustion during effective human anti-leukemia responses to donor lymphocyte infusion," Blood, 123(9):1412-1421 (2013).
Backert et al., "Immunoinformatics and epitope prediction in the age of genomic medicine," Genome Medicine, 7:119 (2015).
Baden et al., "First-in-human evaluation of the safety and immunogenicity of a recombinant adenovirus serotype 26 FflV-1 Env vaccine (IPCAVD 001)," J Infect Dis, 207(2):240-247 (2012).
Balagaan et al., "Stable and efficient intraocular gene transfer using pseudotyped EIAV lentiviral vectors," J Gene Med, 8:275-285 (2005).
Balakrishnan et al., "Novel Somatic and Germline Mutations in Cancer Candidate Genes in Glioblastoma, Melanoma, and Pancreatic Carcinoma," Cancer Res, 67: 3545-3550 (2007).
Balazsi et al., "Cellular decision making and biological noise: from microbes to mammals," Cell, 144(6):910-925 (2011).

Balch et al., "Final version of 2009 AJCC melanoma staging and classification," Journal of clinical oncology, 27(36):6199-6206 (2009).
Barbie et al., "Systematic RNA interference reveals that oncogenic KRAS-driven cancers require TBK1," Nature, 462:108-112 (2009).
Barretina et al., "The Cancer Cell Line Encyclopedia enables predictive modelling of anticancer drug sensitivity," Nature, 483:603-607 (2012).
Baskar et al., "Autologous Lymphoma Vaccines Induce Human T Cell Responses Against Multiple, Unique Epitopes," J Clin Invest, 113:1498-1510 (2004).
Bassani-Sternberg et al., "Mass Spectrometry of Human Leukocyte Antigen Class I Peptidomes Reveals Strong Effects of Protein Abundance and Turnover on Antigen Presentation," Mol Cell Proteomics, 14:658-673 (2015).
Baurain et al., "High Frequency of Autologous Anti-Melanoma CTL Directed Against an Antigen Generated by a Point Mutation in a New Helicase Gene," J Immunol, 164: 6057-6066 (2000).
Baylin, "A decade of exploring the cancer epigenome-biological and translational implications," Nat Rev Cancer, 11:726-734 (2005).
Baylin, "DNA methylation and gene silencing in cancer," Nat Clin Pract Oncol 2, Suppl 1, S4-11 (2005).
Beck et al., "Enterocolitis in Patients With Cancer After Antibody Blockade of Cytotoxicity TLymphocyte-Associated Antigen 4," J Clin Oncol, 24(15): 2283-2289 (2006).
Bediaga et al., "DNA methylation epigenotypes in breast cancer molecular subtypes," Breast Cancer Research, 12:R77 (2010).
Behrends et al., "Network organization of the human autophagy system," Nature, 466(7302):68-76 (2010).
Bellucci et al., "Complete Response to Donor Lymphocyte Infusion in Multiple Myeloma is Associated with Antibody Responses to Highly Expressed Antigens," Blood, 103: 656-663 (2004).
Benson, "Tandem repeats finder: a program to analyze DNA sequences," Nucleic acids research, 27(2):573-580 (1999).
Bentley et al., "Accurate Whole Human Genome Sequencing using Reversible Terminator Chemistry," Nature, 456(7218): 53-59 (2008).
Benton et al., "Screening lambdagt recombinant clones by hybridization to single plaques in situ," Science, 196(4286):180-182 (1977).
Berg et al., "Detection of artifacts and peptide modifications in liquid chromatography/mass spectrometry data using two-dimensional signal intensity map data visualization," Rapid Commun Mass Spectrom, 20(10):1558-1562 (2006).
Berger et al., "The genomic complexity of primary human prostate cancer," Nature, 470:214-220 (2011).
Berger et al., "Melanoma genome sequencing reveals frequent PREX2 mutations," Nature, 485(7399):502 (2012).
Berman et al., "Regions of focal DNA hypermethylation and long-range hypomethylation in colorectal cancer coincide with nuclear lamina-associated domains," Nat Genet, 44:40-46 (2012).
Bettelli et al., "TH-17 cells in the circle of immunity and autoimmunity," Nat Immunol, 8:345-350 (2007).
Bhardwaj et al., "TLR Agonists: Are They Good Adjuvants?," Cancer J, 16:382-391 (2010).
Bindea et al., "Spatiotemporal dynamics of intratumoral immune cells reveal the immune landscape in human cancer," Immunity, 39:782-795 (2013).
Bird, "DNA methylation patterns and epigenetic memory," Genes Dev, 16:6-21 (2002).
Birrell et al., "A genome-wide screen in *Saccharomyces cerevisiae* for genes affecting UV radiation sensitivity," Proceedings of the National Academy of Sciences 98(22):12608-12613 (2001).
Bishop et al., "APOBEC-mediated editing of viral RNA," Science, 305:645 (2004).
Bisht et al., "Severe acute respiratory syndrome coronavirus spike protein expressed by attenuated vaccinia virus protectively immunizes mice," Proc Natl Acad Sci, 101:6641-46 (2004).
Blackwell HE, Grubbs RH (1998). "Highly Efficient Synthesis of Covalently Cross-Linked Peptide Helices by Ring-Closing Metathesis". Angewandte Chemie International Edition. 37 (23): 3281-3284.
Blanchard et al., "Modified vaccinia virus Ankara undergoes limited replication in human cells and lacks several immunomodulatory

(56) References Cited

OTHER PUBLICATIONS proteins: implications for use as a human vaccine," Journal of General Virology, 79(5):1159-1167 (1998).
Bock et al., "BiQ Analyzer: visualization and quality control for DNA methylation data from bisulfite sequencing," Bioinformatics, 21:4067-4068 (2005).
Bock et al., "Reference Maps of human ES and iPS cell variation enable high-throughput characterization of pluripotent cell lines," Cell, 144:439-452 (2011).
Boen et al., "Identification of T Cell Ligands in a Library of Peptides Covalently Attached to HLA-DR4," J Immunol, 165:2040-2047 (2000).
Bogunovic et al., "TLR4 engagement during TLR3-induced proinflammatory signaling in dendritic cells promotes IL-10-mediated suppression of antitumor immunity," Cancer Res, 71(16):5467-5476 (2011).
Boisgerault et al., "Definition of the HLA-A29 peptide ligand motif allows prediction of potential T-cell epitopes from the retinal soluble antigen, a candidate autoantigen in birdshot retinopathy," PNAS, 93:3466-3470 (1996).
Boisguerin et al., "Translation of genomis-guided RNA-based personalised cancer vaccaines: towards the bedside," British J Cancer, 111:1469-1475 (2014).
Boller et al. "Characterization of the antibody response specific for the human endogenous retrovirus HTDV/HERV-K," Journal of virology, 71(6):4581-4588 (1997).
Boni et al. "Adoptive transfer of allogeneic tumor-specific T cells mediates effective regression of large tumors across major histocompatibility barriers," Blood, 112(12):4746-4754 (2008).
Boon et al., "Human T Cell Responses Against Melanoma," Annu Rev Immunol, 24: 175-208 (2006).
Boon, "Toward a Genetic Analysis of Tumor Rejection Antigens," Adv Cancer Res, 58:177-210 (1992).
Boquest et al., "Isolation and transcription profiling of purified uncultured human stromal stem cells: alteration of gene expression after in vitro cell culture," Molecular biology of the cell, 16(3):1131-1141 (2005).
Boscardin et al., "Antigen targeting to dendritic cells elicits long-lived T cell help for antibody responses." Journal of Experimental Medicine, 203(3):599-606 (2006).
Bourdetsky et al., The nature and extent of contributions by defective ribosome products to the HLA peptidome, PNAS, III, E1591-E1599 (2014).
Bowerman et al., "Engineering the binding properties of the T cell receptor:peptide:MHC ternary complex that governs T cell activity." Mol Immunol, 46(15):3000-3008 (2009).
Boyle et al., "Gel-free multiplexed reduced representation bisulfite sequencing for large-scale DNA methylation profiling," Genome Biol, 13:R92 (2012).
Boyle et al., "Tapasin-related protein TAPBPR is an additional component of the MHC class I presentation pathway," Proceedings of the National Academy of Sciences, 110: 3465-3470 (2013).
Bozic et al., "Dynamics of targeted cancer therapy." Trends Mol Med, 18:311-316 (2012).
Bozic et al., "Evolutionary dynamics of cancer in response to targeted combination therapy," Elife, 2:e00747 (2013).
Brahmer et al., "Safety and activity of anti-PD-L1 antibody in patients with advanced cancer," N Engl J Med, 366(26):2455-2465 (2012).
Brandle et al., "A Mutated HLA-A2 Molecule Recognized by Autologous Cytotoxic T Lymphocytes on a Human Renal Cell Carcinoma," J Exp Med, 183: 2501-2508 (1996).
Bremel et al., "An integrated approach to epitope analysis I: Dimensional reduction, visualization and prediction of MHC binding using amino acid principal components and regression approaches," Immunome Res, 6:7 (2010).
Brinckerhoff et al., "Melanoma Vaccines," Curr Opin Oncol, 12:163-173 (2000).
Broad Institute Article, Jan. 29, 2009, "Turning Cancer's Strength Into Weakness," (2009).
Brochier et al., "Large-scale eradication of rabies using recombinant vaccinia-rabies vaccine," Nature, 354:520-552 (1991).
Brown et al., "Integrative genomic analysis implicates gain of PIK3CA at 3g26 and MYC at 8q24 in chronic lymphocytic leukemia," Clin Cancer Res, 8:3791-802 (2012).
Brown et al., "Neo-antigens predicted by tumor genome meta-analysis correlate with increased patient survival," Genome Res, 24(5):743-750 (2014).
Brunsvig et al., "Telomerase Peptide Vaccination: A Phase I/II Study in Patients with Non-Small Cell Lung Cancer," Cancer Immunol Immunother, 55(12): 1553-1564 (2006).
Buchschacher et al., "Human immunodeficiency virus vectors for inducible expression of foreign genes." Journal of virology, 66(5):2731-2739 (1992).
Buckwalter et al., "It is the antigen(s), stupid' and other lessons from over a decade of vaccitherapy of human cancer," Seminar in Immunology, 20(5):296-300 (2008).
Buller et al., "Decreased virulence of recombinant vaccinia virus expression vectors is associated with a thymidine kinase-negative phenotype," Nature, 317:813-815 (1985).
Buller et al., "Deletion of the vaccinia virus growth factor gene reduces virus virulence," Journal of virology, 62(3):866-874 (1988).
Burger et al., "B cell receptor signaling in chronic lymphocytic leukemia," Trends Immunol, 34:592-601 (2013).
Burger et al., "Safety and activity of ibrutinib plus rituximab for patients with high-risk chronic lymphocytic leukaemia: a single-arm, phase 2 study," Lancet Oncology, 15(10):1090-1099 (2014).
Burkhardt et al., "Autologous CLL cell vaccination early after transplant induces leukemia-specific T cells," The Journal of clinical investigation, 123(9):3756-3765 (2013).
Buser et al., "Unique composite hematolymphoid tumor consisting of a pro-T lymphoblastic lymphoma and an indeterminate dendritic cell tumor: evidence for divergent common progenitor cell differentiation," Pathobiology, 81:199-205 (2014).
Byrd et al., "Targeting BTK with ibrutinib in relapsed chronic lymphocytic leukemia," The New England journal of medicine, 369:32-42 (2013).
Bystryn et al., "Double-blind trial of a polyvalent, shed-antigen, melanoma vaccine," Clin Cancer Res, 7(7):1882-1887 (2001).
Böhm et al., DNA vector constructs that prime hepatitis B surface antigen-specific cytotoxic T lymphocyte and antibody responses in mice after intramuscular injection. Journal of immunological methods 193(1): 29-40 (1996).
Cahill et al., "450K-array analysis of chronic lymphocytic leukemia cells reveals global DNA methylation to be relatively stable over time and similar in resting and proliferative compartments," Leukemia, 27:150-158 (2013).
Cai et al., "Mutated BCR-ABL Generates Immunogenic T-Cell Epitopes in CML Patients," Clinical Cancer Research, 18(20):5761-5772 (2012).
Cai et al., "Peptides Derived From Mutated BCR-ABL Elicit T Cell Immunity In CML Patients," BLOOD, 116(21): 388-388 (2010).
Callahan et al., "Nivolumab Plus Ipilimumab in Patients With Advanced Melanoma: Updated Survival, Response, and Safety Data in a phase I Dose-Escalation Study," J Clin Oncol, 36(4): 391-398 (2018).
Cancer Genome Atlas Network, "Comprehensive molecular characterization of human colon and rectal cancer," Nature, 487:330-337 (2012).
Cancer Genome Atlas Network, "Comprehensive molecular portraits of human breast tumours," Nature, 490:61-70 (2012).
Cancer Genome Atlas Research Network, "Comprehensive genomic characterization defines human glioblastoma genes and core pathways," Nature, 455(7216):1061-1068 (2008).
Cancer Genome Atlas Research Network, "Comprehensive genomic characterization of squamous cell lung cancers," Nature, 489, 519-525 (2012).
Cancer Genome Atlas Research Network, "Comprehensive molecular characterization of clear cell renal cell carcinoma," Nature, 499:43-49 (2013).
Cancer Genome Atlas Research Network, "Comprehensive molecular characterization of gastric adenocarcinoma," Nature, 513:202-209 (2014).

(56) References Cited

OTHER PUBLICATIONS

Cancer Genome Atlas Research Network, "Genomic and epigenomic landscapes of adult de novo acute myeloid leukemia," New England Journal of Medicine, 368(22):2059-2074 (2013).

Cancer Genome Atlas Research Network, "Integrated genomic analyses of ovarian carcinoma," Nature, 474: 609-615 (2011).

Cardarella et al., "Clinical, Pathologic, and Biologic Features Associated with BRAF Mutations in Non-Small Cell Lung Cancer," Clin Cancer Res, 19(16):4532-4540 (2013).

Caron et al., "Analysis of MHC immunopeptidomes using mass spectrometry," Mol Cell Proteomics (2015), doi: 10.1074/mcp.OI 15.052431.

Carpten et al., "A transforming mutation in the pleckstrin homology domain of AKT1 in cancer," Nature, 448(26):439-444 (2004).

Carreno et al., "A dendritic cell vaccine increases the breadth and diversity of melanoma neoantigen-specific T cells." Science, 348(6239):803-808 (2015).

Carreno et al., "IL-12p70-producing patient DC vaccine elicits Tc1-polarized immunity," Journal of Clinical Investigation, 123(8):3383-94 (2013).

Carter et al., "Absolute quantification of somatic DNA alterations in human cancer," Nat Biotechnol, 30:413-21 (2012).

Carter et al., "Accurate estimation of homologue-specific DNA concentration-ratios in cancer samples allows long-range haplotyping," Nature Precedings, 59-87 (2011).

Carter et al., "Identification and validation of cell surface antigens for antibody targeting in oncology," Endocrine-Related Cancer, 11:659-687 (2004).

Caskey et al., "Synthetic double-stranded RNA induces innate immune responses similar to a live viral vaccine in humans," The Journal of experimental medicine, 208(12):2357-2366 (2011).

Castle et al., "Exploiting the mutanome for tumor vaccination," Cancer research, 72(5):1081-1091 (2012).

CBOL Plant Working Group, "A DNA barcode for land plants," PNAS, 106(31):12794-12797 (2009).

Certified Priority Document for U.S. Appl. No. 61/334,866, filed May 14, 2010.

Chang et al., "Immune selection of hot-spot beta 2-microglobulin gene mutations, HLA-A2 allospecificity loss, and antigen-processing machinery component down-regulation in melanoma cells derived from recurrent metastases following immunotherapy," Journal of immunology, 174:1462-1471 (2005).

Chang et al., "Peptide length-based prediction of peptide-MHC class II binding," Bioinformatics, 22(22): 2761-2767 (2006).

Chang et al., "Use of tumor genomic profiling to reveal mechanisms of resistance to the BTK inhibitor ibrutinib in chronic lymphocytic leukemia (CLL)." J Clin Oncol, 31(15S):Abstract 7014 (2013).

Chapman et al., "Initial genome sequencing and analysis of multiple myeloma," Nature, 471:467-472 (2011).

Chatila, "The Regulatory T Cell Transcriptosome: E Pluribus Unum," Immunity, 27(5):693-695 (2007).

Cheever, "Twelve immunotherapy drugs that could cure cancers," Immunological reviews, 222:357-368 (2008).

Chen et al., "Impact of replication timing on non-CpG and CpG substitution rates in mammalian genomes," Genome Res, 20:447-457 (2010).

Chen et al., "Langerhans Cell Sarcoma Arising from Chronic Lymphocytic Lymphoma/Small Lymphocytic Leukemia: Lineage Analysis and BRAF V600E Mutation Study," N Am J Sci, 5:386-91 (2013).

Chen et al., "Molecular mechanisms of T cell co-stimulation and co-inhibition," Nature reviews Immunology, 13:227-242 (2013).

Chen et al., "Recombinant modified vaccinia virus Ankara expressing the spike glycoprotein of severe acute respiratory syndrome coronavirus induces protective neutralizing antibodies primarily targeting the receptor binding region," Journal of virology, 79.5:2678-2688 (2005).

Chen et al., Molecular Pharmaceutics, 3:109-111 (2010).

Chen et al., "Induction of CD8+ T cell responses to dominant and subdominant epitopes and protective immunity to Sendai virus infection by DNA vaccination," The Journal of Immunology, 160(5):2425-2432 (1998).

Chianese-Bullock et al., "Multi-peptide vaccines vialed as peptide mixtures can be stable reagents for use in peptide-based immune therapies," Vaccine, 27(11):1764-1770 (2009).

Chiari et al., "Two Antigens Recognized by Autologous Cytolytic T Lymphocytes on a Melanoma Result from a Single Point Mutation in an Essential Housekeeping Gene," Cancer Res, 59: 5785-5792 (1999).

Child et al., "Insertional inactivation of the large subunit of ribonucleotide reductase encoded by vaccinia virus is associated with reduced virulence in vivo," Virology, 174(2):625-629 (1990).

Chim et al., "Epigenetic dysregulation of the Wnt signalling pathway in chronic lymphocytic leukaemia," J Clin Pathol, 61:1214-1219 (2008).

Chinese Office Action dated Jun. 12, 2017 in corresponding CN Application No. 2014800322910.

Chiron et al., "Cell-cycle reprogramming for PI3K inhibition overrides a relapse-specific C4815 BTK mutation revealed by longitudinal functional genomics in mantle cell lymphoma," Cancer Discov, 4:1022-35 (2014).

Chowell et al., "TCR contact residue hydrophobicity is a hallmark of immunogenic CD8(+) T cell epitopes," PNAS, 112:E1754-E1762 (2015).

Christian et al., "Targeting DNA double-strand breaks with TAL effector nucleases," Genetics, 186(2):757-761 (2010).

Christianson et al., "Defining human ERAD networks through an integrative mapping strategy," Nat Cell Biol, 14:93-105 (2012).

Chroboczek et al., "The Sequence of the Genome of Adenovirus Type 5 and Its Comparison with the Genome of Adenovirus Type 2," Virology, 186:280-285 (1992).

Church, "Genomes for all," Sci Am, 294(1):46-54 (2006).

Cibulskis et al., "ContEst: estimating cross-contamination of human samples in next-generation sequencing data," Bioinformatics, 27:2601-2602 (2011).

Cibulskis et al., "Sensitive detection of somatic point mutations in impure and heterogeneous cancer samples," Nat Biotechnol, 31:213-9 (2013).

Ciofani et al., "A Validated Regulatory Network for Th17 Cell Specification," Cell, 151(2):289-303 (2012).

Cleveland, "LOWESS: A program for smoothing scatterplots by robust locally weighted regression," The American Statistician, 35:54 (1981).

Clinical trial NCT 01970358, Patrick Ott, A Phase I Study With a Personalized NeoAntigen Cancer Vaccine in Melanoma, p. 1-6, Retrieved from https://clinicaltrials.gov/ct2/show/NCT01970358 downloaded Jun. 20, 2017.

CNBC news article posted online on Mar. 1, 2019 entitled "Bill Gates: These breakthrough technologies are going to profoundly change the world".

Coffman et al., "Vaccine Adjuvants: Putting Innate Immunity to Work," Immunity 33:492-503 (2010).

Conlon et al., "Mouse, but not Human STING, Binds and Signals in Response to the Vascular Disrupting Agent 5,6-Dimethylxanthenone-4-Acetic Acid," Journal of Immunology, 190:5216-25 (2013).

Consolidated Table of Documents filed in Opposition to date in Response to Notices of Opposition of EP2569633 dated Jun. 28, 2017.

Corbett et al., "Aerosol immunization with NYVAC and MVA vectored vaccines is safe, simple, and immunogenic," Proc Natl Acad Sci, 105(6):2046-51 (2008).

Coulie et al., "A mutated intron sequence codes for an antigenic peptide recognized by cytolytic T lymphocytes on a human melanoma," Proc Natl Acad Sci USA, 92(17):7976-7980 (1995).

Cox et al., "Induction of cytotoxic T lymphocytes by recombinant canarypox (ALVAC) and attenuated vaccinia (NYVAC) viruses expressing the HIV-1 envelope glycoprotein," Virology, 195(2):845-850 (1993).

(56) References Cited

OTHER PUBLICATIONS

Crozat et al., "The XC chemokine receptor 1 is a conserved selective marker of mammalian cells homologous to mouse CD8α+ dendritic cells," Journal of Experimental Medicine, 207(6):1283-1292 (2010).
Daheshia et al., "Suppression of ongoing ocular inflammatory disease by topical administration of plasmid DNA encoding IL-10," The Journal of Immunology 159(4):1945-1952 (1997).
Dai et al., "Prediction of soluble heterologous protein expression levels in *Escherichia colifrom* sequence-based features and its potential in biopharmaceutical process development," Pharmaceutical Bioprocessing, 2(3): 253-266 (2014).
Dana-Farber Cancer Institute; Feb. 20, 2013 publication of the Dana-Farber Cancer Institute entitled, "Inside the Institute'; and the article Study tracks evolution of leukemia."
Datasheet for the decision of May 31, 2007, Boards of Appeal of The European Patent Office, T 1396/06.
De et al., "Aberration in DNA methylation in B-cell lymphomas has a complex origin and increases with disease severity," PLOS Genet. 9:e1003137 (2013).
De Magalhaes et al., "Next-generation sequencing in aging research: emerging applications, problems, pitfalls and possible solutions," Ageing Research Reviews, 9(3):315-323 (2010).
De Plaen et al., "Immunogenic (tum-) Variants of Mouse Tumor P815: Cloning of the Gene of Tum- Antigen P91A and Identification of the Tum- Mutation," PNAS, 85: 2274-2278 (1988).
Declaration by Professor John Haanen, M.D., Ph.D. on Mar. 8, 2019.
Declaration by Stephen Johnston filed during the prosecution of granted U.S. Pat. No. 8,796,414 dated Nov. 20, 2013.
Declaration of Dr Nir Hacohen on Feb. 16, 2014.
Declaration of Dr. John C. Castle executed on Nov. 9, 2016.
Dekosky et al., "High-throughput sequencing of the paired human immunoglobulin heavy and light chain repertoire," Nature Biotech 166-170 (2013).
DeLuca et al., "RNA-SeQC: RNA-seq metrics for quality control and process optimization," Bioinformatics, 28:1530-2 (2012).
Dengjel et al., "Glycan side chains on naturally presented MHC class II ligands," J. Mass Spectrom, 40:100-104 (2005).
DePristo et al., "A framework for variation discovery and genotyping using next-generation DNA sequencing data," Nature Genetics, 43:491-498 (2011).
Dermer et al., "Another Anniversary for the War on Cancer," Biotech, 12:320 (1994).
Di Nicolantonio et al., "Wild-Type Is Required for Response to Panitumumab or Cetuximab in Metastatic Colorectal Cancer," Journal of Clinical Oncology, 26(35):5705-5712 (2008).
Di Stasi et al., "Inducible apoptosis as a safety switch for adoptive cell therapy," New England Journal of Medicine, 365(18):1673-1683 (2011).
Diaz et al., "The molecular evolution of acquired resistance to targeted EGFR blockade in colorectal cancers," Nature, 486: 537-540 (2012).
Didierlaurent et al., "Attenuated poxviruses expressing a synthetic HIV protein stimulate HLA-A2-restricted cytotoxic T-cell responses," Vaccine, 22(25-26):3395-3403 (2004).
Ding et al., "Genome remodelling in a basal-like breast cancer metastasis and xenograft," Nature, 464:999-1005 (2010).
Ding et al., "Somatic mutations affect key pathways in lung adenocarcinoma," Nature, 455:1069-1075 (2008).
Dohner et al., "Genomic aberrations and survival in chronic lymphocytic leukemia," The New England journal of medicine, 343:1910-1916 (2000).
Donkena et al., "Oxidative Stress and DNA Methylation in Prostate Cancer," Obstetrics and Gynecology International, 2010(Article ID 302051):14 pages (2010).
Doody et al., "PRDMI/BLIMP-1 Modulates IFN-—Dependent Control of the MHC Class I Antigen-Processing and Peptide-Loading Pathway," The Journal of Immunology, 179:7614-7623 (2007).
Dreicer et al., "MVA-MUC1-IL2 vaccine immunotherapy (TG4010) improves PSA doubling time in patients with prostate cancer with biochemical failure," Investigational new drugs, 27(4):379-386 (2009).
Dressman et al., "Gene expression profiles of multiple breast cancer phenotypes and response to neoadjuvant chemotherapy," Clin Cancer Res, 12(3):819-826 (2006).
Du et al., "The Significance and Therapeutic Potential of GATA3 Expression and Mutation in Breast Cancer: A Systematic Review," Med Res Rev, 35(6):1300-1315 (2015).
Duarte "Milestone 21 Individualized neoantigen vaccines" Nature Milestones, Nov. 2020: S3-S25.
Dubey et al., "The immunodominant antigen of an ultraviolet-induced regressor tumor is generated by a somatic point mutation in the DEAD (SEQ ID No. 62) box helicase p68," The Journal of experimental medicine, 185(4):695-705 (1997).
Dudley et al., "Cancer Regression and Autoimmunity in Patients After Clonal Repopulation with Antitumor Lymphocytes," Science, 298: 850-854 (2002).
DuPage et al., "Expression of tumour-specific antigens underlies cancer immunoediting," Nature, 482(7385):405-409 (2012).
Dupuis et al., "Dendritic Cells Internalize Vaccine Adjuvant after Intramuscular Injection," Cell Immunol, 186(1): 18-27 (1998).
Dössinger et al., "MHC multimer-guided and cell culture-independent isolation of functional T cell receptors from single cells facilitates TCR identification for immunotherapy," PloS one, 8(4):e61384 (2013).
Earl et al., "Immunogenicity of a highly attenuated MVA smallpox vaccine and protection against monkeypox," Nature, 428:182 (2004).
Eckhardt et al., "DNA methylation profiling of human chromosomes 6, 20 and 22, " Nat Genet, 38:1378-1385 (2006).
Eden et al., "Discovering motifs in ranked lists of DNA sequences," PLOS computational biology, 3, e39 (2007).
Eden et al., "GOrilla: a tool for discovery and visualization of enriched GO terms in ranked gene lists," BMC bioinformatics, 10:48 (2009).
Eggermont et al., "Ulceration and stage are predictive of interferon efficacy in melanoma: results of the phase III adjuvant trials EORTC 18952 and EORTC 18991," Eur J Cancer, 48(2):218-225 (2012).
Ehrlich, "DNA hypomethylation in cancer cells," Epigenomics, 1:239-259 (2009).
Eichmann et al., "Identification and characterisation of peptide binding motifs of six autoimmune disease-associated human leukocyte antigen-class I molecules including HLA-B*39:06," Tissue Antigens 84(4):378-388 (2014).
Elias et al., Target-decoy search strategy for increased confidence in large-scale protein identifications by mass spectrometry, Nat Meth, 4:207-214 (2007).
Engelhard, "Structure of peptides associated with MHC class I molecules," Curr Opin Immunol, 6(1):13-23 (1994).
Engler et al., "A one pot, one step, precision cloning method with high throughput capability," PloS one 3(11):e3647 (2008).
Engler et al., "Golden gate shuffling: a one-pot DNA shuffling method based on type IIs restriction enzymes," PloS one, 4(5):e5553 (2009).
Erlich et al., "Next-generation sequencing for HLA typing of class I loci," BMC Genomics, 12:42 (2011).
Escobar et al., "Bayesian density estimation and inference using mixtures," Journal of the American Statistical Association, 90:577-588 (1995).
Esteban, "Attenuated poxvirus vectors MVA and NYVAC as promising vaccine cadidates against HIV/AIDS," Human vaccines, 5(12):867-871 (2009).
Estep et al., "Mutation Analysis of BRAF, MEK1 and MEK2 in 15 Ovarian Cancer Cell Lines: Implications for Therapy," PLOS ONE, 12:e1279 (2007).
Extended European Search Report dated Apr. 11, 2016, which issued during prosecution of EP Application No. 15198284.0.
Extended European Search Report for EP Application No. 19219395.1 dated Jul. 23, 2020.
Extended European Search Report for EP Application No. EP 20179960 dated Nov. 9, 2020.

(56) References Cited

OTHER PUBLICATIONS

Extended European Search Report received for EP patent application No. EP11781409, dated Apr. 10, 2014.
Extended Search Report in Corresponding European Application No. 11781409.5, dated Apr. 14, 2014.
Eyers et al., "CONSeQuence: prediction of reference peptides for absolute quantitative proteomics using consensus machine learning approaches," Mol Cell Proteomics (2011); 10(11):M110.003384. doi: 10.1074/mcp.MI 10.003384. Epub Aug. 3, 2011.
Ezzell, "Cancer 'Vaccines': An idea whose time has come?," J NIH Res, 7:46 (1995).
Fais et al., "Chronic lymphocytic leukemia B cells express restricted sets of mutated and unmutated antigen receptors," The Journal of clinical investigation, 102:1515-25 (1998).
Fan et al., "The multi substrate adapter Gab1 regulates hepatocyte growth factor (scatter factor)-c-Met signaling for cell survival and DNA repair," Molecular and cellular biology, 21:4968-4984 (2001).
Fantom Consortium et al., "A promoter-level mammalian expression atlas," Nature, 507:462-470 (2014).
Farsaci et al., "Consequence of dose scheduling of sunitinib on host immune response elements and vaccine combination therapy," Int J Cancer, 130:1948-1959 (2012).
Felgner et al., "Lipofection: A Highly Efficient, Lipid-Mediated DNA-Transfection Procedure," PNAS, 84(21): 7413-7417 (1987).
Ferrier-Rembert et al., "Short-and long-term immunogenicity and protection induced by non-replicating smallpox vaccine candidates in mice and comparison with the traditional 1st generation vaccine," Vaccine, 26(14):1794-1804 (2008).
Filatreau et al., "Technische Universitat Berlin, Fakultat III—Prozesswissenschaften Direct comparasion of T cell receptor avidity of auto-antigen specific conventional and regulatory T cells," Abstract, 1-6.
Final Office Action for U.S. Appl. No. 15/735,566, "Formulations for Neoplasia Vaccines and Methods of Preparing Thereof," dated Feb. 3, 2021.
Final Office Action for U.S. Appl. No. 15/800,732, "Compositions and Methods of Identifying Tumor Specific Neoantigens," dated Dec. 17, 2020.
Final Office Action for U.S. Appl. No. 16/813,371, "Formulations for Neoplasia Vaccines," dated Oct. 13, 2020.
Final Rejection for U.S. Appl. No. 14/794,449, "Compositions and Methods of Identifying Tumor Specific Neoantigens," dated Apr. 5, 2019.
Final Rejection for U.S. Appl. No. 14/877,125, "Compositions and Methods for Personalized Neoplasia Vaccines," dated May 24, 2019.
Final Rejection for U.S. Appl. No. 13/108,610, "Compositions and Methods of Identifying Tumor Specific Neoantigens," dated May 12, 2014.
Final Rejection for U.S. Appl. No. 14/794,449, "Compositions and Methods of Identifying Tumor Specific Neoantigens," dated Sep. 13, 2017.
Final Rejection for U.S. Appl. No. 14/877,125, "Compositions and Methods for Personalized Neoplasia Vaccines," dated Oct. 25, 2017.
Final Rejection for U.S. Appl. No. 15/038,504 , "Compositions and Methods for Diagnosing, Evaluating and Treating Cancer by Means of the DNA Methyl," dated Apr. 30, 2018.
Final Rejection for U.S. Appl. No. 15/038,504 , "Compositions and Methods for Diagnosing, Evaluating and Treating Cancer by Means of the DNA Methyl," dated Dec. 21, 2018.
Final Rejection for U.S. Appl. No. 15/102,129, "Formulations for Neoplasia Vaccines," dated Aug. 15, 2019.
Final Rejection for U.S. Appl. No. 15/102,129, "Formulations for Neoplasia Vaccines," dated Sep. 14, 2018.
Final Rejection for U.S. Appl. No. 15/105,961, "Combination Therapy With Neoantigen Vaccine," dated Aug. 23, 2019.
Final Rejection for U.S. Appl. No. 15/105,961, "Combination Therapy With Neoantigen Vaccine," dated Jul. 5, 2018.
Final Rejection for U.S. Appl. No. 15/187,174, "Compositions and Methods of Identifying Tumor Specific Neoantigens," dated May 25, 2017.
Final Rejection for U.S. Appl. No. 15/187,174, "Compositions and Methods of Identifying Tumor Specific Neoantigens," dated Oct. 12, 2018.
Final Rejection for U.S. Appl. No. 15/513,127, "Use of Clonal Evolution Analysis for Ibrutinib Resistance in Chronic Lymphocytic Leukemia Patients," dated May 17, 2019.
Final Rejection for U.S. Appl. No. 15/537,785, "Methods for Profiling the T Cell Repertoire," dated Jul. 18, 2019.
Final Rejection for U.S. Appl. No. 15/537,839, "Molecular Biomarkers for Cancer Immunotherapy," dated May 1, 2020.
Final Rejection for U.S. Appl. No. 15/575,328, "Shared Neoantigens," dated Oct. 23, 2019.
Final Rejection for U.S. Appl. No. 16/181,098, "Compositions and Methods of Identifying Tumor Specific Neoantigens," dated Jun. 17, 2019.
Finke et al., "Sunitinib Reverses Type-1 Immune Suppression and Decreases T-Regulatory Cells in Renal Cell Carcinoma Patients," Clin Cancer Res, 14(20):6674-6682 (2008).
Fisher et al., "A scalable, fully automated process for construction of sequence-ready human exome targeted capture libraries," Genome Biol, 12:R1 (2011).
Flaherty et al., "From genes to drugs: targeted strategies for melanoma," Nat Rev Cancer, 12(5):349-361 (2012).
Flexner et al., "Prevention of vaccinia virus infection in imiminodeficient mice by vector-directed IL-2 expression," Nature, 330(6145):259-262 (1987).
Flynn et al., "Immunization with HIV Gag targeted to dendritic cells followed by recombinant New York vaccinia virus induces robust T-cell immunity in nonhuman primates," Proc Natl Acad Sci, 108(17):7131-7136 (2011).
Forconi et al., "Genome-wide DNA analysis identifies recurrent imbalances predicting outcome in chronic lymphocytic leukaemia with 17p deletion," British journal of haematology. 143:532-6 (2008).
Fransen et al., "Controlled local delivery of CTLA-4 blocking antibody induces CD8+ T-cell-dependent tumor eradication and decreases risk of toxic side effects," Clin Cancer Res, 19(19):5381-5389 (2013).
Frederick et al., "BRAF inhibition is associated with enhanced melanoma antigen expression and a more favorable tumor microenvironment in patients with metastatic melanoma," Clin Cancer Res, 19:1225-1231 (2013).
Friedberg et al., "Inhibition of Syk with fostamatinib disodium has significant clinical activity in non-Hodgkin lymphoma and chronic lymphocytic leukemia," Blood, 115:2578-2585 (2011).
Fritsch et al., "HLA-Binding Properties of Tumor Neoepitopes in Humans," Cancer Immunol Res, 2(6):522-529 (2014).
Fritsch et al., "Personal Neoantigen Cancer Vaccines: A Road Not Fully Paved," Cancer Immunology Research, 8: 1465-9 (2020).
Fritsch et al., "Personal neoantigen cancer vaccines: The momentum builds," Oncoimmunology, 3(6):e29311 (2014).
Fritsch et al., "Translational repression of MCL-1 couples stress-induced eIF2 alpha phosphorylation to mitochondrial apoptosis initiation," The Journal of biological chemistry. 282:22551-62 (2007).
Fruci et al., "Altered expression of endoplasmic reticulum aminopeptidases ERAP1 and ERAP2 in transformed non-lymphoid human tissues," J Cell Physiol, 216(3):742-749 (2008).
Furman et al., "Ibrutinib resistance in chronic lymphocytic leukemia," New Engl J Med, 370(24):2352 (2014).
Furman et al., "Idelalisib and rituximab in relapsed chronic lymphocytic leukemia," The New England journal of medicine, 370:997-1007 (2014).
Fusaro et al., "Prediction of high-responding peptides for targeted protein assays by mass spectrometry" Nat Biotechnol, 27(2):190-198 (2009).
Fynan et al., "DNA vaccines: protective immunizations by parenteral, mucosal, and gene-gun inoculations," PNAS, 90 (24): 11478-82 (1993).

(56) References Cited

OTHER PUBLICATIONS

Gabrilovich et al., "IL-12 and Mutant P53 Peptide-Pulsed Dendritic Cells for the Specific Immunotherapy of Cancer," J Immunother Emphasis Tumor Immunol, 19(6): 414-418 (1996).
Gallego-Gomez et al., "Differences in virus-induced cell morphology and in virus maturation between MVA and other strains (WR, Ankara, and NYCBH) of vaccinia virus in infected human cells," Journal of virology, 77(19):10606-10622 (2003).
Gallois et al., "A needle in the 'cancer vaccine' haystack," Nature medicine, 16(8):854-856 (2010).
Ganesan et al., "Tumor-Infiltrating Regulatory T Cells Inhibit Endogenous Cytotoxic T Cell Responses to Lung Adenocarcinoma," The Journal of Immunology, 191(4): 2009-2017 (2013).
Gao et al., "Integrative analysis of complex cancer genomics and clinical profiles using the cBioPortal," Science signaling, 6(269):pi1 (2013).
Garcia-Marco et al., "Frequent Somatic Deletion of the 13q12.3 locus Encompassing BRCA2 in Chronic Lymphocytic Leukemia," Blood, 88: 1568-1575 (1996).
Garimella et al., "Identification of novel molecular regulators of tumor necrosis factor-related apoptosis-inducing ligand (TRAIL)-induced apoptosis in breast cancer cells by RNAi screening," Breast cancer research, 16(2):R41 (2014).
Garofalo et al., "miR-221&222 regulate TRAIL resistance and enhance tumorigenicity through PTEN and TIMP3 downregulation," Cancer Cell, 16(6):498-509 (2009).
Garraway et al., "Lessons from the cancer genome," Cell, 153:17-37 (2013).
Gascoigne et al., "Allelic exclusion of the T cell receptor a-chain: developmental regulation of post-translational event," Semin Immunol, 11:337-347 (1999).
Gaucher et al., "Yellow fever vaccine induces integrated multilineage and polyfunctional immune responses," The Journal of experimental medicine, 205(13):3119-3131 (2008).
Gazdar, "Activating and resistance mutations of EGFR in non-small-cell lung cancer: role in clinical response to EGFR tyrosine kinase inhibitors," Oncogene, 28:S24-S31 (2009).
Gevaert et al., "Protein identification methods in proteomics," Electrophoresis: An International Journal, 21(6):1145-1154 (2000).
Gherardi et al., "Prime-boost immunization schedules based on influenza virus and vaccinia virus vectors potentiate cellular immune responses against human immunodeficiency virus Env protein systemically and in the genitorectal draining lymph nodes," Journal of virology, 77(12):7048-7057 (2003).
Ghiringhelli et al., "Metronomic cyclophosphamide regimen selectively depletes CD4+CD25+ regulatory T cells and restores T and NK effector functions in end stage cancer patients," Cancer Immunol Immunother, 56:641-648 (2007).
Giaever et al., "Functional profiling of the Saccharomyces cerevisiae genome," Nature, 418(6896):387-391 (2002).
Giannopoulos et al., "Peptide vaccination elicits leukemia-associated antigen-specific cytotoxic CD8+ T-cell responses in patients with chronic lymphocytic leukemia," Leukemia, 24(4):798-805 (2010).
Gibbs et al., "Abundant quantitative trait loci exist for DNA methylation and gene expression in human brain," PLOS genetics, 6:e1000952 (2010).
Gibney et al., "Safety and efficacy of adjuvant anti-PD1 therapy (nivolumab) in combination with vaccine in resected high-risk metastatic melanoma.," J Clin Oncol, Abstract 9056 (2013).
Gilboa, "The Makings of a Tumor Rejection Antigen," Immunity, 11: 263-270 (1999).
Gluzman, "SV40-transformed simian cells support the replication of early SV40 mutants," Cell, 23:175-182 (1981).
Gnirke et al., "Solution Hybrid Selection with Ultra-Long Oligonucleotides for Massively Parallel Targeted Sequencing," Nat Biotechnol, 27(2): 182-189 (2009).
Goebel et al., "The complete DNA sequence of vaccinia virus," Virology, 179(1):247-266 (1990).
Goh et al., "Mining the Structural Genomics Pipeline: Identification of Protein Properties that Affect High-throughput Experimental Analysis," Journal of Molecular Biology, 336(1): 115-130 (2004).
Gomez et al., "Efficient CD8+ T cell response to the HIV-env V3 loop epitope from multiple virus isolates by a DNA prime/vaccinia virus boost (rWR and rMVA strains) immunization regime and enhancement by the cytokine IFN-γ," Virus research, 105:11-22 (2004).
Gomez et al., "Head-to-head comparison on the immunogenicity of two HIV/AIDS vaccine candidates based on the attenuated poxvirus strains MVA and NYVAC co-expressing in a single locus the HIV-1BX08 gp120 and HIV-1IIIB Gag-Pol-Nef proteins of clade B," Vaccine, 25(15):2863-2885 (2007).
Gomez et al., "MVA and NYVAC as vaccines against emergent infectious diseases and cancer," Current gene therapy, 11(:3):189-217 (2011).
Gomez et al., "The poxvirus vectors MVA and NYVAC as gene delivery systems for vaccination against infectious diseases and cancer," Current gene therapy, 8(2):97-120 (2008).
Gomez et al., "Virus distribution of the attenuated MVA and NYVAC poxvirus strains in mice," Journal of General Virology, 88(9):2473-2478 (2007).
Gotter et al., "Medullary Epithelial Cells of the Human Thymus Express a Highly Diverse Selection of Tissue-specific Genes Colocalized in Chromosomal Clusters," J Exp Med, 199(2): 155-166 (2004).
Goya et al., "SNVMix:predicting single nucleotide variants from next-generation sequencing of tumors." Bioinformatics. Original Paper, 26(6): 730-736 (2010).
Greco et al., "Improving the safety of cell therapy with the TK-suicide gene," Front Pharmacol, 6:95 (2015).
Greenman et al., "Patterns of somatic mutation in human cancer genomes," Nature, 446:153-158 (2007).
Gregoriadis et al., "Improving the therapeutic efficacy of peptides and proteins: A role for polysialic acids," Int J Pharmaceutics, 300(1-2):125-30 (2005).
Gros et al., "PD-1 identifies the patient-specific CD8+ tumor-reactive repertoire infiltrating human tumors." The Journal of clinical investigation, 124(5):2246-2259 (2014).
Grunstein et al., "Colony hybridization: a method for the isolation of cloned DNAs that contain a specific gene," PNAS, 72(10):3961-3965 (1975).
GTEx Consortium, The Genotype-Tissue Expression (GTEx) project, Nature genetics, 45:580-585 (2013).
Guasp et al., "The Peptidome of Behcet's Disease-Associated HLA-B*51 :01 Includes Two Subpeptidomes Differentially Shaped by Endoplasmic Reticulum Aminopeptidase 1," Arthritis Rheumatol, 68:505-515 (2016).
Gubin et al., "Checkpoint blockade cancer immunotherapy targets tumor-specific mutant antigens," Nature, 515:577-581 (2014).
Gueguen et al., "An Antigen Recognized by Autologous CTLs on a Human Bladder Carcinoma," J Immunol, 160(12): 6188-6194 (1998).
Guo et al., "Different length peptids bind to HLA-Aw68 similarity at their ends but bulge on in the middle," Nature, 360:364-366 (1992).
Guo et al., "Droplet microfluidics for high-throughput biological assays," Lab Chip, 12:2146-55 (2012).
Guruprasad et al., "Correlation between stability of a protein and its dipeptide composition: a novel approach for predicting in vivo stability of a protein from its primary sequence," Protein Eng, 4(2):155-161 (1990).
Guthals et al., "Shotgun Protein Sequencing with Meta-contig Assembly," Molecular and Cellular Proteomics, 1(10):1084-96 (2012).
Haanen et al., "Immunotherapy of melanoma," Euro J Canc Supp 11:97-105 (2013).
Hacohen et al., "Getting Personal with Neoantigen-Based Therapeutic Cancer Vaccines," Cancer Immunol. Res, 1(1):11-15 (2013).
Hadrup et al., "Parallel detection of antigen-specific T-eeil responses by multidimensional encoding of MHC multimers," Nature Methods, 6(7):520-26 (2009).
Halabi et al., "Prognostic model for predicting survival in men with hormone-refractory metastatic prostate cancer," Journal of Clinical Oncology, 21(7):1232-1237 (2003).

(56) References Cited

OTHER PUBLICATIONS

Hall, "Advanced sequencing technologies and their wider impact in microbiology," Journal of experimental biology, 210(9):1518-1525 (2007).
Hamid et al., "Safety and Tumor Responses with Lambrolizumab (Anti-PD-1) in Melanoma," The New England Journal of Medicine, 369(2):134-144 (2013).
Han et al., "Linking T-Cell Receptor Sequence to Fucntional Phenotype at the Single-Cell Level," Nat Biotechnol, 32:684-692 (2014).
Hanahan et al., "Hallmarks of cancer: the next generation," Cell, 144:646-674 (2011).
Hansen et al., "Increased methylation variation in epigenetic domains across cancer types," Nat Genet, 43:768-775 (2011).
Hanzelmann et al., "GSVA: gene set variation analysis for microarray and RNA-Seq data," BMC bioinformatics, 14:7 (2013).
Harndahl et al., "Peptide-MHC class I stability is a better predictor than peptide affinity of CTL immunogenicity," Eur J Immunol, 42:1405-1416 (2012).
Harndahl et al., "Real-time, High-Throughput Measurements of Peptide-MHC-I Dissociation Using a Scintillation Proximity Assay," J Immunol Methods, 374:5-12 (2011).
Harris et al., "Comparison of sequencing-based methods to profile DNA methylation and identification of monoallelic epigenetic modifications," Nat Biotechnol, 28:1097-1105 (2010).
Harris et al., "RNA editing enzyme APOBEC1 and some of its homologs can act as DNA mutators," Molecular cell. 1095):1247-1253 (2002).
Heemskerk et al., "The cancer antigenome," EMBO Journal, 32(2):194-203 (2013).
Hel et al., "Potentiation of simian immunodeficiency virus (SIV)-specific CD4+ and CD8+ T cell responses by a DNA-SIV and NYVAC-SIV prime/boost regimen," The Journal of Immunology, 167(12):7180-7191 (2001).
Herbeuval et al., "HAART reduces death ligand but not death receptors in lymphoid tissue of HIV-infected patients and simian immunodeficiency virus-infected macaques," AIDS, 23:35-40 (2009).
Herbst et al., "Predictive Correlates of Response to the Anti-PD-L1 Antibody MPDL3280A in Cancer Patients," Nature, 515(7528):563-567 (2014).
Herman et al., "Differences in the Recognition by CTL of Peptides Presented by the HLAB* 4402 and the HLA-B*4403 Molecules Which Differ by a Single Amino Acid," Tissue Antigens, 53: 111-121 (1999).
Herman et al., "ibrutinib-induced lymphocytosis in patients with chronic lymphocytic leukemia: correlative analyses from a phase II study," Leukemia, 28:2188 (2014).
Hersey et al., "Phase I/II study of treatment with dendritic cell vaccines in patient with disseminated melanoma," Cancer Immunol Immunoother, 53:125-134 (2004).
Hickman et al., "Toward a Definition of Self: Proteomic Evaluation of the Class I Peptide Repertoire," J Immunol, 172:2944-2952 (2004).
Hinrichs et al., "Exploiting the curative potential of adoptive T-cell therapy for cancer," Immunological reviews, 257:56-71 (2014).
History of Changes for Study: NCT01176461, Vaccine Therapy and Monoclonal Antibody Therapy in Treating Patients with Stage III or Stage IV Melanoma That Cannot Be Ren by Surgery, (6 pages) (2010).
Hocker et al., "Ultraviolet Radiation and Melanoma: A Systematic Review and Analysis of Reported Sequence Variants," Hum Mutat, 28(6): 578-588 (2007).
Hodi et al., "Biologic Activity of Cytotoxic T Lymphocyte-Associated Antigen 4 Antibody Blockade in Previously Vaccinated Metastatic Melanoma and Ovarian Carcinoma Patients," PNAS, 100: 4712-4717 (2003).
Hodi et al., "Immunologic and Clinical Effects of Antibody Blockade of Cytotoxic T Lymphocyte-Associated Antigen 4 in Previously Vaccinated Cancer Patients," PNAS, 105: 3005-3010 (2008).

Hodi et al., "Improved Survival with Ipilimumab in Patients with Metastatic Melanoma," New Engl J Med, 363:711-723 (2010).
Hofmann et al., "Presence of the BCR-ABL mutation Glu255Lys prior to STI571 (imatinib) treatment in patients with Ph+ acute lymphoblastic leukemia," Blood, 102(2): 659-661 (2003).
Hombrink et al., "High-Throughput Identification of Potential Minor Histocompatibility Antigens by MHC Tetramer-Based Screening: Feasibility and Limitations," Plos One, 6(8):1-11 (2011).
Hombrink et al., "Identification of Biological Relevant Minor Histocompatibility Antigens within the B-lymphocyte-Derived HLA-Ligandome Using a Reverse Immunology Approach," Clin Cancer Res, 21(9):2177-2186 (2015).
Honigberg et al., "The Bruton tyrosine kinase inhibitor PCI-32765 blocks B-cell activation and is efficacious in models of autoimmune disease and B-cell malignancy," PNAS, 107:13075-13080 (2010).
Hoof et al., "NetMHCpan, a method for MHC class I binding prediction beyond humans." Immunogenetics, 61:1-13 (2009).
Horig et al., "Phase 1 clinical trial of a recombinant canarypoxvirus (ALVAC) vaccine expressing human carcinoembryonic antigen and the B7.1 co-stimulatory molecule," Cancer Immunol Immunother, 49:504-514 (2000).
Huang et al., "Mucosal priming with replicative Tiantan vaccinia and systemic boosting with DNA vaccine raised strong mucosal and systemic HIV-specific immune responses," Vaccine, 25(52):8874-8884 (2007).
Huang et al., "T Cells Associated With Tumor Regression Recognize Frameshifted Products of the CDKN2A Tumor Suppressor Gene Locus and a Mutated HLA Class I Gene Product," J Immunol, 172(10):6057-6064 (2004).
Humphries et al., "Lineage tracing reveals multipotent stem cells maintain human adenomas and the pattern of clonal expansion in tumor evolution," PNAS, 110(27):e2490-e2499 (2013).
Hunt et al., "Characterization of peptides bound to the class I MHC molecule HLA-A2.1 by mass spectrometry," Science, 255:1261-1263 (1992).
Hutchings et al., "Combination of protein and viral vaccines induces potent cellular and humoral immune responses and enhanced protection from murine malaria challenge," Infect Immun, 75(12):5819-26 (2007).
IEDB Analysis Resource for MHC-I binding predictions (printed Oct. 2019).
IEDB Analysis Resource for MHC-II binding predictions (printed Oct. 2019).
Illingworth et al., "Orphan CpG islands identify numerous conserved promoters in the mammalian genome," PLOS Genet, 6(9):e1001134 (2010).
Illumina, "Immunotherapy, the Next Generation of Cancer Treatment, NGS-guided assessment of interactions between tumors and the immune system leads to new discoveries in immuno-oncology," (2016).
Inokuchi et al., "DCC protein expression in hematopoietic cell populations and its relation to leukemogenesis," J Clin Invest, 97:852-857 (1996).
Intellectual Property Policy for Partners-Affiliated Hospitals and Institutions, Aug. 15, 2002.
International Preliminary Report on Patentability for International Application No. PCT/US2011/036665 dated Nov. 20, 2012.
International Preliminary Report on Patentability for International Application No. PCT/US2014/033185 dated Oct. 22, 2015.
International Preliminary Report on Patentability for International Application No. PCT/US2014/067146 dated May 31, 2016.
International Preliminary Report on Patentability for International Application No. PCT/US2014/068746 dated Jun. 7, 2016.
International Preliminary Report on Patentability for International Application No. PCT/US2014/068893 dated Jun. 7, 2016.
International Preliminary Report on Patentability for International Application No. PCT/US2014/071707 dated Jun. 21, 2016.
International Preliminary Report on Patentability for International Application No. PCT/US2015/067143 dated Jun. 20, 2017.
International Preliminary Report on Patentability for International Application No. PCT/US2017/028122 dated Oct. 23, 2018.
International Search Report and Written Opinion for International Application No. PCT/US/2015/051340 dated Dec. 21, 2015.

(56) References Cited

OTHER PUBLICATIONS

International Search Report and Written Opinion for International Application No. PCT/US/2016/033452 dated May 20, 2016.
International Search Report and Written Opinion for International Application No. PCT/US/2016/036605 dated Jan. 16, 2017.
International Search Report and Written Opinion for International Application No. PCT/US2011/036665 dated Jul. 2, 2012.
International Search Report and Written Opinion for International Application No. PCT/US2014/033185 dated Nov. 5, 2014.
International Search Report and Written Opinion for International Application No. PCT/US2014/067146 dated Mar. 31, 2015.
International Search Report and Written Opinion for International Application No. PCT/US2015/067143 dated Apr. 12, 2016.
International Search Report and Written Opinion for International Application No. PCT/US2017/028122 dated Apr. 18, 2016.
International Search Report and Written Opinion for International Application No. PCT/US2018/014831 dated Apr. 4, 2018.
International Search Report for International Application No. PCT/US2014/068746 dated Mar. 23, 2015.
International Search Report for International Application No. PCT/US2014/068893 dated Apr. 9, 2015.
International Search Report for International Application No. PCT/US2014/071707 dated Sep. 10, 2015.
Invention Agreement of the Dana-Farber Cancer Institute, Jul. 1, 1997.
Ishihama et al., "Exponentially Modified Protein Abundance Index (emPAI) for Estimation of Absolute Protein Amount in Proteomics by the Number of Sequenced Peptides per Protein," Mol Cell Proteomics, 4:1265-1272 (2005).
Itoh et al., "Personalized peptide vaccines: A new therapeutic modality for cancer," Cancer Sci, 97:970-976 (2006).
Izeradjene et al., "Casein kinase II (CK2) enhances death-inducing signaling complex (DISC) activity in TRAIL-induced apoptosis in human colon carcinoma cell lines," Oncogene, 24:2050-2058 (2005).
Jaatinen et al., "Global gene expression profile of human cord blood-derived CD133+ cells," Stem Cells, 24:631-641 (2006).
Japanese Office Action dated Jan. 22, 2018, which issured during prosecution of JP 2016-507587.
Japanese Office Action from Application No. 2013-510360 dated Apr. 28, 2015.
Jarmalavicius et al., "High Immunogenicity of the Human Leukocyte Antigen Peptidomes of Melanoma Tumor Cells," J Biol Chem, 287(40):33401-33411 (2012).
Jeffery et al., "The Influence of HLA Class I Alleles and Heterozygosity on the Outcome of Human T Cell Lymphotropic Virus Type I Infection," J Immunol, 165:7278-7284 (2000).
Jemal et al., "Cancer statistics, 2007," CA: a cancer journal for clinicians, 57:43-66 (2007).
Jennewein et al., "Sumoylation of peroxisome proliferator-activated receptor gamma by apoptotic cells prevents lipopolysaccharide-induced NCoR removal from kappaB binding sites mediating transrepression of proinflammatory cytokines," Journal of immunology, 181:5646-5652 (2008).
Jensen et al., "Design and implementation of adoptive therapy with chimeric antigen receptor-modified T cells," Immunol Rev, 257(1):127-144 (2014).
Ji et al., "An immune-active tumor microenvironment favors clinical response to ipilimumab," Cancer Immunol Immunother, 61(7):1019-1031 (2011).
Jiang et al., "GATA3 Mutations Define a Unique Subtype of Luminal-Like Breast Cancer With Improved Survival," Canc 120:1329-1337 (2014).
Jocham et al., "Adjuvant Autologous Renal Tumour Cell Vaccine and Risk of Tumour Progression in Patients with Renal-Cell Carcinoma After Radical Nephrectomy: Phase III, Randomised Controlled Trial," Lancet, 363: 594-599 (2004).
Johann et al., "GLVR1, a receptor for gibbon ape leukemia virus, is homologous to a phosphate permease of Neurospora crassa and is expressed at high levels in the brain and thymus," Journal of Virology, 66(3):1635-1640 (1992).

Johnson et al., "Discovery of Naturally Processed and HLA-Presented Class I Peptides from Vaccinia Virus Infection using Mass Spectrometry for Vaccine Development," Vaccine, 28(1):38-47 (2009).
Johnson et al., "Single-cell perforin and granzyme expression reveals the anatomical localization of effector CD8+ T cells in influenza virus-infected mice," PNAS, 100:2657-2662 (2003).
Jones et al., "Functions of DNA methylation: islands, start sites, gene bodies and beyond," Nat Rev Genet, 13:484-492 (2012).
Jones et al., "InterProScan 5: genome-scale protein function classification," Bioinformatics, 30:1236-1240 (2014).
Jones et al., "The epigenomics of cancer," Cell, 128:683-692 (2007).
Jorgensen et al., "NetMHC stab—predicting stability of peptide-MHC-I complexes; impacts for cytotoxic T lymphocyte epitope discovery," Immunology 141:18-26 (2014).
Jun et al., "Progress in T cell adoptive Immunotherapy for Malignant Solid Tumors," Chin Med Biotechnol, 3(1):1-7 (2008).
Kalaora et al., "Use of HLA peptidomics and whole exome sequencing to identify human immunogenic neo-antigens," Oncotarget, 7(5):5110-5117 (2016).
Kandoth et al., "Mutational landscape and significance across 12 major cancer types," Nature, 502:333-339 (2013).
Kanduri et al., "Differential genome-wide array-based methylation profiles in prognostic subsets of chronic lymphocytic leukemia," Blood, 115(2):296-305 (2010).
Kannan et al., "Vaccination strategies in follicular lymphoma," Current hematologic malignancy reports, 4(4):189-195 (2009).
Kantoff et al. "Overall survival analysis of a phase II randomized controlled trial of a Poxviral-based PSA-targeted immunotherapy in metastatic castration-resistant prostate cancer," Journal of Clinical Oncology, 28(7):1099-1105 (2010).
Kanzler et al., "Therapeutic Targeting of Innate Immunity with Toll-like Receptor Agonists and Antagonists," Nat Med, 13: 552-559 (2007).
Karanikas et al., "High frequency of cytolytic T lymphocytes directed against a tumor-specific mutated antigen detectable with HLA tetramers in the blood of a lung carcinoma patient with long survival," Cancer Res, 61:3718-3724 (2001).
Karnani et al., "Pan-S replication patterns and chromosomal domains defined by genome-tiling arrays of ENCODE genomic areas," Genome research, 17:865-876 (2007).
Karolchik et al., "The UCSC Table Browser data retrieval tool," Nucleic acids research, 32:D493-496 (2004).
Kaufman et al., "Phase II randomized study of vaccine treatment of advanced prostate cancer (E7897): a trial of the Eastern Cooperative Oncology Group," Journal of Clinical Oncology, 22(11):2122-2132 (2004).
Kawai et al., "TLR signaling," Seminars in immunology, 19(1):24-32 (2007).
Kawakami et al., "Identification of human tumor antigens and its implications for diagnosis and treatment of cancer," Cancer Sci, 95(10): 784-791 (2004).
Keats et al., "Promiscuous Mutations Activate the Noncanonical NF-KB Pathway in Multiple Myeloma," Cancer Cell, 12: 131-144 (2007).
Kenter et al., "Phase I Immunotherapeutic Trial with Long Peptides Spanning the E6 and E7 Sequences of High-Risk Human Papillomavirus 16 in End-Stage Cervical Cancer Patients Show Low Toxicity and Robust Immunogenicity," Clin. Cancer Research, 14(1):169-177 (2008).
Kenter et al., "Vaccination against HPV-16 oncoproteins for vulvar intraepithelial neoplasia," New England Journal of Medicine, 361(19):1838-1847 (2009).
Keogh et al., "Identification of New Epitopes from Four Different Tumor-Associated Antigens: Recognition of Naturally Processed Epitopes Correlates with HLA-A□0201-Binding Affinity," J Immunol, 167:787-796 (2001).
Keskin et al., "Direct identification of an HPV-16 tumor antigen from cervical cancer biopsy specimens," Front Immunol, 2:75 (2011).
Keskin et al., "Neoantigen vaccine generates intratumoral T cell responses in phase lb glioblastoma trial," Nature, 565(7738):234-239 (2019).

(56) References Cited

OTHER PUBLICATIONS

Keskin et al., "Physical detection of influenza A epitopes identifies a stealth subset on human lung epithelium evading natural CD8 immunity," PNAS, 112(7):2151-2156 (2015).
Kesmir et al., "Prediction of proteasome cleavage motifs by neural networks," Protein Eng, 15(4):287-296 (2002).
Kessler et al., "Identification of T-cell epitopes for cancer immunotherapy," Leukemia, 21:1859-1874 (2007).
Khalili et al., "In silico prediction of tumor antigens derived from functional missense mutations of the cancer gene census," Oncoimmunology, 1(8):1281-1289 (2012).
Khammari et al., "Treatment of metastatic melanoma with autologous melan-A/mart-1-specific cytotoxic t lymphocyte clones," Journal of Investigative Dermatology, 129(12): 2835-2842 (2009).
Khong et al., "Natural selection of tumor variants in the generation of "tumor escape" phenotypes," Nature immunology, 3:999-1005 (2002).
Kim et al., "A Myc network accounts for similarities between embryonic stem and cancer cell transcription programs," Cell, 143:313-324 (2010).
Kim et al., "Anticancer flavonoids are mouse-selective STING agonists," ACS chemical biology, 8(7):1396-1401 (2013).
Kim et al., "Derivation of an amino acid similarity matrix for peptide:MHC binding and its application as a Bayesian prior," BMC Bioinformatics, 10:1-11 (2009).
Kim et al., "Inactivating mutations of caspase-8 in colorectal carcinomas," Gastroenterology, 125:708-715 (2003).
Kim et al., "mTOR inhibitors radiosensitize PTEN-deficient non-small-cell lung cancer cells harboring an EGFR activating mutation by inducing autophagy," J Cell Biochem, 114(6):1248-1256 (2013).
Kim et al., "Positional Bias of MHC Class I Restricted T-Cell Epitopes in Viral Antigens Is Likely due to a Bias in Conservation," PLOS Comput Biol, 9:e1002884 (2013).
Kim et al., "TopHat2: accurate alignment of transcriptomes in the presence of insertions, deletions and gene fusions," Genome biology, 14:R36 (2013).
Kim et al., "TroVax, a recombinant modified vaccinia Ankara virus encoding 5T4: lessons learned and future development," Human vaccines, 6(10):784-791 (2010).
Kimmel et al., "[54] Identification and characterization of specific clones: Strategy for confirming the validity of presumptive clones," Methods in enzymology, 152:507-511 (1987).
Kirkwood et al., "High- and Low-dose Interferon Alpha-2b in High-isk Melanoma: First Analysis of Intergroup Trial E1690/S9111/C9190," J Clin Oncol, 18:2444-2458 (2000).
Kirkwood et al., "Interferon alfa-2b Adjuvant Therapy of High-Risk Resected Cutaneous Melanoma: The Eastern Cooperative Oncology Group Trial EST 1684," J Clin Oncol, 14:7-17 (1996).
Klebanoff et al., "Therapeutic cancer vaccines:are we there yet?," Immunol Rev, 239(1):27-44 (2011).
Klein et al., "Droplet Barcoding for Single-Cell Transcriptomics Applied to Embryonic Stem Cells," Cell, 161:1187-1201 (2015).
Kloor et al., "Immune evasion of microsatellite unstable colorectal cancers," International journal of cancer, 127:1001-1010 (2010).
Klug et al., "Characterization of MHC Ligands for Peptide Based Tumor Vaccination," Current Pharmaceutical Design, 15(28): 3221-3236 (2009).
Kobayashi et al., "DNA methylation profiling reveals novel biomarkers and important roles for DNA methyltransferases in prostate cancer," Genome Research, 21:1017-1027 (2011).
Kobayashi et al., "Peptide epitope identification for tumor-reactive CD4 T cells," Current opinion in immunology, 20(2):221-227 (2008).
Koch, "Combining morphology and DNA barcoding resolves the taxonomy of Western Malagasy Liotrigona Moure, 1961," African Invertebrates, 51(2):413-421 (2010).
Koh et al., "Immunological consequences of using three different clinical/laboratory techniques of emulsifying peptide-based vaccines in incomplete Freund's adjuvant," J Translational Med, 4:42 (2006).
Komarova et al., "Evolution of Ibrutinib Resistance in Chronic Lymphcytic Leukemia (CLL)," Proceedings of the National Academy of Sciences, 111(38):13906-13911 (2014).
Kornher et al., "Mutation Detection Using Nucleotide Analogs That Alter Electrophoretic Mobility," Nucleic Acids Res, 17(19): 7779-7784 (1989).
Kotwal et al., "Vaccinia virus encodes two proteins that are structurally related to members of the plasma serine protease inhibitor superfamily," Journal of virology, 63(2):600-606 (1989).
Kreiter et al., "Mutant MHC Class II epitopes drive therapeutic immune responses to cancer," Nature, 520:692 (2015).
Kreiter et al., "Targeting the tumor mutanome for personalized vaccination therapy," OncoImmunology, 1(5):768-769 (2012).
Kreso et al., "Variable clonal repopulation dynamics influence chemotherapy response in colorectal cancer," Science, 339:543-548 (2013).
Kress et al., "DNA barcodes: Genes, genomics, and bioinformatics," PNAS, 105(8):2761-2762 (2008).
Kress et al., "Use of DNA barcodes to identify flowering plants," PNAS, 102(23):8369-8374 (2005).
Krieg, "Therapeutic potential of Toll-like receptor 9 activation," Nature reviews Drug discovery, 5(6):471-484 (2006).
Kronenberger et al., "A Polyvalent Cellular Vaccine Induces T-cell Responses Against Specific Self-antigens Overexpressed in Chronic Lymphocytic B-cell Leukemia," J Immunother, 31(8): 723-730 (2008).
Kronke et al. "Lenalidomide causes selective degradation of IKZFI and IKZF3 in multiple myeloma cells," Science, 343(6168): 301-305 (2014).
Kronke et al. "Lenalidomide induces ubiquitination and degradation of CKla in del(5q) MDS," Nature, 523(7559):183-188 (2015).
Kulis et al., "Epigenomic analysis detects widespread gene-body DNA hypomethylation in chronic lymphocytic leukemia," Nat Genet, 44:1236-1242 (2012).
Kuppuswamy et al., "Single Nucleotide Primer Extension to Detect Genetic Diseases: Experimental Application to Hemophilia B (Factor IX) and Cystic Fibrosis Genes," PNAS, 88(4): 1143-1147 (1991).
Kyte et al., "A Simple Method for Displaying the Hydropathic Character of a Protein," J. Mol. Biol., 157: 105-132 (1982).
Kyte et al., "Telomerase Peptide Vaccination Combined with Temozolomide: A Clinical Trial in Stage IV Melanoma Patients," Clin Cancer Res, 17(13):4568-4580 (2011).
Ladetto et al., "Real-Time Polymerase Chain Reaction in Multiple Myeloma: Quantitative Analysis of Tumor Contamination of Stem Cell Harvests," Exp Hematol, 30: 529-536 (2002).
Lahaye et al., "DNA barcoding the floras of biodiversity hotspots," PNAS, 105(8):2923-2928 (2008).
Landan et al., "Epigenetic polymorphism and the stochastic formation of differentially methylated regions in normal and cancerous tissues," Nat Genet, 44:1207-1214 (2012).
Landau et al., "Chronic lymphocytic leukemia: molecular heterogeneity revealed by high-throughput genomics," Genome Med, 5:47 (2013).
Landau et al., "Clonal evolution in hematological malignancies and therapeutic implications," Leukemia, 28:34-43 (2014).
Landau et al., "Evolution and Impact of Subclonal Mutations in Chronic Lymphocytic Leukemia," Cell, 152:714-726 (2013).
Landau et al., "Increased Local Disorder of DNA Methylation Forms the Basis of High Intra-Leukemic Epigenetic Heterogeneity and Enhances CLL Evolution," Blood, 122:596 (2013).
Landau et al., "The evolutionary landscape of chronic lymphocytic leukemia treated with ibrutinib targeted therapy," Nat Commun, 8(1):2185 (2017).
Langmead et al., "Fast gapped-read alignment with Bowtie 2," Nat Meth, 9:357-359 (2012).
Langmead et al., "Ultrafast and memory-efficient alignment of short DNA sequences to the human genome," Genome Biology, 10:R25 (2009).
Larsen et al., "Large-scale validation of methods for cytotoxic T-lymphocyte epitope prediction," BMC Bioinformatics, 8:424-424 (2007).

(56) References Cited

OTHER PUBLICATIONS

Lata et al., "MHCBN 4.0: A database of MHC/TAP binding peptides and T-cell epitopes," BMC Research Notes, 2(1): 61 (2009).
Lavranos Declaration dated Jan. 12, 2022.
Lavranos Declaration dated Jan. 17, 2022.
Lawrence et al., "Discovery and saturation analysis of cancer genes across 21 tumour types," Nature, 505:495-501 (2014).
Lawrence et al., "Mutational heterogeneity in cancer and the search for new cancer-associated genes," Nature, 499:214-218 (2013).
Le et al., "Evaluation of Ipilimumab in combination with allogeneic pancreatic tumor cells transfected with a GM-CSF gene in previously treated pancreatic cancer," J Immunother, 36(7):382-389 (2013).
Le et al., "Next-Generation Cancer Vaccine Approaches: Integrating Lessons Learned From Current Successes With Promising Biotechnologic Advances," J Natl Compr Cancer Network, 11:766-772 (2013).
Le Mercier et al., "Beyond CTLA-4 and PD-1, the generation Z of negative checkpoint regulators," Front Immunol, 6:418 (2015).
Lee et al., "Monocyte-derived dendritic cells from HLA-matched allogenic donors showed a greater ability to induce leukemic cell-specific T cells in comparison to leukemic cell-derived dendritic cells or monocyte-derived dendritic cells from AML patients," Leukemia Research, 32: 1653-1660 (2008).
Lee et al., "Sequential amplification of cloned DNA as tandem multimers using class-IIS restriction enzymes," Genetic Analysis: Biomolecular Engineering, 13(6):139-145 (1996).
Lee, "Identification of Neo-antigens for a Cancer Vaccine by Transcriptome Analysis", PhD Thesis, Arizona State University (2012).
Leffers et al., "Immunization with a P53 synthetic long peptide vaccine induces P53 ⌐ specific immune responses in ovarian cancer patients, a phase II trial," Int J Cancer, 125(9):2104-2113 (2009).
Leffers et al., "Long-term clinical and immunological effects of p53?SLP® vaccine in patients with ovarian cancer," Int J Cancer, 130(1):105-112 (2012).
Leitner et al., "Immune responses induced by intramuscular or gene gun injection of protective deoxyribonucleic acid vaccines that express the circumsporozoite protein from Plasmodium berghei malaria parasites," J Immunol, 159(12):6112-6119 (1997).
Lemay et al., "Dok-3, a Novel Adapter Molecule Involved in the Negative Regulation of Immunoreceptor Signaling," Mol Cell Biol, 20:2743-2754 (2000).
Lemmel et al., "Differential quantitative analysis of MHC ligands by mass spectrometry using stable isotope labeling," Nature Biotechnology, 22(4):450-454 (2004).
Lennerz et al., "The Response of Autologous T Cells to a Human Melanoma is Dominated by Mutated Neoantigens," PNAS, 102(44):16013-16018 (2005).
Letter from Mathys & Squire dated Jun. 28, 2017 accompanying Response to Notices of Opposition of EP2569633.
Letter from Mathys & Squire dated Jun. 29, 2017+B245:B256.
Lewin et al., "DNA is the Genetic Material: Mutations Change the Sequence of DNA," Genes IV, 4:68-69 (1990).
Lewintre et al., "Analysis of chronic lymphotic leukemia transcriptomic profile: differences between molecular subgroups," Leuk Lymphoma, 50:68-79 (2009).
Lewis et al., "DNA Vaccines: A Review," Advances in Virus Research, 54:129-88 (1999).
Ley et al., "DNA sequencing of a cytogenetically normal acute myeloid leukaemia genome," Nature, 456: 66-72 (2008).
Ley et al., "DNMT3A Mutations in Acute Myeloid Leukemia", The New England Journal of Medicine, 363: 2423-2433 (2010).
Li et al., "Cancer Genome Sequencing and Its Implications for Personalized Cancer Vaccines," Cancers 3(4):4191-4211 (2011).
Li et al., "Fast and accurate short read alignment with Burrows-Wheeler Transform," Bioinformatics, 25(14):1754-1760 (2009).
Li et al., "Inactivating mutations of the chromatin remodeling gene ARID2 in hepatocellular carcinoma," Nature Genetics, 43:828-829 (2011).

Li et al., "Mapping short DNA sequencing reads and calling variants using mapping quality scores," Genome Res, 18:1851-1858 (2008).
Li et al., "RSEM: accurate transcript quantification from RNA-Seq data with or without a reference genome," BMC Bioinformatics, 12:323 (2011).
Li et al., "The Sequence Alignment/Map format and SAMtools," Bioinformatics, 25(16):2078-2079 (2009).
Li et al., "Fast and accurate long-read alignment with Burrows-Wheeler transform," Bioinformatics, 26(5):589-595 (2010).
Liggins et al., "MORC4, a novel member of the MORC family, is highly expressed in a subset of diffuse large B-cell lymphomas," Brit J Haematol, 138:479-486 (2007).
Lim et al., "Transcriptome analyses of mouse and human mammary cell subpopulations reveal multiple conserved genes and pathways," Breast Cancer Res, 12:R21 (2010).
Lin et al., "Evaluation of MHC-II Peptide Binding Prediction Servers: Applications for Vaccine Research," BMC Bioinformatics, 9: S22 (2008).
Lin et al., "Relevance of the immunoglobulin VH somatic mutation status in patients with chronic lymphocytic leukemia treated with fludarabine, cyclophosphamide, and rituximab (FCR) or related chemoimmunotherapy regimens," Blood, 113:3168-71 (2009).
Linard et al., "A ras-Mutated Peptide Targeted by CTL Infiltrating a Human Melanoma Lesion," J Immunol, 168:4802-4808 (2002).
Linardou et al., "Assessment of somatic k-RAS mutations as a mechanism associated with resistance to EGFR-targeted agents: a systematic review and meta-analysis of studies in advanced non-small-cell lung cancer and metastatic colorectal cancer," Lancet Oncol, 9(10):962-972 (2008).
Linardou et al., "Somatic EGFR mutations and efficacy of tyrosine kinase inhibitors in NSCLC," Nat Rev Clin Oncol, 6(6):352-366 (2009).
Lindhout et al., "Site-specific enzymatic polysialylation of therapeutic proteins using bacterial enzymes," PNAS, 108(18):7397-7402 (2011).
Link et al., "Electric control of droplets in microfluidic devices," Angew Chem Int Ed Engl. 45(16):2556-2560 (2006).
Linnemann et al., "High-throughput epitope discovery reveals frequent recognition of neo-antigens by CD4+ T cells in human melanoma," Nat Med, 21:81-85 (2015).
Linnemann et al., "High-throughput identification of antigen-specific TCRs by TCR gene capture," Nat Med, 19(11):1534-1541 (2013).
Liu et al., "Athlates:accurate typing of human leukocyte antigen through exome sequencing," Nucleic Acids Res, 41(14):e142 (2013).
Liu et al., "Systematic identification of type I and type II interferon-induced antiviral factors," PNAS, 109(11):4239-4244 (2012).
Livak et al. "Methods for qPCR gene expression profiling applied to 1440 lymphoblastoid single cells," Methods, 59(1):71-79 (2013).
Llano et al., "Best-Characterized HIV-1 CTL Epitopes: The 2013 Update," HIV Mol Immunol , 3-25 (2013).
Llobet et al., "CK2 controls TRAIL and Fas sensitivity by regulating FLIP levels in endometrial carcinoma cells," Oncogene, 27:2513-2524 (2008).
Lohr et al., "Discovery and prioritization of somatic mutations in diffuse large B-cell lymphoma (DLBCL) by whole-exome sequencing," PNAS, 109(10):3879-3884 (2012).
Lorente et al., "Diversity of Natural Self-Derived Ligands Presented by Different HLA Class I Molecules in Transporter Antigen Processing-Deficient Cells," PLoS ONE 8:e59118 (2013).
Loveridge et al., "The genetic contribution to human T-cell receptor repertoire," Immunology, 74:246-250 (1991).
Lu et al., "Mutated regions of nucleophosmin 1PPP1R3B Is Recognized by T Cells Used To Treat a Melanoma Patient Who Experienced a Durable Complete Tumor Regression," J Immunol, 190(12):6034-6042 (2013).
Lucas et al., "About human tumor antigens to be used in immunotherapy." Semin Immunol, 20(5):301-307 (2008).
Luckow et al.,"Trends in the Development of Baculovirus Expression Vectors," Nat Biotechnol, 6:47-55 (1988).
Lund et al., "Coordination of early protective immunity to viral infection by regulatory T cells," Science, 320(5880):1220-1224 (2008).

(56) References Cited

OTHER PUBLICATIONS

Lundegaard et al., "NetMHC-3.0: accurate web accessible predictions of human, mouse and monkey MHC class I affinities for peptides of length 8-11," Nucleic Acids Research, 36: W509. W512(2008).
Lundegaard et al., "Prediction of epitopes using neural network based methods," J Immunol Methods, 374(1-2):26-34 (2011).
Lundegaard et al., "State of the art and challenges in sequence based T-cell epitope prediction," Immunome Research, 6(Suppl 2): S3 (2010).
Luo et al. "Machine learning methods for Predicting hla-Peptide Binding activity," Bioinformatics and Biology Insights, 9(s3):21-29 (2015).
Ma, "Novor: Real-Time Peptide de Novo Sequencing Software," J Am Soc Mass Spectrom, 26:1885-1894 (2015).
Macconaill et al., Profiling Critical Cancer Gene Mutations in Clinical Tumor Samples, PLoS One, 4(11):e7887 (2009).
Machiels et al., "Peptide-Based Cancer Vaccines," Seminars in Oncology, 29(5):494-502 (2002).
Mackall et al., "Targeting tumor specific translocations in sarcomas in pediatric patients for immunotherapy," Clinical Orthopaedics and Related Research, 373:25-31 (2000).
Mackett et al., "Vaccinia virus: a selectable eukaryotic cloning and expression vector," PNAS, 79:7415-7419 (1982).
Macosko et al., "Highly Parallel Genome-wide Expression Profiling of Individual Cells Using Nanoliter Droplets," Cell, 161(5):1202-1214 (2015).
Maegawa et al., "Age-related epigenetic drift in the pathogenesis of MDS and AML," Genome Res, 24:580-591 (2014).
Maeurer et al., "New treatment options for patients with melanoma: review of melanoma-derived T-cell epitopebased peptide vaccines," Melanom Research, 6:11-24 (1996).
Maker et al., "Intrapatient Dose Escalation of Anti-CTLA-4 Antibody in Patients With Metastatic Melanoma," J Immunother, 29: 455-463 (1997).
Malavolta et al., "Interpretation of the dissolution of insoluble peptide sequences based on the acid-base properties of the solvent," Protein Sci, 15(6):1476-1488 (2006).
Malcikova et al., "Identification of somatic hypermutations in the TP53 gene in B-cell chronic lymphocytic leukemia," Molecular Immunol, 45(5):1525-1529 (2008).
Mandelboim et al., "Regression of Established Murine Carcinoma Metastases Following Vaccination with Tumor-Associated Antigen Peptides," Nature Medicine, 1(11):1179-1183 (1995).
Mandl et al., "Immunotherapy with MVA-BN®-HER2 induces HER-2-specific Th1 immunity and alters the intratumoral balance of effector and regulatory T cells," Cancer Immunol Immunother, 61(1):19-29 (2012).
Mandruzzato et al., "A CASP-8 Mutation Recognized by Cytolytic T Lymphocytes on a Human Head and Neck Carcinoma," J Exp Med, 186: 785-793 (1997).
Manghera et al., "Endogenous retrovirus-K promoter: a landing strip for inflammatory transcription factors?," Retrovirol, 10:16 (2013).
Mannino et al., "Liposome Mediated Gene Transfer," Biotechniques, 6(7): 682-690 (1988).
Marabelle et al., "Depleting tumor-specific Tregs at a single site eradicates disseminated tumors," J Clin Invest, 1123(6):2447-2463(2013).
Maratea et al. "Deletion and fusion analysis of the phage φX174 lysis gene E," Gene 40(1):39-46 (1985).
Marcais et al., "A fast, lock-free approach for efficient parallel counting of occurrences of k-mers," Bioinformatics, 27(6):764-770 (2011).
Mardis et al., "Cancer genome sequencing: a review," Human Molecular Genetics, 18(2): R163-R168 (2009).
Mardis et al., "Recurring Mutations Found by Sequencing an Acute Myeloid Leukemia Genome," New Engl J Med, 361:1058-1066 (2009).
Mardis, "The impact of next-generation sequencing technology on genetics," Trends in Genetics, 24(3):133-141 (2007).
Margulies et al., "Genome Sequencing in Open Microfabricated High Density Picoliter Reactors," Nature, 15:437(7057): 376-380 (2005).
Marijt et al., "Hematopoiesis-Restricted Minor Histocompatibility Antigens HA-1 - or HA -2- specific T Cells can Induce Complete Remissions of Relapsed Leukemia," PNAS, 100: 2742-2747 (2003).
Marina et al., "Serologic Markers of Effective Tumor Immunity Against Chronic Lymphocytic Leukemia Include Nonmutated B-Cell Antigens," Cancer Res, 70(4): 1344-1355 (2010).
Mark et al., "Site-specific mutagenesis of the human fibroblast interferon gene," PNAS, 81(18):5662-5666 (1984).
Marshall et al., "Phase I Study in Cancer Patients of a Replication-Defective Avipox Recombinant Vaccine That Expresses Human Carcinoembryonic Antigen," J Clin Oncol, 17:332-337 (1999).
Matsushita et al., "Cancer Exome Analysis Reveals a T Cell Dependent Mechanism of Cancer Immunoediting," Nature, 482(7385):400-404 (2012).
Maus et al., "Adoptive Immunotherapy for Cancer or Viruses," Annual Review of Immunology, 32:189-225 (2014).
Mayer et al., "A revised nomenclature for transcribed human endogenous retroviral loci," Mobile DNA, 2:7 (2011).
Mayr et al., "Abstammung, Eigenschaften und Verwendung des attenuierten Vaccinia-Stammes MVA (Translated Summary)," Infection, 3(1):6-14 (1975).
Mayr, "The smallpox vaccination strain MVA: marker, genetic structure, experience gained with the parenteral vaccination and behavior in organisms with a debilitated defence mechanism (author's transl)," Zentralbl Bakteriol 167(5-6):375-9 (1978).
Mazutis et al., "Single-cell analysis and sorting using droplet-based microfluidics," Nat Protoc, 8:870-891 (2013).
McCleskey et al., "GATA-3 Expression in Advanced Breast Cancer: Prognostic Value and Organ-Specific Relapse," Amer J Clin Pathol 144:756-763 (2015).
McCormack et al., "HLA-A*3101 and Carbamazepine-Induced Hypersensitivity Reactions in Europeans," New Engl J Med, 364:1134-1143 (2011).
McCurdy et al., "Modified Vaccinia Ankara: Potential as an Alternative Smallpox Vaccine," Clin Infect Dis, 38:1749-1753 (2004).
McDermott et al., "Immune Therapy for Kidney Cancer: A Second Dawn?," Semin Oncol, 40(4):492-498 (2013).
McFadden et al., "Genetic and clonal dissection of murine small cell lung carcinoma progression by genome sequencing." Cell, 156(6):1298-1311 (2014).
McKenna et al., "The Genome Analysis Toolkit: a MapReduce framework for analyzing next-generation DNA sequencing data," Genome Res, 20(9):1297-1303 (2010).
McMurtrey et al., "Toxoplasma gondii peptide ligands open the gate of the HLA class I binding groove," eLife 5:e12556 (2016).
Medema et al., "Immune Escape of Tumors in Vivo by Expression of Cellular Flice-Inhibitory Protein," J Exp Med, 190:1033-1038 (1999).
Meissner et al., "Genome-scale DNA methylation maps of pluripotent and differentiated cells," Nature, 454:766-770 (2008).
Melief et al., "Immunotherapy of established (pre)malignant disease by synthetic long peptide vaccines," Nature Rev Cancer, 8:351-360 (2008).
Men et al., "Assessment of Immunogenicity of Human Melan-A Peptide Analogues in HLA-A*0201/Kb Transgenic Mice," J Immunol, 162:3566-3573 (1999).
Menke et al., "Genetic interactions between the Wilms' tumor 1 gene and the p53 gene," Cancer Res, 62(22):6615-6620 (2002).
Mermel et al., "GISTIC2.0 facilitates sensitive and confident localization of the targets of focal somatic copy-number alteration in human cancers," Genome Biol, 12:R41 (2011).
Merrifield, "Solid Phase Peptide Synthesis. I. The Synthesis of a Tetrapeptide," J Am Chem Soc, 85(14):2149-2154 (1963).
Messmer et al., "In vivo measurements document the dynamic cellular kinetics of chronic lymphocytic leukemia B cells," J Clin Invest, 115(3):755-764 (2005).

(56) References Cited

OTHER PUBLICATIONS

Meyer et al., "Mapping of deletions in the genome of the highly attenuated vaccinia virus MVA and their influence on virulence," J Gen Virol, 72:1031-1038 (1991).
Meyerson et al., "Advances in understanding cancer genomes through second-generation sequencing," Nat Rev Genetics, 11:685-696 (2010).
Midgley, "Vaccinia virus strain NYVAC induces substantially lower and qualitatively different human antibody responses compared with strains Lister and Dryvax," J Gen Virol, 89:2992-2997 (2008).
Mikeska et al., "The implications of heterogeneous DNA methylation for the accurate quantification of methylation," Epigenomics, 2(4):561-573 (2010).
Miller et al., "Construction and properties of retrovirus packaging cells based on gibbon ape leukemia virus," Virol, 65:2220-2224 (1991).
Milner et al., "The Effect of Proteasome Inhibition on the Generation of the Human Leukocyte Antigen (HLA) Peptidome," Mol Cell Proteomics, 12:1853-1864 (2013).
Milner et al., "The Turnover Kinetics of Major Histocompatibility Complex Peptides of Human Cancer Cells*," Mol Cell Proteomics, 5:357-365 (2006).
Missale et al., "HLA-A31- and HLA-Aw68-restricted cytotoxic T cell responses to a single hepatitis B virus nucleocapsid epitope during acute viral hepatitis," J Exp Med, 177(3):751-762 (1993).
Miyamoto et al., "GATA binding protein 3 is down-regulated in bladder cancer yet strong expression is an independent predictor of poor prognosis in invasive tumor," Human Pathology, 43:2033-2040 (2012).
Mkrtichyan et al., "B117 Defining a novel mechanism of a-PD1 synergy with vaccine to induce potent anti-tumor effects," Clinical Exp. Metastasis, 28, Abstract #B117(247-248): 157-259 (2011).
Mocellin et al., "Interferon Alpha Adjuvant Therapy in Patients With High-Risk Melanoma: A Systematic Review and Meta-analysis," JNCI, 102(7):493-501 (2010).
Mommen et al., "Expanding the detectable HLA peptide repertoire using electron-transfer/higher-energy collision dissociation (EThcD)," PNAS III, 4507-4512 (2014).
Mommen et al., "Sampling From the Proteome to the Human Leukocyte Antigen-DR (HLA-DR) Ligandome Proceeds Via High Specificity." Mol Cell Proteomics MCP, 15:1412-1423 (2016).
Mooij, "Differential CD4+ versus CD8+ T-Cell Responses Elicited by Different Poxvirus-Based Human Immunodeficiency Virus Type 1 Vaccine Candidates Provide Comparable Efficacies in Primates," J Virol, 82(6):2975-2988 (2008).
Mor et al., "Complexity of the cytokine and antibody response elicited by immunizing mice with Plasmodium yoelii circumsporozoite protein plasmid DNA," J Immunol, 155(4):2039-2046 (1995).
Morison et al., "A census of mammalian imprinting," Trends Genet, 21(8):457-465 (2005).
Morozov et al., "The Transmembrane Protein of the Human Endogenous Retrovirus-K (HERV-K) Modulates Cytokine Release and Gene Expression," PloS one 8(8):e70399 (2013).
Morton et al., "Prolonged Survival of Patients Receiving Active Immunotherapy With Canvaxin Therapeutic Polyvalent Vaccine After Complete Resection of Melanoma Metastatic to Regional Lymph Nodes," Ann Surg, 236(4):438-448 (2002).
Mosmann et al., "TH1 and TH2 Cells: Different Patterns of Lymphokine Secretion Lead to Different Functional Properties," Ann Rev Immunol, 7:145-173 (1989).
Moss, "Reflections on the early development of poxvirus vectors," Vaccine, 31(39): 4220-4222 (2013).
Mullally et al., "Beyond HLA: The Significance of Genomic Variation for Allogeneic Hematopoietic Stem Cell Transplantation," Blood, 109: 1355-1362 (2007).
Muntel et al., "Abundance-based Classifier for the Prediction of Mass Spectrometric Peptide Detectability Upon Enrichment (PPA)," Mol Cell Proteomics, 14:430-440 (2015).
Murphy et al., "Antigen Presentation to T Lymphocytes," Janeway's Immunobiology, 7th Edition, 5:182-83 & 197 (2008).

Murphy et al., "Genetic construction, expression, and melanoma-selective cytotoxicity of a diphtheria toxin-related alpha-melanocyte-stimulating hormone fusion protein," PNAS, 83:8258-8262 (1986).
Murphy et al., "Phase I Clinical Trial: T-Cell Therapy for Prostate Cancer Using Autologous Dendritic Cells Pulsed with HLA-A0201-Specific Peptides from Prostate-Specific Membrane Antigen," Prostate, 29(6): 371-380 (1996).
Musey et al., "HIV-1 Vaccination Administered Intramuscularly Can Induce Both Systemic and Mucosal T Cell Immunity in HIV-1-Uninfected Individuals," J Immunol, 171(2):1094-1101 (2003).
Najera et al., "Cellular and Biochemical Differences between Two Attenuated Poxvirus Vaccine Candidates (MVA and NYVAC) and Role of the C7L Gene," J Virol, 80(12):6033-6047 (2006).
Nam et al., "Different contribution of co-stimulatory molecules B7.1 and B7.2 to the immune response to recombinant modified vaccinia virus ankara vaccine expressing prM/E proteins of Japanese encephalitis virus and two hepatitis B virus vaccines," Acta Virol, 51:125-30 (2007).
Ng et al., "Dereplication and de novo sequencing of nonribosomal peptides," Nat Meth, 6:596-599 (2009).
Nielsen et al., "NetMHCpan, a Method for Quantitative Predictions of Peptide Binding to Any HLA-A and -B Locus Protein of Known Sequence," PloS one, 2:e796 (2007).
Nielsen et al., "NetMHCpan-3.0; improved prediction of binding to MHC class Imolecules integrating information from multiple receptor and peptide length datasets," Genome Medicine, 8:33 (2016).
Nielsen et al., "The role of the proteasome in generating cytotoxic T-cell epitopes: insights obtained from improved predictions of proteasomal cleavage," Immunogenetics, 57:33-41 (2005).
Nishimura et al., "Distinct Role of Antigen-Specific T Helper Type 1 (Th1) and Th2 Cells in Tumor Eradication in Vivo," J Ex Med, 190(5):617-27 (1999).
Niwa et al., "Bimodal protein solubility distribution revealed by an aggregation analysis of the entire ensemble of *Escherichia coli* proteins," PNAS, 106(11): 4201-4206 (2009).
Nocentini et al., "A new member of the tumor necrosis factor/nerve growth factor receptor family inhibits T cell receptor-induced apoptosis," PNAS, 94(12):6216-6221 (1997).
Non-Final Office Action for U.S. Appl. No. 13/108,610, "Compositions and Methods of Identifying Tumor Specific Neoantigens," dated Aug. 15, 2013.
Non-Final Office Action for U.S. Appl. No. 13/108,610, "Compositions and Methods of Identifying Tumor Specific Neoantigens," dated Dec. 3, 2014.
Non-Final Office Action for U.S. Appl. No. 14/794,449, "Compositions and Methods of Identifying Tumor Specific Neoantigens," dated Dec. 29, 2016.
Non-Final Office Action for U.S. Appl. No. 14/794,449, "Compositions and Methods of Identifying Tumor Specific Neoantigens," dated Jul. 24, 2018.
Non-Final Office Action for U.S. Appl. No. 14/877,125, "Compositions and Methods for Personalized Neoplasia Vaccines," dated Mar. 27, 2017.
Non-Final Office Action for U.S. Appl. No. 14/877,125, "Compositions and Methods for Personalized Neoplasia Vaccines," dated Nov. 2, 2018.
Non-Final Office Action for U.S. Appl. No. 15/038,504, "Compositions and Methods for Diagnosing, Evaluating and Treating Cancer by Means of the DNA Methyl," dated Sep. 6, 2017.
Non-Final Office Action for U.S. Appl. No. 15/102,129, "Formulations for Neoplasia Vaccines," dated Apr. 26, 2019.
Non-Final Office Action for U.S. Appl. No. 15/102,129, "Formulations for Neoplasia Vaccines," dated Dec. 17, 2018.
Non-Final Office Action for U.S. Appl. No. 15/102,129, "Formulations for Neoplasia Vaccines," dated Jul. 28, 2017.
Non-Final Office Action for U.S. Application No. 15/102, 129, "Formulations for Neoplasia Vaccines," dated Mar. 7, 2018.
Non-Final Office Action for U.S. Appl. No. 15/105,961, "Combination Therapy With Neoantigen Vaccine," dated Jan. 21, 2021.
Non-Final Office Action for U.S. Appl. No. 15/105,961, "Combination Therapy With Neoantigen Vaccine," dated Jan. 8, 2019.
Non-Final Office Action for U.S. Appl. No. 15/105,961, "Combination Therapy with Neoantigen Vaccine," dated Nov. 20, 2017.

(56) References Cited

OTHER PUBLICATIONS

Non-Final Office Action for U.S. Appl. No. 15/187,174, "Compositions and Methods of Identifying Tumor Specific Neoantigens," dated Dec. 5, 2016.
Non-Final Office Action for U.S. Appl. No. 15/187,174, "Compositions and Methods of Identifying Tumor Specific Neoantigens," dated Jan. 22, 2018.
Non-Final Office Action for U.S. Appl. No. 15/513,127, "Use of Clonal Evolution Analysis for Ibrutinib Resistance in Chronic Lymphocytic Leukemia Patients," dated Dec. 4, 2020.
Non-Final Office Action for U.S. Appl. No. 15/513,127, "Use of Clonal Evolution Analysis for Ibrutinib Resistance in Chronic Lymphocytic Leukemia Patients," dated Nov. 26, 2018.
Non-Final Office Action for U.S. Appl. No. 15/537,785, "Methods for Profiling the T Cell Repertoire," dated Dec. 21, 2018.
Non-Final Office Action for U.S. Appl. No. 15/575,328, "Shared Neoantigens," dated Jun. 27, 2019.
Non-Final Office Action for U.S. Appl. No. 16/181,098, "Compositions and Methods of Identifying Tumor Specific Neoantigens," dated Jan. 31, 2019.
Non-Final Office Action for U.S. Appl. No. 16/181,098, "Compositions and Methods of Identifying Tumor Specific Neoantigens," dated Oct. 29, 2020.
Non-Final Rejection for U.S. Appl. No. 14/877,125, "Compositions and Methods for Personalized Neoplasia Vaccines," dated Feb. 3, 2020.
Non-Final Rejection for U.S. Appl. No. 15/038,504, "Compositions and Methods for Diagnosing, Evaluating and Treating Cancer by Means of the DNA Methylation Status," dated Feb. 4, 2020.
Non-Final Rejection for U.S. Appl. No. 15/105,961, "Combination Therapy With Neoantigen Vaccine," dated Jun. 2, 2020.
Non-Final Rejection for U.S. Appl. No. 15/513,127, "Use of Clonal Evolution Analysis for Ibrutinib Resistance in Chronic Lymphocytic Leukemia Patients," dated Oct. 29, 2019.
Non-Final Rejection for U.S. Appl. No. 15/537,785, "Methods for Profiling the T Cell Repertoire," dated May 11, 2020.
Non-Final Rejection for U.S. Appl. No. 15/537,839, "Molecular Biomarkers for Cancer Immunotherapy," dated Oct. 8, 2019.
Non-Final Rejection for U.S. Appl. No. 15/735,566, "Formulations for Neoplasia Vaccines and Methods of Preparing Thereof," dated May 28, 2020.
Non-Final Rejection for U.S. Appl. No. 15/800,732, "Compositions and Methods of Identifying Tumor Specific Neoantigens," dated Apr. 10, 2020.
Notice of Allowance for U.S. Appl. No. 13/108,610, "Compositions and Methods of Identifying Tumor Specific Neoantigens," dated Jun. 11, 2015.
Notice of Allowance for U.S. Appl. No. 13/108,610, "Compositions and Methods of Identifying Tumor Specific Neoantigens," dated May 12, 2015.
Notice of Allowance for U.S. Appl. No. 15/102,129, "Formulations for Neoplasia Vaccines," dated Oct. 12, 2018.
Notice of Allowance for U.S. Appl. No. 15/575,328, "Shared Neoantigens," dated Jan. 23, 2020.
Notice of Allowance for U.S. Appl. No. 16/188,737, "Compositions and Methods of Identifying Tumor Specific Neoantigens," dated Jul. 25, 2019.
Notice of Opposition to European Patent No. EP2569633—Agenus Inc. (Opponent) dated Nov. 9, 2016.
Notice of Opposition to European Patent No. EP2569633—Dr. Christian Muller (Opponent) dated Nov. 9, 2016.
Notice of Opposition to European Patent No. EP2569633—Gritstone Oncology, Inc. (Opponent) dated Nov. 7, 2016.
Notice of Opposition to European Patent No. EP2569633—James Poole Limited (Opponent) dated Nov. 9, 2016.
Notice of Opposition to European Patent No. EP2569633—Strawman Limited (Opponent) dated Nov. 10, 2016.
Novellino et al., "A listing of human tumor antigens recognized by T cells: Mar. 2004 update," Cancer Immunol Immunother, 54(3):187-207 (2005).

Novershtern et al., "Densely Interconnected Transcriptional Circuits Control Cell States in Human Hematopoiesis," Cell, 144(2):296-309 (2011).
Nyren et al., "Solid Phase DNA Minisequencing by an Enzymatic Luminometric Inorganic Pyrophosphate Detection Assay," Anal Biochem, 208(1): 171-175 (1993).
O'Mahony et al., "A Pilot Study of CTLA-4 Blockade after Cancer Vaccine Failure in Patients with Advanced Malignancy" Clin Canc Res 13(3):958-964 (2007).
O'Shea et al., "Signal transduction and Th17 cell differentiation," Microbes Infect, 11(5):599-611 (2009).
Oakes et al., "Evolution of DNA Methylation Is Linked to Genetic Aberrations in Chronic Lymphocytic Leukemia," Cancer Discov, 4(3):348-361 (2014).
Oakes et al., "Heterogeneity and Evolution of DNA Methylation in Chronic Lymphocytic Leukemia," Blood, 122(21):1626 (2013).
Oates et al., "D(2)P(2): database of disordered protein predictions," Nucleic Acids Res, 41:D508-D516 (2013).
Ofran et al., "Identification of Human Minor Histocompatibility Antigens (MHA) by Combining Bioinformatic Prediction of Peptide Epitopes with Validation of T Cell Reactivity in Patient Blood Samples after Allogeneic Hematopoietic Stem Cell Transplantation," Biol Bone Marrow Transplant, 14:1 (Abstract #2) (2008).
Oh et al., "Neutrophil isolation protocol," J Vis Exp (2008).
Ohashi et al., "Lung cancers with aquired resistance to EGFR inhibitors occasionally harbor BRAF gene mutations but lack mutations in KRAS, NRAS, or MEK1," PNAS, E2127-E2133 (2012).
Ohnishi et al., "Premature Termination of Reprogramming In Vivo Leads to Cancer Development through Altered Epigenetic Regulation," Cell, 156(4):663-677 (2014).
Okada et al., "Induction of CD8+ T-Cell Responses Against Novel Glioma-Associated Antigen Peptides and Clinical Activity by Vaccinations With α-Type 1 Polarized Dendritic Cells and Polyinosinic-Polycytidylic Acid Stabilized by Lysine and Carboxymethylcellulose in Patients With Recurrent Malignant Glioma," J Clin Oncol, 29(3):330-336 (2011).
Opavsky et al., CpG Island Methylation in a Mouse Model of Lymphoma Is Driven by the Genetic Configuration of Tumor Cells, PLOS Genetics, 3(9):e167 (2007).
Opposition Letter—Agenus Inc. (Opponent) in European Patent 2569633, dated Nov. 9, 2016.
Opposition Letter—Dr. Christian Muller (Opponent) in European Patent No. 2569633, dated Nov. 9, 2016.
Opposition Letter—Gritstone Oncology Inc. (Opponent) in European Application No. 11781409.5 dated Nov. 7, 2016.
Opposition Letter—James Poole Limited (Opponent) in European Patent No. 2569633, dated Nov. 9, 2016.
Opposition Letter—Strawman Limited (Opponent) in European Patent No. 2569633 dated Nov. 10, 2016.
Oshiumi et al., "DEAD/H BOX 3 (DDX3) helicase binds the RIG-I adaptor IPS-1 to up-regulate IFN-beta-inducing potential," Eur J Immunol, 40:940-948 (2010).
Osorio et al., "Stability Analysis of Antimicrobial Peptides in Solvation Conditions by Molecular Dynamics," Adv Comp Bio, 232:127-131 (2014).
Ott et al., "A Phase Ib Trial of Personalized Neoantigen Therapy Plus Anti-PD-1 in Patients with Advanced Melanoma, Non-small Cell Lung Cancer, or Bladder Cancer," Cell, 183(2):347-362 (2020).
Ott et al., "An Immunogenic personal neoantigen vaccine for patients with melanoma," Nature, 547:217-221 (2017).
Ott et al., "CTLA-4 and PD-1/PD-L1 Blockade: New Immunotherapeutic Modalities with Durable Clinical Benefit in Melanoma Patients," Clin Cancer Res, 19(19):5300-5309 (2013).
Ott et al., "Vaccines and Melanoma," Hematol Oncol Clin N Am, 28(3):559-569 (2014).
Oudard et al., "A phase II study of the cancer vaccine TG4010 alone and in combination with cytokines in patients with metastatic renal clear-cell carcinoma: clinical and immunological findings," Cancer Immunol Immunother, 60(2): 261-271 (2011).
Padgett et al., "Creating seamless junctions independent of restriction sites in PCR cloning," Gene, 168:31-35 (1996).

(56) References Cited

OTHER PUBLICATIONS

Page et al., "Immune Modulation in Cancer with Antibodies," Annu Rev Med, 65:185-202 (2014).
Pages, et al., "Effector Memory T Cells, Early Metastasis, and Survival in Colorectal Cancer," New Engl J Med, 353:2654-2666 (2005).
Assignment Register extract (accessed Oct. 20, 2016).
Patent Assignment Abstract of Title of U.S. Appl. No. 13/108,610, filed May 16, 2011.
Pan et al., "Epigenomic Evaluation in diffuse Large B-Cell Lymphomas," Blood, Nov. 15, 2013, 122(21) XP55174946.
Panicali et al., "Construction of live vaccines by using genetically engineered poxviruses: biological activity of recombinant vaccinia virus expressing influenza virus hemagglutinin," PNAS, 80(17):5364-5368 (1983).
Panicali et al., "Construction of poxviruses as cloning vectors: insertion of the thymidine kinase gene from herpes simplex virus into the DNA of infectious vaccinia virus," PNAS, 79(16):4927-4931 (1982).
Pantaleo et al., "Poxvirus vector-based HIV vaccines," Curr Opin HIV-AIDS, 5:391-396 (2010).
Paoletti, "Applications of pox virus vectors to vaccination: an update," PNAS, 93(21):11349-53 (1996).
Parker et al., "Scheme for Ranking Potential HLA-A2 Binding Peptides Based on Independent Binding of Individual Peptide Side-Chains," J Immunol, 152(1): 163-175 (1994).
Parkhurst et al., "Improved induction of melanoma-reactive CTL with peptides from the melanoma antigen gp100 modified at HLA-A*0201-binding residues", The Journal of Immunology, 157: 2539-2548 (1996).
Parmiani et al., "Unique Human Tumor Antigens: Immunobiology and Use in Clinical Trials," J Immunol, 178: 1975-1979 (2007).
Pasmant et al., "Characterization of a Germ-Line Deletion, Including the Entire INK4/ARF Locus, in a Melanoma-Neural System Tumor Family: Identification of ANRIL, an Antisense Noncoding RNA Whose Expression Coclusters with ARF," Cancer Res, 67(8):3963-3969 (2007).
Pei et al., "Genome-wide DNA methylation analysis reveals novel epigenetic changes in chronic lymphocytic leukemia," Epigenetics, 7:567-578 (2012).
Peng et al., "DOK3 Negatively Regulates LPS Responses and Endotoxin Tolerance," PloS one 7:e39967 (2012).
Perez et al., "A new era in anticancer peptide vaccines," Cancer, 116(9):2071-2080 (2010).
Perez et al., "p63 consensus DNA-binding site: identification, analysis and application into a p63MH algorithm," Oncogene, 26:7363-7370 (2007).
Perkvs et al., "Poxvirus based vaccine candidates for cancer, AIDS, and other infectious diseases," J Leukocyte Biol, 58(1):1-13 (1995).
Perreau et al., "DNA/NYVAC Vaccine Regimen Induces HIV-Specific CD4 and CD8 T-Cell Responses in Intestinal Mucosa," J Virol, 85(19):9854-9862 (2011).
Peters et al., "A Community Resource Benchmarking Predictions of Peptide Binding to MHC-I Molecules," PLOS Computational Biology, 2(6): e65 (2006).
Peters et al., "Accurate whole-genome sequencing and haplotyping from 10 to 20 human cells," Nature 487:190-195 (2012).
Peters et al., "The Immune Epitope Database and Analysis Resource: From Vision to Blueprint," PLoS Biol, 3(3): e91 (2005).
Peters et al., "The many faces of TH-17 Cells," Curr Opin Immunol, 23(6):702-706 (2011).
Petsch et al., "Protective efficacy of in vitro synthesized, specific mRNA vaccines against influenza A virus infection," Nat Biotechnol, 30(12):1210-1216 (2012).
Phan et al., "Cancer regression and autoimmunity induced by cytotoxic T lymphocyte-associated antigen 4 blockade in patients with metastatic melanoma," PNAS, 100(14):8372-8377 (2003).
Pieters et al., "On guard: coronin proteins in innate and adaptive immunity," Nat Rev Immunol, 13:510-518 (2013).
Pietras, "Biologic Basis of Sequential and Combination Therapies for Hormone-Responsive Breast Cancer," Oncologist, 11:704-717 (2006).
Pilla et al., "Multipeptide vaccination in cancer patient," Expert Opin Biol Ther, 9(8):1043-1055 (2009).
Pirard et al., "Interferon Alpha as Adjuvant Postsurgical Treatment of Melanoma: A Meta-Analysis," Dermatology, 208(1):43-48 (2004).
Piros et al., "Market Opportunity for Molecular Diagnostics in Personalized Cancer Therapy," Handbook of Clinical Nanomedicine: Law, Business, Regulation, Safety and Risk, Chapter 14: 1-29 (2016).
Pleasance et al., "A comprehensive catalogue of somatic mutations from a human cancer genome," Nature, 463:191-196 (2010).
Pleasance et al., "A small-cell lung cancer genome with complex signatures of tobacco exposure," Nature, 463: 184-190 (2010).
Poirot et al., "Multiplex genome edited T-cell manufacturing platform for "off-the-shelf" adoptive T-cell immunotherapies," Cancer Res, 75(18):3853 (2015).
Policy Reallocating Ownership of Intellectual Property Covered by the Intellectual Property Policy, Sep. 18, 2002.
Poulet, "Development and registration of recombinant veterinary vaccines: The example of the canarypox vector platform," Vaccine, 25(30):5606-5612 (2007).
Powell et al., "NCoR1 Mediates Papillomavirus E8/\E2C Transcriptional Repression," J Virol, 84:4451-4460 (2010).
Prezant et al., "Trapped-Oligonucleotide Nucleotide Incorporation (TONI) Assay, a Simple Method for Screening Point Mutations," Hum Mutat, 1(2): 159-164 (1992).
Prints-outs from the UniProtKB database concerning the CEP170, PARVA and FLT3 genes.
Pritchard et al., "Exome Sequencing to Predict Neoantigens in Melanoma," Cancer Immunol Res, 3:992-998 (2015).
Provan et al., "Eradication of Polymerase Chain Reaction-Detectable Chronic Lymphocytic Leukemia Cells is Associated with Improved Outcome After Bone Marrow Transplantation," Blood, 88: 2228-2235 (1996).
U.S. Appl. No. 61/334,866, filed May 14, 2010.
Pujadas et al., "Regulated noise in the epigenetic landscape of development and disease," Cell, 148(6):1123-1131 (2012).
Qin et al., "Soft lithography for micro- and nanoscale patterning," Nat Protoc, 5:491-502 (2010).
Quesada et al., "Exome sequencing identifies recurrent mutations of the splicing factor SF3B1 gene in chronic lymphocytic leukemia," Nat Genet, 44:47-52 (2012).
Quezada et al.,"CTLA4 blockade and GM-CSF combination immunotherapy alters the intratumor balance of effector and regulatory T cells," J Clin Invest, 116(7):1935-1945 (2006).
Rajasagi et al., "Systematic Identification of Personal Mutated Tumor-Specific Neoantigens in CLL," Blood, 120(21):954 (2012).
Rajasagi et al., "Systematic identification of personal tumor-specific neoantigens in chronic lymphocytic leukemia," Blood, 124(3):453-462 (2014).
Rammensee et al., "Cancer Vaccines: Some Basic Considerations," Genomic and Personalized Medicine, 5:573-589 (2009).
Rammensee et al., "MHC ligands and peptide motifs: first listing," Immunogenetics, 41:178 (1995).
Rammensee et al., "SYFPEITHI: Database for MHC Ligands and Peptide Motifs," Immunogenetics, 50(3-4): 213-219 (1999).
Rammensee et al., "Towards Patient-Specific Tumor Antigen Selection for Vaccination," Immunological Reviews, Blackwell Publishing Munksgaard, 188:164-176 (2002).
Ramos et al., "An Inducible Caspase 9 Suicide Gene to Improve the Safety of Mesenchymal Stromal Cell Therapies," Stem Cells, 28(6):1107-1115 (2010).
Ramskold et al., "Full-length mRNA-Seq from single-cell levels of RNA and individual circulating tumor cells," Nat Biotechnol, 30:777-782 (2012).
Rappsilber et al., "Protocol for micro-purification, enrichment, pre-fractionation and storage of peptides for proteomics using StageTips," Nat Protoc, 2(8):1896-1906 (2007).
Rassenti et al., "Relative value of ZAP-70, CD38, and immunoglobulin mutation status in predicting aggressive disease in chronic lymphocytic leukemia," Blood, 112:1923-1930 (2008).

(56) References Cited

OTHER PUBLICATIONS

Raval et al., "Downregulation of Death-Associated Protein Kinase 1 (DAPK1) in Chronic Lymphocytic Leukemia," Cell, 129(5):879-890 (2007).
Ravi et al., "Sensitization of Tumor Cells to Apo2 Ligand/TRAIL-induced Apoptosis by Inhibition of Casein Kinase II," Cancer Res, 62(15):4180-4185 (2002).
Reche et al., "Elicitation from virus-naive individuals of cytotoxic T lymphocytes directed against conserved HIV-1 epitopes," Med Immunol, 5:1 (2006).
Reifenberger et al., "Frequent Alterations of Ras Signaling Pathway Genes in Sporadic Malignant Melanomas," Int J Cancer, 109: 377-384 (2004).
Response to Notices of Opposition of EP2569633, dated Jun. 28, 2017.
Ressing et al., "Human CTL epitopes encoded by human papillomavirus type 16 E6 and E7 identified through in vivo and in vitro immunogenicity studies of HLA-A*0201-binding peptides.," J Immunol, 154(11):5934-5943 (1995).
Restifo et al., "Adoptive immunotherapy for cancer: harnessing the T cell response," Nat Rev Immunol, 12(4):269-281 (2015).
Restriction Requirement for U.S. Appl. No. 13/108,610, "Compositions and Methods of Identifying Tumor Specific Neoantigens," dated Mar. 7, 2013.
Restriction Requirement for U.S. Appl. No. 14/794,449, "Compositions and Methods of Identifying Tumor Specific Neoantigens," dated Oct. 26, 2016.
Restriction Requirement for U.S. Appl. No. 14/877,125, "Compositions and Methods for Personalized Neoplasia Vaccines," dated Nov. 18, 2016.
Restriction Requirement for U.S. Appl. No. 15/038,504, "Compositions and Methods for Diagnosing, Evaluating and Treating Cancer by Means of the DNA Methyl," dated Jun. 22, 2017.
Restriction Requirement for U.S. Appl. No. 15/102,129, "Formulations for Neoplasia Vaccines," dated May 8, 2017.
Restriction Requirement for U.S. Appl. No. 15/105,961, "Combination Therapy With Neoantigen Vaccine," dated Jul. 13, 2017.
Restriction Requirement for U.S. Appl. No. 15/187,174, "Compositions and Methods of Identifying Tumor Specific Neoantigens," dated Sep. 9, 2016.
Restriction Requirement for U.S. Appl. No. 15/513,127, "Use of Clonal Evolution Analysis for Ibrutinib Resistance in Chronic Lymphocytic Leukemia Patients," dated Aug. 13, 2018.
Restriction Requirement for U.S. Appl. No. 15/537,785, "Methods for Profiling the T Cell Repertoire," dated Mar. 22, 2018.
Restriction Requirement for U.S. Appl. No. 15/537,839, "Molecular Biomarkers for Cancer Immunotherapy," dated Jun. 20, 2019.
Restriction Requirement for U.S. Appl. No. 15/575,328, "Shared Neoantigens," dated Feb. 7, 2019.
Ribas et al., "Antitumor Activity in Melanoma and Anti-Self Responses in a Phase I Trial with the Anti-Cytotoxic T Lymphocyte-Associated Antigen 4 Monoclonal Antibody CP-675,206," J Clin Oncol. 23(35): 8968-8977 (2005).
Richter et al., "Mechanistic Determinants of Biotherapeutics Absorption Following SC Administration," The AAPS Journal, 14(3):559-568 (2012).
Rini et al., "Biology and Treatment of Advanced Renal Cell Carcinoma: A Global Perspective," Semin Oncol, 40(4):419-420 (2013).
Rizvi et al., "Mutational landscape determines sensitivity to PD-1 blockade in non-small cell lung cancer," Science, 348(6230):124-128 (2015).
Robbins et al., "A mutated beta-catenin gene encodes a melanoma-specific antigen recognized by tumor infiltrating lymphocytes," J Exp Med, 183(3):1185-1192 (1996).
Robbins et al., "Mining exomic sequencing data to identify mutated antigens recognized by adoptively transferred tumor-reactive T cells," Nat Med, 19(6):747-752 (2013).
Robinson et al., "A phase I-II trial of multiple-dose polyriboinosic-polyribocytidylic acid in patieonts with leukemia or solid tumors," J Natl Cancer Inst, 57(3):599-602 (1976).
Robinson et al., "DNA vaccines for viral infections: Basic studies and applications," Adv Virus Res, 55:1-74 (2000).
Robinson et al., "edgeR: a Bioconductor package for differential expression analysis of digital gene expression data," Bioinformatics, 26(1):139-140 (2010).
Robinson et al., "Integrative genomics viewer," Nat Biotechnol, 29:24-26 (2011).
Robinson et al., "The IPD and FMGT/HLA database: allele variant databases," Nucleic Acids Res, 43:D423-D431 (2015).
Rock et al., "Re-examining class-I presentation and the DRIP hypothesis," Trends Immunol, 35(4):144-152 (2014).
Rolph et al., "Recombinant viruses as vaccines and immunological tools," Curr Opin Immunol, 9(4):517-524 (1997).
Ronchetti et al., "Frontline:GITR, a member of the TNF receptor superfamily, is costimulatory to mouse T lymphocytesubpopulations," Eur J Immunol, 34(3):613-622 (2004).
Rondon et al., "Graft-versus-Leukemia Effect After Allogeneic Bone Marrow Transplantation for Chronic Lymphocytic Leukemia," Bone Marrow Transplant, 18: 669-672 (1996).
Rooney et al., "Molecular and Genetic Properties of Tumors Associated with Local Immune Cytolytic Activity," Cell, 160(1-2):48-61 (2015).
Rosenberg et al., "Adoptive cell transfer as personalized immunotherapy for human cancer," Science, 348(6230):62-68 (2015).
Rosenberg et al., "Cancer Immunotherapy: Moving Beyond Current Vaccines," Nat Med, 10: 909-915 (2004).
Rosenberg, "Raising the Bar: The Curative Potential of Human Cancer Immunotherapy," Sci Transl Med, 4(127):127ps128 (2012).
Rossi et al., "Integrated mutational and cytogenetic analysis identifies new prognostic subgroups in chronic lymphocytic leukemia," Blood, 121:1403-1412 (2013).
Rubin et al., "Mutation patterns in cancer genomes," PNAS, 106(51):21766-21770 (2009).
Rubinfeld et al., "Stabilization of Beta-Catenin by Genetic Defects in Melanoma Cell Lines," Science, 275(5307):1790-1792 (1997).
Rubio-Moscardo et al., "Characterization of 8p21.3 chromosomal deletions in B-cell lymphoma: TRAIL-R1 and TRAIL-R2 as candidate dosage-dependent tumor suppressor genes," Blood, 106:3214-3222 (2005).
Ruggles et al., "An analysis of the sensitivity of proteogenomic mapping of somatic mutations and novel splicing events in cancer," Cell Proteomics, 15(3):1060-1071 (2015).
Rupprecht et al., "Oral immunization and protection of raccoons (*Procyon lotor*) with a vaccinia-rabies glycoprotein recombinant virus vaccine," PNAS, 83:7947-7950 (1986).
Rutledge et al., "Tumor-Infiltrating Lymphocytes in Glioblastoma Are Associated with Specific Genomic Alterations and Related to Transcriptional Class," Clin Cancer Res, 19:4951-4960 (2013).
Sabado et al., "Preparation of Tumor Antigen-loaded Mature Dendritic Cells for Immunotherapy," J Vis Exp, 78:50085 (2013).
Sabbatini et al., "Phase I trial of overlapping long peptides from a tumor self-antigen and Poly-ICLC shows rapid induction of integrated immune response in ovarian cancer patients," Clin Cancer Res, 18:6497-6508 (2012).
Sadelain, "Eliminating Cells Gone Astray," New Engl J Med, 365:1735-1737 (2011).
Sahin et al., "Personalized RNA mutanome vaccines mobilize poly-specific therapeutic immunity against cancer," Nature, 547(7662):222-226 (2017).
Salem et al., "Defining the Antigen-Specific T-Cell Response to Vaccination and Poly(I:C)/TLR3 Signaling: Evidence of Enhanced Primary and Memory CD8 T-Cell Responses and Antitumor Immunity." J Immunother, 28(3):220-228 (2005).
Sampson et al., "An epidermal growth factor receptor variant III-targeted vaccine is safe and immunogenic in patients with glioblastomas multiforme," Mol Cancer Ther, 8(10):2773-2779 (2009).
Sampson et al., "Greater chemotherapy-induced lymphopenia enhances tumor-specific immune responses that eliminate EGFRvIII-expressing tumor cells in patients with glioblastoma," Neuro-Oncology, 13(3):324-333 (2011).

(56) References Cited

OTHER PUBLICATIONS

Sampson et al., "Immunologic Escape After Prolonged Progression-Free Survival With Epidermal Growth Factor Receptor Variant III Peptide Vaccination in Patients With Newly Diagnosed Glioblastoma," J Clin Oncol, 28(31):4722-4729 (2010).
Samuels et al., "Oncogenic PI3K and its role in cancer," Curr Opin Oncol, 18:77-82n (2006).
Sancho, "The Block in Assembly of Modified Vaccinia Virus Ankara in Hela Cells Reveals New Insights into Vaccinia Virus Morphogenesis," J Virol, 76(16):8313-8334 (2002).
Sanderson et al., "Autoimmunity in a Phase I Trial of a Fully Human Anti-Cytotoxic T-Lymphocyte Antigen-4 Monoclonal Antibody With Multiple Melanoma Peptides and Montanide ISA 51 for Patients With Resected Stages III and IV Melanoma," J Clin Oncol, 23(4):741-750 (2005).
Saterdal et al., "Frameshift-mutation-derived peptides as tumor-specific antigens in inherited and spontaneous colorectal cancer," Proceedings of the National Academy of Sciences 98(23): 13255-13260 (2001).
Sato et al., "Discovery of Novel Targets for Aberrant Methylation in Pancreatic Carcinoma Using High-Throughput Microarrays." Cancer Res, 63(13):3735-3742 (2003).
Sato et al., "Intraepithelial CD8+ tumor-infiltrating lymphocytes and a high CD8+/regulatory T cell ratio are associated with favorable prognosis in ovarian cancer," PNAS, 102(51):1838-18543 (2005).
Saturno et al., "Combining TRAIL with PI3 Kinase or HSP90 inhibitors enhances apoptosis in colorectal cancer cells via suppression of survival signaling," Oncotarget, 4(8):1185-1198 (2013).
Saunders et al., "Strelka: accurate somatic small-variant calling from sequenced tumor-normal sample pairs," Bioinformatics, 28(14):1811-1817 (2012).
Saveanu et al., "Concerted peptide trimming by human ERAP1 and ERAP2 aminopeptidase complexes in the endoplasmic reticulum," Nat Immunol, 6:689-697 (2005).
Saxova et al., "Predicting proteasomal cleavage sites: a comparison of available methods," Int Immunol, 15:781-787 (2003).
Schaffner et al., "Somatic ATM Mutations Indicate a Pathogenic Role of ATM in B-Cell Chronic Lymphocytic Leukemia," Blood, 94: 748-753 (1999).
Scheibenbogen et al., "Analysis of the T Cell Response to Tumor and Viral Peptide Antigens by an IFNy-ELISPOT Assay," Int. J. Cancer, 71:932-936 (1997).
Schietinger et al., "Specificity in cancer immunotherapy," Semin. Immunol, 20(5)276-285 (2008).
Schmitt et al., "Transcriptional Profiling of Human Endogenous Retrovirus Group HERV-K(HML-2) Loci in Melanoma," Genome Biol Evol, 5(2):307-328 (2013).
Schneider et al., "Induction of CD8+ T cells using heterologous prime-boost immunisation strategies," Immunol Rev, 170(1):29-38 (1999).
Schreiber et al., "Cancer Immunoediting: Integrating Immunity's Roles in Cancer Suppression and Promotion," Science, 331(6024):1565-1570 (2011).
Schuh et al., "Monitoring chronic lymphocytic leukemia progression by whole genome sequencing reveals heterogeneous clonal evolution patterns," Blood, 120(20):4191-4196 (2012).
Schumacher et al., "Neoantigens in cancer immunotherapy," Science, 348:69-74 (2015).
Schumacher et al., "Prognostic Significance of Activated CD8+ T Cell Infiltrations within Esophageal Carcinomas," Cancer Res, 61(10):3932-3936 (2001).
Schuster et al., "Vaccination With Patient-Specific Tumor-Derived Antigen in First Remission Improves Disease-Free Survival in Follicular Lymphoma," J Clin Oncol, 29(20):2787-2794 (2011).
Schwitalle et al., "Immunogenic peptides generated by frameshift mutations in DNA mismatch repair-deficient cancer cells," Cancer Immunity, 4(1):14 (2004).

Scriba et al., "Modified vaccinia Ankara expressing Ag85A, a novel tuberculosis vaccine, is safe in adolescents and children, and induces polyfunctional CD4+ T cells," Eur J Immunol, 40(1):279-290 (2010).
Searle et al., "Using Data Independent Acquisition (DIA) to Model High-responding Peptides for Targeted Proteomics Experiments," Mol Cell Proteomics, 14:2331-2340 (2015).
Seberg et al., "How Many Loci Does it Take to DNA Barcode a Crocus?," PLOS One 4(2):e4598 (2009).
Secchiero et al., "Aberrant expression of TRAIL in B chronic lymphocytic leukemia (B-CLL) cells," J Cell Physiol, 205(2):246-252 (2005).
Sedegah et al., "Protection against malaria by immunization with plasmid DNA encoding circumsporozoite protein," PNAS, 91(21):9866-9870 (1994).
Segal et al., "Epitope Landscape in Breast and Colorectal Cancer," Cancer Res, 68: 889-892 (2008).
Sensi et al., "Unique Tumor Antigenesis: Evidence for Immune Control of Genome Integrity and Immunogenic for T Cell-Mediated Patient-Specific Immunotherapy," Clin Cancer Res, 12(7): :5023-5032 (2006).
Sette et al., "Peptide binding to the most frequent HLA-A class I alleles measured by quantitative molecular binding assays," Molecular Immunology, 31(11): 813-822 (1994).
Sette et al., "The relationship between class I binding affinity and immunogenicity of potential cytotoxic T cell epitopes," J Immunol, 153:5586-5592 (1994).
Shah et al., "Multiple BCR-ABL kinase domain mutations confer polyclonal resistance to the tyrosine kinase inhibitor imatinib (STI571) in chronic phase and blast crisis chronic myeloid leukemia," Cancer Cell, 2(2):117-125 (2002).
Shalek et al., "Single-cell RNA-seq reveals dynamic paracrine control of cellular variation," Nature, 510(7505):363-369 (2014).
Shames et al., "A Genome-Wide Screen for Promoter Methylation in Lung Cancer Identifies Novel Methylation Markers for Multiple Malignancies," PLOS Med, 3(12):e486 (2006).
Shannon, "A Mathematical Theory of Communication," Bell System Technical Journal, 27(3):379-423 (1948).
Shao et al., "Clonally related histiocytic/dendritic cell sarcoma and chronic lymphocytic leukemia/small lymphocytic lymphoma: a study of seven cases," Mod Pathol, 24:1421-1432 (2011).
Sharei et al., "Ex Vivo Cytosolic Delivery of Functional Macromolecules to Immune Cells," PLOS ONE, 10(4):e0118803 (2015).
Sharma et al., "A Chromatin-Mediated Reversible Drug-Tolerant State in Cancer Cell Subpopulations," Cell, 141:69-80 (2010).
Sharma et al., "Novel cancer immunotherapy agents with survival benefit: recent successes and next steps," Nat Rev Cancer, 11(11):805-812 (2011).
Shastri et al., "Presentation of endogenous peptide/MHC class I complexes is profoundly influenced by specific C-terminal flanking residues," J Immunol, 155:4339 (1995).
Shen et al., "Integrated genetic and epigenetic analysis identifies three different subclasses of colon cancer," PNAS, 104(47):18654-18659 (2007).
Shendure et al., "Next-generation DNA sequencing," Nat Biotechnol, 26(10):1135-1145 (2008).
Shida, "Effects and virulences of recombinant vaccinia viruses derived from attenuated strains that express the human T-cell leukemia virus type I envelope gene," J Virol, 62(12):4474-4480 (1988).
Shimizu et al., "Production of human cells expressing individual transferred HLA-A,-B,-C genes using an HLA-A,- B,-C null human cell line," J Immunol, 142(9):3320-3328 (1989).
Shimizu et al., "Transfer of cloned human class I major histocompatibility complex genes into HLA mutant human lymphoblastoid cells," Mol Cell Biol, 6(4):1074-1087 (1986).
Shipony et al., "Dynamic and static maintenance of epigenetic memory in pluripotent and somatic cells," Nature, 513:115-119 (2014).
Shukla et al., "Topics in Cancer Genomics," Graduate Theses and Dissertations, Paper 13796 (2014). [accessed online] https://search.proquest.com/docview/1558874754.

(56) References Cited

OTHER PUBLICATIONS

Sidney et al., "HLA class I supertypes: a revised and updated classification," BMC Immunol, 9:1 (2008).
Sidney et al., "Measurement of MHC/Peptide Interactions by Gel Filtration or Monoclonal Antibody Capture," Curr Protoc Immunol: 18.3.1-18.3.36 (2013).
Sidney et al., "Measurement of MHC/Peptide Interactions by Gel Filtration" Curr Prot Immunol, 31(1):18.3.1-18.3.19 (1999).
Siegel et al., "Cancer statistics, 2013," CA, 63(1):11-30 (2013).
Siegmund et al., "Inferring clonal expansion and cancer stem cell dynamics from DNA methylation patterns in colorectal cancers," PNAS, 106(12):4828-4833 (2009).
Simmons et al., "Local secretion of anti-CTLA-4 enhances the therapeutic efficacy of a cancer immunotherapy with reduced evidence of systemic autoimmunity," Cancer Immunol Immunother, 57(8):1263-1270 (2008).
Simpson et al., "Cancer/testis antigens, gametogenesis and cancer," Nat Rev Cancer, 5:615-625 (2005).
Simpson et al., "Fc-dependent depletion of tumor-infiltrating regulatory T cells co-defines the efficacy of anti-CTLA-4 therapy against melanoma," J Exp Med, 210(9):1695-1710 (2013).
Singh et al., "CIMT 2010: Report on the eighth annual meeting of the association for cancer immunotherapy, May 26-28, 2010, Mainz, Germany," Cancer Immunol. Immunother., 60: 443-450 (2011).
Singh-Jasuga et al., "Correlation of T-cell response, clinical activity and regulatory T-cell levels in renal cell carcinoma patients treated with IMA901, a novel multi-peptide vaccine," J Clin Conology, 25:18S, Abstract #3017 (2007).
Sizemore, "Attenuated Shigella as a DNA Delivery Vehicle for DNA-Mediated Immunization," Science, 270(5234):299-303 (1995).
Sjoblom et al., "The Consensus Coding Sequences of Human Breast and Colorectal Cancers," Science, 314(5797):268-274 (2006).
Slingluff et al., "Immunologic and Clinical Outcomes of a Randomized Phase II Trial of Two Multipeptide Vaccines for Melanoma in the Adjuvant Setting," Clin Cancer Res, 13(21):6386-6395 (2007).
Slingluff et al., "Randomized Multicenter Trial of the Effects of Melanoma-Associated Helper Peptides and Cyclophosphamide on the Immunogenicity of a Multipeptide Melanoma Vaccine," J Clin Oncol, 29(21):2924-2932 (2011).
Smialowsky et al., "Protein solubility: sequence based prediction and experimental verification," Bioinformatics, 23(19):2356-3542 (2007).
Smith et al., "Comparison of biosequences," Adv Appl Math, 2(4):482-489 (1981).
Smith et al., "Construction and characterization of an infectious vaccinia virus recombinant that expresses the influenza hemagglutinin gene and induces resistance to influenza virus infection in hamsters," PNAS, 80(23):7155-7159 (1983).
Smith et al., "Infectious vaccinia virus recombinants that express hepatitis B virus surface antigen," Nature, 302:490-495 (1983).
Smoley et al., "Standardization of fluorescence in situ hybridization studies on chronic lymphocytic leukemia (CLL) blood and marrow cells by the CLL Research Consortium," Cancer Genet Cytogenet, 203(2):141-148 (2010).
Snyder et al., "Genetic Basis for Clinical Response to CTLA-4 Blockade in Melanoma," New Engl J Med, 371(23):2189-2199 (2014).
Snyder et al., "Immunogenic peptide discovery in cancer genomes," Cuff Opin Genet Dev, 30: 7-16 (2015).
Soares et al. "A subset of dendritic cells induces CD4+ T cells to produce IFN-gamma by an IL-12-independent but CD70-dependent mechanism in vivo." J Exp Med, 2215(11):1095-1106 (2007).
Soiffer et al., "Vaccination with irradiated autologous melanoma cells engineered to secrete human granulocyte-macrophage colony-stimulating factor generates potent antitumor immunity in patients with metastatic melanoma," PNAS, 95(22):13141-13146 (1998).
Soiffer et al., "Vaccination With Irradiated, Autologous Melanoma Cells Engineered to Secrete Granulocyte-Macrophage Colony-Stimulating Factor by Adenoviral-Mediated Gene Transfer Augments Antitumor Immunity in Patients With Metastatic Melanoma," J Clin Oncol, 21(17):3343-3350 (2003).
Soininen et al., "Analysing diet of small herbivores: the efficiency of DNA barcoding coupled with high-throughput pyrosequencing for deciphering the composition of complex plant mixtures," Front Zool, 6:16 (2009).
Sokolov., "Primer Extension Technique for the Detection of Single Nucleotide in Genomic DNA," Nucleic Acids Res. 18(12): 3671 (1990).
Somasundaram et al., "Human Leukocyte Antigen-A2-Restricted CTL Responses to Mutated BRAF Peptides in Melanoma Patients," Cancer Res, 66(6): 3287-3293 (2006).
Sommnerfeit et al., "Receptor interference groups of 20 retroviruses plating on human cells," Virol, 176:58-59 (1990).
Song et al., "c-Cbl acts as a mediator of Src-induced activation of the PI3K-Akt signal transduction pathway during TRAIL treatment," Cellular Signalling, 22(3):377-385 (2010).
Song et al., "Full screening and accurate subtyping of HLA-A*02 alleles through group-specific amplification and mono-allelic sequencing," Cell Mol Immunol, 10:490-496 (2013).
Sosman et al., "A phase 2 trial of complete resection for stage IV melanoma: results of Southwest Oncology Group Clinical Trial S9430," Cancer, 117(20):4740-4706 (2011).
Soung et al., "Capase-8 gene is frequently inactivated by the frameshift somatic mutation 1225_1226delTG in hepatocellular carcinomas," Oncogene, 24:141-147 (2005).
Sowa et al., "Defining the Human Deubiquitinating Enzyme Interaction Landscape," Cell, 138(2):389-403 (2009).
Speetjens et al., "Induction of p53-Specific Immunity by a p53 Synthetic Long Peptide Vaccine in Patients Treated for Metastatic Colorectal Cancer," Clin Cancer Res, 15(3):1086-1095 (2009).
Speiser et al., "Molecularly defined vaccines for cancer immunotherapy, and protective T cell immunity," Semin Immunol, 22(3):144-154 (2010).
Spencer et al., "Non-genetic origins of cell-to-cell variability in TRAIL-induced apoptosis," Nature, 459:428-432 (2009).
Spitler, "Cancer Vaccines: The Interferon Analogy," Cancer Biother, 10:1-3 (1995).
Spranger et al., "Up-regulation of PD-LI, IDO, and Tregs in the melanoma tumor microenvironment is driven by CD8+ T cells," Sci Transl Med, 5(200):200ra116 (2013).
Srivastava et al., "Modeling the Repertoire of True Tumor-Specific MHC I Epitopes in a Human Tumor," PLOS ONE, 4(7):e6094 (2009).
Srivastava, "Therapeutic Cancer Vaccines," Curr Opin Immunol, 18: 201-205 (2006).
Staehler et al., "An open label study to evaluate the safety and immunogenicity of the peptide based cancer vaccine IMA901," ASCO meeting 2007; Abstract No. 3017.
Stahl-Hennig et al., "Synthetic double-stranded RNAs are adjuvants for the induction of T helper 1 and humoral immune responses to human papillomavirus in rhesus macaques," PLoS pathogens, 5(4):e1000373 (2009).
Stankovic et al., "Microarray Analysis Reveals that TP53- and ATM-Mutant B-CLLs Share a Defect in Activating Proapoptotic Responses after DNA Damage but are Distinguished byMajor Differences in Activating Prosurvival Responses," Blood, 103: 291-300 (2004).
Stover et al., "New Use of BCG for Recombinant Vaccines," Nature, 351(6326): 456-460 (1991).
Stransky et al., "The Mutational Landscape of Head and Neck Squamous Cell Carcinoma," Science, 333:1157-1160 (2011).
Stranzl et al., "NetCTLpan: pan-specific MHC class I pathway epitope predictions," Immunogenetics, 62(6):357-368 (2010).
Stratton et al., "The Cancer Genome," Nature, 458(7239):719-724 (2009).
Su et al., "Immunological and Clinical Responses in Metastatic Renal Cancer Patients Vaccinated with Tumor RNA-Transfected Dendritic Cells," Cancer Res, 63: 2127-2133 (2003).
Su et al., "Next-generation sequencing and its applications in molecular diagnostics" Exp Rev Mol Diagn, 11(3):333-343 (2011).
Submission in opposition proceedings of EP 2569633, dated Jun. 28, 2017.

(56) References Cited

OTHER PUBLICATIONS

Subramanian et al., "Gene set enrichment analysis: a knowledge-based approach for interpreting genome-wide expression profiles," PNAS, 102:15545-15550 (2005).
Sullivan et al., "Expression and Characterization of Herpes Simplex Virus Type 1 (HSV-1) Glycoprotein G (gG) by Recombinant Vaccinia Virus: Neutralization of HSV-1 Infectivity with Anti-gG Antibody," Gen Vir, 68:2587-2598 (1987).
Sun et al., Material bionics and Thinking Innovation, 176-177 (2012).
Supplementary Materials from Third Party Observation in EP Application No. 15198284.0.
Suzuki et al., "A Novel Glycosylphosphatidyl Inositol-Anchored Protein on Human Leukocytes: A Possible Role for Regulation of Neutrophil Adherence and Migration," J Immunol, 162(7):4277-4284 (1999).
Sykulev et al., "Evidence that a Single Peptide-MHC Complex on a Target Cell Can Elicit a Cytolytic T Cell Response," Immunity, 4:565-571 (1996).
Syvanen et al., "A Primer-Guided Nucleotide Incorporatiopn Assay in the Genotyping of Apoliprotein E," Genomics, 8(4): 684-692 (1990).
Syvanen et al., "Identification of Individuals by Analysis of Biallelic DNA Markers, Using PCR and Solid-Phase Minisequencing," Am J Hum Genet, 52(1): 46-59 (1993).
Table S4 Somatic mutations Identified in Breast or Colorectal Cancers filed on Nov. 7, 2016 in Notice of Opposition by Gritstone Oncology Inc. to EP 2569633.
Table S5 Breast CAN-genes, filed on Nov. 7, 2016, in Notice of Opposition by Gritstone Oncology Inc., to EP Patent No. 2569633.
Table S6 Colorectal CAN-genes, filed on Nov. 7, 2016 in Notice of Opposition by Gritstone Oncology Inc. to EP Patent No. 2569633.
Tang et al., "NeoantigenR: An annotation based pipeline for tumor neoantigen identification from sequencing data," bioRxiv preprint first posted online Aug. 8, 2017.
Tang et al., "The landscape of viral expression and host gene fusion and adaptation in human cancer," Nat Commun, 4:2513 (2013).
Tartaglia et al., "NYVAC: A highly attenuated strain of vaccinia virus," Virology, 188(1):217-232 (1992).
Ten Bosch et al., "Keeping Up With the Next Generation: Massively Parallel Sequencing in Clinical Diagnostics," J Mol Diagn, 10(6):484-492 (2008).
Teng et al., "A human TAPBP (TAPASIN)-related gene, TAPBP-R," Eur J Immunol, 32:1059-1068 (2002).
Testori et al., "Phase III comparison of vitespen, an autologous tumor-derived heat shock protein gp96 peptide complex vaccine, with physician's choice of treatment for stage IV melanoma: the C-100-21 Study Group," J Clin Oncol, 26(6):955-962 (2008).
Textor et al., "Human NK cells are alerted to induction of p53 in cancer cells by upregulation of the NKG2D ligands ULBPI and ULBP2," Cancer Res, 71:5998-6009 (2011).
Thomas et al., "High-Throughput Oncogene Mutation Profiling in Human Cancer," Nat Genet, 39: 347-351 (2007).
Thompson et al., "Aberrations of the B-Cell Receptor B29 (CD79b) Gene in Chronic Lymphocytic Leukemia," Blood, 90(4):1387-1394 (1997).
Thon et al., "Personalized treatment strategies in glioblastoma: MGMT promoter methylation status," Onco Targets and Therapy, 6:1363-1372 (2013).
Thornton et al., "Characterisation of TP53 Abnormalities in Chronic Lymphocytic Leukaemia," Hematol J, 5: 47-54 (2004).
Timmerman et al., "Idiotype-Pulsed Dendritic Cell Vaccination for B-Cell Lymphoma: Clinical and Immune Responses in 35 Patients," Blood, 99: 1517-1526 (2002).
Timp et al., "Cancer as a dysregulated epigenome allowing cellular growth advantage at the expense of the host," Nat Rev Cancer, 13:497-510 (2013).
Tjernberg et al., "DMSO-Related Effects in Protein Characterization," Journal of Biomolecular Screening, 11(2): 131-137 (2006).
Tjoa et al., "Follow-Up Evaluation of Prostate Cancer Patients Infused with Autologous Dendritic Cells Pulsed with PSMA Peptides," Prostate, 32(4): 272-278 (1997).
Tong et al., "Methods and protocols for prediction of immunogenic epitopes", Briefings In Bioinformatics, 8(2): 96-108 (2008).
Topalian et al., "Five-Year Survival and Correlates Among Patients With Advanced Melanoma, Renal Cell Carcinoma, or Non-Small Cell Lung Cancer Treated With Nivolumab," JAMA Oncol., 5(10): 1411-1420 (2019).
Topalian et al., "Safety, Activity, and Immune Correlates of Anti-PD-1 Antibody in Cancer," N Engl J Med, 366(26):2443-2454 (2012).
Topalian et al., "Survival, Durable Tumor Remission, and Long-Term Safety in Patients With Advanced Melanoma Receiving Nivolumab," J Clin Oncol, 32(10):1020-1030 (2014).
Topalian et al., "Targeting the PD-1/B7-H1(PD-L1) pathway to activate anti-tumor immunity," Current Opinion in Immunology, 24:207-212 (2012).
Tough et al., "Induction of bystander T cell proliferation by viruses and type I interferon in vivo," Science, 272(5270):1947-1950 (1996).
Tourdot et al., "A general strategy to enhance immunogenicity of low-affinity HLA-A2.1-associated peptides: implication in the identificatiioonn of cryptic tumor epitopes," Eur. J. Immunol, 30:3411-3421 (2000).
Toze et al., "Myeloablative Allografting for Chronic Lymphocytic Leukemia: Evidence for Potent Graft-versus-Leukemia Effect Associated with Graft-versus-Host Disease," Bone Marrow Transplant, 36: 825-830 (2005).
Tran et al., "Cancer Immunotherapy Based on Mutation-Specific CD4+ T Cells in a Patient with Epithelial Cancer," Science, 344(6184):641-645 (2014).
Trolle et al., "Automated benchmarking of peptide-MHC class I binding predictions," Bioinformatics, 31(13):2174-2181 (2015).
Trolle et al., "The Length Distribution of Class I-Restricted T Cell Epitopes Is Determined by Both Peptide Supply and MHC Allele-Specific Binding Preference," J Immunol (2016), doi: 10.4049/jimmunol.1501721.
Trumpfheller et al., "Intensified and protective CD4+ T cell immunity in mice with anti-dendritic cell HIV gag fusion antibody vaccine," J Exp Med, 203(3):607-617 (2006).
Trumpfheller et al., "The microbial mimic poly IC induces durable and protective CD4+ T cell immunity together with a dendritic cell targeted vaccine," PNAS, 105(7):2574-2579 (2008).
Tucker et al., "Massively Parallel Sequencing: The Next Big Thing in Genetic Medicine," Am J Hum Genet, 85(2):142-154 (2009).
Tumeh et al., "PD-1 blockade induces responses by inhibiting adaptive immune resistance," Nature, 515(7528):568-571 (2014).
Turchaninova et al., "Pairing of T-cell receptor chains via emulsion PCR," Eur J Immunol, 43:2507-2515 (2013).
Turke et al., "Preexistence and Clonal Selection of MET Amplification in EGFR Mutant NSCLC," Cancer Cell, 17: 77-88 (2010).
Tynan et al., "T cell receptor recognition of a "super-bulged" major histocompatibility complex class I-bound peptide," Nat Immunol, 6:1114-1122 (2005).
U.S. Final Office Action dated May 25, 2017 and issued in U.S. Appl. No. 15/187,174.
U.S. Final Rejection dated Sep. 13, 2017 and issued in U. S. U.S. Appl. No. 14/794,449.
U.S. Non-Final Office Action dated Jan. 22, 2018 and issued in U.S. Appl. No. 15/187,174.
U.S. Non-Final Office Action dated Mar. 7, 2019 and issued in U.S. Appl. No. 15/037,394.
U.S. Non-Final Office Action dated Oct. 2, 2020 and issued in U.S. Appl. No. 15/037,394.
U.S. Non-Final Office Action dated Dec. 5, 2016 and issued in U.S. Appl. No. 15/187,174.
U.S. Non-Final Office Action dated Dec. 29, 2016 and issued in U.S. Appl. No. 14/794,449.
Uderhardt et al., "12/15-lipoxygenase orchestrates the clearance of apoptotic cells and maintains immunologic tolerance," Immunity, 36(5):834-846 (2012).

(56) References Cited

OTHER PUBLICATIONS

Udeshi et al., "Methods for quantification of in vivo changes in protein ubiquitination following proteasome and deubiquitinase inhibition," Mol Cell Proteomics, 11:148-159 (2012).
Ueda et al., "Germ Line and Somatic Mutations of BRAF V599E in Ovarian Carcinoma," Int J Gynecol Cancer, 17: 794-797 (2007).
Ugozzoli et al., "Detection of Specific Alleles by Using Allele-Specific Primer Extension Followed by Capture on Solid Support," Genet Anal Tech AppL, 9(4): 107-112 (1992).
UniProtKB Printouts—Q5SW79 filed on Nov. 2016 in Muller Opposition to EP 2569633.
Ushijima et al., "Fidelity of the methylation pattern and its variation in the genome," Genome research, 13:868-874 (2005).
Uyttenhove et al., "Evidence for a tumoral immune resistance mechanism based on tryptophan degradation by indoleamine 2,3-dioxygenase," Nature medicine, 9:1269-1274 (2003).
Vaishampayan et al., "Active immunotherapy of metastatic melanoma with allogeneic melanoma lysates and interferon alpha," Clin Cancer Res, 8(12):3696-3701 (2002).
Van Buuren et al., "High sensitivity of cancer exome-based CD8 T cell neo-antigen identification," OncoImmunology, 3(5):e28836 (2014).
Van de Roemer et al., "P1737:IVAC: Individualized vaccines for cancer," Immunology 137(Suppl. 1):715, Sep. 2012.
Van Den Broeke et al., "Identification and Epitope Enhancement of a PAX-FKHR Fusion Protein Breakpoint Epitope in Alveolar Rhabdomyosarcoma Cells Created by a Tumorigenic Chromosomal Translocation Inducing CTL Capable of Lysing Human Tumors," American Association for Cancer Research, 66(3):1818-1823 (2006).
Van der Bruggen et al., "A Gene Encoding an Antigen Recognized by Cytolytic T Lymphocytes on a Human Melanoma," Science, 254: 1643-1647 (1991).
Van Elsas et al., "Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation," Journal of Experimental Medicine, 190(3):355-366 (1999).
Van Pel et al., "Tumor Cell Variants Obtained by a Mutageneis of a Lewis Lung Carcinoma Cell Line: Immune Rejection by Syngeneic Mice," PNAS, 76(10): 5282-5285 (1979).
Van Poelgeest et al., "HPV16 synthetic long peptide (HPV16-SLP) vaccination therapy of patients with advanced or recurrent HPV16-induced gynecological carcinoma, a phase II trial," J Transl Med, 11:88 (2013).
Van Rooij et al., "Tumor Exome Analysis Reveals Neoantigen-Specific T-Cell Reactivity in an 1pilimumab-Responsive Melanoma," Journal of Clinical Oncology, 31(32):e439-e442 (2013).
Van Trappen et al., "Somatic Mitochondrial DNA Mutations in Primary and Metastatic Ovarian Cancer," Gynecol Oncol, 104: 129-133 (2007).
Vandenberghe et al., "Heparin binding directs activation of T cells against adeno-associated virus serotype 2 capsid," Nature Medicine, 12(8): 967-971 (2006).
Vandrovcova et al., "Somatic BRAF-V600E Mutations in Familial Colorectal Cancer," Cancer Epidemio Biomarkers Prev, 15(11):2270-2273 (2006).
Varley et al., "Intra-tumor heterogeneity of MLH1 promoter methylation revealed by deep single molecule bisulfite sequencing," Nucleic Acids Research, 37(14):4603-4612 (2009).
Verardi et al., "A vaccinia virus renaissance: new vaccine and immunotherapeutic uses after smallpox eradication," Human vaccines & immunotherapeutics, 8(7):961-970 (2012).
Verhoef et al., "Des-enkephalin-v-endorphin (DEyE): Biotransformation in rat, dog and human plasma," Eur J Drug Metab Ph, 11(4):291-302 (1986).
Vermeij et al., "Potentiation of a p53-SLP vaccine by cyclophosphamide in ovarian cancer: a single-arm phase II study," Int J Cancer, 131(5):E670-680 (2012).
Vita et al., "The immune epitope database (IEDB) 3.0," Nucleic Acids Res, 43:D405-D412 (2015).
Vita et al., "The Immune Epitope Database 2.0," Nucleic Acids Res, 38:D854-D862 (2010).
Vogel et al., "Mass Spectrometry Reveals Changes in MHC I Antigen Presentation After Lentivector Expression of a Gene Regulation System," Molecular Therapy—Nucleic Acids, 2:e75 (2013).
Vogelstein et al., "Cancer Genome Landscapes," Science, 339(6127): 1546-1558 (2013).
Volpe et al., "Alternative BCR/ABL Splice Variants in Philadelphia Chromosome-Positive Leukemias Result in Novel Tumor-Specific Fusion Proteins that May Represent Potential Targets for Immunotherapy Approaches," Cancer Res, 67(11):5300-5307 (2007).
Von Krempelhuber et al., "A randomized, double-blind, dose-finding Phase II study to evaluate immunogenicity and safety of the third generation smallpox vaccine candidate IMVAMUNE®," Vaccine, 28(5):1209-1216 (2010).
Von Mehren et al., "Pilot study of a dual gene recombinant avipox vaccine containing both carcinoembryonic antige (CEA.) and B7.1 transgenes in patients with, recurrent CEA-expressing adenocarcinomas," Clin Cancer Res, 6:2219-28 (2000).
Vonderheide et al., "Immunotherapy at Large: The road to personalized cancer vaccines," Nature Medicine 19(9) 1098-1100 (2013).
Wahl et al., "[43] Molecular hybridization of immobilized nucleic acids: Theoretical concepts and practical considerations," Methods in enzymology, Academic Press, 152:399-407 (1987).
Walter et al., "DNA Methylation Profiling Defines Clinically Relevant Biological Subsets of Non-small Cell Lung Cancer," Clin Cancer Res, 18(8):2360-2373 (2012).
Walter et al., "Multipeptide immune response to cancer vaccine IMA901 after single-dose cyclophosphamide associates with longer patient survival," Nature medicine, 18(8):1254 (2012).
Walz et al., "The antigenic landscape of multiple myeloma: mass spectrometry (re)defines targets for T-cell-based immunotherapy," Blood 126:1203-1213 (2015).
Wang et al., "Role of protein kinase CK2 in the regulation of tumor necrosis factor-related apoptosis inducing ligand-induced apoptosis in prostate cancer cells," Cancer research, 66:2242-2249 (2006).
Wang et al., "SF3B1 and other novel cancer genes in chronic lymphocytic leukemia," N Engl J Med, 365:2497-2506 (2011).
Wang et al., "Widespread plasticity in CTCF occupancy linked to DNA methylation," Genome Res, 22:1680-1688 (2012).
Wang et al., Functional Polymeric Material, 1-44 (2010).
Wang, "Tumor Antigens Discovery: Perspectives for Cancer Therapy", Molecular Medicine, 3(11): 716-731 (1997).
Watson et al., "SHP-1: the next checkpoint target for cancer immunotherapy?," Biochem Soc Trans, 44(2):356-362 (2016).
Weber et al., "Assembly of Designer TAL Effectors by Golden Gate Cloning," PLoS ONE, 6:e19722 (2001).
Weber et al., "Safety, Efficacy, and Biomarkers of Nivolumab With Vaccine in Ipilimumab- Refractory or -Naive Melanoma," J Clin Oncol, 31:4311-4318 (2013).
Webster et al., "Enhanced T cell-mediated protection against malaria in human challenges by using the recombinant poxviruses FP9 and modified vaccinia virus Ankara," Proceedings of the National Academy of Sciences, 102(13):4836-4841 (2005).
Weiner et al., "Genetic vaccines," Scientific American, 281(1):50-57 (1999).
Weinschenk et al., "Integrated Functional Genomics Approach for the Design of Patientindividual Antitumor Vaccines," Cancer Res, 62: 5818-5827 (2002).
Welters et al., "Induction of tumor-specific CD4+ and CD8+ T-cell immunity in cervical cancer patients by a human papillomavirus type 16 E6 and E7 long peptides vaccine," Clinical cancer research, 14(1):178-187 (2008).
Welters et al., "Success or failure of vaccination for HPV16-positive vulvar lesions correlates with kinetics and phenotype of induced T-cell responses," PNAS, 107(26):11895-11899 (2010).
Weyer et al., "Generation and evaluation of a recombinant modified vaccinia virus Ankara vaccine for rabies," Vaccine, 25(21):4213-4222 (2007).
Weyer et al., "Poxvirus-vectored vaccines for rabies—a review," Vaccine, 27(51):7198-7201 (2009).

(56) References Cited

OTHER PUBLICATIONS

Wheatley et al., "Does adjuvant interferon-alpha for high-risk melanoma provide a worthwhile benefit?A meta-analysis of the randomised trials," Cancer treatment reviews, 29(4):241-252 (2003).
Whelan et al., "Safety and immunogenicity of boosting BCG vaccinated subjects with BCG: comparison with boosting with a new TB vaccine, MVA85A," PLoS One, 4(6):e5934 (2009).
Widschwendter et al., "Epigenetic stem cell signature in cancer," Nat Genet, 39:157-158 (2007).
Wierda et al., "Multivariable model for time to first treatment in patients with chronic lymphocytic leukemia," J Clin Oncol, 29:4088-4095 (2011).
Wiktor et al., "Protection from rabies by a vaccinia virus recombinant containing the rabies virus glycoprotein gene," Proceedings of the National Academy of Sciences, 81(22):7194-7198 (1984).
Willmore-Payne et al., "Human Malignant Melanoma: Detectection of BRAF- and c-kit-Activating Mutations by High-Resolution Amplicon Melting Analysis," Hum Pathol, 36: 486-493 (2005).
Wilson et al., "Formation of infectious hybrid virions with gibbon ape leukemia virus and human T-cell leukemia virus retroviral envelope glycoproteins and the gag and pol proteins of Moloney murine leukemia virus," Journal of virology, 63(5):2374-2378 (1989).
Winzeler et al., "Functional characterization of the *S. cerevisiae* genome by gene deletion and parallel analysis," science, 285(5429):901-906 (1999).
Wolchok et al., "Nivolumab plus ipilimumab in advanced melanoma," N Engl J Med, 369(2):122-133 (2013).
Wolfel et al., "A p16INK4a-insensitive CDK4 mutant targeted by cytolytic T lymphocytes in a human melanoma," Science, 269(5228):1281-1284 (1995).
Wolff et al., "Direct Gene Transfer into Mouse Muslce in Vivo," Science, 247(4949):1465-1468 (1990).
Wong et al., "Module map of stem cell genes guides creation of epithelial cancer stem cells," Cell Stem Cell, 2:333-344 (2008).
Wood et al., "The Genomic Landscapes of Human Breast and Colorectal Cancers," Science, 318: 1108-1113 (2007).
Woodbury et al., "Introduction to Macromolecular Binding Equilibria," CRC Press, 13:978 (2007).
Woodfine et al., "Quantitative analysis of DNA methylation at all human imprinted regions reveals preservation of epigenetic stability in adult somatic tissue," Epigenetics & chromatin, 4:1 (2011).
Woyach et al., "Resistance mechanisms for the Bruton's tyrosine kinase inhibitor ibrutinib," The New England journal of medicine, 370:2286-94 (2014).
Wraith, "The Future of Immunotherapy: A 20-Year Perspective," Front Immunol, 8(1668): 1-6 (2017).
Wu et al., "Detection of a potent humoral response asscoiated with immune-induced remission of chronic myelogenous leukemia," J Clin Invest, 106(5):705-714 (2000).
Wu et al., "Graft-versus-Leukemia Target Antigens in Chronic Myelogenous Leukemia Are Expressed on Myeloid Progenitor Cells," Clin Cancer Res, 11(12):4504-4511 (2005).
Wu et al., "Induction of Tumor Immunity Following Allogeneic Stem Cell Transplantation," Adv Immunol, 90: 133-173 (2006).
Wu et al., "Mouse Model of Human Ovarian Endometrioid Adenocarcinoma Based on Somatic Defects in the Wnt/6-Catenin and PI3K/Pten Signaling Pathways," Cancer Cell, 11: 321-333 (2007).
Wu et al., "Reconstitution of T-Cell Receptor Repertoire Diversity Following T-Cell Depleted Allogeneic Bone Marrow Transplantation is Related to Hematopoietic Chimerism," Blood, 95: 352-359 (2000).
Wu et al., "Structure-based engineering of a monoclonal antibody for improved solubility," Protein Engineering, Design & Selection, 23(8): 643-651 (2010).
Wyatt et al., "Marker rescue of the host range restriction defects of modified vaccinia virus Ankara," Virology, 251(2):334-342 (1998).

Wyatt et al., "Multiprotein HIV type 1 clade B DNA and MVA vaccines: construction, expression, and immunogenicity in rodents of the MVA component," AIDS research and human retroviruses, 20(6):645-653 (2004).
Xi et al., "BSMAP: whole genome bisulfite sequence MAPping program," BMC bioinformatics, 10:232 (2009).
Xie et al., "Stepwise reprogramming of B cells into macrophages," Cell, 117(5):663-676 (2004).
Xu et al., "Design of 240,000 orthogonal 25mer DNA barcode probes," Proceedings of the National Academy of Sciences, pnas-0812506106 (2009).
Yan et al., "PBAF chromatin-remodeling complex requires a novel specificity subunit, BAF200, to regulate expression of selective interferon-responsive genes," Genes & development, 19(14):1662-1667 (2005).
Yang et al. "CML66, a broadly immunogenic tumor antigen, elicits a humoral immune response associated with remission of chronic myelogenous leukemia," PNAS, 98(13):7492-7497 (2001).
Yang et al., "Meta-analysis followed by replication identifies loci in or near CDKN1B, TET3, CD80, DRAM1, and ARID5B as associated with systemic lupus erythematosus in Asians," American journal of human genetics, 92:41-51 (2013).
Yao et al., "Advances in targeting cell surface signalling molecules for immune modulation," Nature Rev Drug Discov, 12:130-146 (2013).
Yee et al., "Adoptive T cell therapy using antigen-specific CD8 T cell clones for the treatment of patients with metastatic melanoma: In vivo persistence, migration, and antitumor effect of transferred T cells," PNAS, 99(25): 16168-16173 (2002).
Yewdell, "DRiPs solidify: progress in understanding endogenous MHC class I antigen processing," Trends Immunol, 32(11):548-558 (2011).
Yilma, "Prospects for the total eradication of rinderpest," Vaccine, 7(6):484-485 (1989).
Yokoyama et al., "Matrilysin (MMP-7) Is a Novel Broadly Expressed Tumor Antigen Recognized by Antigen-Specific T Cells," Clin Cancer Res, 14(17): 5503-5511 (2008).
Yosef et al., "Dynamic regulatory network controlling TH17 cell differentiation," Nature, 496(7446):461-468 (2013).
Yoshihara et al., Inferring tumour purity and stromal and immune cell admixture from expression data,: Nature communications 4:2612 (2013).
Yoshitake et al., "Cross☐linking of GPI☐80, a possible regulatory molecule of cell adhesion, induces up☐regulation of CD11b/CD18 expression on neutrophil surfaces and shedding of L☐selectin," Journal of leukocyte biology, 71(2):205-211 (2002).
You et al., "Understanding Prediction Systems for HLA-Binding Peptides and T-Cell Epitope Identification," Pattern Recognition in Bioinformatics, Lecture Notes in Computer Science, 4474: 337-348 (2007).
Young et al., "Resurrection of endogenous retroviruses in antibody-deficient mice," Nature, 491(7426):774 (2012).
Yu et al., "Nucleic acid-sensing Toll-like receptors are essential for the control of endogenous retrovirus viremia and ERV-induced tumors," Immunity, 37(5):867-879 (2012).
Yuille et al., "TCL1 is activated by chromosomal rearrangement or by hypomethylation," Genes, Chromosomes and Cancer, 30(4):336-341 (2001).
Zeestraten et al., "Addition of interferon-alpha to the p53-SLP(R) vaccine results in increased production of interferon-gamma in vaccinated colorectal cancer patients: a phase 1/11 clinical trial," Int J Cancer, 132(7):1581-1591 (2013).
Zhang et al., "Dana-Farber repository for machine learning in immunology," J Immunol Methods, 374(1-2):18-25 (2011).
Zhang et al., "Graft-versus-Leukemia Antigen CML66 Elicits Coordinated B-Cell and T-Cell Immunity after Donor Lymphocyte Infusion," Clin Cancer Res, 16: 2729-2739 (2010).
Zhang et al., "Intratumoral T Cells, recurrence, and survival in epithelial ovarian cancer," New Engl J Med, 348(3):203-213 (2003).
Zhang et al., "Machine learning competition in immunology-prediction of HLA class I binding peptides," J Immunol Methods 374:1-4 (2009).

(56) References Cited

OTHER PUBLICATIONS

Zhang et al., "The impact of next-generation sequencing on genomics," J Genet Genomics, 38(3):95-109 (2011).
Zhang et al., Oncology, 1-44 (2005).
Zhou et al., "A hypermorphic missense mutation in PLCG2, encoding phospholipase Cgamma2, causes a dominantly inherited autoinflammatory disease with immunodeficiency," Am J Hum Genet, 91:713-20 (2012).
Zhou et al., "Diverse CD8+ T-Cell Responses to Renal Cell Carcinoma Antigens in Patients Treated with an Autologous Granulocyte-Macrophage Colony-Stimulating Factor Gene-Transduced Renal Tumor Cell Vaccine," Cancer Res, 65: 1079-1088 (2005).
Zhou et al., "Long-term outcome after haploidentical stem cell transplant and infusion of T cells expressing the inducible caspase 9 safety transgene," Blood, 123(25):3895-3905 (2014).
Zhou et al., "Transcriptional regulatory networks in Th17 cell differentiation," Curr Opin Immunol, 21(2):146-152 (2009).
Zhou et al., Persistance of Multiple Tumor-Specific T-Cell Clones is Associated with Complete Tumor Regression in a Melanoma Patient Receiving Adoptive Cell transfer Therapy, J Immunother, 28(1):53-62 (2005).
Zhu et al., "Toll like receptor-3 ligand poly-ICLC promotes the efficacy of peripheral vaccinations with tumor antigen-derived peptide epitopes in murine CNS tumor models," Journal of translational medicine, 5:10 (2007).
Ziller et al., "Charting a dynamic DNA methylation landscape of the human genome," Nature, 500:477-481 (2013).
Zitvogel et al., "Immunological aspects of cancer chemotherapy," Nature reviews immunology, 8:59 (2008).
Zorn et al., "A natural cytotoxic T cell response in a spontaneously regressing human melanoma targets a neoantigen resulting from a somatic point mutation," Eur J Immunol, 29(2):592-601 (1999).
Zwaveling et al., "Established human papillomavirus type 16-expressing tumors are effectively eradicated following vaccination with long peptides," J Immunol, 169(1):350-358 (2002).
Carlino et al., "Immune checkpoint inhibitors in melanoma," Lancet, 398: 1002-1014 (2021).
Coulie et al., "Genes Coding for Antigens Recognized on Human Tumors by Autologous Cytolytic T Lymphocytes," Annals of New York Academy of Sciences: 113-119 (1993).
Coulie et al., "Tumour antigens recognized by T lymphocytes: at the core of cancer immunotherapy," Nature Review, 14: 135-146 (2014).
Extended European Search Report for EP Application No. 22162718.5 dated Jul. 1, 2022.
Gaynor et al., "GATA3 Mutations Found in Breast Cancers May Be Associated with Aberrant Nuclear Localization, Reduced Transactivation and Cell Invasiveness", Hormones and Cancer, 4: 123-139 (2013).
Kantoff et al., "Sipuleucel-T Immunotherapy for Castration-Resistant Prostate Cancer," The New England Journal of Medicine, 363: 411-422 (2010).
Kirstensen et al., "The Antigenicity of the Tumor Cell-Context Matters," The New England Journal of Medicine, 376(5): 491-493 (2017).
McGranahan et al., "Clonal neoantigens elicit T cell immunoreactivity and sensitivity to immune checkpoint blockade," Science, 351(6280): 1463-1469 (2016).
Melief., "Cancer Immunotherapy by Dendritic Cells" Immunity, 29: 372-383 (2008).
Melief., "Precision T-cell therapy targets tumours," Nature, 547(7662): 165-167 (2017).
Reck et al., "First-Line Immunotherapy for Non-Smalll-Cell Lung Cancer," Journal of Clinical Oncology, 40(6): 586-597 (2022).
Shrock et al., "Tumor mutational burden is predictive of response to immune checkpoint inhibitors in MSI-high metastatic colorectal cancer," Annals of Oncology, 30: 1096-1103 (2019).
Velez et al., "BNT221, an Autologous Neoantigen-Specific T cell Product for Adoptive Cell Therapy of Metastatic Ovarian Cancer" poster presented Oct. 2021 at SITC.

* cited by examiner

FIG. 2A
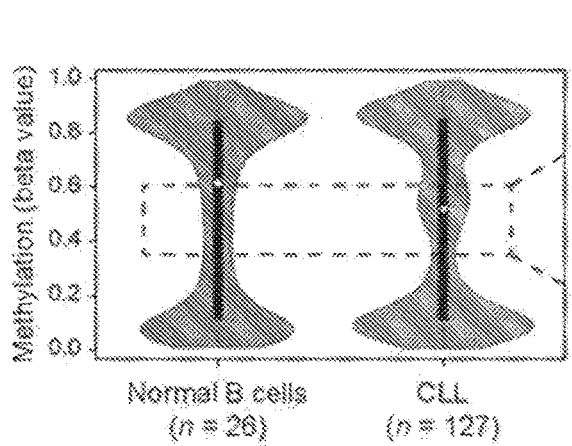
FIG. 2B
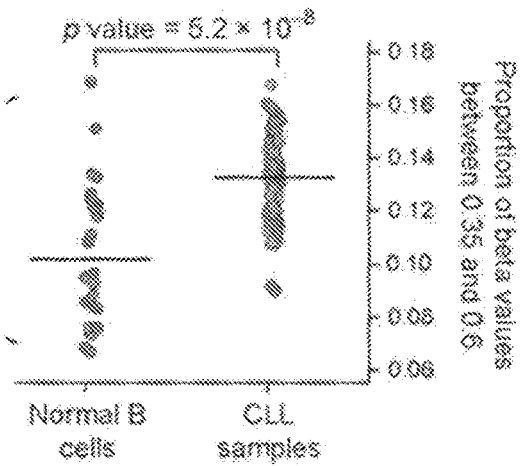
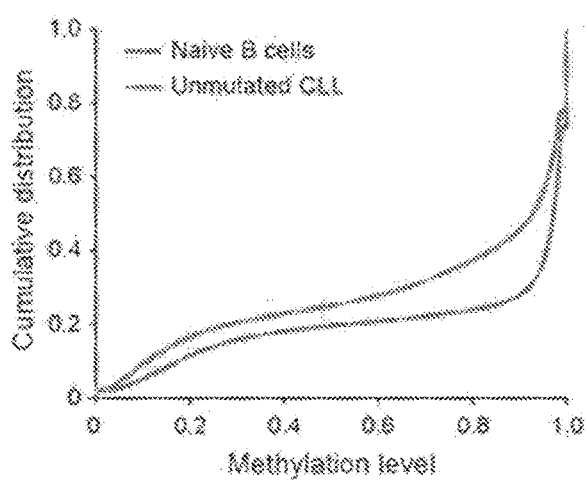
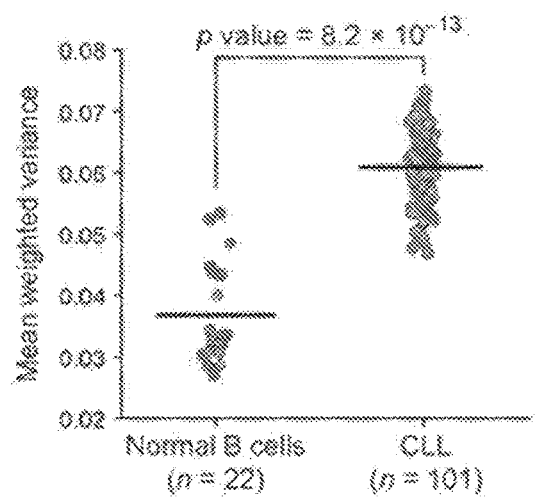
FIG. 2C
FIG. 2D
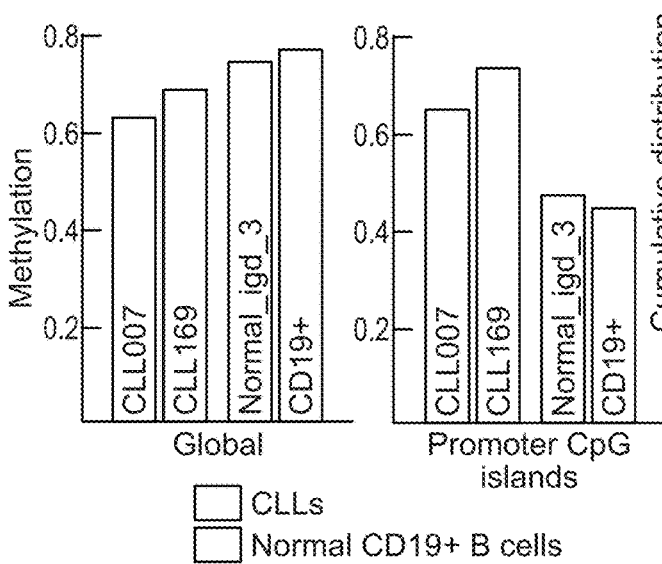
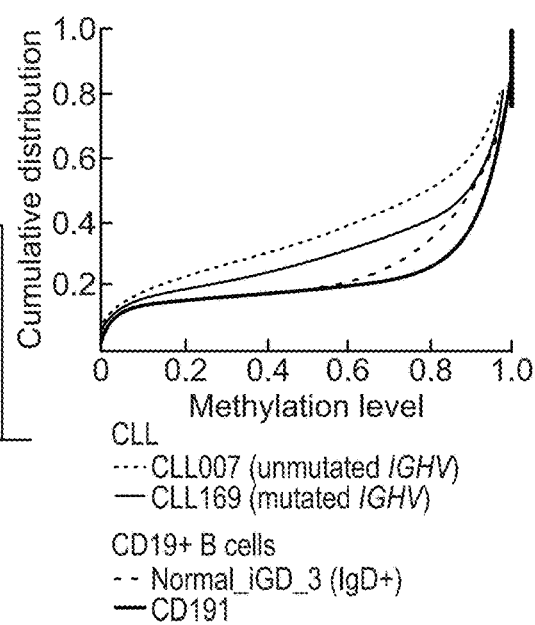
FIG. 3A

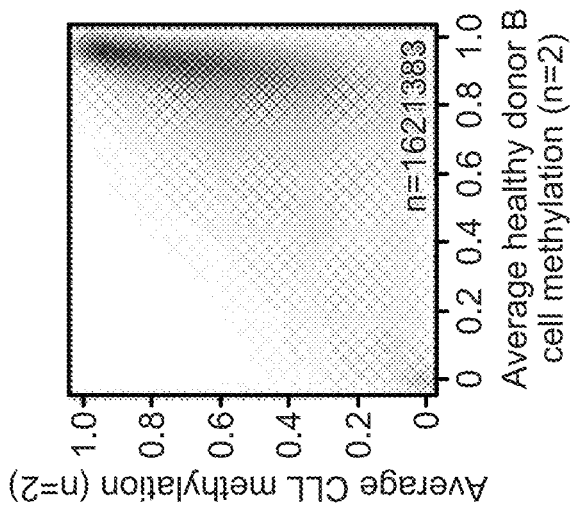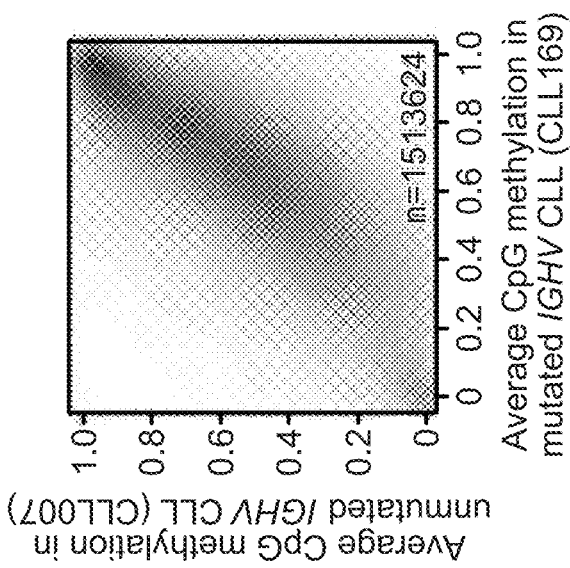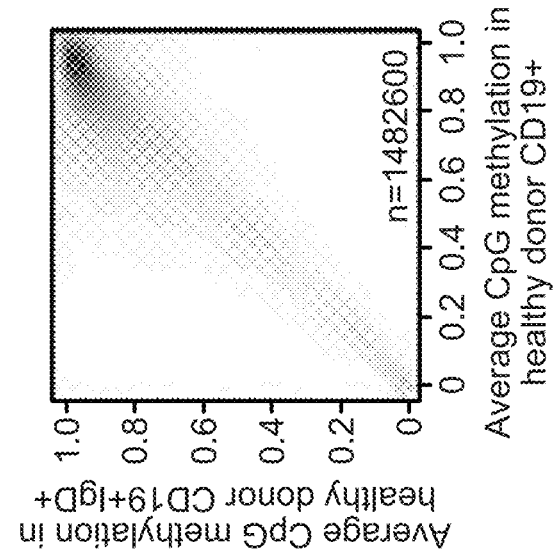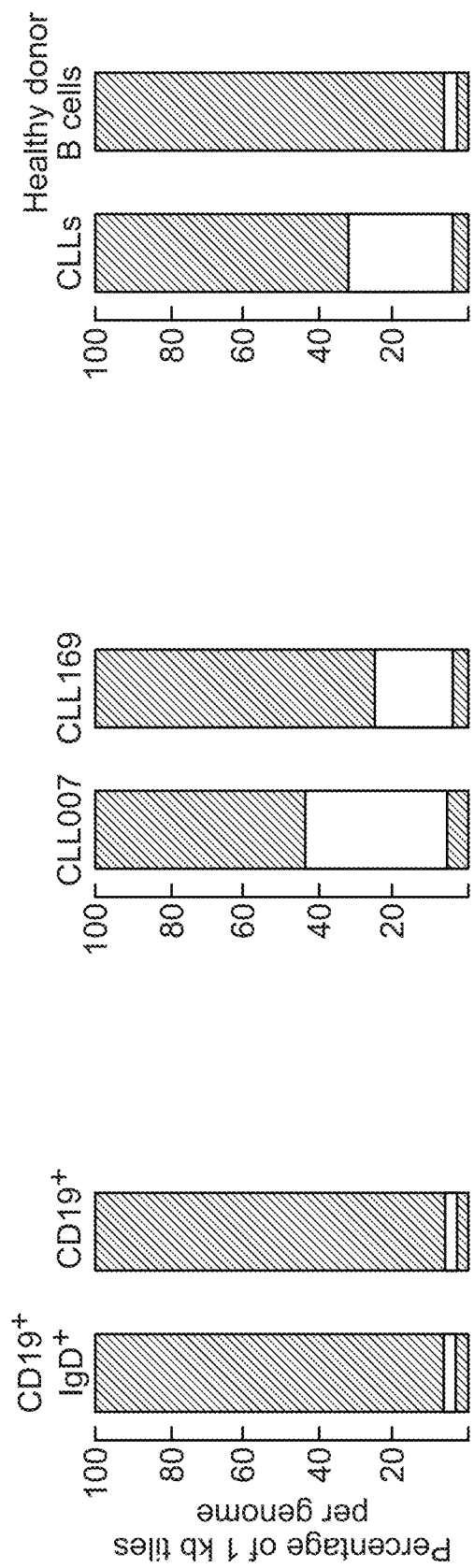
FIG. 4A  FIG. 4B  FIG. 4C

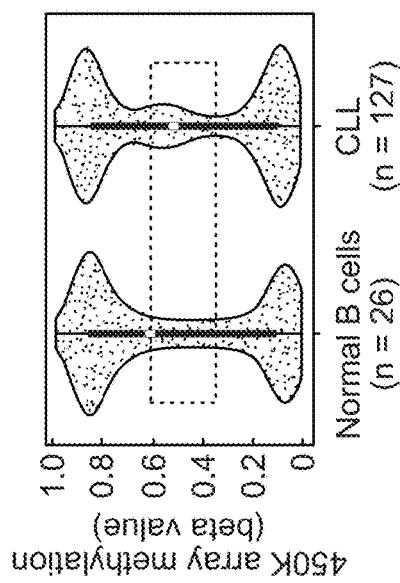
FIG. 4G
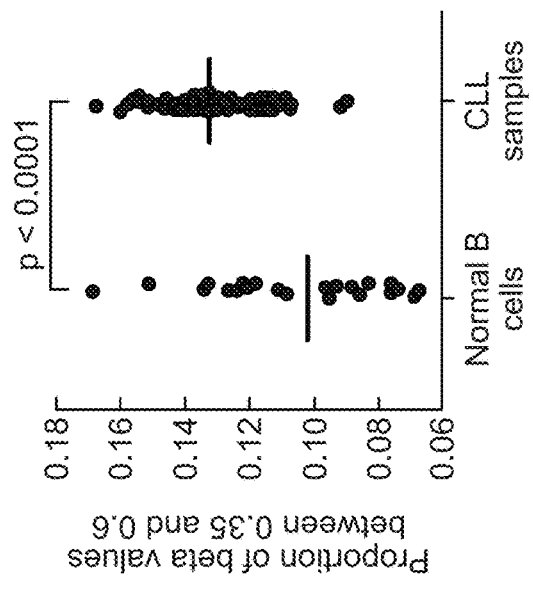
FIG. 4H
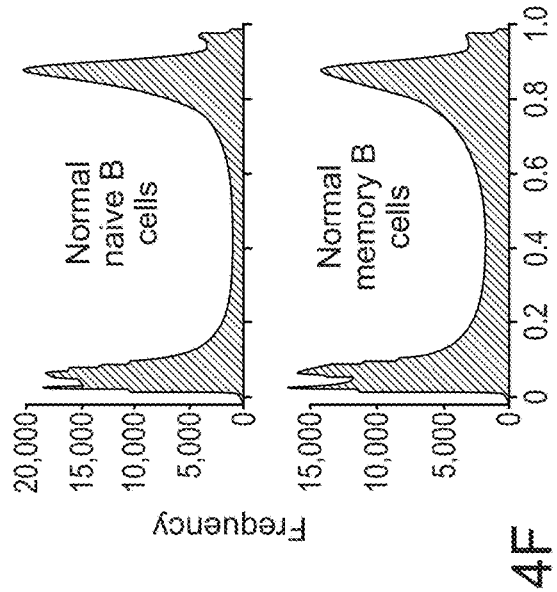
FIG. 4F
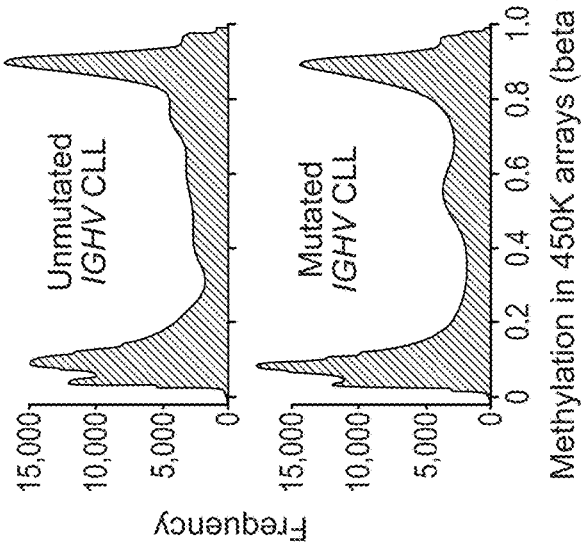

FIG. 5A
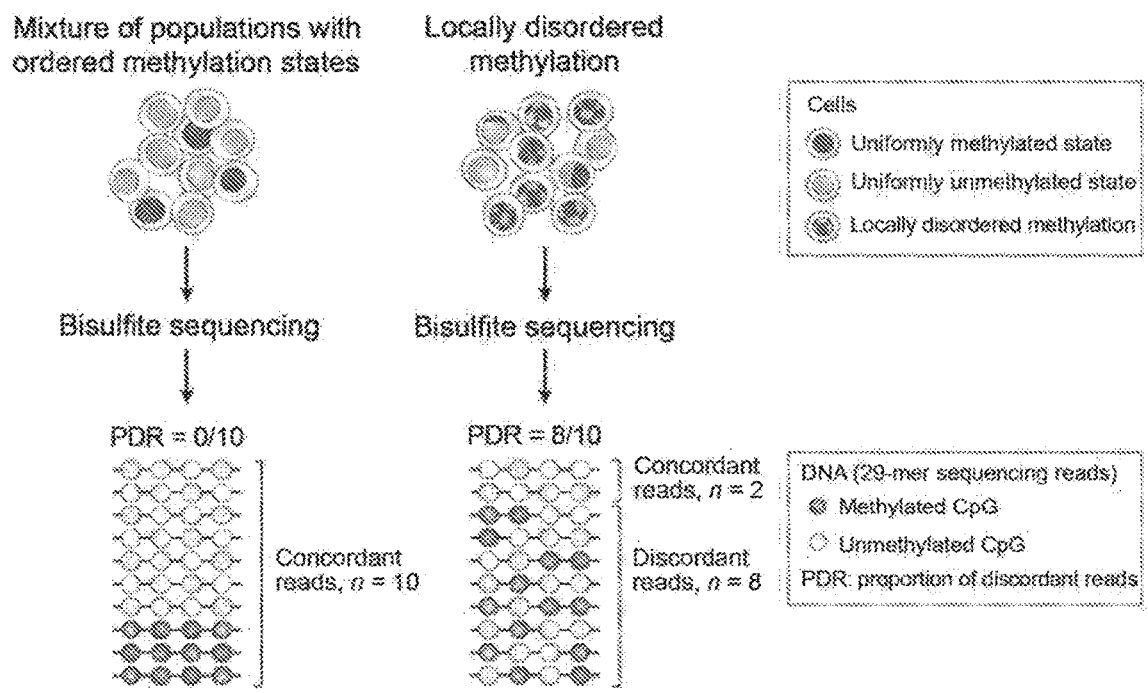
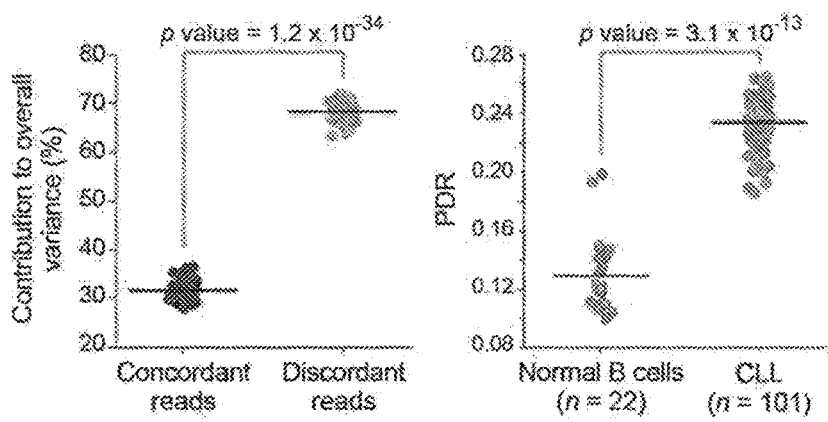
FIG. 5B
FIG. 5C

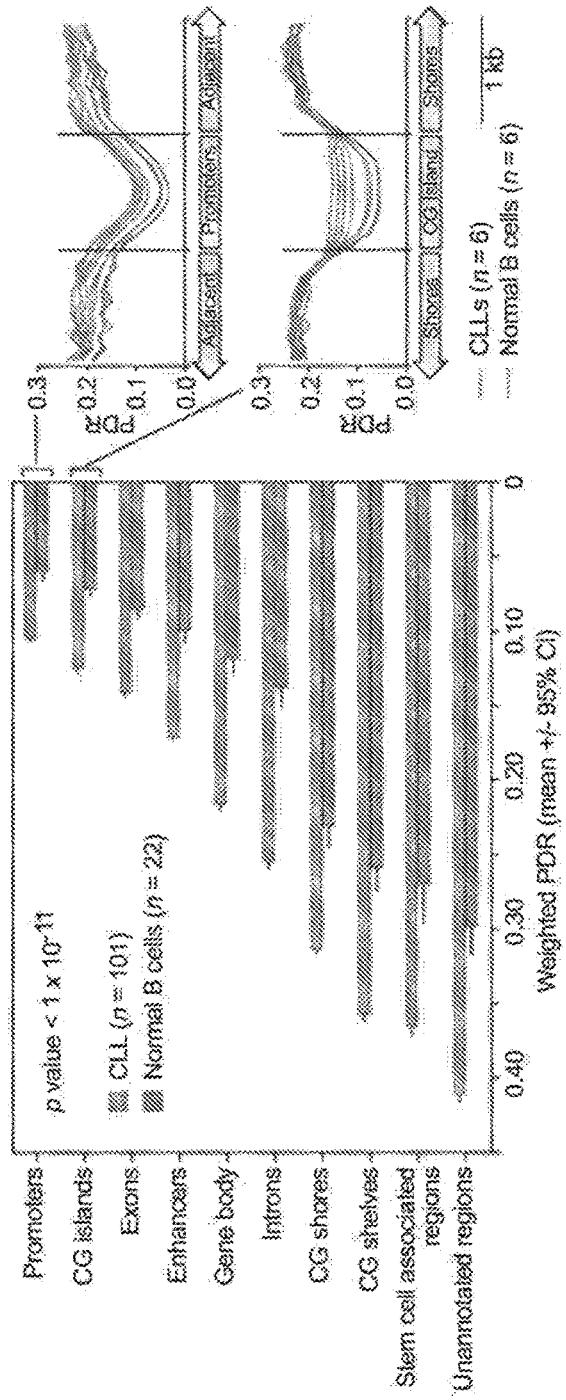
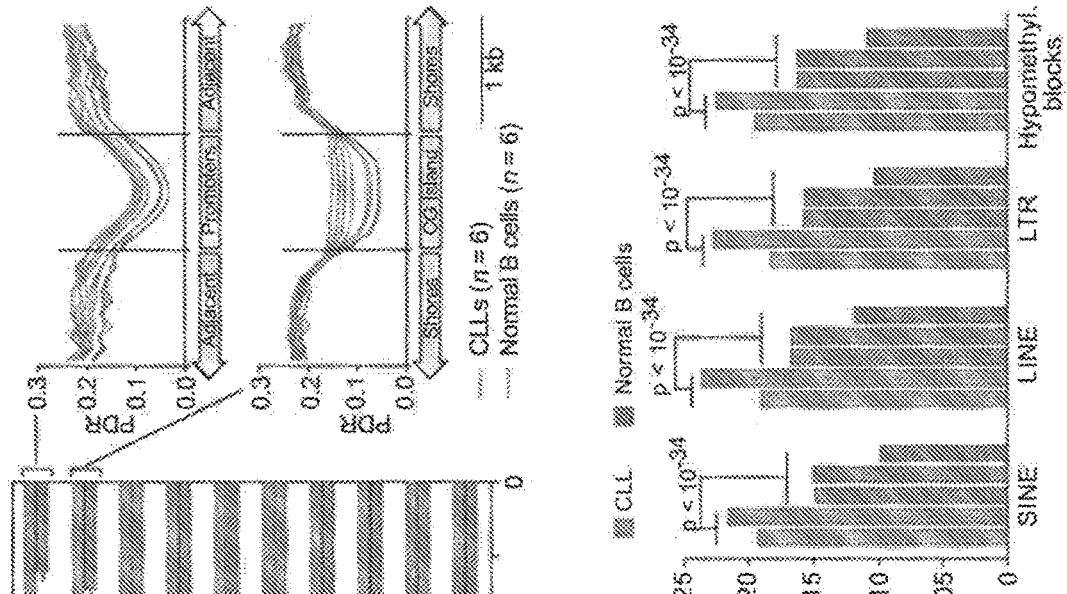
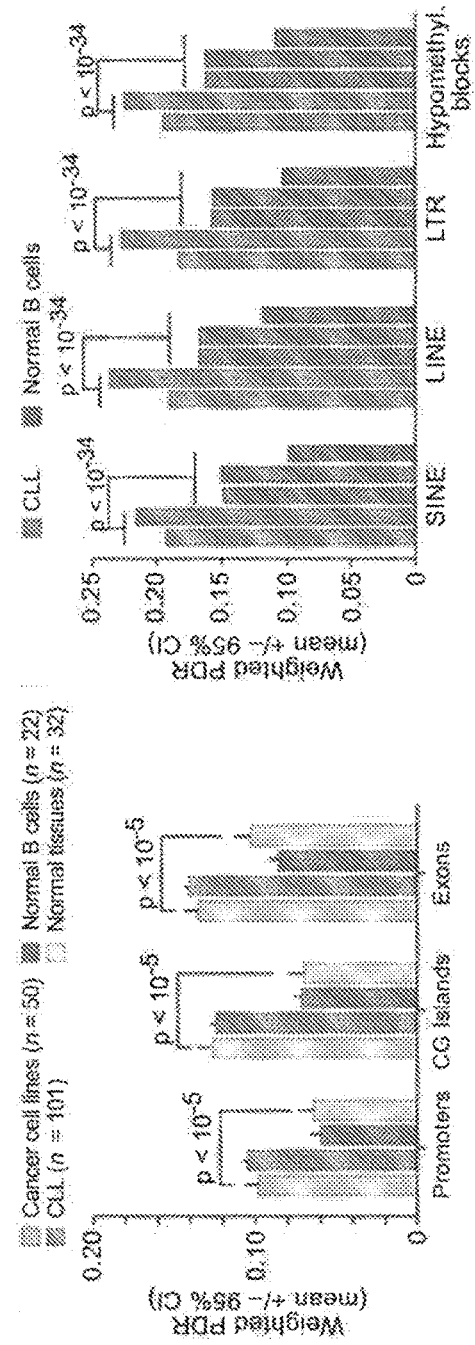
FIG. 6A, FIG. 6B, FIG. 6C, FIG. 6D

FIG. 9E
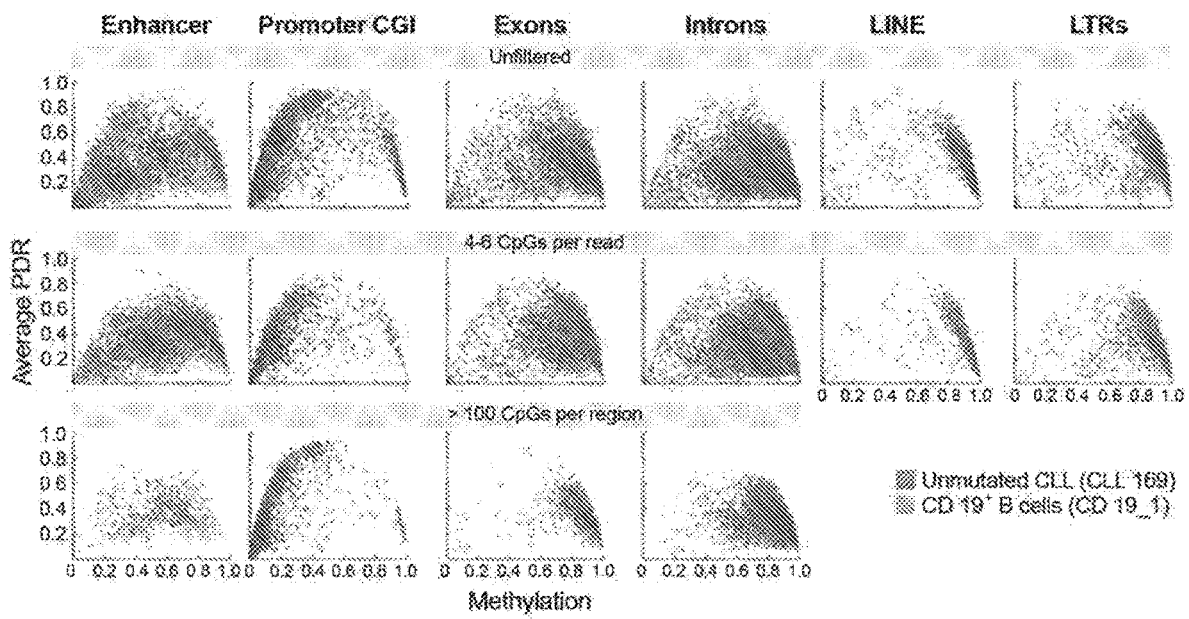
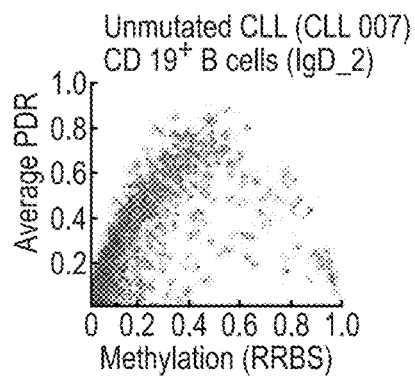
FIG. 9F
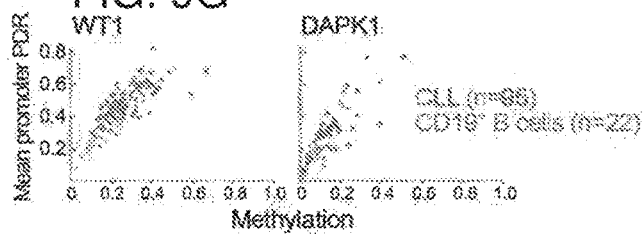
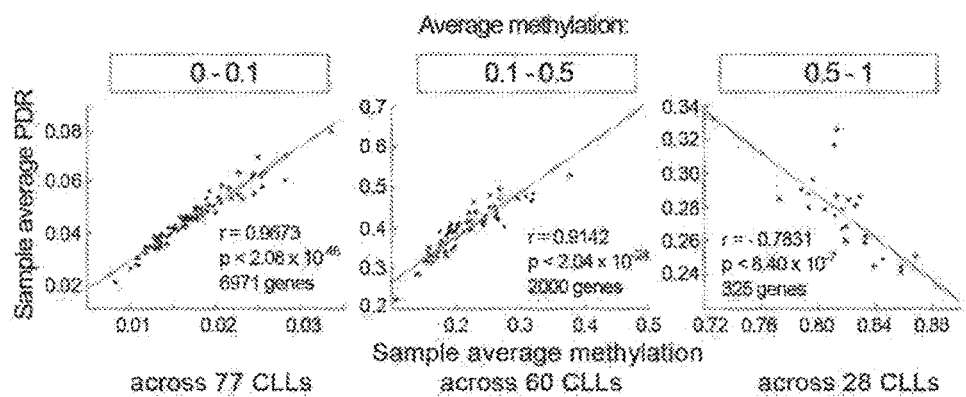
FIG. 9H

FIG. 11A
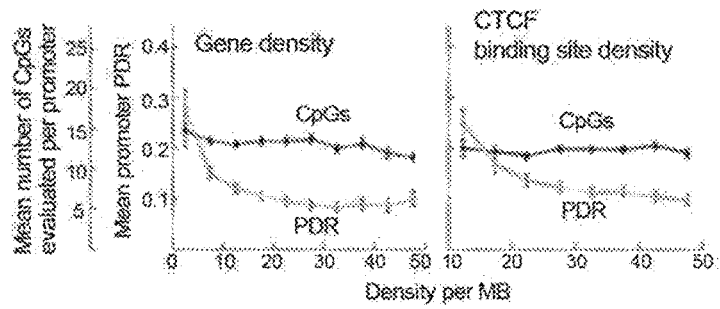
FIG. 11C
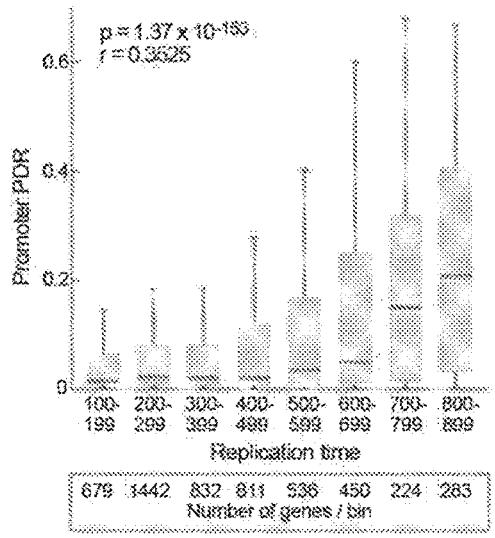
FIG. 11B
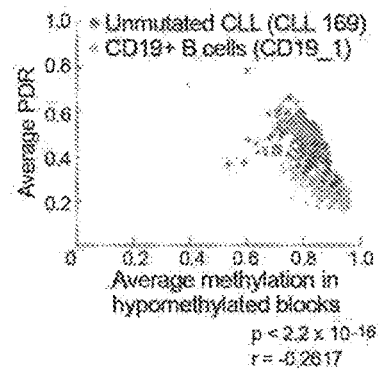
FIG. 11D
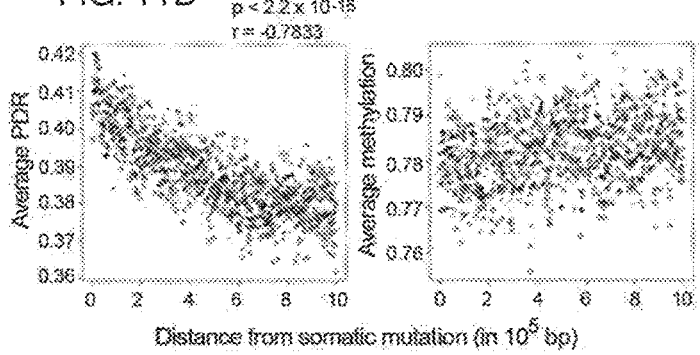
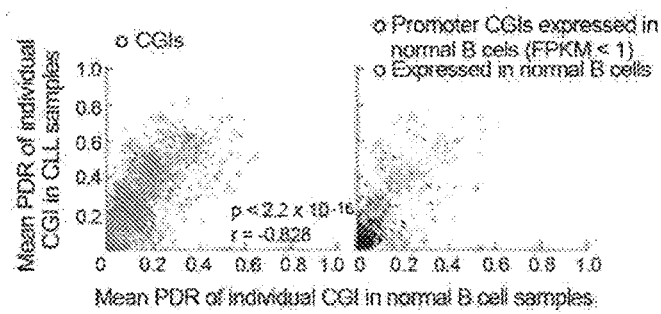
FIG. 11E FIG. 12A
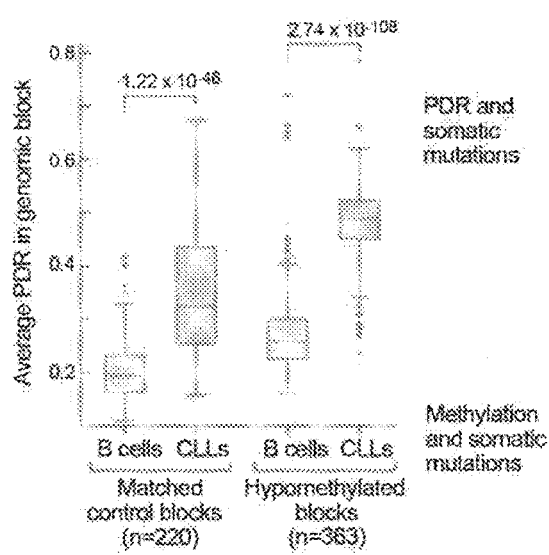
FIG. 12B
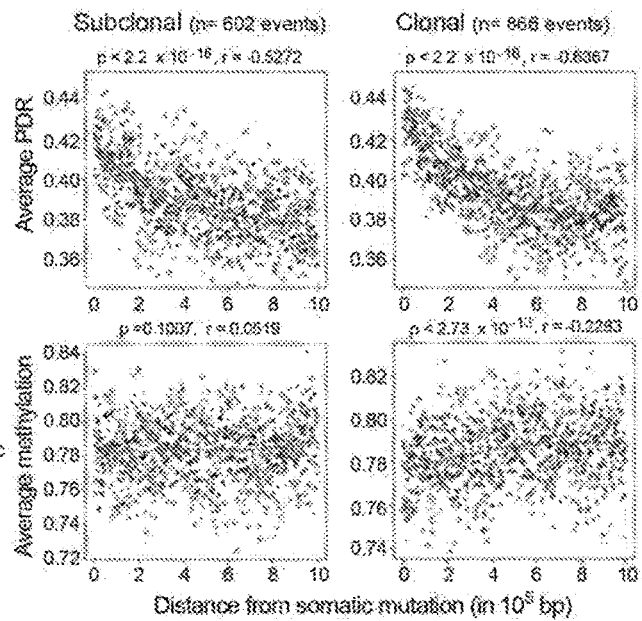
FIG. 12C
FIG. 13A
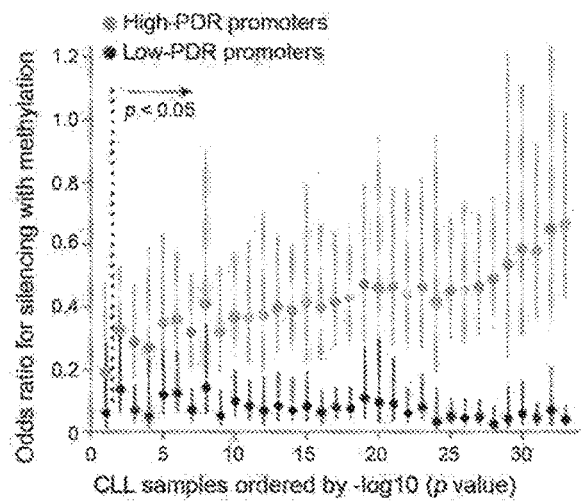
FIG. 13B
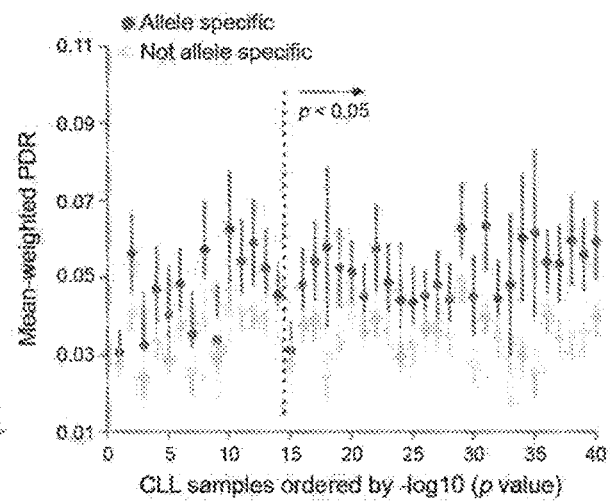
FIG. 14A
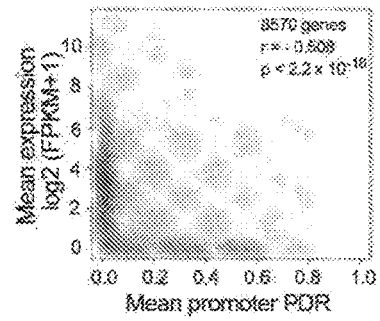
FIG. 14B
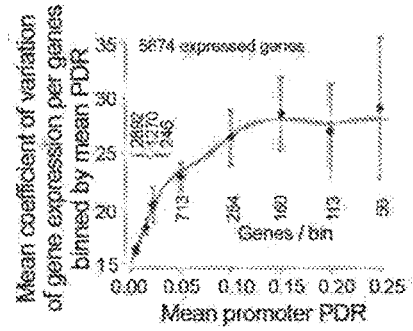

FIG. 18A
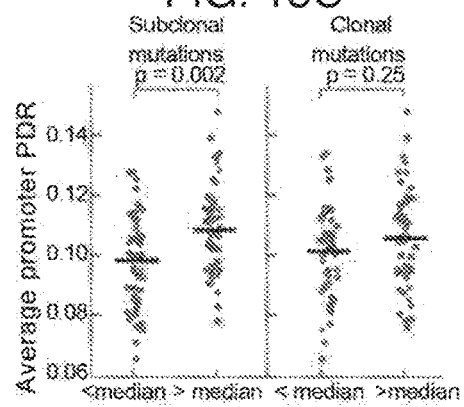
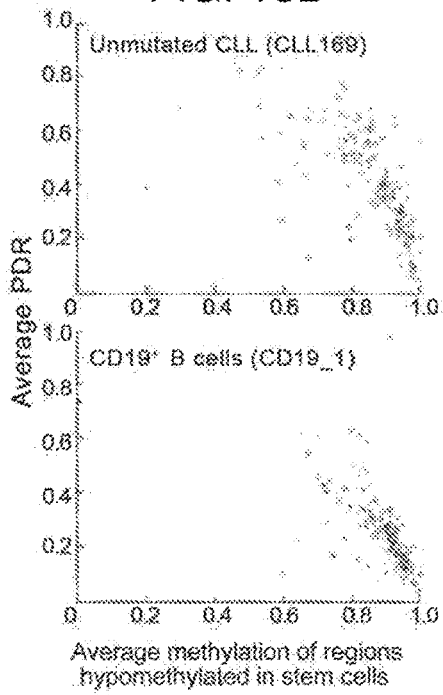
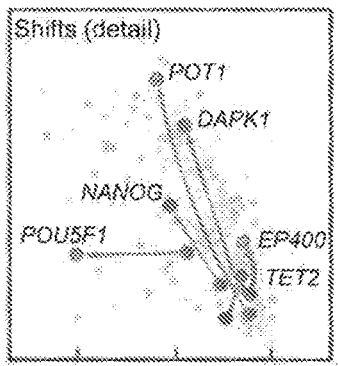
FIG. 18B
FIG. 18C
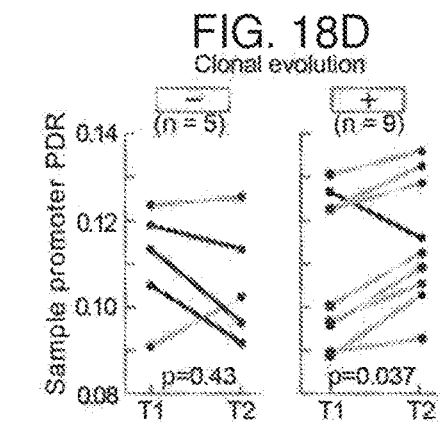
FIG. 18D
FIG. 18E FIG. 19A
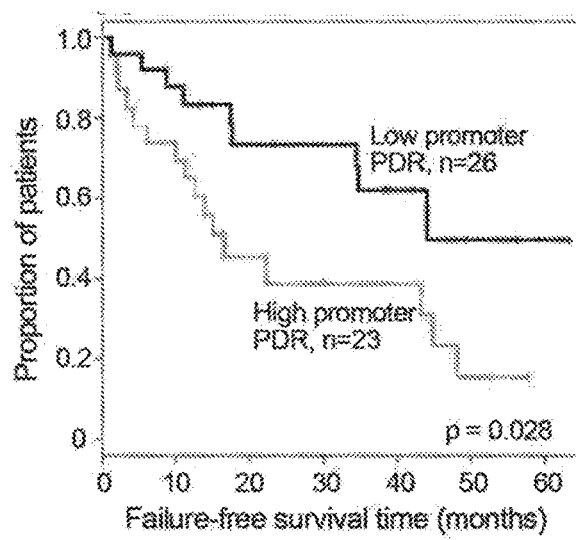
FIG. 19B
FIG. 20A
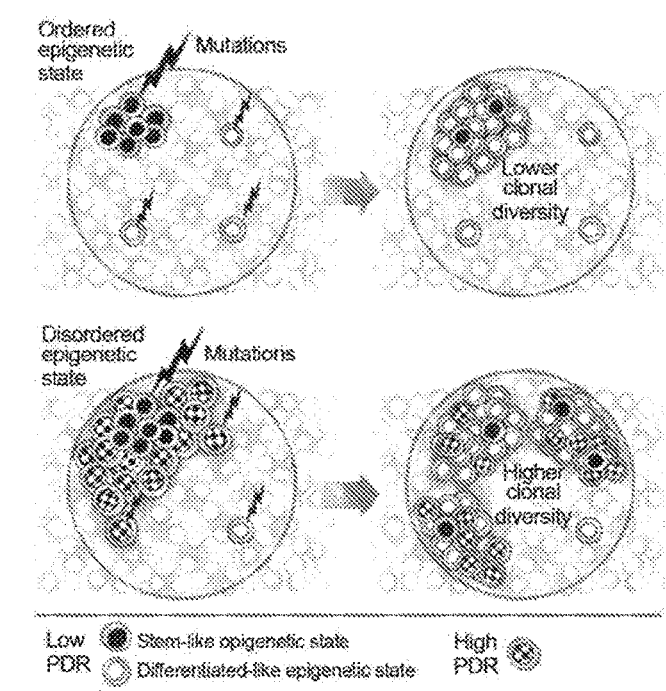
FIG. 20B
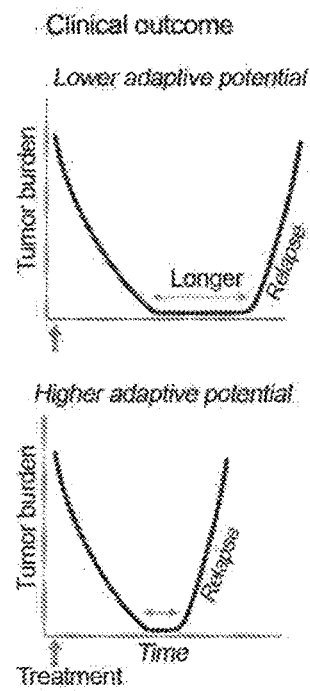

COMPOSITIONS AND METHODS FOR DIAGNOSING, EVALUATING AND TREATING CANCER BY MEANS OF THE DNA METHYLATION STATUS

RELATED APPLICATIONS AND INCORPORATION BY REFERENCE

This application is a Division application of U.S. application Ser. No. 15/038,504, filed on May 23, 2016, now allowed, which is a national stage filing under 35 U.S.C. § 371 of PCT/US14/67146, filed Nov. 24, 2014, which claims benefit of and priority to U.S. provisional patent application Ser. No. 61/908,316, filed Nov. 25, 2013. The entire contents of these applications are incorporated herein by reference in their entirety.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to methods for diagnosing, evaluating and treating cancer.

BACKGROUND OF THE INVENTION

In recent years, multiple effective treatment modalities for cancer have been introduced. Nevertheless, in many cases, despite striking initial responses, the malignant process evolves and adapts to the therapy, leading to disease recurrence. Therefore, an important barrier to curative cancer therapy is the plasticity of cancer, its ability to adapt to treatment. Chronic lymphocytic leukemia (CLL) constitutes an informative case study to dissect this phenomenon. Despite highly effective therapies, this common leukemia remains incurable. For example, chemoimmunotherapy with fludarabine, cyclophosphamide and rituximab (FCR) leads to a 44% complete response rate, yet the disease invariably recurs, often after evolving to a more aggressive and treatment-refractory form.

Cancer subpopulations compete and mold the malignant genetic landscape to yield adaptation to therapy. In CLL, the presence of co-existing cell subpopulations, distinguished on the basis of genetic differences, was first demonstrated using cytogenetic technologies and SNP arrays. Recently, massively parallel sequencing (MPS) has allowed genetic heterogeneity to be studied in CLL at an unprecedented resolution. Such studies demonstrated that evolution in response to therapy is the rule rather than the exception. Using this approach, a clear impact of pre-treatment heterogeneity on the rapidity of clonal evolution and the overall clinical outcome has been shown.

Genome-wide methylation assays, such as arrays and MPS with bisulfite conversion, have revealed that aberrant DNA methylation, in addition to dysregulated genes and pathways, is involved in CLL pathogenesis. In CLL and other cancers it has been previously reported that there is a global decrease in DNA methylation and an increase in methylation specifically at CpG islands (CGI) (Baylin and Jones, 2011; Kulis et al., 2012). Specifically, it has been thought that in a normal cell the CpG islands are completely unmethylated at the CpG sites within a CpG island and when the cell becomes a tumor cell the CpG island becomes completely methylated at every CpG. Moreover, CpG islands, which are normally located near the promoters of genes and contain a higher than expected CG content, are normally kept hypomethylated. Presumably, this is to create an active euchromatin environment as well as preventing C to T mutations caused by deamination of methylated cytosine. In an unmethylated state cytosine is converted to uracil after deamination, which is recognized by the cell's repair machinery and is removed, while in a methylated state deamination of cytosine results in the formation of thymine which is not recognized by the repair machinery. Therefore, the presence or absence of hypermethylation at these CpG islands can be used to detect tumor cells. As cancer cells are constantly evolving to avoid treatment regimens, there is a need for a method to not only detect a tumor cell, but to detect tumor cell plasticity. Determining plasticity of a tumor can allow a personalized treatment for a patient in need thereof.

Methylation profiles were also shown to have independent prognostic value in CLL. Like genetic alterations, DNA methylation modifications are heritable and therefore subject to natural selection in cancer. Furthermore, genetically uniform cell subpopulations can contain profound epigenetic differences leading to phenotypic differences in their survival capacity and proliferative potential. Together, these observations suggest that an integrative model of cancer evolution is warranted, which accounts for both epigenetic heterogeneity of genetically uniform subpopulations, and genetic heterogeneity of epigenetically uniform subpopulations.

Citation or identification of any document in this application is not an admission that such document is available as prior art to the present invention.

SUMMARY OF THE INVENTION

A first aspect of the present invention provides a method of assessing a subject's tumor plasticity or the ability to acquire treatment resistance mutations. In another embodiment the method assesses a subject's cancer treatment prognosis. In some embodiments, the method comprises detecting DNA methylation status at one or more regions of neighboring CpG sites in a plurality of cells in a tumor sample from the subject; comparing the DNA methylation status of neighboring CpG sites along a sequence of CpG sites in DNA of the plurality of cells and/or comparing the DNA methylation status of corresponding CpG sites across multiple gene copies in the plurality of cells; and assessing the consistency of methylation status along the sequences of neighboring CpG sites and/or across multiple gene copies in the plurality of cells. In one embodiment there are at least 2 neighboring CpG sites. In another embodiment there are at least 3, or 4, or 5, or 6, or 7, or 8, or 9, or 10 neighboring CpG sites, preferably greater than 4. Consistency can mean that all of the neighboring CpG sites along a sequence of CpG sites in DNA or CpG sites across multiple gene copies are methylated or all of the neighboring CpG sites along a sequence of CpG sites in DNA are unmethylated. It may mean that greater than 50%, or 60% or 70%, or 75%, or 80%, or 85%, or 90%, or 95% of the CpG's are methylated or unmethylated. Inconsistency can mean that any sequence of neighboring CpG sites or CpG sites across multiple gene copies contain at least one methylated and at least one unmethylated CpG site. The presence or prevalence of inconsistent methylation status along the sequences or across the multiple gene copies may indicate that the subject is more likely to (1) develop resistance to an antitumor agent; (2) relapse after treatment with an antitumor agent; (3) develop a metastatic tumor; or (4) any combination thereof. For example, the DNA methylation status of CpG sites along one or more sequencing reads, e.g., operatively linked to each other in a single polynucleotide molecule, may be detected. The neighboring CpG sites along the sequencing read may then be compared to each other or to corresponding positions of different sequencing reads (e.g., at the same genomic location) from the plurality of cells.

The DNA methylation may be detected by methylation-specific PCR, whole genome bisulfite sequence, the HELP assay, ChIP-on-chip assays, restriction landmark genomic scanning, methylated DNA immunoprecipitation, pyrosequencing of bisulfite treated DNA, molecular break light assay for DNA adenine methyltransferase activity, methyl sensitive Southern blotting, methylCpG binding proteins, and reduced representation bisulfite sequencing. In some embodiments, the DNA methylation is detected in a methylation assay utilizing next-generation sequencing. For example, DNA methylation may be detected by massive parallel sequencing with bisulfite conversion. e.g., whole-genome bisulfite sequencing or reduced representation bisulfite sequencing. Optionally, the DNA methylation is detected by microarray, such as a genome-wide microarray.

The methylation status of neighboring CpG sites may be compared by identifying and/or quantifying inconsistently methylated regions, such as by calculating the proportion of discordant reads, calculating variance, calculating epipolymorphism, or calculating information entropy. In some embodiments, a proportion of discordant reads (PDR) is calculated. Optionally, each region of neighboring CpG sites (e.g., within a sequencing read) is assigned a consistent status or an inconsistent status before calculating the proportion of discordant reads, variance, epipolymorphism or information entropy. There may be multiple inconsistent statuses, each representing a distinct methylation pattern or class of similar methylation patterns.

The one or more regions of neighboring CpG sites having a locally disordered methylation status may be in a genomic location selected from a CpG island, a CpG shore, a CpG shelf, a promoter, an enhancer, an exon, an intron, a gene body, a stem cell associated region, a short interspersed element (SINE), a long interspersed element (LINE), and a long terminal repeat (LTR), preferably a CpG island or a promoter.

In some embodiments, the method further comprises detecting a subclonal genetic mutation. Optionally, the subclonal genetic mutation is within the one or more genomic regions having a locally disordered methylation status. A subclonal genetic mutation with the one or more genomic regions having a locally disordered methylation status may indicate that the subject is even more likely to (1) develop resistance to an antitumor agent; (2) relapse after treatment with an antitumor agent; (3) develop a metastatic tumor; or (4) any combination thereof.

The DNA methylation status at the one or more neighboring CpG sites may be detected before treatment with an antitumor agent. Optionally, the DNA methylation status at the one or more neighboring CpG sites is detected after treatment with an antitumor agent. The DNA methylation status at the one or more neighboring CpG sites may be detected both before and after treatment with an antitumor agent. In some embodiments, the DNA methylation status at the one or more neighboring CpG sites is detected throughout a time course of treatment with an antitumor agent. An increase in the number of regions of neighboring CpG sites having a locally disordered methylation status, or the level of inconsistent methylation status in these regions across sequences in a sample, may indicate that the subject is even more likely to (1) develop resistance to an antitumor agent; (2) relapse after treatment with an antitumor agent; (3) develop a metastatic tumor; or (4) any combination thereof.

A second aspect of the present invention provides a method of calculating a proportion of discordant reads (PDR) in a first tumor sample from a subject. In some embodiments, the method comprises detecting DNA methylation status at one or more regions of neighboring CpG sites in a plurality of cells in the tumor sample; comparing the DNA methylation status of sequencing reads in multiple regions of neighboring CpG sites along a sequence of CpG sites in DNA of the plurality of cells; and determining a relative number of cells in the tumor sample having inconsistent methylation status across the sequence of CpG sites as compared to the total number of cells in the tumor sample or a number of cells in the tumor sample having consistent methylation status across the sequence of CpG sites, or determining a level of inconsistent methylation status across the sequence of CpG sites in cells in the tumor sample.

The DNA methylation may be detected by methylation-specific PCR, whole genome bisulfite sequence, the HELP assay and other methods using methylation-sensitive restriction endonucleases, ChIP-on-chip assays, restriction landmark genomic scanning, COBRA, Ms-SNuPE, methylated DNA immunoprecipitation (MeDip), pyrosequencing of bisulfite treated DNA, molecular break light assay for DNA adenine methyltransferase activity, methyl sensitive Southern blotting, methylCpG binding proteins, mass spectrometry, HPLC, and reduced representation bisulfite sequencing. In some embodiments, the DNA methylation is detected in a methylation assay utilizing next-generation sequencing. For example, DNA methylation may be detected by massive parallel sequencing with bisulfite conversion, e.g., whole-genome bisulfite sequencing or reduced representation bisulfite sequencing. Optionally, the DNA methylation is detected by microarray, such as a genome-wide microarray.

The PDR may be calculated before treatment with an antitumor agent. Optionally, the PDR is calculated after treatment with an antitumor agent. The PDR may be calculated both before and after treatment with an antitumor agent. In some embodiments, the PDR is calculated throughout a time course of treatment with an antitumor agent.

In some embodiments, a PDR threshold, such as greater than 0.15, indicates that the patient is more likely to (1) develop resistance to an antitumor agent; (2) relapse after treatment with an antitumor agent; (3) develop a metastatic tumor, or (4) any combination thereof. A PDR threshold, such as less than 0.15, may indicate that the patient is more likely to respond to treatment with an antitumor agent. A change, such as an increase or in some instances a decrease, in PDR following treatment may indicate that the subject is likely to develop resistance to the treatment.

A third aspect of the present invention provides a method of treating a subject suffering from cancer. In some embodiments, the method comprises performing the method of identifying a subject's cancer treatment prognosis described herein and administering an antitumor agent to the subject if no or few inconsistencies in methylation status are identified or b) administering fewer antitumor agents to a subject having a low level of inconsistencies in methylation status and more antitumor agents to a subject having a high level of inconsistencies in methylation status. Optionally, the method comprises ceasing or altering treatment with an antitumor agent, or initiating a non-chemotherapeutic treatment (e.g., surgery or radiation) if a high level of inconsistencies in methylation status is identified.

In another embodiment the treatment is based on the standard of care for a particular cancer. In one embodiment if the standard of care allows a physician to choose between two treatment options, such as surgery or chemotherapy, the addition of detecting plasticity based on DNA methylation discordance can determine the proper option. In another embodiment if the standard of care can be followed using different doses of an antitumor agent DNA methylation discordance may be used to select the proper dose.

In some embodiments, the method comprises, performing a prognostic method as described herein; administering an antitumor agent to the subject; and repeating the prognostic method, wherein the treatment is administered between the initial and subsequent prognostic methods. In some embodiments, the method comprises continuing to treat the subject with the antitumor agent if the level of inconsistent methylation status is substantially the same in the initial and subsequent prognostic methods or lower in the subsequent prognostic method than in the initial prognostic method. In some embodiments, the method comprises ceasing or altering treatment with an antitumor agent, or initiating a non-chemotherapeutic treatment (e.g., surgery or radiation) if the level of inconsistent methylation status is different in the subsequent prognostic method compared to the initial prognostic method. The antitumor agent may be administered to the subject for at least 3 months, at least 6, months, at least 9 months, at least 12 months, at least 24 months, or at least 36 months before performance of the second prognostic method, preferably at least 12 months.

The methylation status of neighboring CpG sites may be compared by calculating the proportion of discordant reads, calculating variance, calculating epipolymorphism, or calculating information entropy.

The method of treatment may further comprise detecting a genetic mutation. The genetic mutation may be a clonal mutation or a subclonal mutation, preferably a subclonal mutation. In some embodiments, the method comprises treating or continuing to treat the subject with the antitumor agent if no region of neighboring CpG sites having locally disordered methylation status also comprises a genetic mutation, such as a subclonal mutation. Optionally, the method comprises ceasing or altering treatment with an antitumor agent, or initiating a non-chemotherapeutic treatment (e.g., surgery or radiation) if one or more regions of neighboring CpG sites having locally disordered methylation status also comprises a genetic mutation, such as a subclonal mutation.

In some embodiments, the method comprises determining the genomic location of the one or more regions of neighboring CpG sites having locally disordered methylation status. The genomic location may be selected from a CpG island, a CpG shore, a CpG shelf, a promoter, an enhancer, an exon, an intron, a gene body, a stem cell associated region, a short interspersed element (SINE), a long interspersed element (LINE), and a long terminal repeat (LTR), preferably a CpG island or a promoter. Optionally, the method comprises ceasing or altering treatment with an antitumor agent, or initiating a non-chemotherapeutic treatment (e.g., surgery or radiation) if one or more regions of neighboring CpG's having locally disordered methylation status is located in a CpG island, a promoter or an exon. The method may comprise treating or continuing to treat the subject with the antitumor agent if no or few regions of neighboring CpG sites having locally disordered methylation status are within a CpG island, a promoter, or an exon.

In some embodiments, the method of treatment comprises calculating a PDR from a tumor sample in a subject as described herein, and administering an antitumor agent to the subject if the PDR is less than a PDR threshold, such as 0.15. Optionally, the method comprises ceasing or altering treatment with an antitumor agent, or initiating a non-chemotherapeutic treatment (e.g., surgery or radiation) if the PDR is greater than a PDR threshold, such as 0.15.

In some embodiments, the method of treatment comprises calculating a PDR from a sample of cells shed from a tumor in a subject as described herein, and administering an antitumor agent to the subject if the PDR is less than a PDR threshold, such as 0.15. The shed cells can be collected from the colon, from the bladder, from the kidney's, from the prostate, or from the lungs. The shed cells could be in the urine, sputum, semen, or stool. In one embodiment, the PDR may determine that a lung, or bladder, or kidney, or colon, or prostate should be removed. In one aspect, removal is based on the plasticity of the tumor cells as determined by the PDR. In one aspect the plasticity indicates that the tumor may become invasive. In another aspect, determining the PDR allows the tumor to be removed before it becomes invasive. Optionally, the method comprises ceasing or altering treatment with an antitumor agent, or initiating a non-chemotherapeutic treatment (e.g., surgery or radiation) if the PDR is greater than a PDR threshold, such as 0.15.

In some embodiments, the method of treatment comprises calculating a first PDR from a first tumor sample obtained from the subject according to the methods described herein; treating the subject with an antitumor agent; and calculating a second PDR from a second tumor sample obtained from the subject according to the methods described herein. The method may comprise continuing to treat the subject with the antitumor agent if the second PDR is substantially the same as the first PDR. Optionally, the method comprises ceasing or altering treatment with an antitumor agent, or initiating a non-chemotherapeutic treatment (e.g., surgery or radiation) if the second PDR is different than the first PDR. The first and second tumor sample may be from the same tumor. The first and second tumor sample may be from a first tumor sample that was treated such that no further tumor was detectable and the second tumor is from a relapse tumor or a tumor from a cancer that was in remission.

The subject may be treated with the antitumor agent for at least 3 months, at least 6 months, at least 9 months, at least 12 months, at least 24 months or at least 36 months before calculating the second PDR, preferably at least 12 months.

A fourth aspect of the present invention provides a method for identifying an antitumor agent that decreases the potential evolutionary capacity of cancer and, thus, the risk of relapse. In some embodiments the antitumor agent targets epigenetic proteins. In another embodiment the antitumor agent targets the DNA methylation machinery of the cell. In another embodiment the antitumor agent causes reprogramming of the DNA methylation within a cell. In another embodiment, the antitumor agent preferentially kills cells with a high potential evolutionary capacity as determined by calculating a PDR.

In some embodiments, the method comprises growing a first culture of hyperproliferative cells and a second culture of hyperproliferative cells, wherein the first culture is grown in the presence of an antitumor agent and the second culture is grown in the absence of the antitumor agent; detecting DNA methylation status at one or more regions of neighboring CpG sites in a plurality of cells from the first culture and a plurality of cells from the second culture; comparing the DNA methylation status of neighboring CpG sites along one or more sequences of neighboring CpG sites in DNA of the plurality of cells and/or comparing the DNA methylation status of corresponding CpG sites across multiple gene copies in the plurality of cells of the first culture; comparing the DNA methylation status of neighboring CpG sites along one or more sequences of neighboring CpG sites in DNA of the plurality of cells and/or comparing the DNA methylation status of corresponding CpG sites across multiple gene copies in the plurality of cells of the second culture; and assessing the consistency of methylation status along the sequences of neighboring CpG sites and/or across multiple gene copies in the plurality of cells.

In some embodiments, the method comprises treating an animal model of a cancer, wherein a first animal is treated with an antitumor agent and the second animal is treated with a placebo or no antitumor agent; detecting DNA methylation status at one or more regions of neighboring CpG sites in a plurality of cells from the first animal and a plurality of cells from the second animal; comparing the DNA methylation status of neighboring CpG sites along one or more sequences of neighboring CpG sites in DNA of the plurality of cells and/or comparing the DNA methylation status of corresponding CpG sites across multiple gene copies in the plurality of cells of the first animal; comparing the DNA methylation status of neighboring CpG sites along one or more sequences of neighboring CpG sites in DNA of the plurality of cells and/or comparing the DNA methylation status of corresponding CpG sites across multiple gene copies in the plurality of cells of the second animal; and assessing the consistency of methylation status along the sequences of neighboring CpG sites and/or across multiple gene copies in the plurality of cells. The antitumor agent decreases the potential evolutionary capacity of cancer if the level of inconsistent methylation status is less in the first animal than in the second animal. In another embodiment the antitumor agent is administered to more than one cell or animal model using a range of doses.

The methylation status of neighboring CpG sites may be compared by calculating the proportion of discordant reads, calculating variance, calculating epipolymorphism, or calculating information entropy. In some embodiments, the method comprises calculating a PDR, variance, epipolymorphism or information entropy in the first and second culture, wherein the antitumor agent decreases the potential evolutionary capacity of cancer if the PDR, variance, epipolymorphism or information entropy of the first culture is less than the PDR, variance, epipolymorphism or information entropy of the second culture.

The hyperproliferative cells in the first and second cultures may comprise cells from a cell line, e.g., a tumor cell line. Alternatively, the hyperproliferative cells in the first and second cultures may be cells from a tumor sample obtained from a subject, preferably a human, or cells cultured from such a sample. In some embodiments, the first and second cultures are the same culture, wherein the second culture is a sample of the hyperproliferative cells before addition of the antitumor agent and the first culture is a sample of the hyperproliferative cells after addition of the antitumor agent.

The animal model may be a model of any cancer. The animal model may be a mammal, more specifically a rodent, preferably a rat, and more preferably a mouse.

The first culture may be cultured in the presence of the antitumor agent for at least 6 hours, at least 12 hours, at least 18 hours, at least one day, at least two days, at least three days, at least four days, at least five days, at least six days or at least one week, preferably at least one day, prior to detecting methylation status.

The first animal may be treated with the antitumor agent for at least one day, one week, a month, 12 month's, 18 month's, 2 years, preferably at least one day, prior to detecting methylation status.

In some embodiments, the method comprises performing a first prognostic method on a first tumor sample from a subject, such as a laboratory animal, as described herein; administering an antitumor agent to the subject; and performing a second prognostic method on a second tumor sample form the subject as described herein, wherein the treatment is administered between the first and second prognostic methods. The antitumor agent decreases the potential evolutionary capacity of cancer if the level of inconsistent methylation status is less in the second tumor sample than in the first tumor sample.

The methylation status of neighboring CpG sites may be compared by calculating the proportion of discordant reads, calculating variance, calculating epipolymorphism, or calculating information entropy. In some embodiments, the method comprises calculating a first PDR, variance, epipolymorphism or information entropy from a first tumor sample obtained from the subject, such as a laboratory animal, according to the methods described herein; treating the subject with an antitumor agent; and calculating a second PDR, variance, epipolymorphism or information entropy from a second tumor sample obtained from the subject according to the methods described herein. The antitumor agent decreases the potential evolutionary capacity of cancer if the second PDR, variance, epipolymorphism or information entropy is less than the first PDR, variance, epipolymorphism or information entropy.

The antitumor agent may be administered to the subject for at least one day, at least two days, at least three days, at least 4 days, at least five days, at least six days, at least one week, at least two weeks, at least three weeks, at least one month, preferably at least one week.

In any of the methods described herein, the tumor sample may be a solid tumor, such as carcinomas, sarcomas and lymphomas. In some embodiments, the solid tumor is selected from adrenocortical carcinoma, bone tumors, brain cancer, breast cancer, cervical cancer, colorectal carcinoma, desmoid tumors, desmoplastic small round cell tumors, endocrine tumors, esophageal cancer, Ewing sarcoma family tumors, gastric cancer, germ cell tumors, head or neck cancer, hepatoblastoma, hepatocellular carcinoma, lung cancer, melanoma, mesothelioma, nasopharyngeal carcinoma, neuroblastoma, non-rhabdomyosarcoma soft tissue sarcoma, osteosarcoma, ovarian cancer, pancreatic cancer, prostate cancer, retinoblastoma, rhabdomyosarcoma, skin carcinoma, testicular cancer, thyroid carcinoma, uterine cancer and Wilms tumors. The tumor sample may be a hematological cancer, such as leukemia, preferably CLL.

In any of the methods described herein, the antitumor agent may be selected from an angiogenesis inhibitor, such as angiostatin K1-3, DL-α-Difluoromethyl-ornithine, endostatin, fumagillin, genistein, minocycline, staurosporine, and thalidomide; a DNA intercaltor/cross-linker, such as Bleomycin, Carboplatin, Carmustine, Chlorambucil, Cyclophosphamide, cis-Diammineplatinum(II) dichloride (Cisplatin), Melphalan, Mitoxantrone, and Oxaliplatin; a DNA synthesis inhibitor, such as (±)-Amethopterin (Methotrexate), 3-Amino-1,2,4-benzotriazine 1,4-dioxide, Aminopterin, Cytosine β-D-arabinofuranoside, 5-Fluoro-5'-deoxyuridine, 5-Fluorouracil, Ganciclovir, Hydroxyurea, and Mitomycin C; a DNA-RNA transcription regulator, such as Actinomycin D, Daunorubicin, Doxorubicin, Homoharringtonine, and Idarubicin; an enzyme inhibitor, such as S(+)-Camptothecin, Curcumin, (−)-Deguelin, 5,6-Dichlorobenzimidazole 1-R-D-ribofuranoside, Etoposide, Formestane, Fostriecin, Hispidin, 2-Imino-1-imidazoli-dineacetic acid (Cyclocreatine), Mevinolin, Trichostatin A, Tyrphostin AG 34, and Tyrphostin AG 879; a gene regulator, such as 5-Aza-2'-deoxycytidine, 5-Azacytidine, Cholecalciferol (Vitamin D3), 4-Hydroxytamoxifen, Melatonin, Mifepristone, Raloxifene, all trans-Retinal (Vitamin A aldehyde), Retinoic acid, all trans (Vitamin A acid), 9-cis-Retinoic Acid, 13-cis-Retinoic acid, Retinol (Vitamin A), Tamoxifen, and Troglitazone; a microtubule inhibitor, such as Colchicine, docetaxel, Dolastatin 15, Nocodazole, Paclitaxel, Podophyllotoxin, Rhizoxin, Vinblastine, Vincristine, Vindesine, and Vinorelbine (Navelbine); and an unclassified antitumor agent, such as 17-(Allylamino)-17-demethoxygeldanamycin, 4-Amino-1,8-naphthalimide, Apigenin, Brefeldin A. Cimetidine, Dichloromethylene-diphosphonic acid, Leuprolide (Leuprorelin), Luteinizing Hormone-Releasing Hormone, Pifithrin-α, Rapamycin, Sex hormone-binding globulin, Thapsigargin, and Urinary trypsin inhibitor fragment (Bikunin). The antitumor agent may be a monoclonal antibody such as rituximab (Rituxan®), alemtuzumab (Campath®), Ipilimumab (Yervoy®), Bevacizumab (Avastin®), Cetuximab (Erbitux®), panitumumab (Vectibix®), and trastuzumab (Herceptin®), Vemurafenib (Zelboraf®) imatinib mesylate (Gleevec®), erlotinib (Tarceva®), gefitinib (Iressa®), Vismodegib (Erivedge™), 90Y-ibritumomab tiuxetan, 131I-tositumomab, ado-trastuzumab emtansine, lapatinib (Tykerb®), pertuzumab (Perjeta™), ado-trastuzumab emtansine (Kadcyla®), regorafenib (Stivarga®), sunitinib (Sutent®), Denosumab (Xgeva®), sorafenib (Nexavar®), pazopanib (Votrient®), axitinib (Inlyta®), dasatinib (Sprycel®), nilotinib (Tasigna®), bosutinib (Bosulif®), ofatumumab (Arzerra®), obinutuzumab (Gazyva™), ibrutinib (Imbruvica™), idelalisib (Zydelig®), crizotinib (Xalkori®), erlotinib (Tarceva®), afatinib dimaleate (Gilotrif®), ceritinib (LDK378/Zykadia), Tositumomab and 131I-tositumomab (Bexxar®), ibritumomab tiuxetan (Zevalin®), brentuximab vedotin (Adcetris®), bortezomib (Velcade®), siltuximab (Sylvant™), trametinib (Mekinist®), dabrafenib (Tafinlar®), pembrolizumab (Keytruda®)), carfilzomib (Kyprolis®), Ramucirumab (Cyramza™), Cabozantinib (Cometriq™), vandetanib (Caprelsa®), Optionally, the antitumor agent is a neoantigen. The antitumor agent may be a neoantigen. Neoantigens are tumor-associated peptides that serve as active pharmaceutical ingredients of vaccine compositions which stimulate antitumor responses and are described in US 2011-0293637, which is incorporated by reference herein in its entirety. The antitumor agent may be a cytokine such as interferons (INFs), interleukins (ILs), or hematopoietic growth factors. The antitumor agent may be INF-α, IL-2, Aldesleukin IL-2, Erythropoietin, Granulocyte-macrophage colony-stimulating factor (GM-CSF) or granulocyte colony-stimulating factor. The antitumor agent may be a targeted therapy such as toremifene (Fareston®), fulvestrant (Falodex®), anastrozole (Arimidex®), exemestane (Aromasin®), letrozole (Femara®), ziv-aflibercept (Zaltrap®), Alitretinoin (Panretin®), temsirolimus (Torisel®), Tretinoin (Vesanoid®), denileukin diftitox (Ontak®), vorinostat (Zolinza®), romidepsin (Istodax®), bexarotene (Targretin®), pralatrexate (Folotyn®), lenaliomide (Revlimid®), belinostat (Beleodaq™), lenaliomide (Revlimid®), pomalidomide (Pomalyst®), Cabazitaxel (Jevtana®), enzalutamide (Xtandi®), abiraterone acetate (Zytiga®), radium 223 chloride (Xofigo®), or everolimus (Afinitor®). The antitumor agent may be a checkpoint inhibitor such as an inhibitor of the programmed death-1 (PD-1) pathway, for example an anti-PD1 antibody (Nivolumab). The inhibitor may be an anti-cytotoxic T-lymphocyte-associated antigen (CTLA-4) antibody. The inhibitor may target another member of the CD28 CTLA4 Ig superfamily such as BTLA, LAG3, ICOS, PDL1 or KIR. A checkpoint inhibitor may target a member of the TNFR superfamily such as CD40, OX40, CD137, GITR, CD27 or TIM-3. Additionally, the antitumor agent may be an epigenetic targeted drug such as HDAC inhibitors, kinase inhibitors, DNA methyltransferase inhibitors, histone demethylase inhibitors, or histone methylation inhibitors. The epigenetic drugs may be Azacitidine (Vidaza), Decitabine (Dacogen), Vorinostat (Zolinza), Romidepsin (Istodax), or Ruxolitinib (Jakafi).

In any of the methods herein, the subject may be a mammal, preferably a human. In some embodiments, the subject may be a laboratory animal, such as a mouse, a rabbit, a rat, a guinea pig, and a hamster. In other embodiments the subject may be a primate or ungulate.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 2A-D demonstrates differential methylation between normal B cells and CLL samples. (A) and (B) 450K methylation arrays showing different distribution in CLL vs. normal B cells, resulting in higher proportion of markers with intermediate methylation state. (C) Higher cumulative distribution of intermediate methylation seen in WGBS of a CLL sample vs. a normal B cell; data generated by Kulis et al. Nat Genet 2012; 44:1236-42. (D) Higher methylation heterogeneity in CLL demonstrated with RRBS.

FIG. 3A-F illustrates that higher DNA methylation intra-sample heterogeneity in CLL arises from locally disordered methylation. A. CLL Global and CGI methylation compared with normal B cells, measured with WGBS (top). Cumulative distribution analysis (bottom) enables the comparison of the proportion of intermediate methylation values in WGBS data of CLL and B cells from healthy adult volunteers. B. Mean intra-sample CpG variance measured with RRBS. C. Methylation patterns from RRBS data of a CLL sample (CLL007), show two patterns of methylation (black circles—methylated CpGs; white circles—unmethylated): (1) A pattern compatible with a mixture of cell populations with clear but distinct methylation states for a particular non-imprinted locus (left-SDHAP3 promoter [chr5: 1594239-1594268]), and (2) a pattern compatible with an admixture of cells with locally disordered methylation (right-PIK3R5 promoter [chr17:8869616-8869640]). D. A comparison between the intra-sample CpG variance that arises from discordant compared with concordant reads across the 104 CLLs. E. CpG methylation and the proportion of discordant reads (PDR) were calculated as shown. F. Sample average PDR for CLL, cancer cell lines, normal B cells and a collection of primary healthy human tissues. To enable an accurate comparison between samples, sample average PDR is calculated based on a consensus set of 63,443 CpGs that are covered with greater than 10 reads in >75% of all 202 RRBS samples.

FIG. 5A-C demonstrates that increased locally disordered DNA methylation is the predominant source of the epigenetic heterogeneity in CLL. (A) Bisulfite MPS distinguishes between two sources of methylation heterogeneity. (B) Most of the overall variance in DNA methylation results from discordant reads. (C) The proportion of discordant reads (PDR) is higher in CLL.

FIG. 6A-D demonstrates the genomic location of locally disordered methylation. (A) Higher PDR affects most genomic features, with unique patterns in CpG islands and promoters, as seen in (B). (C) Similarly increased PDR is seen in cancer cell lines compared with normal human tissues. (D) Increased PDR in repetitive regions shown with WGBS.

FIG. 9A-H illustrates that locally disordered methylation in CLL is consistent with a stochastic process. A. As an additional measure of methylation disorder in individual reads, Applicants calculated Shannon's information entropy (Shannon, 1948) for intra-sample methylation variation. Information entropy was calculated for each read and then averaged across all reads for each CpG as shown. B. Increased average Shannon's information entropy was observed in CLL and cancer cell line samples compared with normal B cells and primary healthy diverse human tissue samples, demonstrating an increase in stochastic methylation variation. C. An increase in information entropy is seen across all measured regions in RRBS data from CLL samples (red) compared with B cells from healthy adult volunteers (blue). Error bars indicate upper 95% CI. Relative increase in average entropy from B cells to CLL samples and p value for Wilcoxon rank sum test are shown. D. Analysis of outlier genes falling outside of the expected distribution of PDR in relation to methylation level. Left panels—Outlier genes (black) were identified by the Tukey method in which promoter CGI PDR was lower then expected given the methylation level. Right panel—the comparative location of selected gene promoters in CLL (red) compared with normal B cells (blue). This plot highlights the considerable CLL hypermethylation without a significant concomitant change in PDR in tumor suppressor genes (WIF1, DCC, DUSP22; solid circles). In contrast, imprinted genes (empty circles, e.g., GNAS) show relative little difference between CLL and normal B cells. E. Scatter plots for methylation and PDR values were generated for a CLL sample (CLL169) and a normal B cell sample (Normal_CD19_1). Values were calculated for each element (enhancers, promoter CGIs, exons, introns, LINE family repeat elements and LTR family repeat elements) as long as at least 20 evaluable CpGs were contained in the specific element, with at least 4 CpG per read and read depth>10 ('unfiltered'). The same data were analyzed with filtering such that only CpGs covered by reads with 4-6 CpGs per read (similar to RRBS data) were examined (second row), or such that a more stringent criteria on the number of evaluable CpGs (>100) per evaluated element was used. Together the plots follow the same distribution of PDR to methylation values suggestive of a stochastic change in methylation (FIG. 3A). F. A scatter plot for methylation and PDR values for promoter CGIs utilizing RRBS data (CLL007 compared with Normal_IGD_2). G. Similar distribution can be seen for the methylation and PDR values of promoter regions of the key tumor suppressor genes DAPK1 and WT1 across CLL samples. H. The strong correlation between average promoter CGI PDR and methylation across 104 CLL samples in shown separately for 3 groups of genes, arranged according to their average methylation values across 104 CLLs (0-0.1, left; 0.1-0.5, center; 0.5-1.0, right).

Figure 1A:
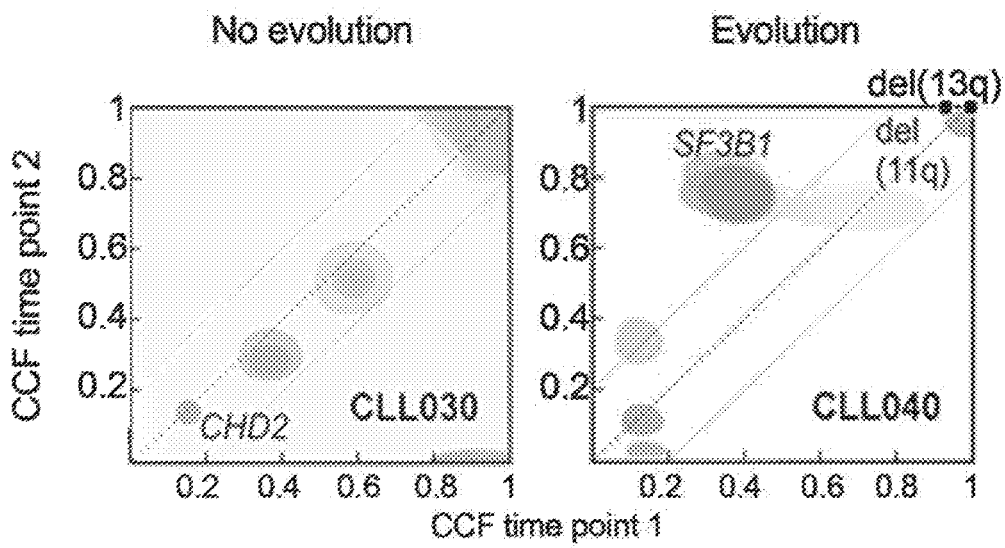
FIG. 1A-B demonstrates the effect of clonal evolution on treatment of CLL. (A) Comparing cancer cell fractions (CCF) at two timepoints can distinguish CLL with and without clonal evolution. (B) Pre-treatment subclonal driver presence is associated with shorter time to retreatment or death.

normal physiological state changes. G. To confirm this finding across the entire dataset, random pairings were performed in each category listed on the X-axis, avoiding repeated use of any individual sample within a category. This procedure was repeated 100 times, and the means of the correlation coefficients for each iteration are plotted and compared.

FIG. 11A-E illustrates that locally disordered methylation affects preferentially gene-poor regions and can be traced back to non-expressed genes in normal B cells. A. Promoter PDR (orange, error bars represent 95% CI of means) in relation to gene density (genes/MB, left) and CTCF binding site density (right) regions. As reference, the CpG content is also provided (black). B. PDR and methylation in hypomethylated blocks (Hansen et al., 2011) is plotted for CLL and normal B cells (shown are blocks with >1,000 CpGs in WGBS). C. Replication time and PDR are correlated; PDR was averaged for each promoter covered in >70% of 104 CLLs, and these values were grouped in replication time bins. D. To assess the relationship between somatic mutations and PDR, sSNVs were identified with whole genome sequencing of matched tumor and germline DNA (CLL169). Average PDR (left) and methylation (right) were measured in 1,000 bp increments from each somatic mutation. Values of CpGs in each 1,000 bp bin were averaged over 4,973 sSNVs, and plotted as a function of the distance from the somatic mutation. Orange lines—the LOWESS (locally weighted scatterplot smoothing). E. Left—promoter CGI PDR is correlated between CLL and normal B cells samples (Pearson, evaluated with 5,811 consistently covered CGIs). Right—Promoter CGI PDR in B cells and CLL % is shown for genes expressed and non-expressed in normal B cells (FPKM<, n=1,002 from RNAseq data of 7 healthy donor B cell samples).

FIG. 12A-C illustrates the association between PDR and distance from somatic mutation is similar for clonal and subclonal mutations. A. To study the specificity of the PDR increase in the previously defined hypomethylated blocks (Hansen et al., 2011), Applicants identified size, GC and repeat content matched regions at random from the genome. Of these regions, Applicants retained only those that harbored more than 1000 CpGs each (covered with greater than 10 reads and 4 or more CpGs per read in the CLL169 and Normal_CD19_1 WGBS data). Compared to the control genomic regions, the hypomethylated blocks exhibit higher PDR in both CLL and normal B cells, as well as a greater increase in CLL compared to the normal B cells. To assess for a relationship between somatic mutations and PDR, somatic single nucleotide variants (sSNVs) were identified with WGS of CLL169 and matched germline DNA. Subsequently, sSNVs with sufficient read depth (>40) were classified as clonal (n=866) or subclonal (n=602) based on the allelic frequency (above or below 0.2, respectively, analysis limited to sSNVs with greater than 40 reads and that do not involve sCNVs to enhance the confidence in the clonal vs. subclonal classification). Average PDR (B) and methylation (C) were measured in 1000 bp increments from each somatic mutation. Values for each 1000 bp bin were averaged over sSNVs, and plotted as a function of the distance from the somatic mutation. Red lines—the LOWESS (locally weighted scatterplot smoothing).

FIG. 13A-B demonstrates that locally disordered methylation contributes to the increase transcriptional variation found to be associated with epigenetic heterogeneity. (A) The likelihood of methylation associated gene silencing is lower in genes with high PDR. (B) Allele-specific expression is associated with higher promoter PDR.

FIG. 14A-F illustrates that locally disordered methylation is associated with transcriptional variation. A. Mean promoter PDR and gene expression are correlated (evaluated with 8,570 genes that had promoter RRBS coverage in >70% of 33 samples with matched RRBS and RNAseq. B. PDR and expression variability as measured with coefficient of variation (CV) of 5,874 transcribed genes (FPKM>1). Black circles (brackets)—mean CV (95% CI) for genes within PDR bins (number of genes per bin in blue). Red line—cubic smoothing spline of CV and PDR values (unbinned). Note that the analysis was limited to transcribed genes to avoid an artificial enhancement of CV that occurs with very low mean expression values. As >97.5% of transcribed genes had PDR<0.3, Applicants limited the X axis to PDR<0.3. C. Left—Odds ratio (bars—95% CI) for gene expression (FPKM>1) with a methylated promoter (average methylation >0.8) versus unmethylated promoter (average methylation <0.2) is calculated for genes with high (orange, 27.5±2.6% of genes) or low promoter PDR (black). Right—Linear models that combine information from all 33 CLLs as continuous variables to predict expression. D. PDR and intra-sample gene expression heterogeneity (assessed by Shannon's information entropy) across the range of population average expression (FPM—fragments per million), by single cell RNA sequencing of 84 cells from CLL005. Local regression lines for genes with low PDR (0-0.05, blue), intermediate PDR (0.05-0.2, purple) and high PDR (0.2-1.0, red) are shown. E. Results of generalized additive regression tests that model single cell gene expression Shannon's information entropy based on PDR, population average expression, and transcript length across the 4 CLL samples. F. Single cell gene expression patterns for genes within a narrow population average expression range of 1.0-1.2 (black rectangle in panel D). Consistent with the higher gene expression Shannon's information entropy observed in genes with higher PDR (top), genes with low PDR (bottom left) tend to be expressed at high magnitude (larger dot size) in fewer cells, while genes with high PDR (bottom right) are frequently expressed at low expression magnitudes across many cells.

FIG. 15A-E illustrates that locally disordered methylation is linked to transcriptional variation. A. Genes were divided into 9 bins according to their mean expression over 33 samples (starting from 0, and then in increments of 1 until 9; log 2[FPKM+1]). PDR is shown for each bin in boxplots, demonstrating that PDR is highest in genes with low expression values (bottom). The number of genes in each expression bin is shown (top). B. Density scatter plot of mean promoter methylation in relation to mean expression (log 2(FPKM+1)), showing that these features are negatively correlated. 8,570 genes were evaluated that had promoter RRBS coverage in at least 70% of 33 samples with matched RRBS and RNAseq. C. An example is shown of the promoter region of ZNF718 from two samples (CLL062 and CLL74) with similar promoter methylation values but different PDR and different expression as measured by RNAseq (bottom right). ZNF718 promoter RRBS reads for CLL062 and CLL074 are shown (top). The number of concordantly methylated (grey background) or discordantly methylated (orange background) sequencing reads for each distinct methylation pattern is indicated to the right of each read pattern. D. Gene expression Shannon's information entropy (y-axis) in relation to the population average gene expression (x-axis, log 10[FPM]) for each gene covered in single cells of CLL032, CLL096 and CLL146, evaluated by single cell transcriptome sequencing. Colored lines—local regression curves for genes with low PDR (0-0.05, blue), intermediate PDR (0.05-0.2, purple), and high PDR (0.2-1.0, red). 90% of genes with higher promoter PDR (PDR>0.1) have lower population average expression (bounded by the yellow highlighted line). Right panels—Boxplots of the gene expression Shannon's information entropy for each of the three PDR bins for genes with population average gene expression of 1.0-1.5 (to control for differences in this variable). E. Generalized additive regression tests that model gene expression Shannon's information entropy based on: PDR, population average gene expression (locally smoothed), transcript length and promoter methylation across the 4 CLL samples that underwent single-cell transcriptome sequencing.

Figure 16C:
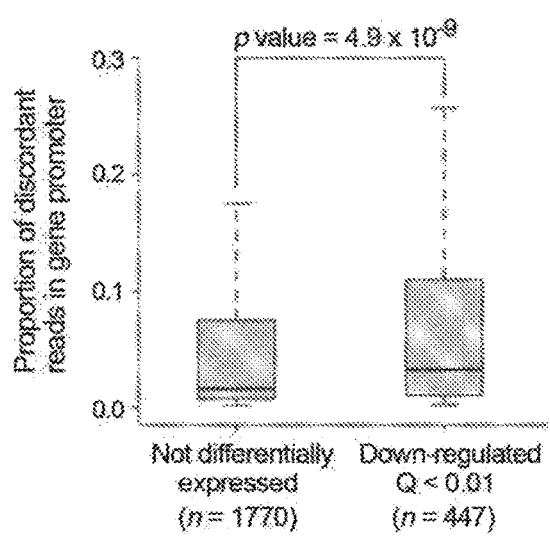
Figure 16C:
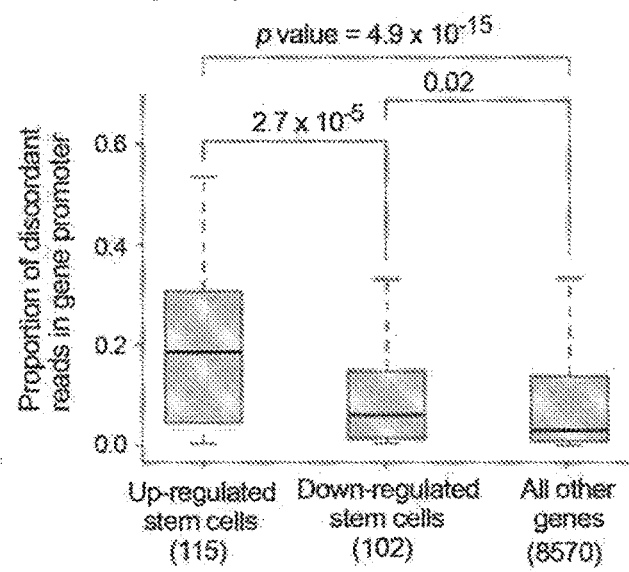
Figure 16C:
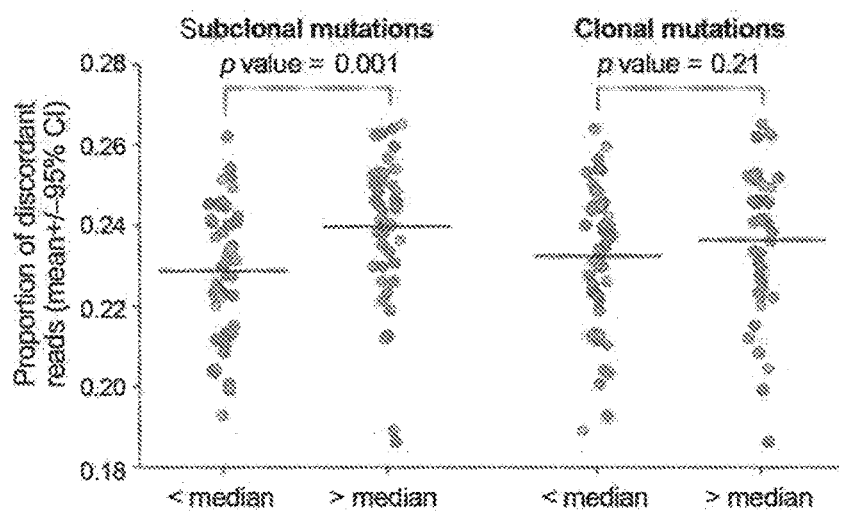

FIG. 16A-C demonstrates that locally disordered methylation creates a rich substrate for CLL evolution by stochastic variation amenable to positive selection. (A) Higher PDR in genes down-regulated in CLL. (B) Higher PDR in genes known to be up-regulated in stem cells. (C) Higher PDR in samples with a higher number of subclonal mutations, but not clonal mutations.

Figure 17A:
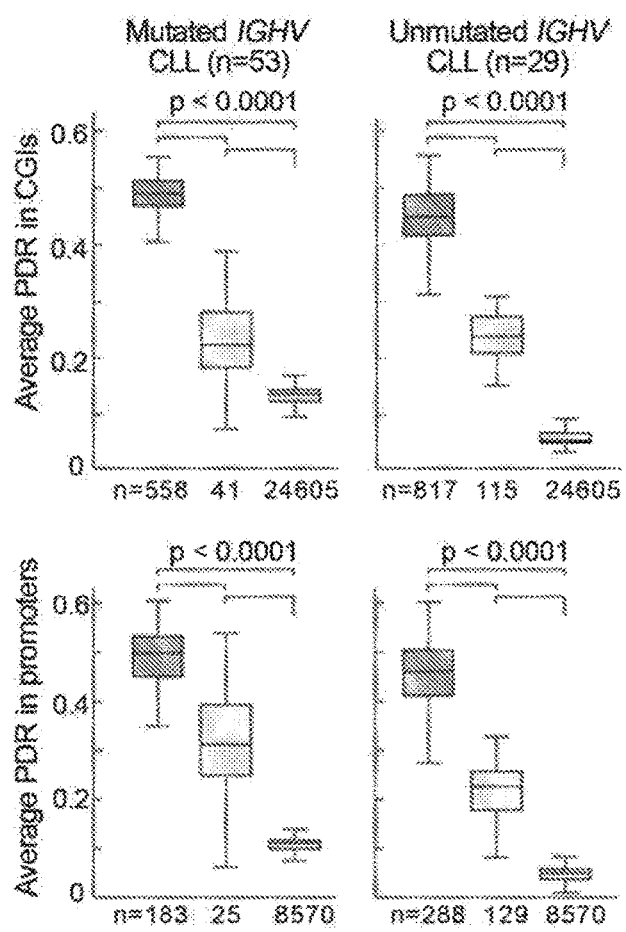
Figure 17B:
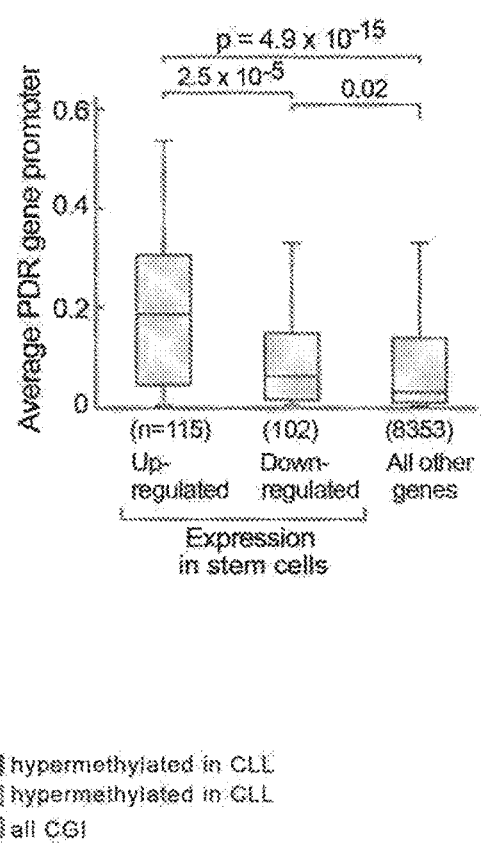

FIG. 17A-B illustrates that increased locally disordered methylation involves differentially methylated regions and affects stem cell related genes. A. Two sets of differentially methylated CpG islands and promoter regions were identified by comparing methylation across: i) unmutated IGHV CLL vs. normal naive B cell samples, and ii) across mutated IGHV CLL vs. normal memory B cell samples. Significantly differentially methylated regions were defined as having a >10% average methylation change with a t-test p value <0.01. Average PDR was then calculated for each one of these regions. Higher PDR was measured in differentially methylated (both increased and decreased methylation) promoters and CpG islands compared with regions that are not differentially methylated between CLL and normal B cells (Wilcoxon rank sum test). B. Average promoter PDR is highest in promoters of 115 genes up-regulated in stromal stem cells compared with 102 genes down-regulated in stromal stem cells (Boquest et al., 2005) as well as the average for 8,353 genes without a differential expression in stem cells (all comparisons by Wilcoxon rank sum test). Boxes represent median and interquartile range (IQR). Whiskers represent 1.5 times IQR.

FIG. 18A-E illustrates that locally disordered methylation may interact with evolution through drift towards a stem-like state. A. Gene set enrichment analysis comparing 1,668 genes with consistently high promoter PDR (>0.1 in >75% of samples) to 5,392 genes with consistently low promoter PDR (<0.1 in >75% of samples, selected 10 gene sets displayed). Enrichment in genes with consistently high PDR was calculated for hypergeometric distribution followed by BH-FDR ('Q(high)'). In addition, enrichment in high PDR genes vs. low PDR genes was calculated using Fisher's exact test followed by BH-FDR ('Q(high vs low)'). B. PDR and methylation in regions hypomethylated in embryonic stem cells (Ziller et al., 2013), in CLL compared with normal B cells (WGBS data). Regions include 91 enhancers (e.g., POU5F1, NANOG), 41 enhancer CGIs (e.g., TET2, EP400), 6 CGIs (e.g., DAPK1), 6 promoters and 84 other putative regulatory elements (e.g., DEC and POT1) (Ziller et al., 2013). The inset shows individual changes of selected regions. C. PDR in CLLs with high vs. low number of subclonal (median=7.5 sSNVs) and clonal mutations (median=10 sSNVs). D. Fourteen CLLs were sampled longitudinally at two time points (T1, T2; median interval time—3.5 years), and change in PDR over time was compared between CLLs that underwent genetic clonal evolution (n=9) and those without genetic evolution (n=5, paired t test). E. Gene set enrichment of the 899 genes from the 14 cases with significant promoter methylation change between timepoints T1 and T2 (absolute change >10%, FDR BH Q<0.1) in genes with promoter demethylation over time (456 genes), and in genes with promoter methylation over time (443 genes) see Table 6 for top 30 enrichments).

FIG. 19A-B illustrates that locally disordered methylation is associated with adverse clinical outcome. A. Kaplan-Meier plot showing failure free survival time (failure defined as retreatment or death from the time of first therapy after RRBS analysis) in CLLs with higher versus lower than average promoter PDR. Note that the analysis could only be performed for the 49 patients who received therapy after RRBS sampling. B. Multivariable analysis for this association with the addition of well-established poor outcome predictors in CLL (IGHV unmutated status, del(17p) and del(11q)), as well as with the addition of the presence of a subclonal driver (including somatic copy number changes, sSNVs and indels), as previously described (Landau et al., 2013)) to the model.

FIG. 20A-B illustrates a model of the interaction between methylation disorder and clonal evolution. A novel somatic mutation (depicted with lightning bolts) would have to coincide with an epigenetic state that will be permissive to the propagation of the new genotype to a progeny population. In a cellular population with limited stochastic methylation changes (top panel), the proportion of cells that are therefore able to actively participate in the evolutionary process is small. However, in a more malleable epigenetic landscape resulting from high level of locally disordered methylation, a greater proportion of cells can give birth to new subclones, increasing the diversity and the adaptive capacity of the cancer population, resulting in adverse clinical outcome with therapy.

DETAILED DESCRIPTION OF THE INVENTION

In order that the invention described herein may be fully understood, the following detailed description is set forth.

Unless defined otherwise, all technical and scientific terms used herein have the same meaning as those commonly understood by one of skill in the art to which this invention belongs. Although methods and materials similar or equivalent to those described herein can be used in the practice or testing of the present invention, suitable methods and materials are described below. The materials, methods and examples are illustrative only, and are not intended to be limiting. All publications, patents and other documents mentioned herein are incorporated by reference in their entirety.

Throughout this specification, the word "comprise" or variations such as "comprises" or "comprising" will be understood to imply the inclusion of a stated integer or groups of integers but not the exclusion of any other integer or group of integers.

The terms "antitumor agent" and "chemotherapeutic agent" are used interchangeably herein and refer to an agent for the treatment of cancer. Typically, an antitumor agent is a cytotoxic anti-neoplastic drug, which is administered as part of a standardized regimen. Without being bound by theory, antitumor agents act by killing cells that divide rapidly, one of the main properties of most cancer cells. Preferably, the antitumor agent is not indiscriminately cytotoxic, but rather targets proteins that are abnormally expressed in cancer cells and that are essential for their growth. Non-limiting examples of antitumor agents include:

angiogenesis inhibitors, such as angiostatin K1-3, DL-α-Difluoromethyl-ornithine, endostatin, fumagillin, genistein, minocycline, staurosporine, and (±)-thalidomide; DNA intercaltor/cross-linkers, such as Bleomycin, Carboplatin, Carmustine, Chlorambucil, Cyclophosphamide, cis-Diammineplatinum(II) dichloride (Cisplatin), Melphalan, Mitoxantrone, and Oxaliplatin; DNA synthesis inhibitors, such as (±)-Amethopterin (Methotrexate), 3-Amino-1,2,4-benzotriazine 1,4-dioxide, Aminopterin, Cytosine β-D-arabinofuranoside, 5-Fluoro-5'-deoxyuridine, 5-Fluorouracil, Ganciclovir, Hydroxyurea, and Mitomycin C; DNA-RNA transcription regulators, such as Actinomycin D, Daunorubicin, Doxorubicin, Homoharringtonine, and Idarubicin; enzyme inhibitors, such as S(+)-Camptothecin, Curcumin, (−)-Deguelin, 5,6-Dichlorobenzimidazole 1-β-D-ribofuranoside, Etoposide, Formestane, Fostriecin, Hispidin, 2-Imino-1-imidazoli-dineacetic acid (Cyclocreatine), Mevinolin, Trichostatin A, Tyrphostin AG 34, and Tyrphostin AG 879; gene regulators, such as 5-Aza-2'-deoxycytidine, 5-Azacytidine, Cholecalciferol (Vitamin D3), 4-Hydroxytamoxifen, Melatonin, Mifepristone, Raloxifene, all trans-Retinal (Vitamin A aldehyde), Retinoic acid, all trans (Vitamin A acid), 9-cis-Retinoic Acid, 13-cis-Retinoic acid, Retinol (Vitamin A), Tamoxifen, and Troglitazone; microtubule inhibitors, such as Colchicine, Dolastatin 15, Nocodazole, Paclitaxel, Podophyllotoxin, Rhizoxin, Vinblastine, Vincristine, Vindesine, and Vinorelbine (Navelbine); and unclassified antitumor agents, such as 17-(Allylamino)-17-demethoxygeldanamycin, 4-Amino-1,8-naphthalimide, Apigenin, Brefeldin A, Cimetidine, Dichloromethylene-diphosphonic acid, Leuprolide (Leuprorelin), Luteinizing Hormone-Releasing Hormone, Pifithrin-α, Rapamycin, Sex hormone-binding globulin, Thapsigargin, and Urinary trypsin inhibitor fragment (Bikunin). The antitumor agent may be a neoantigen. Neoantigens are tumor-associated peptides that serve as active pharmaceutical ingredients of vaccine compositions which stimulate antitumor responses and are described in US 2011-0293637, which is incorporated by reference herein in its entirety. The antitumor agent may be a monoclonal antibody such as rituximab (Rituxan®), alemtuzumab (Campath®), Ipilimumab (Yervoy®), Bevacizumab (Avastin®), Cetuximab (Erbitux®), panitumumab (Vectibix®), and trastuzumab (Herceptin®), Vemurafenib (Zelboraf®) imatinib mesylate (Gleevec®), erlotinib (Tarceva®), gefitinib (Iressa®), Vismodegib (Erivedge™), 90Y-ibritumomab tiuxetan, 131I-tositumomab, ado-trastuzumab emtansine, lapatinib (Tykerb®), pertuzumab (Perjeta™), ado-trastuzumab emtansine (Kadcyla™), regorafenib (Stivarga®), sunitinib (Sutent®), Denosumab (Xgeva®), sorafenib (Nexavart®), pazopanib (Votrient®), axitinib (Inlyta®), dasatinib (Sprycel®), nilotinib (Tasigna®), bosutinib (Bosulif®), ofatumumab (Arzerra®), obinutuzumab (Gazyva™), ibrutinib (Imbruvica™), idelalisib (Zydelig®), crizotinib (Xalkori®), erlotinib (Tarceva®), afatinib dimaleate (Gilotrif®), ceritinib (LDK378/Zykadia), Tositumomab and 131I-tositumomab (Bexxar®), ibritumomab tiuxetan (Zevalin®), brentuximab vedotin (Adcetris®), bortezomib (Velcade®), siltuximab (Sylvant™), trametinib (Mekinist®), dabrafenib (Tafinlar®), pembrolizumab (Keytruda®)), carfilzomib (Kyprolis®), Ramucirumab (Cyramza™), Cabozantinib (Cometriq™), vandetanib (Caprelsa®), The antitumor agent may be a cytokine such as interferons (INFs), interleukins (ILs), or hematopoietic growth factors. The antitumor agent may be INF-α, IL-2, Aldesleukin, IL-2, Erythropoietin, Granulocyte-macrophage colony-stimulating factor (GM-CSF) or granulocyte colony-stimulating factor. The antitumor agent may be a targeted therapy such as toremifene (Fareston®), fulvestrant (Faslodex®), anastrozole (Arimidex®), exemestane (Aromasin®), letrozole (Femara®), ziv-aflibercept (Zaltrap®), Alitretinoin (Panretin®), temsirolimus (Torisel®), Tretinoin (Vesanoid®), denileukin diftitox (Ontak®), vorinostat (Zolinza®), romidepsin (Istodax®), bexarotene (Targretin®), pralatrexate (Folotyn®), lenaliomide (Revlimid®), belinostat (Beleodaq™), lenaliomide (Revlimid®), pomalidomide (Pomalyst®) Cabazitaxel (Jevtana®), enzalutamide (Xtandi®), abiratrone acetate (Zytiga®), radium 223 chloride (Xofigo®), or cycrolimus (Afinitor®). The antitumor agent may be a checkpoint inhibitor such as an inhibitor of the programmed death-1 (PD-1) pathway, for example an anti-PD1 antibody (Nivolumab). The inhibitor may be an anti-cytotoxic T-lymphocyte-associated antigen (CTLA-4) antibody. The inhibitor may target another member of the CD28 CTLA4 Ig superfamily such as BTLA, LAG3, ICOS, PDL1 or KIR. A checkpoint inhibitor may target a member of the TNFR superfamily such as CD40, OX40, CD137, GITR, CD27 or TIM-3. Additionally, the antitumor agent may be an epigenetic targeted drug such as HDAC inhibitors, kinase inhibitors, DNA methyltransferase inhibitors, histone demethylase inhibitors, or histone methylation inhibitors. The epigenetic drugs may be Azacitidine (Vidaza), Decitabine (Dacogen), Vorinostat (Zolinza), Romidepsin (Istodax), or Ruxolitinib (Jakafi).

The term "chemotherapy" refers to the treatment of cancer with an antitumor or chemotherapeutic agent as part of a standardized regimen. Chemotherapy may be given with a curative intent or it may aim to prolong life or to palliate symptoms. It may be used in conjunction with other cancer treatments, such as radiation therapy or surgery.

The term "clonal genetic mutation" refers an alteration of genetic sequence of one or more cells to create a clone (i.e., a progenitor cell) from which a population of identical cells is derived. For example, a clonal genetic mutation can be the genetic change that changes a healthy cell into a cancerous cell in a subject, giving rise to a tumor in the subject through clonal expansion. In such cases, the clonal genetic mutation may change the nucleotide sequence of an oncogene or a tumor suppressor gene.

The term "CpG" refers to a dinucleotide sequence, wherein a cytosine nucleotide occurs next to a guanine nucleotide in the linear sequence of bases along its length. In a CpG sequence, the cytosine nucleotide is 5' to the guanine nucleotide, and the two nucleotides are connected by a phosphate molecule. Cytosines in CpG dinucleotides can be methylated to form 5-methylcytosine. In mammals, methylation of the cytosine within a gene or promoter can affect transcriptional regulation of the gene. Enzymes that add a methyl group are called DNA methyltransferases.

The term "CpG" island refers to a genomic region that contains a high frequency of CpG sites. A CpG island is characterized by CpG dinucleotide content of at least 60% of that which would be statistically expected (about 0.4-6%), whereas the rest of the genome has a much lower CpG frequency (about 0.1%).

The term "epipolymorphism" refers to the probability that two randomly sampled DNA molecules differ in their methylation pattern. Epipolymorphism can be determined by calculating the probability that two reads, selected at random from a collection of overlapping reads will be not be methylated identically. This probability will increase with higher locally disordered methylation. See, e.g., Landan et al., Nat. Genetics, 2012, vol. 44: 1207-1216, incorporated by reference herein in its entirety.

The terms "information entropy" and "methylation entropy" are used interchangeably herein and refer to a measure of the randomness of DNA methylation patterns in a cell population. For example, information entropy can be calculated by computing Shannon's entropy for the methylation state of neighboring CpGs. Entropies may be combined in a variety of ways. See, e.g., Xie et al., (Nucleic Acids Research, 2011, vol. 39, 4099-4108), incorporated by reference herein in its entirety.

The term "likely to respond" to a therapy refers to the plasticity of a tumor. A tumor with greater heterogeneity is less likely to respond to an antitumor agent because there is a greater possibility of a resistant subclone being present or spontaneously arising within the tumor. Similarly, a tumor that is likely to undergo subclonal evolution is less likely to respond to an antitumor agent because the tumor may develop resistance to the treatment.

The terms "locally disordered methylation" and "discordant methylation" are used interchangeably and refer alterations of CpG methylation patterns over a short genetic distance or within a genomic feature. Typically, short-range concordance is expected to be very high in non-disease states, as DNA methylation generally changes by feature (e.g., a specific gene promoter, or a CG island) rather than by individual CpG. These terms may also refer, in a stricter sense, to the concordance status of CpGs on the same sequencing read. If all CpGs contained within one sequencing read are uniformly methylated or uniformly unmethylated, the read is classified as concordantly methylated. Otherwise the read is classified as discordantly methylated. A sequencing read may be over a short genetic distance, such as 25 basepairs (bp); 30 bp; 35 bp; 40 bp; 45 bp; 50 bp; 60 bp; 70 bp; 80 bp; 90 bp; 100 bp; 250 bp; 500 bp; 750 bp or 1000 bp, preferably less than 50 bp, or even less than 40 or less than 30 bp. FIG. 3 provides a graphical depiction of discordant and concordant methylation patterns.

The term "methylation" refers to the addition of a methyl group to the 5' carbon of the cytosine base in a deoxyribonucleic acid sequence of CpG within a genome.

The term "methylation status" refers to the presence or absence of a methylated cytosine base at a CpG site.

The term "neighboring CpG site" refers to the collection of CpG sites within a genomic feature or over a short genetic distance. The genomic feature may be a promoter, an enhancer, an exon, an intron, a 5'-untranslated region (UTR), a 3'-UTR, a gene body, a stem cell associated region, a CpG island, a CpG shelf, a CpG shore, a LINE, a SINE, or an LTR. The short genetic distance may be 10 bp, 11 bp, 12 bp, 13 bp, 14 bp, 15 bp, 16 bp, 17 bp, 18 bp, 19 bp, 20 bp, 21 bp, 22 bp, 23 bp, 24 bp, 25 bp, 26 bp, 27 bp, 28 bp, 29 bp, 30 bp, 31 bp, 32 bp, 33 bp, 34 bp, 35 bp, 36 bp, 37 bp, 38 bp, 39 bp, 40 bp, 41 bp, 42 bp, 43 bp, 44 bp, 45 bp, 46 bp, 47 bp, 48 bp, 49 bp, 50 bp, 51 bp, 52 bp, 53 bp, 54 bp, 55 bp, 56 bp, 57 bp, 58 bp, 59 bp, 60 bp, 61 bp, 62 bp, 63 bp, 64 bp, 65 bp, 66 bp, 67 bp, 68 bp, 69 bp, 70 bp, 71 bp, 72 bp, 73 bp, 74 bp, 75 bp, 76 bp, 77 bp, 78 bp, 79 bp, 80 bp, 81 bp, 82 bp, 83 bp, 84 bp, 85 bp, 86 bp, 87 bp, 88 bp, 89 bp, 90 bp, 91 bp, 92 bp, 93 bp, 94 bp, 95 bp, 96 bp, 97 bp, 98 bp, 99 bp, 100 bp, 250 bp, 500 bp, 750 bp or 1,000 bp, preferably 29 bp. Optionally, neighboring CpG sites occur within a sequencing read.

The terms "proportion of discordant reads" and "PDR" are used interchangeably and refer to the ratio of discordant reads of the total number of overlapping reads for a specific genomic location. FIG. 3 provides a sample calculation of the proportion of discordant reads in a tumor sample.

The term "sodium bisulfite" refers to sodium hydrogen sulfite having the chemical formula of $NaHSO_3$. Sodium bisulfite functions to deaminate cytosine into uracil; but does not affect 5-methylcytosine (a methylated form of cytosine with a methyl group attached to carbon 5). When the bisulfite-treated DNA is amplified via polymerase chain reaction, the uracil is amplified as thymine and the methylated cytosine is amplified as cytosine.

The term "subclonal genetic mutation" refers an alteration in a genetic sequence of one or more cells of a clonal population. Accordingly, a subclonal genetic mutation occurs subsequently to a clonal genetic mutation. Typically, individual cancer samples are genetically heterogeneous and contain subclonal populations. In cancer, subclonal genetic alterations may have an impact on clinical course. For example, a subclonal genetic mutation may arise in response to a selective pressure, such as treatment with an antitumor agent, to confer resistance. Similarly, in a heterogeneous tumor, a subclonal population, comprising a subclonal genetic mutation, may thrive and emerge as dominant, while other subclonal populations will decline, in response to selective pressure. Subclonal genetic mutations that permit a subclonal population to overcome a selective pressure are known as "subclonal driver mutations" or "subclonal drivers."

The term "subject" refers to a vertebrate or invertebrate animal. In some embodiments, the subject is a vertebrate animal, e.g., a mammal, preferably a human. In some embodiments, a subject is a domestic or laboratory animal, including but not limited to, household pets, such as dogs, cats, pigs, rabbits, rats, mice, gerbils, hamsters, guinea pigs, and ferrets. In some embodiments, a subject is a livestock animal. Non-limiting examples of livestock animals include: alpaca, bison, camel, cattle, deer, pigs, horses, llamas, mules, donkeys, sheep, goats, rabbits, reindeer, and yak.

The term "variance" refers to a statistical measurement of how far a set of numbers is spread out. A variance of zero indicates that all the values are identical. A non-zero variance is always positive. A small variance indicates that the data points tend to be very close to the mean (expected value, e.g., concordance) and hence to each other, while a high variance indicates that the data points are very spread out from the mean and from each other. Variance may be calculated as a sum of variance that stems from discordant reads and the variance that stems from concordant reads. One can then estimate which contributes more to CpG variance.

As noted herein, genetically uniform cell subpopulations can contain profound epigenetic differences leading to phenotypic differences in their survival capacity and proliferative potential. The proportion of cells that ultimately participate in the evolutionary process may be limited by the fact that in order to form a new subclone, a novel somatic mutation would need to coincide with an epigenetic state permissive to its propagation. Applicants data shows that CLL cells have substantially increased epigenetic stochasticity, which results in a more malleable epigenetic landscape and likely increases the pool of cells that serve as substrate for the evolutionary process. These results demonstrate the mechanistic effects of epigenetic stochasticity on transcriptional regulation and chromatin modification. In addition, these results indicate the need to determine how genetic and epigenetic characteristics cooperate in CLL clonal evolution in a large clinical trial cohort. Indeed, these results define locally disordered methylation as a key evolution-enabling feature of cancer and a predictive biomarker.

Importantly, they may pave the way for the future development of therapeutic modalities to address the cancer's evolutionary adaptive capacity.

This phenomenon is defined as locally disordered methylation. For example, the degree of methylation disorder as measured in DNA fragments that are sequenced in shotgun sequencing (up to 100 bases long) is higher in leukemia and cancer cell line samples than in normal samples. In certain embodiments, locally disordered methylation may be measured by identifying the overlapping reads (corresponding to DNA fragments originating from individual cells) for each genomic location covered by massive parallel sequencing; identifying the CpGs and their methylation status within each sequencing read (DNA fragment); if all CpGs contained within one sequencing read are uniformly methylated or uniformly unmethylated, the read may be classified as concordantly methylated, otherwise the read is classified as discordantly methylated.

Prognostic Methods

A first aspect of the present invention provides a method of assessing a subject's cancer treatment prognosis. In some embodiments, the method comprises detecting DNA methylation status at one or more regions of neighboring CpG sites in a plurality of cells in a tumor sample from the subject; comparing the DNA methylation status of neighboring CpG sites along a sequence of CpG sites in DNA of the plurality of cells and/or comparing the DNA methylation status of corresponding CpG sites across multiple gene copies in the plurality of cells; and assessing the consistency of methylation status along the sequences of neighboring CpG sites and/or across multiple gene copies in the plurality of cells. The presence or prevalence of inconsistent methylation status along the sequences or across the multiple gene copies may indicate that the subject is more likely to (1) develop resistance to an antitumor agent; (2) relapse after treatment with an antitumor agent; (3) develop a metastatic tumor; or (4) any combination thereof. For example, the DNA methylation status of CpG sites along one or more sequencing reads, e.g., operatively linked to each other in a single polynucleotide molecule, may be detected. The neighboring CpG sites along the sequencing read may then be compared to each other or to corresponding positions of different sequencing reads (e.g., at the same genomic location) from the plurality of cells.

DNA methylation may be detected by any method known in the art, including methylation-specific PCR, whole genome bisulfite sequence, the HELP assay and other methods using methylation-sensitive restriction endonucleases, ChIP-on-chip assays, restriction landmark genomic scanning, COBRA, Ms-SNuPE, methylated DNA immunoprecipitation (MeDip), pyrosequencing of bisulfite treated DNA, molecular break light assay for DNA adenine methyltransferase activity, methyl sensitive Southern blotting, methylCpG binding proteins, mass spectrometry, HPLC, and reduced representation bisulfite sequencing.

In some embodiments methylation is detected at specific sites of DNA methylation using pyrosequencing after bisulfite treatment and optionally after amplification of the methylation sites. Pyrosequencing technology is a method of sequencing-by-synthesis in real time. It is based on an indirect bioluminometric assay of the pyrophosphate (PPi) that is released from each deoxynucleotide (dNTP) upon DNA-chain elongation. This method presents a DNA template-primer complex with a dNTP in the presence of an exonuclease-deficient Klenow DNA polymerase. The four nucleotides are sequentially added to the reaction mix in a predetermined order. If the nucleotide is complementary to the template base and thus incorporated, PPi is released. The PPi and other reagents are used as a substrate in a luciferase reaction producing visible light that is detected by either a luminometer or a charge-coupled device. The light produced is proportional to the number of nucleotides added to the DNA primer and results in a peak indicating the number and type of nucleotide present in the form of a pyrogram. Pyrosequencing can exploit the sequence differences that arise following sodium bisulfite-conversion of DNA.

In some embodiments, the DNA methylation is detected in a methylation assay utilizing next-generation sequencing. For example, DNA methylation may be detected by massive parallel sequencing with bisulfite conversion, e.g., whole-genome bisulfite sequencing or reduced representation bisulfite sequencing. Optionally, the DNA methylation is detected by microarray, such as a genome-wide microarray. Microarrays, and massively parallel sequencing, have enabled the interrogation of cytosine methylation on a genome-wide scale (Zilberman D, Henikoff S. 2007. Genome-wide analysis of DNA methylation patterns. Development 134(22): 3959-3965). Genome wide methods have been described previously (Deng, et al. 2009. Targeted bisulfite sequencing reveals changes in DNA methylation associated with nuclear reprogramming. Nat Biotechnol 27(4): 353-360; Meissner, et al. 2005. Reduced representation bisulfite sequencing for comparative high-resolution DNA methylation analysis. Nucleic Acids Res 33(18): 5868-5877; Down, et al. 2008. A Bayesian deconvolution strategy for immunoprecipitation-based DNA methylome analysis. Nat Biotechnol 26(7): 779-785; Gu et al. 2011. Preparation of reduced representation bisulfite sequencing libraries for genome-scale DNA methylation profiling. Nat Protoc 6(4): 468-481).

The most comprehensive, highest resolution method for detecting DNA methylation is whole genome bisulfite sequencing (WGBS) (Cokus, et al. 2008. Shotgun bisulphite sequencing of the *Arabidopsis* genome reveals DNA methylation patterning. Nature 452(7184): 215-219; Lister, et al. 2009. Human DNA methylomes at base resolution show widespread epigenomic differences. Nature 462(7271): 315-322; Harris, et al. 2010. Comparison of sequencing-based methods to profile DNA methylation and identification of monoallelic epigenetic modifications. Nat Biotechnol 28(10): 1097-1105).

To detect DNA methylation, a preferred embodiment provides for first converting the DNA to be analyzed so that the unmethylated cytosine is converted to uracil. In one embodiment, a chemical reagent that selectively modifies either the methylated or non-methylated form of CpG dinucleotide motifs may be used. Suitable chemical reagents include hydrazine and bisulphite ions and the like. Preferably, isolated DNA is treated with sodium bisulfite ($NaHSO_3$) which converts unmethylated cytosine to uracil, while methylated cytosines are maintained. Without wishing to be bound by a theory, it is understood that sodium bisulfite reacts readily with the 5,6-double bond of cytosine, but poorly with methylated cytosine. Cytosine reacts with the bisulfite ion to form a sulfonated cytosine reaction intermediate that is susceptible to deamination, giving rise to a sulfonated uracil. The sulfonated group can be removed under alkaline conditions, resulting in the formation of uracil. The nucleotide conversion results in a change in the sequence of the original DNA. It is general knowledge that the resulting uracil has the base pairing behavior of thymine, which differs from cytosine base pairing behavior. To that end, uracil is recognized as a thymine by DNA polymerase. Therefore after PCR or sequencing, the resultant product contains cytosine only at the position where 5-methylcytosine occurs in the starting template DNA. This makes the discrimination between unmethylated and methylated cytosine possible.

The methylation status of neighboring CpG sites may be compared by calculating the proportion of discordant reads, calculating variance, or calculating information entropy identifying differentially methylated regions, by quantifying methylation difference, or by gene-set analysis (i.e., pathway analysis), preferably by calculating the proportion of discordant reads, calculating variance, or calculating information entropy. Optionally, information entropy is calculated by adapting Shannon entropy. In some embodiments, gene-set analysis is performed by tools such as DAVID, GoSeq or GSEA. In some embodiments, a proportion of discordant reads (PDR) is calculated. Optionally, each region of neighboring CpG sites (e.g., within a sequencing read) is assigned a consistent status or an inconsistent status before calculating the proportion of discordant reads, variance, epipolymorphism or information entropy. There may be multiple inconsistent statuses, each representing a distinct methylation pattern or class of similar methylation patterns.

The one or more regions of neighboring CpG sites may be a short genetic sequence or a genomic feature. The short genetic sequence may consist of 10 bp, 0.1 bp, 12 bp, 13 bp, 14 bp, 15 bp, 16 bp, 17 bp, 18 bp, 19 bp, 20 bp, 21 bp, 22 bp, 23 bp, 24 bp, 25 bp, 26 bp, 27 bp, 28 bp, 29 bp, 30 bp, 31 bp, 32 bp, 33 bp, 34 bp, 35 bp, 36 bp, 37 bp, 38 bp, 39 bp, 40 bp, 41 bp, 42 bp, 43 bp, 44 bp, 45 bp, 46 bp, 47 bp, 48 bp, 49 bp, 50 bp, 51 bp, 52 bp, 53 bp, 54 bp, 55 bp, 56 bp, 57 bp, 58 bp, 59 bp, 60 bp, 61 bp, 62, bp, 63 bp, 64 bp, 65 bp, 66 bp, 67 bp, 68 bp, 69 bp, 70 bp, 71 bp, 72 bp, 73 bp, 74 bp, 75 bp, 76 bp, 77 bp, 78 bp, 79 bp, 80 bp, 81 bp, 82 bp, 83 bp, 84 bp, 85 bp, 86 bp, 87 bp, 88 bp, 89 bp, 90 bp, 91 bp, 92 bp, 93 bp, 94 bp, 95 bp, 96 bp, 97 bp, 98 bp, 99 bp, 100 bp, 250 bp, 500 bp, or 1,000 bp, preferably 29 bp.

Preferably, an optimal amplicon length when one or more regions of neighboring CpG sites is amplified by PCR is between about 80 base pairs and about 150 base pairs. There is an inverse relationship between the amplicon length and PCR efficiency. The underlying rationale is related to the fact that sodium bisulfite treatment causes degradation of DNA and therefore PCR efficiency decreases as amplicon size gets larger.

Optionally, the region of neighboring CpG sites is a genomic feature selected from a CpG island, a CpG shore, a CpG shelf, a promoter, an enhancer, an exon, an intron, a gene body, a stem cell associated region, a short interspersed element (SINE), a long interspersed element (LINE), and a long terminal repeat (LTR), preferably a CpG island or a promoter.

The one or more regions of neighboring CpG sites having a locally disordered methylation status may be located within a genomic location selected from a CpG island, a CpG shore, a CpG shelf, a promoter, an enhancer, an exon, an intron, a gene body, a stem cell associated region, a short interspersed element (SINE), a long interspersed element (LINE), and a long terminal repeat (LTR), preferably a CpG island or a promoter.

In some embodiments, the method further comprises detecting a subclonal genetic mutation. Optionally, the subclonal genetic mutation is within the one or more genomic regions having a locally disordered methylation status. A subclonal genetic mutation with the one or more genomic regions having a locally disordered methylation status may indicate that the subject is even more likely to (1) develop resistance to an antitumor agent; (2) relapse after treatment with an antitumor agent; (3) develop a metastatic tumor; or (4) any combination thereof. Optionally, the presence of a subclonal mutation in a subject with a prevalence of inconsistent methylation status along the sequences or across the multiple gene copies may indicate that the subject is even more likely to (1) develop resistance to an antitumor agent; (2) relapse after treatment with an antitumor agent; (3) develop a metastatic tumor; or (4) any combination thereof.

The subclonal genetic mutation may be detected by any method known in the art. For example, the subclonal genetic mutation may be detected by Comparative Genomic Hybridization Array, Multiple Ligation-dependent Probe Amplification, Multiplex Amplifiable Probe Hybridization, Single Condition Amplification/Internal Primer, Multiplex PCR, Southern Blot, Sanger gene sequence, Resequencing Array, mRNA analysis, cDNA sequencing, microarray analysis, whole-genome sequence, massively parallel signature sequencing, Polony sequencing, 454 pyrosequencing, SOLiD sequencing, Illumina dye sequencing, ion semiconductor sequence, DNA nanoball sequencing, heliscope single molecule sequencing, single molecule real time sequencing, nanopore DNA sequencing, tunneling currents DNA sequencing, sequencing by hybridization, sequencing with mass spectrometry, transmission electron microscopy sequencing, and RNA polymerase sequencing, preferably massively parallel signature sequencing.

The DNA methylation status at the one or more neighboring CpG sites may be detected before treatment with an antitumor agent. Optionally, the DNA methylation status at the one or more neighboring CpG sites is detected after treatment with an antitumor agent. The DNA methylation status at the one or more neighboring CpG sites may be detected both before and after treatment with an antitumor agent. In some embodiments, the DNA methylation status at the one or more neighboring CpG sites is detected throughout a time course of treatment with an antitumor agent. An increase in the number of genomic regions having a locally disordered methylation status may indicate that the subject is less likely to respond to an antitumor agent.

The tumor sample may be a solid tumor, such as carcinomas, sarcomas and lymphomas. In some embodiments, the solid tumor is selected from adrenocortical carcinoma, bone tumors, brain cancer, breast cancer, cervical cancer, colorectal carcinoma, desmoid tumors, desmoplastic small round cell tumors, endocrine tumors, esophageal cancer, Ewing sarcoma family tumors, gastric cancer, germ cell tumors, head or neck cancer, hepatoblastoma, hepatocellular carcinoma, lung cancer, melanoma, mesothelioma, nasopharyngeal carcinoma, neuroblastoma, non-rhabdomyosarcoma soft tissue sarcoma, osteosarcoma, ovarian cancer, pancreatic cancer, prostate cancer, retinoblastoma, rhabdomyosarcoma, skin carcinoma, testicular cancer, thyroid carcinoma, uterine cancer and Wilms tumors. The tumor sample may be a hematological cancer, such as leukemia, preferably CLL.

The antitumor agent is selected from an angiogenesis inhibitor, such as angiostatin K1-3, DL-α-Difluoromethylornithine, endostatin, fumagillin, genistein, minocycline, staurosporine, and (±)-thalidomide; a DNA intercaltor/crosslinker, such as Bleomycin, Carboplatin, Carmustine, Chlorambucil, Cyclophosphamide, cis-Diammineplatinum (II) dichloride (Cisplatin), Melphalan, Mitoxantrone, and Oxaliplatin; a DNA synthesis inhibitor, such as (±)-Amethopterin (Methotrexate), 3-Amino-1,2,4-benzotriazine 1,4-dioxide, Aminopterin, Cytosine β-D-arabinofuranoside, 5-Fluoro-5'-deoxyuridine, 5-Fluorouracil, Ganciclovir, Hydroxyurea, and Mitomycin C; a DNA-RNA transcription regulator, such as Actinomycin D, Daunorubicin, Doxorubicin, Homoharringtonine, and Idarubicin; an enzyme inhibitor, such as S(+)-Camptothecin, Curcumin, (−)-Deguelin, 5,6-Dichlorobenzimidazole 1-β-D-ribofuranoside, Etoposide, Formestane, Fostriccin, Hispidin, 2-Imino-1-imidazoli-dineacetic acid (Cyclocreatine), Mevinolin, Trichostatin A, Tyrphostin AG 34, and Tyrphostin AG 879; a gene regulator, such as 5-Aza-2'-deoxycytidine, 5-Azacytidine, Cholecalciferol (Vitamin D3), 4-Hydroxytamoxifen, Melatonin, Mifepristone, Raloxifene, all trans-Retinal (Vitamin A aldehyde), Retinoic acid, all trans (Vitamin A acid), 9-cis-Retinoic Acid, 13-cis-Retinoic acid, Retinol (Vitamin A), Tamoxifen, and Troglitazone; a microtubule inhibitor, such as Colchicine, Dolastatin 15, Nocodazole, Paclitaxel, Podophyllotoxin, Rhizoxin, Vinblastine, Vincristine, Vindesine, and Vinorelbine (Navelbine); and an unclassified antitumor agent, such as 17-(Allylamino)-17-demethoxygeldanamycin, 4-Amino-1,8-naphthalimide, Apigenin, Brefeldin A, Cimetidine, Dichloromethylene-diphosphonic acid, Leuprolide (Leuprorelin), Luteinizing Hormone-Releasing Hormone, Pifithrin-α, Rapamycin, Sex hormone-binding globulin, Thapsigargin, and Urinary trypsin inhibitor fragment (Bikunin). The antitumor agent may be a monoclonal antibody such as rituximab (Rituxan®), alemtuzumab (Campath®), Ipilimumab (Yervoy®), Bevacizumab (Avastin®), Cetuximab (Erbitux®), panitumumab (Vectibix®), and trastuzumab (Herceptin®), Vemurafenib (Zelboraf®) imatinib mesylate (Gleevec®), erlotinib (Tarceva®), gefitinib (Iressa®), Vismodegib (Erivedge™), 90Y-ibritumomab tiuxetan, 131I-tositumomab, ado-trastuzumab emtansine, lapatinib (Tykerb®), pertuzumab (Perjeta™), ado-trastuzumab emtansine (Kadcyla™), regorafenib (Stivarga®), sunitinib (Sutent®), Denosumab (Xgeva®), sorafenib (Nexavar®), pazopanib (Votrient®), axitinib (Inlyta®), dasatinib (Sprycel®), nilotinib (Tasigna®), bosutinib (Bosulif®), ofatumumab (Arzerra®), obinutuzumab (Gazyva™), ibrutinib (Imbruvica™), idelalisib (Zydelig®), crizotinib (Xalkori®), erlotinib (Tarceva®), afatinib dimaleate (Gilotrif®), ceritinib (LDK378/Zykadia), Tositumomab and 131I-tositumomab (Bexxar®), ibritumomab tiuxetan (Zevalin®), brentuximab vedotin (Adcetris®), bortezomib (Velcade®), siltuximab (Sylvant™), trametinib (Mekinist®), dabrafenib (Tafinlar®), pembrolizumab (Keytruda®)), carfilzomib (Kyprolis®), Ramucirumab (Cyramza™), Cabozantinib (Cometriq™), vandetanib (Caprelsa®), Optionally, the antitumor agent is a neoantigen. The antitumor agent may be a cytokine such as interferons (INFs), interleukins (ILs), or hematopoietic growth factors. The antitumor agent may be INF-α, IL-2, Aldesleukin, IL-2, Erythropoietin, Granulocyte-macrophage colony-stimulating factor (GM-CSF) or granulocyte colony-stimulating factor. The antitumor agent may be a targeted therapy such as toremifene (Farcston®), fulvestrant (Faslodex®), anastrozole (Arimidex®), exemestane (Aromasin®), letrozole (Femara®), ziv-aflibercept (Zaltrap®), Alitretinoin (Panretin®), temsirolimus (Torisel®), Tretinoin (Vesanoid®), denileukin diftitox (Ontak®), vorinostat (Zolinza®), romidepsin (Istodax®), bexarotene (Targretin®), pralatrexate (Folotyn®), lenaliomide (Revlimid®), belinostat (Beleodaq™), lenaliomide (Revlimid®), pomalidomide (Pomalyst®), Cabazitaxel (Jevtana®), enzalutamide (Xtandi®), abiraterone acetate (Zytiga®), radium 223 chloride (Xofigo®), or everolimus (Afinitor®). The antitumor agent may be a checkpoint inhibitor such as an inhibitor of the programmed death-1 (PD-1) pathway, for example an anti-PD1 antibody (Nivolumab). The inhibitor may be an anti-cytotoxic T-lymphocyte-associated antigen (CTLA-4) antibody. The inhibitor may target another member of the CD28 CTLA4 Ig superfamily such as BTLA, LAG3, ICOS, PDL1 or KIR. A checkpoint inhibitor may target a member of the TNFR superfamily such as CD40, OX40, CD137, GITR, CD27 or TIM-3. Additionally, the antitumor agent may be an epigenetic targeted drug such as HDAC inhibitors, kinase inhibitors, DNA methyltransferase inhibitors, histone demethylase inhibitors, or histone methylation inhibitors. The epigenetic drugs may be Azacitidine (Vidaza), Decitabine (Dacogen), Vorinostat (Zolinza), Romidepsin (Istodax), or Ruxolitinib (Jakafi).

The subject may be a mammal, preferably a human. In some embodiments, the subject may be a laboratory animal, such as a mouse, a rabbit, a rat, a guinea pig, a hamster, and a primate.

Methods of Calculating a Proportion of Discordant Reads

A second aspect of the present invention provides a method of calculating a proportion of discordant reads (PDR) in a first tumor sample from a subject. In some embodiments, the method comprises detecting DNA methylation status at one or more regions of neighboring CpG sites in a plurality of cells in the tumor sample; comparing the DNA methylation status of sequencing reads in one or more regions of neighboring CpG sites along a sequence of CpG sites in DNA of the plurality of cells; assessing the consistency of methylation status along the sequences of neighboring CpG sites and/or across multiple gene copies in the plurality of cells; and determining a relative number of cells in the tumor sample having variable methylation status across the sequence of CpG sites as compared to the total number of cells in the tumor sample or a number of cells in the tumor sample having consistent methylation status across the sequence of CpG sites.

The DNA methylation may be detected methylation-specific PCR, whole genome bisulfite sequence, the HELP assay and other methods using methylation-sensitive restriction endonucleases, ChIP-on-chip assays, restriction landmark genomic scanning, COBRA, Ms-SNuPE, methylated DNA immunoprecipitation (MeDip), pyrosequencing of bisulfite treated DNA, molecular break light assay for DNA adenine methyltransferase activity, methyl sensitive Southern blotting, methylCpG binding proteins, mass spectrometry, HPLC, and reduced representation bisulfite sequencing. In some embodiments, the DNA methylation is detected in a methylation assay utilizing next-generation sequencing. For example, DNA methylation may be detected by massive parallel sequencing with bisulfite conversion, e.g., whole-genome bisulfite sequencing or reduced representation bisulfite sequencing. Optionally, the DNA methylation is detected by microarray, such as a genome-wide microarray.

The one or more neighboring CpG sites may be a short genetic sequence or a genomic feature. The short genetic sequence may consist of 10 bp, 11 bp, 12 bp, 13 bp, 14 bp, 15 bp, 16 bp, 17 bp, 18 bp, 19 bp, 20 bp, 21 bp, 22 bp, 23 bp, 24 bp, 25 bp, 26 bp, 27 bp, 28 bp, 29 bp, 30 bp, 31 bp, 32 bp, 33 bp, 34 bp, 35 bp, 36 bp, 37 bp, 38 bp, 39 bp, 40 bp, 41 bp, 42 bp, 43 bp, 44 bp, 45 bp, 46 bp, 47 bp, 48 bp, 49 bp, 50 bp, 51 bp, 52 bp, 53 bp, 54 bp, 55 bp, 56 bp, 57 bp, 58 bp, 59 bp, 60 bp, 61 bp, 62, bp, 63 bp, 64 bp, 65 bp, 66 bp, 67 bp, 68 bp, 69 bp, 70 bp, 71 bp, 72 bp, 73 bp, 74 bp, 75 bp, 76 bp, 77 bp, 78 bp, 79 bp, 80 bp, 81 bp, 82 bp, 83 bp, 84 bp, 85 bp, 86 bp, 87 bp, 88 bp, 89 bp, 90 bp, 91 bp, 92 bp, 93 bp, 94 bp, 95 bp, 96 bp, 97 bp, 98 bp, 99 bp, 100 bp, 250 bp, 500 bp, or 1,000 bp, preferably 29 bp. Optionally, the neighboring CpG sites are located within a genomic feature selected from a CpG island, a CpG shore, a CpG shelf, a promoter, an enhancer, an exon, an intron, a gene body, a stem cell associated region, a short interspersed element (SINE), a long interspersed element (LINE), and a long terminal repeat (LTR), preferably a CpG island or a promoter.

The PDR may be calculated for a genomic location or for a genomic feature, such as a CpG island, a CpG shore, a CpG shelf, a promoter, an enhancer, an exon, an intron, a gene body, a stem cell associated region, a short interspersed element (SINE), a long interspersed element (LINE), and a long terminal repeat (LTR), preferably a CpG island or a promoter.

The PDR may be calculated before treatment with an antitumor agent. Optionally, the PDR is calculated after treatment with an antitumor agent. The PDR may be calculated both before and after treatment with an antitumor agent. In some embodiments, the PDR is calculated throughout a time course of treatment with an antitumor agent.

In some embodiments, a PDR threshold, such as greater than 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.38, 0.37, 0.38, 0.39, or 0.40, preferably 0.15, indicates that the patient is less likely to respond to treatment with an antitumor agent. A PDR threshold, such as less than 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.38, 0.37, 0.38, 0.39, or 0.40, preferably 0.15, may indicate that the patient is more likely to respond to treatment with an antitumor agent. A change in PDR following treatment may indicate that the subject is likely to relapse despite treatment. Without being bound by theory, an increase in PDR may suggest clonal evolution; a decrease in PDR may signal selection of a dominant subclone; and a constant PDR may suggest that an antitumor agent is equally effective across subclones.

The tumor sample may be a solid tumor, such as carcinomas, sarcomas and lymphomas. In some embodiments, the solid tumor is selected from adrenocortical carcinoma, bone tumors, brain cancer, breast cancer, cervical cancer, colorectal carcinoma, desmoid tumors, desmoplastic small round cell tumors, endocrine tumors, esophageal cancer, Ewing sarcoma family tumors, gastric cancer, germ cell tumors, head or neck cancer, hepatoblastoma, hepatocellular carcinoma, lung cancer, melanoma, mesothelioma, nasopharyngeal carcinoma, neuroblastoma, non-rhabdomyosarcoma soft tissue sarcoma, osteosarcoma, ovarian cancer, pancreatic cancer, prostate cancer, retinoblastoma, rhabdomyosarcoma, skin carcinoma, testicular cancer, thyroid carcinoma, uterine cancer and Wilms tumors. The tumor sample may be a hematological cancer, such as leukemia, preferably CLL.

The antitumor agent is selected from an angiogenesis inhibitor, such as angiostatin K1-3, DL-α-Difluoromethylornithine, endostatin, fumagillin, genistein, minocycline, staurosporine, and (±)-thalidomide; a DNA intercaltor/crosslinker, such as Bleomycin, Carboplatin, Carmustine, Chlorambucil, Cyclophosphamide, cis-Diammineplatinum (II) dichloride (Cisplatin), Melphalan, Mitoxantrone, and Oxaliplatin; a DNA synthesis inhibitor, such as (±)-Amethopterin (Methotrexate), 3-Amino-1,2,4-benzotriazine 1,4-dioxide, Aminopterin, Cytosine 1-D-arabinofuranoside, 5-Fluoro-5'-deoxyuridine, 5-Fluorouracil, Ganciclovir, Hydroxyurea, and Mitomycin C; a DNA-RNA transcription regulator, such as Actinomycin D, Daunorubicin, Doxorubicin, Homoharringtonine, and Idarubicin; an enzyme inhibitor, such as S(+)-Camptothecin, Curcumin, (−)-Deguelin, 5,6-Dichlorobenzimidazole 1-β-D-ribofuranoside, Etoposide, Formestane, Fostriecin, Hispidin, 2-Imino-1-imidazoli-dineacetic acid (Cyclocreatine), Mevinolin, Trichostatin A, Tyrphostin AG 34, and Tyrphostin AG 879; a gene regulator, such as 5-Aza-2'-deoxycytidine, 5-Azacytidine, Cholecalciferol (Vitamin D3), 4-Hydroxytamoxifen, Melatonin, Mifepristone, Raloxifene, all trans-Retinal (Vitamin A aldehyde), Retinoic acid, all trans (Vitamin A acid), 9-cis-Retinoic Acid, 13-cis-Retinoic acid, Retinol (Vitamin A), Tamoxifen, and Troglitazone; a microtubule inhibitor, such as Colchicine, Dolastatin 15, Nocodazole, Paclitaxel, Podophyllotoxin, Rhizoxin, Vinblastine, Vincristine, Vindesine, and Vinorelbine (Navelbine); and an unclassified antitumor agent, such as 17-(Allylamino)-17-demethoxygeldanamycin, 4-Amino-1,8-naphthalimide, Apigenin, Brefeldin A, Cimetidine, Dichloromethylene-diphosphonic acid, Leuprolide (Leuprorelin), Luteinizing Hormone-Releasing Hormone, Pifithrin-α, Rapamycin, Sex hormone-binding globulin, Thapsigargin, and Urinary trypsin inhibitor fragment (Bikunin). The antitumor agent may be a monoclonal antibody such as rituximab (Rituxan®), alemtuzumab (Campath®), Ipilimumab (Yervoy®), Bevacizumab (Avastin®), Cetuximab (Erbitux®), panitumumab (Vectibix®), and trastuzumab (Herceptin®), Vemurafenib (Zelboraf®) imatinib mesylate (Gleevec®), erlotinib (Tarceva®), gefitinib (Iressa®), Vismodegib (Erivedge™), 90Y-ibritumomab tiuxetan, 131I-tositumomab, ado-trastuzumab emtansine, lapatinib (Tykerb®), pertuzumab (Perjeta™), ado-trastuzumab emtansine (Kadcyla™), regorafenib (Stivarga®), sunitinib (Sutent®), Denosumab (Xgeva®), sorafenib (Nexavar®), pazopanib (Votrient®), axitinib (Inlyta®), dasatinib (Sprycel®), nilotinib (Tasigna®), bosutinib (Bosulif®), ofatumumab (Arzerra®), obinutuzumab (Gazyva™), ibrutinib (Imbruvica™), idelalisib (Zydelig®), crizotinib (Xalkori®), erlotinib (Tarceva®), afatinib dimaleate (Gilotrif®), ceritinib (LDK378/Zykadia), Tositumomab and 131I-tositumomab (Bexxar®), ibritumomab tiuxetan (Zevalin®), brentuximab vedotin (Adcetris®), bortezomib (Velcade®), siltuximab (Sylvant™), trametinib (Mekinist®), dabrafenib (Tafinlar®), pembrolizumab (Keytruda®)), carfilzomib (Kyprolis®), Ramucirumab (Cyramza™), Cabozantinib (Cometriq™), vandetanib (Caprelsa®), Optionally, the antitumor agent is a neoantigen. The antitumor agent may be a cytokine such as interferons (INFs), interleukins (ILs), or hematopoietic growth factors. The antitumor agent may be INF-α, IL-2, Aldesleukin, IL-2, Erythropoietin, Granulocyte-macrophage colony-stimulating factor (GM-CSF) or granulocyte colony-stimulating factor. The antitumor agent may be a targeted therapy such as toremifene (Fareston®), fulvestrant (Faslodex®), anastrozole (Arimidex®), exemestane (Aromasin®), letrozole (Femara®), ziv-aflibercept (Zaltrap®), Alitretinoin (Panretin®), temsirolimus (Torisel®), Tretinoin (Vesanoid®), denileukin diftitox (Ontak®), vorinostat (Zolinza®), romidepsin (Istodax®), bexarotene (Targretin®), pralatrexate (Folotyn®), lenaliomide (Revlimid®), belinostat (Beleodaq™), lenaliomide (Revlimid®), pomalidomide (Pomalyst®), Cabazitaxel (Jevtana®), enzalutamide (Xtandi®), abiraterone acetate (Zytiga®), radium 223 chloride (Xofigo®), or everolimus (Afinitor®). The antitumor agent may be a checkpoint inhibitor such as an inhibitor of the programmed death-1 (PD-1) pathway, for example an anti-PD1 antibody (Nivolumab). The inhibitor may be an anti-cytotoxic T-lymphocyte-associated antigen (CTLA-4) antibody. The inhibitor may target another member of the CD28 CTLA4 Ig superfamily such as BTLA, LAG3, ICOS, PDL1 or KIR. A checkpoint inhibitor may target a member of the TNFR superfamily such as CD40, OX40, CD137, GITR, CD27 or TIM-3. Additionally, the antitumor agent may be an epigenetic targeted drug such as HDAC inhibitors, kinase inhibitors, DNA methyltransferase inhibitors, histone demethylase inhibitors, or histone methylation inhibitors. The epigenetic drugs may be Azacitidine (Vidaza), Decitabine (Dacogen), Vorinostat (Zolinza), Romidepsin (Istodax), or Ruxolitinib (Jakafi).

The subject may be a mammal, preferably a human. In some embodiments, the subject may be a laboratory animal, such as a mouse, a rabbit, a rat, a guinea pig, a hamster, and a primate.

Methods of Treatment

A third aspect of the present invention provides a method of treating a subject suffering from cancer. In some embodiments, the method comprises performing a prognostic method as described herein and administering an antitumor agent to the subject if no or few regions of neighboring CpG sites having a locally disordered methylation status is identified. Optionally, if the presence or prevalence of regions of neighboring CpG sites having a locally disordered methylation status is identified, the method comprises ceasing or altering treatment with an antitumor agent, or initiating a non-chemotherapeutic treatment (e.g., surgery or radiation).

In some embodiments, the method comprises performing a first prognostic method as described herein; administering an antitumor agent to the subject; and performing a second prognostic method as described herein, wherein the treatment is administered between the first and second prognostic methods. In some embodiments, the method comprises continuing to treat the subject with the antitumor agent if the number of regions of neighboring CpG sites having locally disordered methylation is substantially the same (or, in some instances, is lower than) in the second prognostic method compared to the first prognostic method. In some embodiments, the method comprises ceasing or altering treatment with an antitumor agent, or initiating a non-chemotherapeutic treatment (e.g., surgery or radiation) if the number of regions of neighboring CpG sites having locally disordered methylation is different (e.g., greater than, or in some instances less than) in the second prognostic method compared to the first prognostic method. The antitumor agent may be administered to the subject for at least 3 months, at least 6, months, at least 9 months, at least 12 months, at least 24 months, or at least 36 months before performance of the second prognostic method, preferably at least 12 months.

The methylation status of neighboring CpG sites may be compared by calculating the proportion of discordant reads, calculating variance, calculating epipolymorphism, or calculating information entropy. In some embodiments, a proportion of discordant reads (PDR) is calculated.

The method of treatment may further comprise detecting a genetic mutation. The genetic mutation may be a clonal mutation or a subclonal mutation, preferably a subclonal mutation. In some embodiments, the method comprises treating or continuing to treat the subject with the antitumor agent if no region of neighboring CpG sites having locally disordered methylation status also comprises a genetic mutation or is proximal to a genetic mutation, such as a subclonal mutation. Optionally, the method comprises ceasing or altering treatment with an antitumor agent, or initiating a non-chemotherapeutic treatment (e.g., surgery or radiation) if one or more regions of neighboring CpG sites having locally disordered methylation status also comprises a genetic mutation or is proximal to a genetic mutation, such as a subclonal mutation.

The subclonal genetic mutation may be detected by any method known in the art. For example, the subclonal genetic mutation may be detected by Comparative Genomic Hybridization Array, Multiple Ligation-dependent Probe Amplification, Multiplex Amplifiable Probe Hybridization, Single Condition Amplification/Internal Primer, Multiplex PCR, Southern Blot, Sanger gene sequence, Resequencing Array, mRNA analysis, cDNA sequencing, microarray analysis, whole-genome sequence, massively parallel signature sequencing, Polony sequencing, 454 pyrosequencing, SOLiD sequencing, Illumina dye sequencing, ion semiconductor sequence, DNA nanoball sequencing, heliscope single molecule sequencing, single molecule real time sequencing, nanopore DNA sequencing, tunneling currents DNA sequencing, sequencing by hybridization, sequencing with mass spectrometry, transmission electron microscopy sequencing, and RNA polymerase sequencing, preferably massively parallel signature sequencing.

In some embodiments, the method comprises determining the genomic location of the one or more regions of neighboring CpG sites having locally disordered methylation status. The genomic location may be selected from a CpG island, a CpG shore, a CpG shelf, a promoter, an enhancer, an exon, an intron, a gene body, a stem cell associated region, a short interspersed element (SINE), a long interspersed element (LINE), and a long terminal repeat (LTR), preferably a CpG island or a promoter. Optionally, the method comprises ceasing or altering treatment with an antitumor agent, or initiating a non-chemotherapeutic treatment (e.g., surgery or radiation) if one or more regions of neighboring CpG sites having locally disordered methylation status is located in a CpG island, a promoter or an exon. The method may comprise treating or continuing to treat the subject with the antitumor agent if no region of neighboring CpG sites having locally disordered methylation status is within a CpG island, a promoter, or an exon.

In some embodiments, the method of treatment comprises calculating a PDR from a tumor sample in a subject as described herein, and administering an antitumor agent to the subject if the PDR is less than a PDR threshold, such as 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.38, 0.37, 0.38, 0.39, or 0.40, preferably 0.15. Optionally, the method comprises ceasing or altering treatment with an antitumor agent, or initiating a non-chemotherapeutic treatment (e.g., surgery or radiation) if the PDR is greater than a PDR threshold, such as 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.38, 0.37, 0.38, 0.39, or 0.40, preferably 0.15.

In some embodiments, the method of treatment comprises calculating a first PDR, variance, epipolymorphism or information entropy from a first tumor sample obtained from the subject according to the methods described herein; treating the subject with an antitumor agent; and calculating a second PDR, variance, epipolymorphism or information entropy from a second tumor sample obtained from the subject according to the methods described herein, wherein the antitumor agent is administered between obtaining the first and second tumor samples. The method may comprise continuing to treat the subject with the antitumor agent if the second PDR, variance, epipolymorphism or information entropy has not changed compared to the first PDR. Optionally, the method comprises ceasing or altering treatment with an antitumor agent, or initiating a non-chemotherapeutic treatment (e.g., surgery or radiation) if the second PDR, variance, epipolymorphism or information entropy has changed compared to the first PDR. For example, an increase in PDR may suggest clonal evolution. A decrease in PDR, however, may signal selection of a dominant subclone. A constant PDR may suggest that an antitumor agent is equally effective across subclones. The first and second tumor sample may be from the same tumor.

The subject may be treated with the antitumor agent for at least 3 months, at least 6 months, at least 9 months, at least 12 months, at least 24 months or at least 36 months before calculating the second PDR, variance, epipolymorphism or information entropy, preferably at least 12 months.

The tumor sample may be a solid tumor, such as carcinomas, sarcomas and lymphomas. In some embodiments, the solid tumor is selected from adrenocortical carcinoma, bone tumors, brain cancer, breast cancer, cervical cancer, colorectal carcinoma, desmoid tumors, desmoplastic small round cell tumors, endocrine tumors, esophageal cancer, Ewing sarcoma family tumors, gastric cancer, germ cell tumors, head or neck cancer, hepatoblastoma, hepatocellular carcinoma, lung cancer, melanoma, mesothelioma, nasopharyngeal carcinoma, neuroblastoma, non-rhabdomyosarcoma soft tissue sarcoma, osteosarcoma, ovarian cancer, pancreatic cancer, prostate cancer, retinoblastoma, rhabdomyosarcoma, skin carcinoma, testicular cancer, thyroid carcinoma, uterine cancer and Wilms tumors. The tumor sample may be a hematological cancer, such as leukemia, preferably CLL.

The antitumor agent is selected from an angiogenesis inhibitor, such as angiostatin K1-3, DL-α-Difluoromethyl-ornithine, endostatin, fumagillin, genistein, minocycline, staurosporine, and (±)-thalidomide; a DNA intercaltor/cross-linker, such as Bleomycin, Carboplatin, Carmustine, Chlorambucil, Cyclophosphamide, cis-Diammineplatinum (II) dichloride (Cisplatin), Melphalan, Mitoxantrone, and Oxaliplatin; a DNA synthesis inhibitor, such as (±)-Amethopterin (Methotrexate), 3-Amino-1,2,4-benzotriazine 1,4-dioxide, Aminopterin, Cytosine β-D-arabinofuranoside, 5-Fluoro-5'-deoxyuridine, 5-Fluorouracil, Ganciclovir, Hydroxyurea, and Mitomycin C; a DNA-RNA transcription regulator, such as Actinomycin D, Daunorubicin, Doxorubicin, Homoharringtonine, and Idarubicin; an enzyme inhibitor, such as S(+)-Camptothecin, Curcumin, (−)-Deguelin, 5,6-Dichlorobenzimidazole 1-β-D-ribofuranoside, Etoposide, Formestane, Fostriecin, Hispidin, 2-Imino-1-imidazoli-dineacetic acid (Cyclocreatine), Mevinolin, Trichostatin A, Tyrphostin AG 34, and Tyrphostin AG 879; a gene regulator, such as 5-Aza-2'-deoxycytidine, 5-Azacytidine, Cholecalciferol (Vitamin D3), 4-Hydroxytamoxifen, Melatonin, Mifepristone, Raloxifene, all trans-Retinal (Vitamin A aldehyde), Retinoic acid, all trans (Vitamin A acid), 9-cis-Retinoic Acid, 13-cis-Retinoic acid, Retinol (Vitamin A), Tamoxifen, and Troglitazone; a microtubule inhibitor, such as Colchicine, Dolastatin 15, Nocodazole, Paclitaxel, Podophyllotoxin, Rhizoxin, Vinblastine, Vincristine, Vindesine, and Vinorelbine (Navelbine); and an unclassified antitumor agent, such as 17-(Allylamino)-17-demethoxygeldanamycin, 4-Amino-1,8-naphthalimide, Apigenin, Brefeldin A, Cimetidine, Dichloromethylene-diphosphonic acid, Leuprolide (Leuprorelin), Luteinizing Hormone-Releasing Hormone. Pifithrin-α, Rapamycin, Sex hormone-binding globulin, Thapsigargin, and Urinary trypsin inhibitor fragment (Bikunin). The antitumor agent may be a monoclonal antibody such as rituximab (Rituxan®), alemtuzumab (Campath®), Ipilimumab (Yervoy®), Bevacizumab (Avastin®), Cetuximab (Erbitux®), panitumumab (Vectibix®), and trastuzumab (Herceptin®), Vemurafenib (Zelboraf®) imatinib mesylate (Gleevec®), erlotinib (Tarceva®), gefitinib (Iressa®), Vismodegib (Erivedge™), 90Y-ibritumomab tiuxetan, 131I-tositumomab, ado-trastuzumab emtansine, lapatinib (Tykerb®), pertuzumab (Perjeta™), ado-trastuzumab cmtansine (Kadcyla™), regorafenib (Stivarga®), sunitinib (Sutent®), Denosumab (Xgeva®), sorafenib (Nexavar®), pazopanib (Votrient®), axitinib (Inlyta®), dasatinib (Sprycel®), nilotinib (Tasigna®), bosutinib (Bosulif®), ofatumumab (Arzerra®), obinutuzumab (Gazyva™), ibrutinib (Imbruvica™), idelalisib (Zydelig®), crizotinib (Xalkori®), erlotinib (Tarceva®), afatinib dimaleate (Gilotrif®), ceritinib (LDK378/Zykadia), Tositumomab and 131I-tositumomab (Bexxar®), ibritumomab tiuxetan (Zevalin®), brentuximab vedotin (Adcetris®), bortezomib (Velcade®), siltuximab (Sylvant™), trametinib (Mekinist®), dabrafenib (Tafinlar®), pembrolizumab (Keytruda®)), carfilzomib (Kyprolis®), Ramucirumab (Cyramza™), Cabozantinib (Cometriq™), vandetanib (Caprelsa®), Optionally, the antitumor agent is a neoantigen. The antitumor agent may be a cytokine such as interferons (INFs), interleukins (ILs), or hematopoietic growth factors. The antitumor agent may be INF-α, IL-2, Aldesleukin, IL-2, Erythropoietin, Granulocyte-macrophage colony-stimulating factor (GM-CSF) or granulocyte colony-stimulating factor. The antitumor agent may be a targeted therapy such as toremifene (Fareston®), fulvestrant (Faslodex®), anastrozole (Arimidex®), exemestane (Aromasin®), letrozole (Femara®), ziv-aflibercept (Zaltrap®), Alitretinoin (Panretin®), temsirolimus (Torisel®), Tretinoin (Vesanoid®), denileukin diftitox (Ontak®), vorinostat (Zolinza®), romidepsin (Istodax®), bexarotene (Targretin®), pralatrexate (Folotyn®), lenaliomide (Revlimid®), belinostat (Beleodaq™), lenaliomide (Revlimid®), pomalidomide (Pomalyst®), Cabazitaxel (Jevtana®), enzalutamide (Xtandi®), abiraterone acetate (Zytiga®), radium 223 chloride (Xofigo®), or everolimus (Afinitor®). The antitumor agent may be a checkpoint inhibitor such as an inhibitor of the programmed death-1 (PD-1) pathway, for example an anti-PD1 antibody (Nivolumab). The inhibitor may be an anti-cytotoxic T-lymphocyte-associated antigen (CTLA-4) antibody. The inhibitor may target another member of the CD28 CTLA4 Ig superfamily such as BTLA, LAG3, ICOS, PDL1 or KIR. A checkpoint inhibitor may target a member of the TNFR superfamily such as CD40, OX40, CD137, GITR, CD27 or TIM-3. Additionally, the antitumor agent may be an epigenetic targeted drug such as HDAC inhibitors, kinase inhibitors, DNA methyltransferase inhibitors, histone demethylase inhibitors, or histone methylation inhibitors. The epigenetic drugs may be Azacitidine (Vidaza), Decitabine (Dacogen), Vorinostat (Zolinza), Romidepsin (Istodax), or Ruxolitinib (Jakafi).

The subject may be a mammal, preferably a human. In some embodiments, the subject may be a laboratory animal, such as a mouse, a rabbit, a rat, a guinea pig, a hamster, and a primate.

In another embodiment treatment is consistent with the standard of care for a patient in need thereof. In one embodiment the prognostic methods are used to determine the proper standard of care for a patient in need thereof. The standards of care for the most common cancers can be found on the website of National Cancer Institute (located at cancer.gov/cancertopics). The standard of care is the current treatment that is accepted by medical experts as a proper treatment for a certain type of disease and that is widely used by healthcare professionals. Standard of care is also called best practice, standard medical care, and standard therapy. The prognostic methods of the present invention can be incorporated into a treatment plan by deciding the proper standard of care. The prognostic methods may also be used in treatment plans where the standard of care has changed due to advances in medicine.

In one embodiment the prognostic methods described herein are used to determine the proper treatment in a cancer where the standard of care is primarily surgery followed by treatment to remove possible micro-metastases, such as breast cancer. Breast cancer is commonly treated by various combinations of surgery, radiation therapy, chemotherapy, and hormone therapy based on the stage and grade of the cancer.

In one embodiment the prognostic methods are used to determine the proper treatment consistent with the standard of care in Ductal carcinoma in situ (DCIS). The standard of care for this breast cancer type are:
1. Breast-conserving surgery and radiation therapy with or without tamoxifen.
2. Total mastectomy with or without tamoxifen.
3. Breast-conserving surgery without radiation therapy.

The prognostic methods may be applied to determine whether or not breast conserving surgery or total mastectomy should be performed. In the case where the PDR is below a threshold a treatment plan that includes breast conserving surgery may be chosen. In this case the tumor would be less likely to gain resistance mutations to tamoxifen or radiation. On the contrary, if the tumor has a PDR above the threshold total mastectomy may be chosen.

In another embodiment patients diagnosed with stage I, II, IIIA, and Operable IIIC breast cancer are tested with the prognostic methods as described herein. The standard of care for this breast cancer type are:
1. Local-regional treatment:
   Breast-conserving therapy (lumpectomy, breast radiation, and surgical staging of the axilla).
   Modified radical mastectomy (removal of the entire breast with level I-II axillary dissection) with or without breast reconstruction.
   Sentinel node biopsy.
2. Adjuvant radiation therapy postmastectomy in axillary node-positive tumors:
   For one to three nodes: unclear role for regional radiation (infra/supraclavicular nodes, internal mammary nodes, axillary nodes, and chest wall).
   For more than four nodes or extranodal involvement: regional radiation is advised.
3. Adjuvant systemic therapy In one embodiment the prognostic methods are used to determine the correct surgery type to use. A PDR above the threshold may suggest that the treatment should include a radical mastectomy and a PDR, below the threshold may indicate that breast conserving therapy is chosen. In another embodiment the prognostic methods are used to determine the proper adjuvant therapy.

In another embodiment patients diagnosed with inoperable stage IIIB or IIIC or inflammatory breast cancer are tested with the prognostic methods as described herein. The standards of care for this breast cancer type are:
1. Multimodality therapy delivered with curative intent is the standard of care for patients with clinical stage IIIB disease.
2. Initial surgery is generally limited to biopsy to permit the determination of histology, estrogen-receptor (ER) and progesterone-receptor (PR) levels, and human epidermal growth factor receptor 2 (HER2/neu) overexpression. Initial treatment with anthracycline-based chemotherapy and/or taxane-based therapy is standard. For patients who respond to neoadjuvant chemotherapy, local therapy may consist of total mastectomy with axillary lymph node dissection followed by postoperative radiation therapy to the chest wall and regional lymphatics. Breast-conserving therapy can be considered in patients with a good partial or complete response to neoadjuvant chemotherapy. Subsequent systemic therapy may consist of further chemotherapy. Hormone therapy should be administered to patients whose tumors are ER-positive or unknown. All patients should be considered candidates for clinical trials to evaluate the most appropriate fashion in which to administer the various components of multimodality regimens.

In one embodiment the prognostic methods are used to determine the most appropriate fashion in which to administer the various components of multimodality regimens.

In another embodiment the prognostic methods described herein are used to determine the proper treatment in a cancer where the standard of care is primarily not surgery and is primarily based on systemic treatments, such as CLL.

In another embodiment patients diagnosed with stage 0 Chronic Lymphocytic Leukemia are tested with the prognostic methods as described herein. The standard of care for this cancer type is:
1. Because of the indolent nature of stage 0 chronic lymphocytic leukemia (CLL), treatment is not indicated.

In one embodiment the prognostic methods are used to monitor a patients cancer. In another embodiment a change in PDR may indicate that treatment should be initiated.

In another embodiment patients diagnosed with stage I, II, III, and IV Chronic Lymphocytic Leukemia are tested with the prognostic methods as described herein. The standard of care for this cancer type is:
1. Observation in asymptomatic or minimally affected patients.
2. Rituximab
3. Ofatumomab
4. Oral alkylating agents with or without corticosteroids.
5. Fludarabine, 2-chlorodeoxyadenosine, or pentostatin
6. Bendamustine.
7. Lenalidomide.
8. Combination chemotherapy,
   combination chemotherapy regimens include the following:
   Fludarabine plus cyclophosphamide plus rituximab.
   Fludarabine plus rituximab as seen in the CLB-9712 and CLB-9011 trials.
   Fludarabine plus cyclophosphamide versus fludarabine plus cyclophosphamide plus rituximab.
   Pentostatin plus cyclophosphamide plus rituximab as seen in the MAYO-MC0183 trial, for example.
   Ofatumumab plus fludarabine plus cyclophosphamide.
   CVP: cyclophosphamide plus vincristine plus prednisone.
   CHOP: cyclophosphamide plus doxorubicin plus vincristine plus prednisone.
   Fludarabine plus cyclophosphamide versus fludarabine as seen in the E2997 trial [NCT00003764] and the LRF-CLL4 trial, for example.
   Fludarabine plus chlorambucil as seen in the CLB-9011 trial, for example.
9. Involved-field radiation therapy.
10. Alemtuzumab
11. Bone marrow and peripheral stem cell transplantations are under clinical evaluation.
12. Ibrutinib In one embodiment the prognostic methods are used as a tool to further evaluate the best treatment combination for CLL. In another embodiment the prognostic methods are used to evaluate the best treatment combination for an individual patient in need thereof. In one embodiment a more aggressive treatment strategy is employed when the PDR is above the threshold and in another embodiment a less aggressive treatment strategy is employed.

Methods of Identifying an Antitumor Agent

A fourth aspect of the present invention provides a method for identifying an antitumor agent that decreases the potential evolutionary capacity of cancer (i.e., plasticity) and, thus, the risk of relapse. In some embodiments, the method comprises growing a first culture of hyperproliferative cells and a second culture of hyperproliferative cells, wherein the first culture is grown in the presence of an antitumor agent and the second culture is grown in the absence of the antitumor agent; detecting DNA methylation status at one or more regions of neighboring CpG sites in a plurality of cells from the first culture and a plurality of cells from the second culture; comparing the DNA methylation status of one or more regions of neighboring CpG sites along a sequence of CpG sites in the plurality of cells of the first culture and/or comparing the DNA methylation status of corresponding CpG sites across multiple gene copies in the plurality of cells of the first culture; comparing the DNA methylation status of one or more regions of neighboring CpG sites along a sequence of CpG sites in the plurality of cells of the second culture and/or comparing the DNA methylation status of corresponding CpG sites across multiple gene copies in the plurality of cells in the second culture; and assessing the consistency of methylation status along the sequences of neighboring CpG sites and/or across multiple gene copies in the plurality of cells. For example, the DNA methylation status of CpG sites along one or more sequencing reads, e.g., operatively linked to each other in a single polynucleotide molecule, may be detected. The neighboring CpG sites along the sequencing read may then be compared to each other or to corresponding positions of different sequencing reads (e.g., at the same genomic location) from the plurality of cells. The antitumor agent decreases the potential evolutionary capacity of cancer if the number of regions of neighboring CpG sites having locally disordered methylation status is less in the first culture than in the second culture. In some embodiments, the method comprises calculating a PDR, a variance, an epipolymorphism, or an information entropy in the first and second culture, wherein the antitumor agent decreases the potential evolutionary capacity of cancer if the PDR of the first culture is less than the PDR, the variance, the epipolymorphism, or the information entropy of the second culture. Optionally, each region of neighboring CpG sites (e.g., within a sequencing read) is assigned a consistent status or an inconsistent status before calculating the proportion of discordant reads, variance, epipolymorphism or information entropy. There may be multiple inconsistent statuses, each representing a distinct methylation pattern or class of similar methylation patterns.

In some embodiments, the method comprises treating an animal model of a cancer, wherein a first animal is treated with an antitumor agent and the second animal is treated with a placebo or no antitumor agent; detecting DNA methylation status at one or more regions of neighboring CpG sites in a plurality of cells from the first animal and a plurality of cells from the second animal; comparing the DNA methylation status of neighboring CpG sites along one or more sequences of neighboring CpG sites in DNA of the plurality of cells and/or comparing the DNA methylation status of corresponding CpG sites across multiple gene copies in the plurality of cells of the first animal; comparing the DNA methylation status of neighboring CpG sites along one or more sequences of neighboring CpG sites in DNA of the plurality of cells and/or comparing the DNA methylation status of corresponding CpG sites across multiple gene copies in the plurality of cells of the second animal; and assessing the consistency of methylation status along the sequences of neighboring CpG sites and/or across multiple gene copies in the plurality of cells. The antitumor agent decreases the potential evolutionary capacity of cancer if the level of inconsistent methylation status is less in the first animal than in the second animal. In another embodiment the antitumor agent is administered to more than one cell or animal model using a range of doses. In some embodiments the cancer animal models are selected from the National Cancer Institutes Cancer Model Database (cancermodels.nci.nih.gov/camod/).

The hyperproliferative cells in the first and second cultures may comprise cells from a cell line, e.g., a tumor cell line. Alternatively, the hyperproliferative cells in the first and second cultures may be cells from a tumor sample obtained from a subject, preferably a human, or cells cultured from such a sample. In some embodiments, the first and second cultures are the same culture, wherein the second culture is a sample of the hyperproliferative cells before addition of the antitumor agent and the first culture is a sample of the hyperproliferative cells after addition of the antitumor agent.

The first culture may be cultured in the presence of the antitumor agent for at least 6 hours, at least 12 hours, at least 18 hours, at least one day, at least two days, at least three days, at least four days, at least five days, at least six days or at least one week, preferably at least one day, prior to detecting methylation status.

In some embodiments, the method comprises performing a first prognostic method on a first tumor sample from a subject, such as a laboratory animal, as described herein; administering an antitumor agent to the subject; and performing a second prognostic method on a second tumor sample from the subject as described herein. The antitumor agent decreases the potential evolutionary capacity of cancer if the number of genomic regions having locally disordered methylation status is less in the second tumor sample than in the first tumor sample.

The methylation status of neighboring CpG sites may be compared by calculating the proportion of discordant reads, calculating variance, calculating epipolymorphism, or calculating information entropy. In some embodiments, a proportion of discordant reads (PDR) is calculated. Optionally, each region of neighboring CpG sites (e.g., within a sequencing read) is assigned a consistent status or an inconsistent status before calculating the proportion of discordant reads, variance, epipolymorphism or information entropy. There may be multiple inconsistent statuses, each representing a distinct methylation pattern or class of similar methylation patterns.

In some embodiments, the method comprises calculating a first PDR, variance, epipolymorphism, or information entropy from a first tumor sample obtained from the subject, such as a laboratory animal, according to the methods described herein; treating the subject with an antitumor agent; and calculating a second PDR, variance, epipolymorphism, or information entropy from a second tumor sample obtained from the subject according to the methods described herein, wherein the antitumor agent is administered between obtaining the first and second tumor samples. The antitumor agent decreases the potential evolutionary capacity of cancer if the second PDR, variance, epipolymorphism, or information entropy is less than the first PDR, variance, epipolymorphism, or information entropy.

The antitumor agent may be administered to the subject for at one day, at least two days, at least three days, at least 4 days, at least five days, at least six days, at least one week, at least two weeks, at least three weeks, at least one month, preferably at least one week, e.g., prior to performing the second prognostic method or calculating the second PDR, variance, epipolymorphism, or information entropy.

The tumor sample may be a solid tumor, such as carcinomas, sarcomas and lymphomas. In some embodiments, the solid tumor is selected from adrenocortical carcinoma, bone tumors, brain cancer, breast cancer, cervical cancer, colorectal carcinoma, desmoid tumors, desmoplastic small round cell tumors, endocrine tumors, esophageal cancer, Ewing sarcoma family tumors, gastric cancer, germ cell tumors, head or neck cancer, hepatoblastoma, hepatocellular carcinoma, lung cancer, melanoma, mesothelioma, nasopharyngeal carcinoma, neuroblastoma, non-rhabdomyosarcoma soft tissue sarcoma, osteosarcoma, ovarian cancer, pancreatic cancer, prostate cancer, retinoblastoma, rhabdomyosarcoma, skin carcinoma, testicular cancer, thyroid carcinoma, uterine cancer and Wilms tumors. The tumor sample may be a hematological cancer, such as leukemia, preferably CLL.

The antitumor agent is selected from an angiogenesis inhibitor, such as angiostatin K1-3. DL-α-Difluoromethylornithine, endostatin, fumagillin, genistein, minocycline, staurosporine, and (±)-thalidomide; a DNA intercaltor/cross-linker, such as Bleomycin, Carboplatin, Carmustine, Chlorambucil, Cyclophosphamide, cis-Diammineplatinum (II) dichloride (Cisplatin), Melphalan, Mitoxantrone, and Oxaliplatin; a DNA synthesis inhibitor, such as (±)-Amethopterin (Methotrexate), 3-Amino-1,2,4-benzotriazine 1,4-dioxide, Aminopterin, Cytosine β-D-arabinofuranoside, 5-Fluoro-5'-deoxyuridine, 5-Fluorouracil, Ganciclovir, Hydroxyurea, and Mitomycin C; a DNA-RNA transcription regulator, such as Actinomycin D, Daunorubicin, Doxorubicin, Homoharringtonine, and Idarubicin; an enzyme inhibitor, such as S(+)-Camptothecin, Curcumin, (−)-Deguelin, 5,6-Dichlorobenzimidazole 1-β-D-ribofuranoside, Etoposide, Formestane, Fostriecin, Hispidin, 2-Imino-1-imidazoli-dineacetic acid (Cyclocreatine), Mevinolin, Trichostatin A, Tyrphostin AG 34, and Tyrphostin AG 879; a gene regulator, such as 5-Aza-2'-deoxycytidine, 5-Azacytidine, Cholecalciferol (Vitamin D3), 4-Hydroxytamoxifen, Melatonin, Mifepristone, Raloxifene, all trans-Retinal (Vitamin A aldehyde), Retinoic acid, all trans (Vitamin A acid), 9-cis-Retinoic Acid, 13-cis-Retinoic acid, Retinol (Vitamin A), Tamoxifen, and Troglitazone; a microtubule inhibitor, such as Colchicine, Dolastatin 15, Nocodazole, Paclitaxel, Podophyllotoxin, Rhizoxin, Vinblastine, Vincristine, Vindesine, and Vinorelbine (Navelbine); and an unclassified antitumor agent, such as 17-(Allylamino)-17-demethoxygeldanamycin, 4-Amino-1,8-naphthalimide, Apigenin, Brefeldin A, Cimetidine, Dichloromethylene-diphosphonic acid, Leuprolide (Leuprorelin), Luteinizing Hormone-Releasing Hormone, Pifithrin-α, Rapamycin, Sex hormone-binding globulin, Thapsigargin, and Urinary trypsin inhibitor fragment (Bikunin). The antitumor agent may be a monoclonal antibody such as rituximab (Rituxan®), alemtuzumab (Campath®), Ipilimumab (Yervoy®), Bevacizumab (Avastin®), Cetuximab (Erbitux®)), panitumumab (Vectibix®), and trastuzumab (Herceptin®), Vemurafenib (Zelboraf®) imatinib mesylate (Gleevec®), erlotinib (Tarceva®), gefitinib (Iressa®), Vismodegib (Erivedge™), 90Y-ibritumomab tiuxetan, 131I-tositumomab, ado-trastuzumab emtansine, lapatinib (Tykerb®), pertuzumab (Perjeta™), ado-trastuzumab emtansine (Kadcyla™), regorafenib (Stivarga®), sunitinib (Sutent®), Denosumab (Xgeva®), sorafenib (Nexavar®), pazopanib (Votrient®), axitinib (Inlyta®), dasatinib (Sprycel®), nilotinib (Tasigna®), bosutinib (Bosulif®), ofatumumab (Arzerra®), obinutuzumab (Gazyva™), ibrutinib (Imbruvica™), idelalisib (Zydelig®), crizotinib (Xalkori®), erlotinib (Tarceva®), afatinib dimaleate (Gilotrif®), ceritinib (LDK378/Zykadia), Tositumomab and 131I-tositumomab (Bexxar®), ibritumomab tiuxetan (Zevalin®), brentuximab vedotin (Adcetris®), bortezomib (Velcade®), siltuximab (Sylvant™), trametinib (Mekinist®), dabrafenib (Tafinlar®), pembrolizumab (Keytruda®)), carfilzomib (Kyprolis®), Ramucirumab (Cyramza™), Cabozantinib (Cometriq™), vandetanib (Caprelsa®), Optionally, the antitumor agent is a neoantigen. The antitumor agent may be a cytokine such as interferons (INFs), interleukins (ILs), or hematopoietic growth factors. The antitumor agent may be TNF-α, IL-2, Aldesleukin, IL-2, Erythropoietin, Granulocyte-macrophage colony-stimulating factor (GM-CSF) or granulocyte colony-stimulating factor. The antitumor agent may be a targeted therapy such as toremifene (Fareston®), fulvestrant (Faslodex®), anastrozole (Arimidex®), exemestane (Aromasin®), letrozole (Femara®), ziv-aflibercept (Zaltrap®), Alitretinoin (Panretin®), temsirolimus (Torisel®), Tretinoin (Vesanoid®), denileukin diftitox (Ontak®), vorinostat (Zolinza®), romidepsin (Istodax®), bexarotene (Targretin®), pralatrexate (Folotyn®), lenaliomide (Revlimid®), belinostat (Beleodaq™), lenaliomide (Revlimid®), pomalidomide (Pomalyst®), Cabazitaxel (Jevtana®), enzalutamide (Xtandi®), abiraterone acetate (Zytiga®), radium 223 chloride (Xofigo®), or everolimus (Afinitor®). The antitumor agent may be a checkpoint inhibitor such as an inhibitor of the programmed death-1 (PD-1) pathway, for example an anti-PD1 antibody (Nivolumab). The inhibitor may be an anti-cytotoxic T-lymphocyte-associated antigen (CTLA-4) antibody. The inhibitor may target another member of the CD28 CTLA4 Ig superfamily such as BTLA, LAG3, ICOS, PDL1 or KIR. A checkpoint inhibitor may target a member of the TNFR superfamily such as CD40, OX40, CD137, GITR, CD27 or TIM-3. Additionally, the antitumor agent may be an epigenetic targeted drug such as HDAC inhibitors, kinase inhibitors, DNA methyltransferase inhibitors, histone demethylase inhibitors, or histone methylation inhibitors. The epigenetic drugs may be Azacitidine (Vidaza), Decitabine (Dacogen), Vorinostat (Zolinza), Romidepsin (Istodax), or Ruxolitinib (Jakafi).

In some embodiments, the laboratory animal is a mouse, a rabbit, a rat, a guinea pig, a hamster, or a primate.

An unexpected advantage of the present invention is that the treatment of a patient in need thereof is greatly improved and personalized based on the analysis of DNA methylation discordance. The analysis is based on an unexpected fundamental difference between cancer and normal methylomes: locally disordered methylation arising from a stochastic process, that leads to a high degree of intra-sample methylation heterogeneity.

Another advantage is that the methods of the present invention allow a patient's tumor to be evaluated for stochastic methylation changes that enhance epigenetic plasticity and likewise enable tumor cells to better explore the evolutionary space in search of superior fitness trajectories. Treatment regimens that include this analysis can be made more or less aggressive or use different modalities.

The present invention provides improved methods to identify fitness-enhancing differentially methylated regions.

Although the present invention and its advantages have been described in detail, it should be understood that various changes, substitutions and alterations can be made herein without departing from the spirit and scope of the invention as defied in the appended claims.

The present invention will be further illustrated in the following Examples which are given for illustration purposes only and are not intended to limit the invention in any way.

EXAMPLES

Example 1

Genetic Heterogeneity is Associated with Clonal Evolution

Figure 1B:
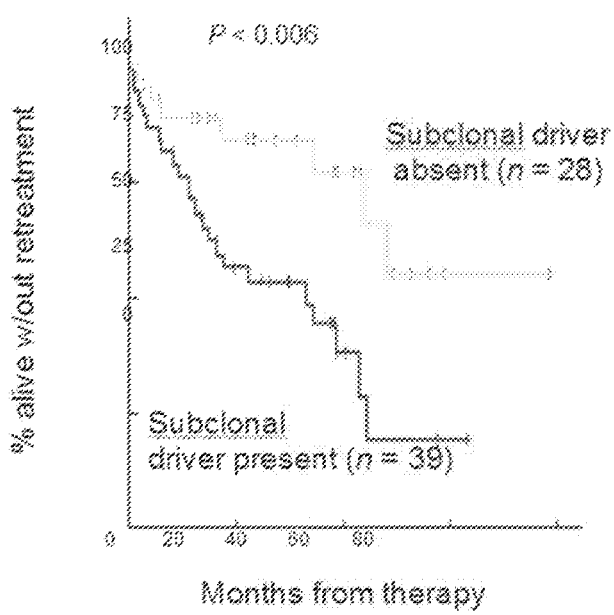

Applicants used an analytic approach in which whole-exome sequencing (WES) was used to infer the fraction of cancer cells (CCF) that harbors each somatic mutation in 149 CLLs by correcting the allelic fraction measured by WES for sample purity and local copy number at the mutated sites. To directly assess clonal evolution (FIG. 1A), Applicants compared CCF for each mutation at 2 time points in 18 CLL cases (median interval between time points 3.5 yrs.). Applicants observed a higher rate of clonal evolution in 12 cases that received treatment between time points compared with 6 continuously untreated cases (P=0.012). Clonal evolution involved the expansion of subclones that harbored mutations highly enriched in driver mutations. These subclonal driver mutations were often already detectable in the pretreatment sample (red clusters, FIG. 1A right). Applicants therefore hypothesized that the pretreatment detection of subclonal drivers would be associated with worse clinical outcome with treatment. Indeed, in a cohort of 67 CLL patients who received CLL treatment, the detection of a subclonal driver mutation was associated with earlier retreatment or death, indicative of a more aggressive disease course (independently of known risk factors, P=0.006, FIG. 1B). Thus, the pre-treatment identification of subclonal mutations can provide information regarding the rapidity and genetic composition of the relapsing leukemia.

Example 2

DNA Methylation Heterogeneity in CLL

While investigations of evolutionary dynamics in cancer have focused primarily on the role of genetic alterations, epigenetic modifications are likely also responsible for the phenotypic differences that ultimately affect fitness.

Applicants therefore assessed the degree of DNA methylation heterogeneity in CLL. Applicants performed a re-analysis of a published set of DNA methylation arrays (Kulis M, et al. Nat Genet, 2012; 44:1236-42) and found that the 127 CLL samples showed a higher degree of DNA methylation heterogeneity compared with 25 normal B cell samples (FIG. 2A-B). Applicants confirmed the higher heterogeneity in CLL by reanalyzing published whole genome bisulfite sequencing (WGBS) data (FIG. 2C). Applicants also studied this question with reduced representation bisulfite sequencing (RRBS) which allowed the use of MPS technology to study DNA methylation in larger cohorts. Applicants found higher methylation heterogeneity in CLL by comparing the mean weighted variance of ~2.5 million CpGs in 101 CLL samples vs. 22 normal B cell samples (FIG. 2D). Similar to other lymphoid malignancies and solid tumors, these data robustly demonstrate that CLL contains increased genome-wide methylation heterogeneity compared with normal B cells.

Example 3

Increased Intra-Sample DNA Methylation Heterogeneity in CLL Arises from Locally Disordered Methylation To measure intra-sample CLL DNA methylation heterogeneity. Applicants compared WGBS data generated from two CLL cases and two healthy donor B cell samples (FIG. 3A). Applicants observed globally decreased methylation in CLL compared to normal B cells, with focally increased methylation of CpG islands (CGI) (FIG. 3A—top, FIG. 4A-C), as previously reported in CLL and other cancers (Baylin and Jones, 2011; Kulis et al., 2012), but also a markedly increased frequency of intermediate methylation values in CLL (FIG. 3A-bottom, FIG. 4A-D), pointing to a large proportion of CpGs that are methylated in some cells in the sample and unmethylated in others. Applicants reanalyzed published WGBS and 450K methylation array data (Kulis et al., 2012) and confirmed the increased cell-to-cell variability in CpG methylation in CLL compared to normal B cells (FIG. 4E-H).

Figure 3B:
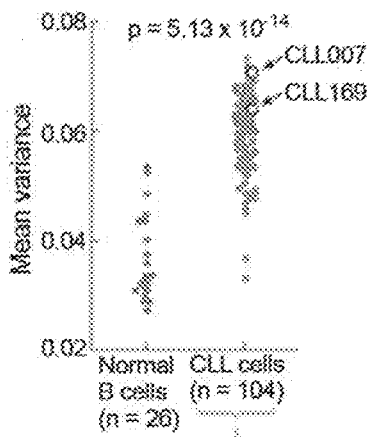
Figure 3C:
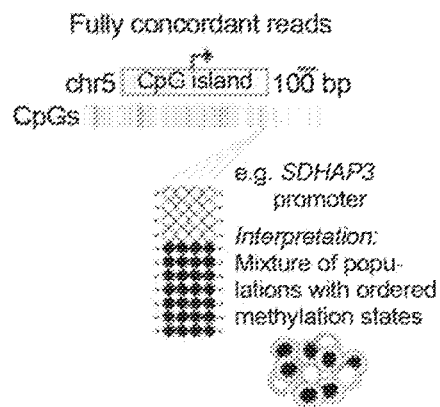
Figure 3D:
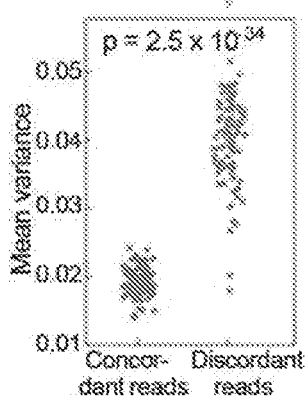

Applicants next applied RRBS to 104 primary CLL samples that had been previously characterized by WES (Landau et al., 2013) (Table 1), and examined mean CpG variance. Consistent with the WGBS data, a greater than 50% increase in intra-sample methylation heterogeneity was detected in CLL cells compared to 26 normal B cell samples ($p=5.13\times10-14$; FIG. 3B). Applicants considered two possible sources for intra-sample heterogeneity: variability between concordantly methylated fragments (i.e., whereby CpGs in an individual fragment are consistently methylated or unmethylated; FIG. 3C, left); or variability within DNA fragments (i.e., discordant methylation by which CpGs in an individual fragment are variably methylated; FIG. 3C, right).

Figure 4D:
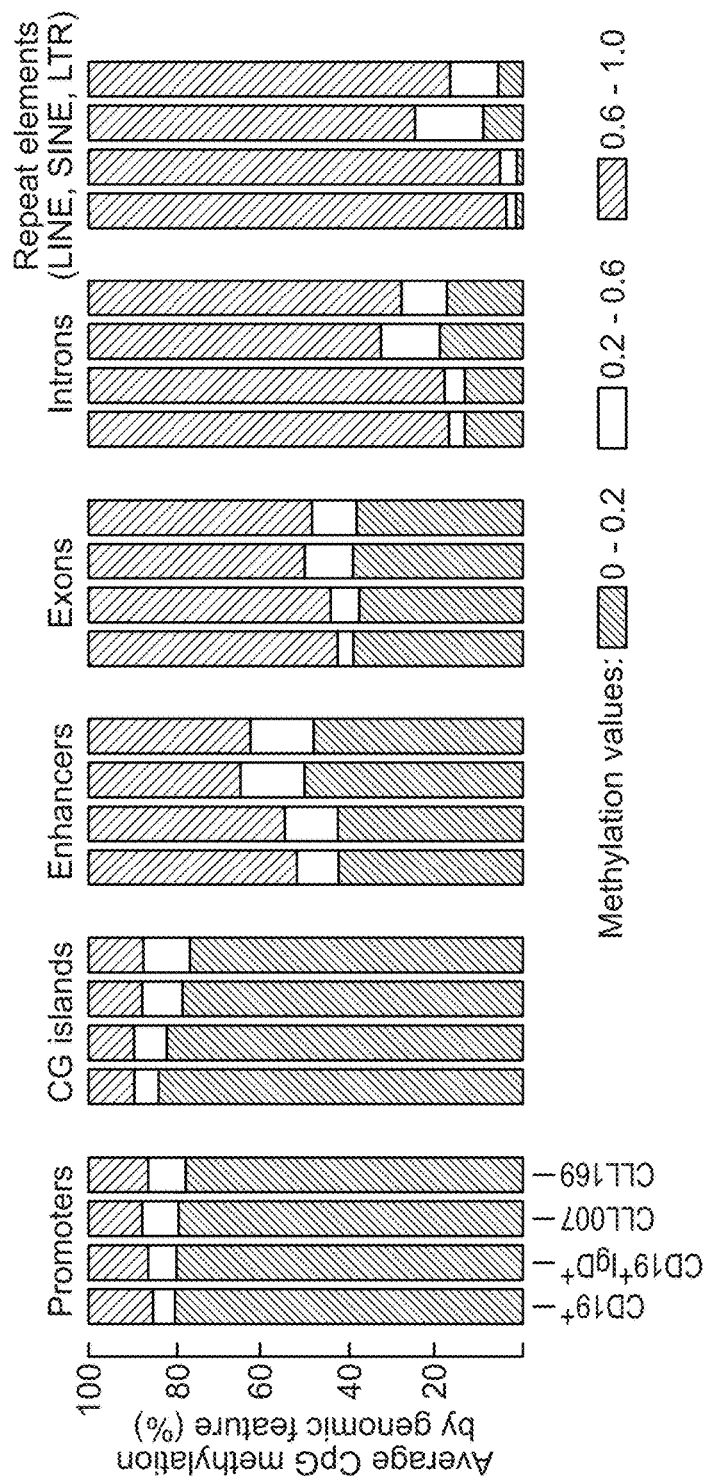
FIG. 4A-O illustrates WGBS and RRBS data from CLLs and normal B cells shows higher Intratumoral DNA methylation heterogeneity that arises from locally disordered methylation. A-C (top). The genome was divided into 1 KB tiles. The analysis was limited to tiles that contained at least 5 CpGs covered with greater than 5 reads. The scatter plots enable the examination of the methylation patterns consistency of the two B cell samples (A), and the two CLL samples (B). Note that the somewhat decreased methylation in CLL007 perhaps results from the DNMT3A nonsense mutation affecting this tumor. A comparison between the average methylation values across the genome in CLL and normal B cells is also shown (C). A-C (bottom). The proportion of genomic 1 KB tiles with intermediate values is compared between CLL and normal B cells. D. The percentage of methylation values falling within each category (0-0.2, 0.2-0.6, 0.6-1.0) is shown for the 4 WGBS samples for different genomic features. Number of CpGs per sample per feature (mean [range]): Promoters—1,737,131 [1,728,620-1,747,890], CG islands—2,031,560 [2,025,376-2,044,203], enhancers—865,820 [860,997-870,134], exons—1,489,549 [1,483,138-1,493,987], introns—6,691,529 [6,599,956-6,739,995] and repeat elements—7,301,495 [7,163,887-7,368,831]. E. Reanalysis of WGBS data (Kulis et al., 2012) for the frequency of CpGs with intermediate methylation in CLL samples compared with B cells from healthy adult volunteers. Shown are cumulative distributions of CpG methylation values in unmutated IGHV CLL compared with naive B cells (left), as well as for mutated IGHV CLL vs. memory B cells (cs—class switched) (middle). The intratumoral DNA methylation heterogeneity in CLL from discordant reads (solid line) versus concordant reads (dashed) (right, analysis of WGBS data from CLL169). F. Histograms of individual normal B cell samples (blue) show bimodal distribution in methylation values as measured by DNA 450K methylation arrays (Kulis et al., 2012), while CLL samples (red) show more CpGs with intermediate methylation values, diverging from a pure bimodal distribution. G-H. Violin plots comparing the proportion of intermediate methylation values from 450K array data (Kulis et al. (Kulis et al., 2012)) from 127 CLL samples and 26 normal B cell samples (beta methylation values between 0.35 and 0.65, average±SEM, 13.7±0.002% vs. 10.1±0.01%, respectively, $p=5 \times 10^{-8}$, Wilcoxon rank sum test). I. While overall purity of the CLL samples was consistently high (median of 90.2%), contaminating non-malignant cells in samples may contribute to the PDR, Applicants therefore compared the PDR in CLL samples with high vs. low tumor purity (above and below the overall average; 86.6%). J. Stochastic disorder in methylation patterns is expected to yield discordant reads that involve both parental alleles in a given locus (in contrast to an allele-specific methylation (ASM) phenomenon). We therefore measured the proportion of germline SNPs for which a discordant read is found to involve both parental alleles (Y axis). As expected, with an increasing number of discordant reads in the studied locus (X axis), the proportion of SNPs with a discordant read involving both parental alleles increases and converges towards 1. K. Even within a given genotype, different methylation patterns were seen. For example, in the left most panel, 3 distinct methylation patterns are seen to affect both the A genotype parental allele and the G genotype parental allele. L. Applicants measured the number of distinct discordant methylation patterns found in each locus (similar to a previous analysis (Landan et al., 2012)). Presence of 1 or 2 patterns of discordancy across all reads covered for a particular locus would be expected of ASM. The plot shows the distribution of the number of methylation patterns in loci with 10-20 discordant reads across 10 randomly selected CLL and normal B cell samples. The distribution shows that there are generally more than 2 discordant methylation patterns per locus for both normal (blue) and CLL (red) samples. In addition, the high number of distinct methylation profiles per locus excludes also the possibility that PDR arises from reads that cover an ordered transition point from one methylation state to another. The shaded distribution (grey) shows the number of distinct patterns if the state of CpG methylation was purely random (with equal frequencies of the number of reads as in the experimental data). The finding that the measured distribution demonstrates less distinct patterns than purely random is consistent with inheritance of discordant patterns to progeny cells. M. To assess for possible amplification biases, the allelic frequencies of germline SNP not involving CpGs was measured and shows a tight distribution around 0.5 compatible with limited amplification biases. N. To assess for possible amplification biases, the methylation of imprinted control regions was measured and shows a tight distribution around 0.5 compatible with limited amplification biases. O. Similar PDR values are seen in regions of somatic copy number variations (sCNV) in the two CLLs that underwent WGBS (CLL169 and CLL007), both for promoter CpGs (top) and for all CpGs (bottom).
Figure 4E:
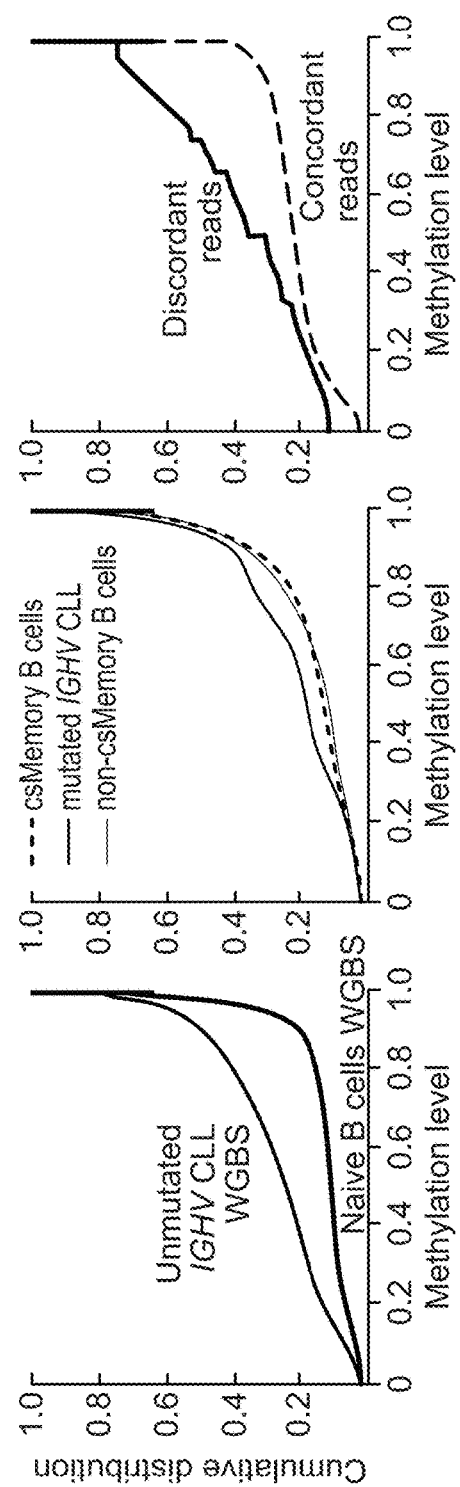

Based on established observations that short-range methylation is highly correlated in normal physiological states (Eckhardt et al., 2006; Jones, 2012), Applicants initially hypothesized that intra-sample heterogeneity in CLL stems from variability between concordantly methylated fragments, reflecting a mixture of subpopulations with distinct but uniform methylation patterns. To test this, Applicants focused on CpGs covered by reads containing 4 or more neighboring CpGs, as previously suggested (Landan et al., 2012), and with sufficient read depth (greater than 10 reads per CpG, with ~6.5 million CpGs/sample covered by 100mer WGBS reads, and an average of 307,041 [range 278.105-335,977] CpGs/sample covered by 29mer RRBS reads). Contrary to the expected hypothesis, Applicants found that 67.6±3.2% (average±SD) of the intra-tumoral methylation variance resulted from discordantly methylated reads across the 104 CLL samples (FIG. 3D; $p=3.24\times10-35$). Similarly, the CLL WGBS confirmed a higher proportion of heterogeneously methylated CpGs in the discordant reads compared with the concordant reads (FIG. 4E, right). These results demonstrate that methylation heterogeneity in CLL primarily arises from variability within DNA fragments, which Applicants have therefore termed 'locally disordered methylation'.

Applicants performed several analyses to exclude potential alternative explanations to these findings, including the impact of contaminating non-malignant cells (FIG. 4I), allele-specific methylation (FIG. 4J-L), the contribution of reads that cover an ordered transition point from one methylation state to another (FIG. 9L) and technical biases (sec Methods). The sex chromosomes were excluded from this analysis to avoid possible confounding sex-chromosome specific effects. In addition, CLL genomes are near diploid (Brown et al., 2012), and therefore the analysis was not significantly impacted by somatic copy number variations (see methods, FIG. 4O).

Figure 3E:
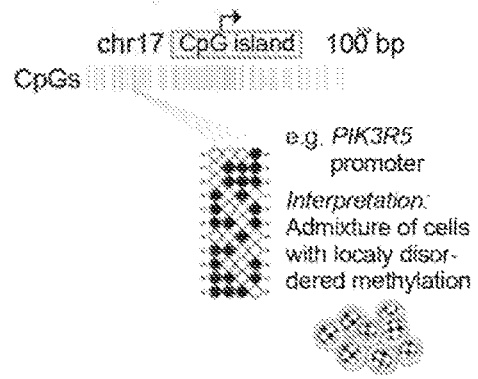
Figure 3E:
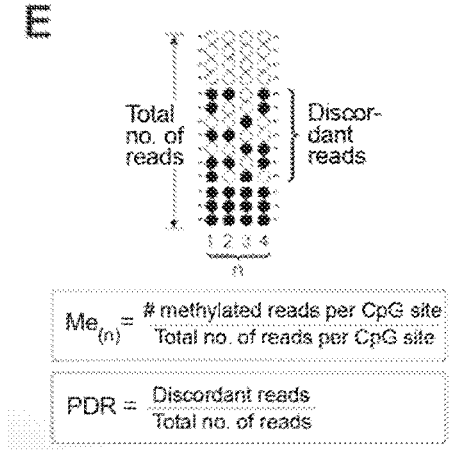
Figure 3F:
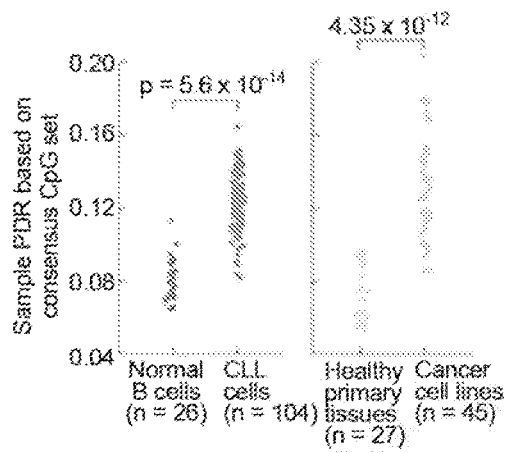

To quantify the magnitude of this phenomenon across large collections of normal and malignant human tissues, Applicants analyzed RRBS data not only from the 104 CLL and 26 B cells samples, but also from 45 solid and blood cancer cell lines and from 27 primary human tissue samples. Applicants then calculated the proportion of discordant reads (PDR) as the number of discordant over the total number of reads for each CpG in the consensus set (FIG. 3E). Applicants found that the average PDR was higher in CLL compared to normal B cells (p=5.60×10−14). Similarly, Applicants found higher PDR in cancer cell lines compared to a diverse collection of healthy human tissue samples (p=4.35×10−12, FIG. 1F). These results support the idea that locally disordered methylation is a general property of the malignant process.

TABLE 1

Characteristics and mean promoter PDR of the 104 CLL patients whose DNA were analyzed by WES and RRBS.

|  | N (%) | Mean Promoter PDR (SD) | p value[†] |
|---|---|---|---|
| N | 104 |  |  |
| Age (median = 54 yrs) |  |  |  |
| <54 yrs. | 46 (44) | 0.101 (0.016) | 0.15 |
| ≥54 yrs. | 58 (56) | 0.105 (0.016) |  |
| Sex |  |  |  |
| Female | 38 (37) | 0.106 (0.016) |  |
| Male | 66 (63) | 0.102 (0.016) | 0.30 |
| Rai Stage at Sample |  |  |  |
| 0-1 | 78 (75) | 0.102 (0.016) | 0.049 |
| 2-4 | 26 (25) | 0.109 (0.015) |  |
| Treatment Status at time of Sample |  |  |  |
| Chemotherapy naïve | 82 (79) | 0.103 (0.017) | 0.59 |
| Prior Treatment | 22 (21) | 0.105 (0.014) |  |
| IGHV status |  |  |  |
| Mutated | 57 (55) | 0.107 (0.017) | 0.035 |
| Not Mutated | 34 (33) | 0.0996 (0.014) |  |
| Unknown | 13 (13) | 0.0977 (0.014) |  |
| FISH Cytogenetics[††] |  |  |  |
| del(13q) present | 67 (67) | 0.105 (0.016) | 0.059 |
| absent | 33 (33) | 0.099 (0.016) |  |
| Trisomy 12 present | 18 (18) | 0.099 (0.015) | 0.21 |
| absent | 82 (82) | 0.104 (0.016) |  |
| del(11q) present | 18 (18) | 0.095 (0.013) | 0.019 |
| absent | 82 (82) | 0.105 (0.016) |  |
| del(17p) present | 14 (14) | 0.105 (0.016) | 0.62 |
| absent | 86 (86) | 0.103 (0.016) |  |
| Mutational Status |  |  |  |
| Subclonal Mutation Present | 49 (47) | 0.105 (0.016) | 0.25 |
| Absent | 55 (53) | 0.102 (0.016) |  |
| TP53 Present | 15 (14) | 0.110 (0.016) | 0.091 |
| Absent | 89 (86) | 0.102 (0.016) |  |
| NOTCH1 Present | 11 (11) | 0.096 (0.016) | 0.097 |
| Absent | 93 (89) | 0.104 (0.016) |  |
| SF3B1 Present | 9 (9) | 0.108 (0.015) | 0.36 |
| Absent | 95 (90) | 0.103 (0.016) |  |
| MYD88 Present | 8 (8) | 0.111 (0.009) | 0.19 |
| Absent | 96 (92) | 0.103 (0.016) |  |
| ATM Present | 6 (6) | 0.112 (0.017) | 0.18 |
| Absent | 98 (94) | 0.103 (0.016) |  |

[†]Testing excludes unknown categories; Welch t-test (variances were not significantly different);
[††]N = 100

Example 4

Epigenetic Variation in CLL is Predominantly Locally Disordered DNA Methylation

Heterogeneity could arise from two possible methylation patterns: 1) mixing of two subpopulations with ordered but distinct methylation states for a particular locus (FIG. 5A left), or 2) admixture of cells with "noisy" disordered methylation at the particular CpG locus (FIG. 5A right). The ability to distinguish between the two relies on the fact that short-range methylation state concordance between neighboring CpGs is expected to be very high in non-disease states, as DNA methylation typically changes by feature (e.g., a specific gene promoter, or a CpG island) rather than by individual CpG. Applicants therefore studied the concordance of methylation status across multiple CpGs contained within an individual 29-bp long sequencing read, and compared the relative contribution of concordant vs. discordant reads to the overall variance. Applicants observed a significantly larger contribution from locally disordered methylation seen in CLL in the RRBS data (FIG. 5B). Applicants also defined the proportion of discordant reads (PDR) for each CpG as a simple measure of locally disordered DNA methylation (FIG. 5C).

Applicants next identified the genomic elements affected by locally disordered methylation. The increase in the PDR in CLL compared to normal samples was prominent in most genomic elements (FIG. 6A), with a more marked degree of change in CpG islands (CGI) compared with their shelves or shores (FIG. 6B). In addition, Applicants studied RRBS data of 50 cancer cell lines (from solid and hematological malignancies included in the CCLE collection) and 32 samples from various normal human tissues, and showed that while locally disordered DNA methylation exists in normal differentiated cells, it is significantly higher in both CLLs and cancer cell lines (FIG. 6C). Performing a similar analysis in WGBS allowed Applicants to probe genomic areas that are not well covered by RRBS. Repetitive regions, showed a marked increase in PDR in CLL, as did the large hypomethylated blocks (FIG. 6D).

While CLLs tended to have uniformly high PDR, the mean-weighted PDR varied between 0.186 and 0.265. RRBS covers, on average, ~2.5 million CpGs, which are enriched in regions important for transcriptional regulation. Therefore, even small differences may signify changes affecting thousands of CpGs genome-wide. For example, when comparing within CLL samples, Applicants found that older age at diagnosis (age>median) was associated with an increase in PDR (average+/−95% CI, 0.24+/−0.005 vs. 0.23+/−0.005, P=0.028), consistent with data showing that aging in itself is associated with epigenetic drift, and suggesting that some of the local methylation disorder may originate prior to the malignant transformation in the leukemia initiating cell. Other clinical factors were not associated with significant differences (e.g., the IGHV mutation status, an important predictor of poor outcome in CLL showed no association with PDR [P=0.175]). Samples with somatic mutations in methylation modulators (DNMT3A, TET1, and IDH1, each n=1) had increased PDR compared with 98 wild type samples (0.251+/−0.01 vs. 0.228+/−0.004, P=0.027). These data suggest that a genotype enhancing the potential for epigenetic drift may be selected for, as was seen in other malignancies. When compared to normal B cells samples (n=32), several methylation regulators were significantly differentially expressed in CLL (n=247) by expression array analysis (Q<0.1, FDR). In particular, although DNMT1 was up-regulated by 2.25-fold in CLL (consistent with reports across cancer37), DNMT3B and TET1 were down-regulated by 3- and 7-fold, respectively. This latter finding suggests that several enzymes that regulate DNA methylation are down-regulated compared to normal B cells, and may contribute to the increase in locally disordered methylation. These results are consistent with previous reports in lymphoid malignancies that suggest that DNMT3A and DNMT3B inhibition may promote the lympho-proliferative process. Collectively, we show that much of the heterogeneity of DNA methylation in CLL results from locally disordered methylation. This form of epigenetic drift may cause some of the epigenetic alterations seen in CLL and cancer.

Example 5

Locally Disordered Methylation Broadly Affects the CLL Genome

To determine whether specific elements in the genome harbor higher levels of locally disordered methylation in CLL compared to normal B cells, Applicants calculated the average PDR across the 104 CLL samples and 26 healthy donor B cell samples (Table 2).

Figure 7A:
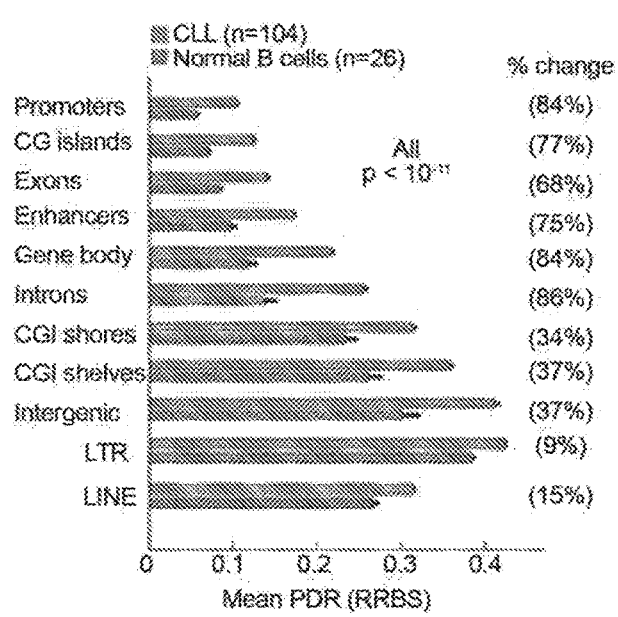
FIG. 7A-C illustrates that locally disordered methylation affects all genomic regions in CLL, including CpG islands (CGIs) and repeat regions. Comparison of mean PDR (A) and mean CpG methylation (B) per genomic region between CLLs and normal B cells using RRBS data (Table 2 provides the average number of CpGs analyzed for each genomic region). Error bars represent upper 95% CI of the mean. C. Top—The distribution of PDR and methylation across all promoters covered by RRBS for randomly selected 6 CLL and 6 normal B cell samples. The distribution was derived by dividing each promoter into 100 bins, and then averaging methylation and PDR for CpGs falling into each bin across all promoters in the sample. The PDR and methylation values in the adjacent 2 KB upstream and downstream are also shown. Bottom—An analogous analysis of CGIs and adjacent shore regions.
Figure 7B:
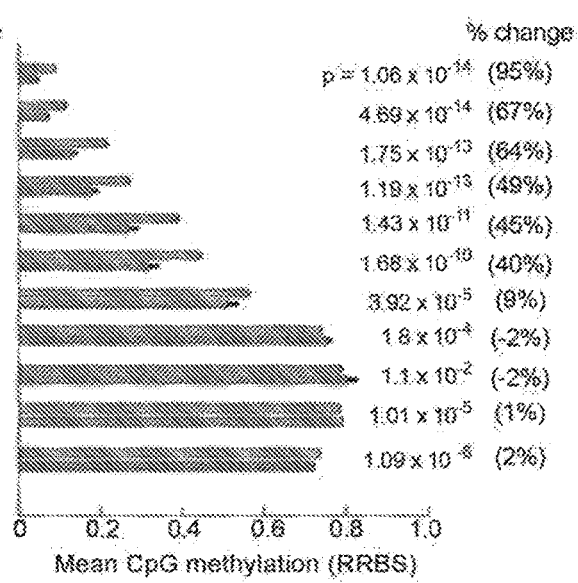
Figure 7C:
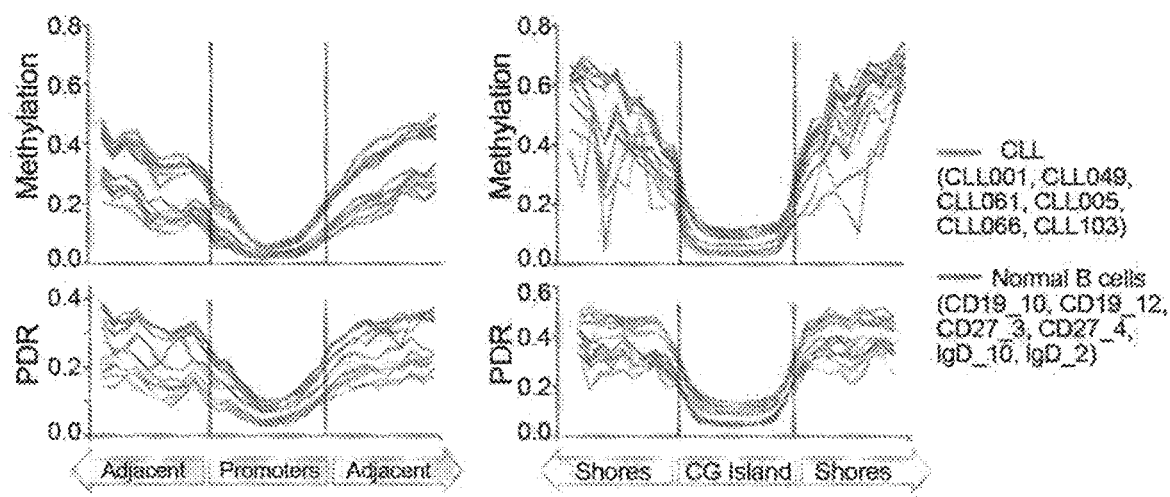
Figure 8A:
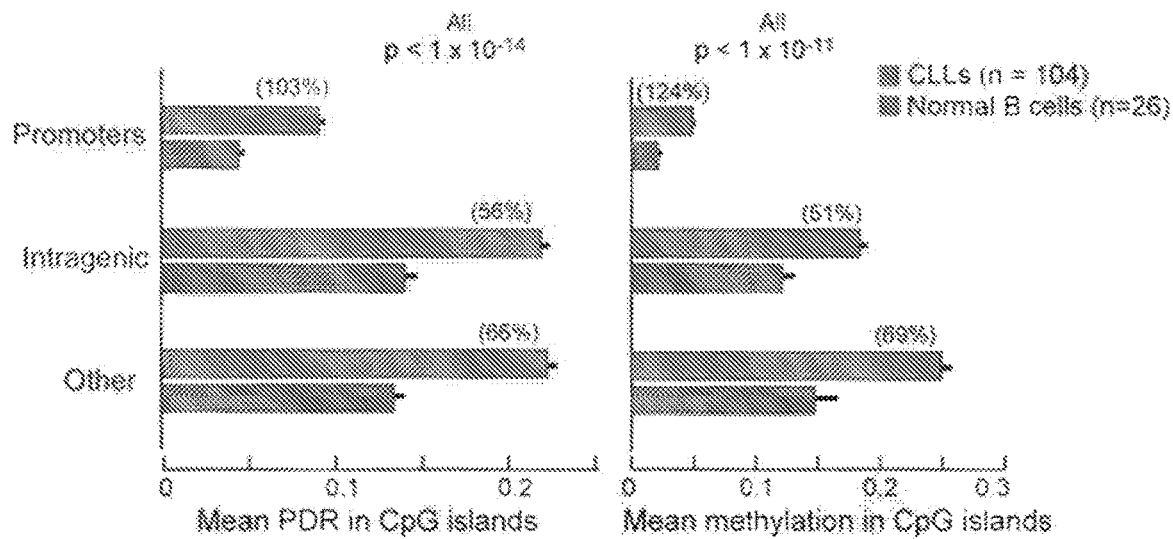
FIG. 8A-C illustrates genomic characterization of locally disordered methylation including analysis of CpG island subtypes and repeat elements based on WGBS. A. Increase in PDR with concomitant increase in methylation in 104 CLLs compared to 26 B cell samples affects all 3 major categories of CpG islands (CGIs: promoters, intragenic, other). B. WGBS based analysis of the 2 CLL samples (CLL007 and CLL169), compared with 2 normal B cell samples (Normal_CD19_1 and Normal_IGD_3) showing increased PDR in repeat elements concomitant with decreased methylation. Comparison between PDR and methylation values individually between each CLL sample and each normal B cell sample yielded a statistically significant difference ($p<1\times10^{-32}$). C. The three of 104 CLL samples with nonsilent mutations in methylation modulators (DNMT3A-Q153*, TET1-N7891, IDH1-S210N) revealed high average PDR by RRBS compared to samples with wildtype alleles for these genes.
Figure 8B:
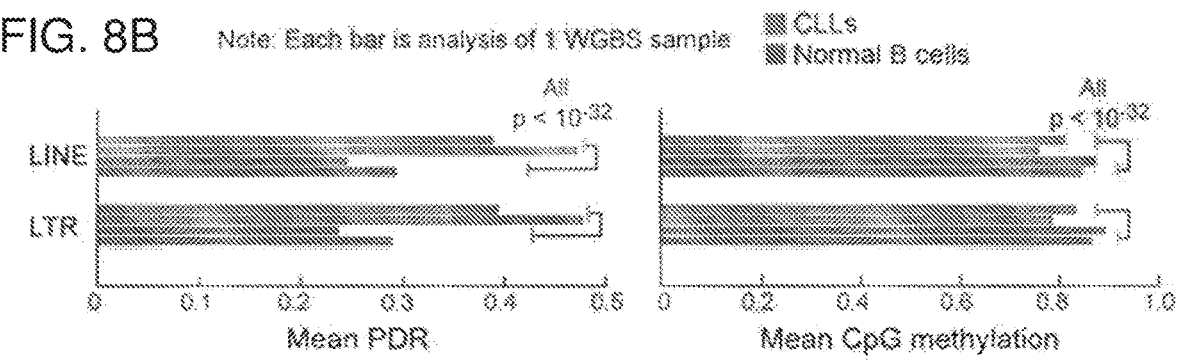

In normal B cells, PDR levels were lowest in regions with a major role in gene regulation (promoters, CGI, exons, enhancers), and higher in regions with presumably less of a regulatory role (CGI shelves and shores, intergenic regions). In CLL. PDR was higher across all measured regions (FIG. 7A), regardless of whether they were relatively hypermethylated (e.g. CGI) or hypomethylated (e.g. intergenic regions) compared to normal B cells (FIG. 7B). This phenomenon appeared to be neither specific to a sub-region of CGIs or promoters (for example, CGI borders, FIG. 7C), nor restricted to a subtype of CGI (FIG. 8A). Increased PDR in CLL was also observed in highly repetitive DNA sequences (e.g., long interspersed elements [LINE] and long terminal repeat [LTR] retrotransposons; FIG. 7A-RRBS data and FIG. 8B—WGBS data), which largely account for the global DNA hypomethylation observed in cancer (Ehrlich, 2009).

Figure 8C:
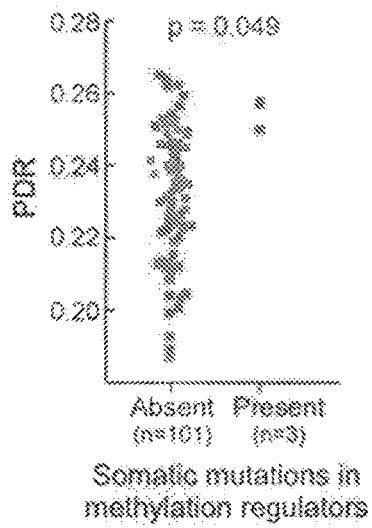

Alterations in the DNA methylation regulatory machinery could impact PDR. Unlike other hematological malignancies (Ley et al., 2010), somatic mutations affecting direct DNA methylation modulators in CLL are rare (Landau et al., 2013). Nonetheless, three CLL samples with such somatic mutations (DNMT3A-Q153*, TET1-N789I, IDH1-S210N) showed increased PDR compared to the 101 CLL samples wildtype for these genes (FIG. 8C).

TABLE 2

Average number of CpGs covered by RRBS with 4 or more CpGs per read, and read depth greater than 10, given by genomic feature.

| Genomic feature | CLL samples | | Normal B cell samples | | Total # of CpGs in the human genome |
|---|---|---|---|---|---|
| | Mean | Standard Dev. | Mean | Standard Dev. | |
| Promoters | 129212.20 | 81086.22 | 163485.80 | 107845.00 | 1954610 |
| CpG islands | 171342.80 | 108393.30 | 215941.40 | 143384.80 | 2124041 |
| Exons | 71536.45 | 45162.34 | 83029.35 | 54823.08 | 1954610 |
| Enhancers | 92322.87 | 62354.34 | 91093.69 | 62145.70 | 1176256 |
| Introns | 155736.40 | 102363.70 | 164236.30 | 110325.50 | 14479789 |
| Genes | 29397.06 | 18483.37 | 34193.31 | 22639.84 | 26917396 |
| LTR | 14222.88 | 9679.65 | 9102.58 | 6533.52 | 2133049 |
| LINE | 5256.03 | 3754.65 | 3055.23 | 2309.95 | 3516060 |

TABLE 2-continued

Average number of CpGs covered by RRBS with 4 or more CpGs per read, and read depth greater than 10, given by genomic feature.

| Genomic feature | CLL samples | | Normal B cell samples | | Total # of CpGs in the human genome |
|---|---|---|---|---|---|
| | Mean | Standard Dev. | Mean | Standard Dev. | |
| Shores | 2488.20 | 1755.74 | 2349.08 | 1801.29 | 3886809 |
| Shelves | 3094.95 | 2403.47 | 4682.19 | 3636.86 | 1259327 |
| Intergenic | 35881.12 | 26900.36 | 18867.27 | 15753.56 | 5087650 |

Example 6

Locally Disordered Methylation Appears to be a Largely Stochastic Process

Figure 9A:
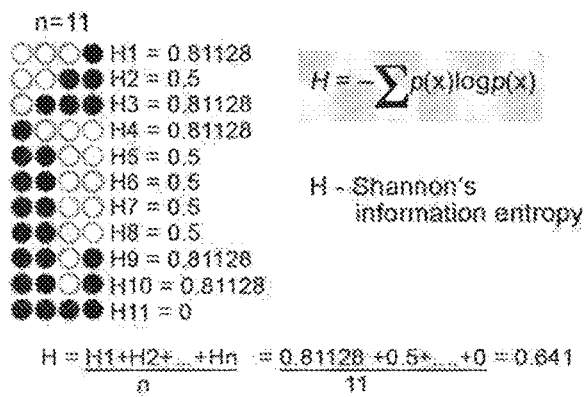
Figure 9B:
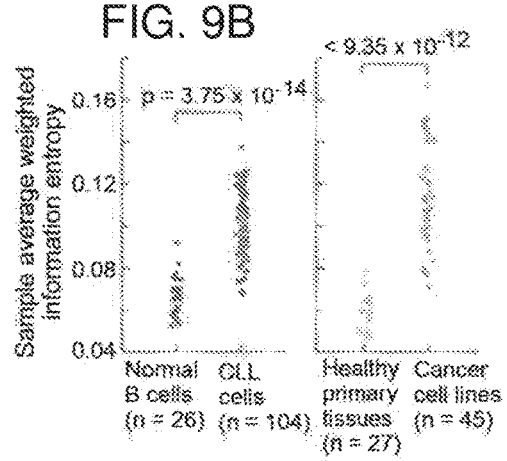
Figure 9C:
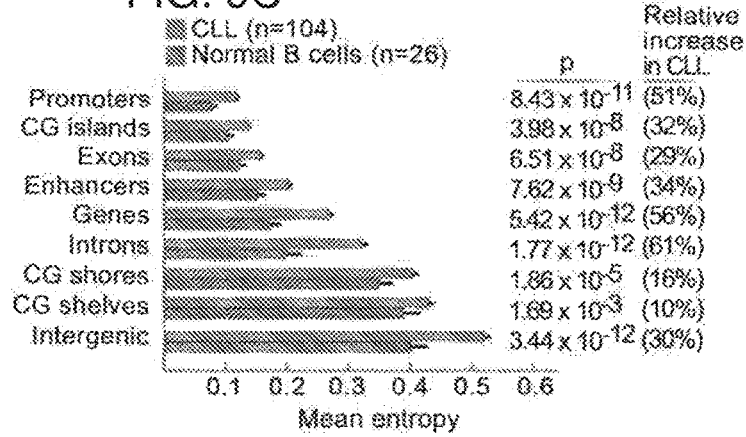

Two observations suggest that PDR measures a process that stochastically increases variation in methylation, a notion which was recently conceptualized as a feature of the cancer epigenome (Pujadas and Feinberg, 2012). First, the pervasiveness of locally disordered methylation across every region evaluated in CLL compared to B cells suggested a stochastic genome-wide process. Second, consistent with a stochastic process, wherein the expected rate of increase in PDR would be related to the starting level of disorder, Applicants observed a larger relative PDR increase in CLL in regions with lower PDR in normal B cells. To formally measure the level of disorder, Applicants undertook a parallel analysis to calculate Shannon's information entropy of intra-sample methylation variation (FIG. 9A). Applicants determined this entropy to be higher in CLL than in normal B cells (as well as higher in cancer cell lines compared to normal tissues), consistent with an increase in stochastic 'noise' (FIG. 9B-C).

Figure 9D:
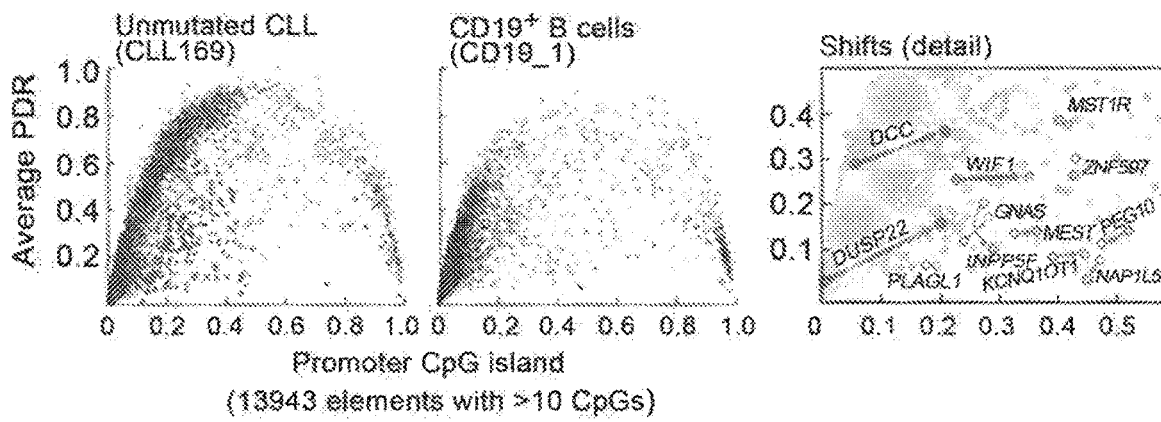
Figure 10A:
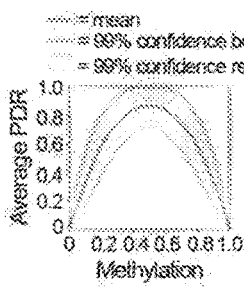
FIG. 10A-G illustrates that locally disordered methylation in CLL is consistent with a stochastic process. A. Applicants developed a model to determine the probability of observing any PDR value in a random CpG methylation state model [given: (1) the total number of reads that cover the locus, (2) the number of neighboring CpGs contained in individual reads, and (3) the locus methylation level]. The plot demonstrates the case in which a locus is covered at a read depth of 30 and each read contains 4 neighboring CpGs. The expected PDR value is shown by the dashed line, and the shaded region represents methylation-PDR tuples with a probability greater than 0.01 under the random model. B. The CLL methylation data are consistent with the stochastic pattern shown in (A). Average promoter CGI methylation and PDR were calculated for 13,943 CGIs covered by WGBS (>10 CpGs per island) in both the CLL and the normal B cell samples. Outliers represent 1.4% of events. C. Average LINE element methylation and PDR were calculated for 1,894 elements covered by WGBS (>20 CpGs per element) in the same samples as in (B). D. The correlation in CLL between sample average of CGI methylation and PDR is shown (8,740.2 (±3,102.8) promoter CGIs per sample were evaluated. E. Similarly, the correlation in CLL between sample average LINE element methylation and PDR are also shown. The RRBS based results of CLL169 are highlighted with a purple square. F. To study the correlation between difference in PDR (ΔPDR) and difference in methylation (ΔMeth). Applicants paired representative CLL and normal B cell samples. For each promoter (>20 CpGs per promoter, n=2119), ΔMeth and ΔPDR were plotted (red). An identical procedure was performed with a pairing of the same normal B cell sample to an adult lung sample (Lung-_normal_BioSam_235, blue). These data enable the comparison between the Pearson's coefficient for the correlation between ΔPDR and ΔMeth in cancer related changes vs.
Figure 10B:
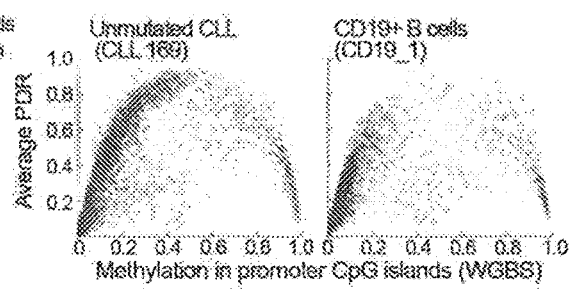

To model the relationship between methylation and PDR under completely stochastic conditions, Applicants plotted the expected distribution of PDR for any level of methylation assuming a purely random assignment of methylation states at each individual CpG (FIG. 10A, sec methods). Strikingly, the distribution of measured PDR and methylation values of ~14,000 individual promoter CGIs from CLL WGBS data closely followed the pattern of the modeled stochastic process (FIG. 10B). In outlier genes (i.e. those with less promoter PDR than expected based on the promoter methylation level; n=195 (1.4%), FIG. 9D), imprinted genes were enriched (Morison et al., 2005) as expected, since these are hemimethylated under normal physiological conditions (n=10, Fishers exact test p=1.94×10). In addition, the outlier genes contained at least three tumor suppressor genes (WIF1, DUSP22 and DCC) that have an established role in hematopoietic malignancies (Chim et al., 2008; Inokuchi et al., 1996; Jantus Lewintre et al., 2009), and also had >10% higher methylation in the CLL169 sample compared with the normal CD19$^+$ B cell sample.

Figure 10C:
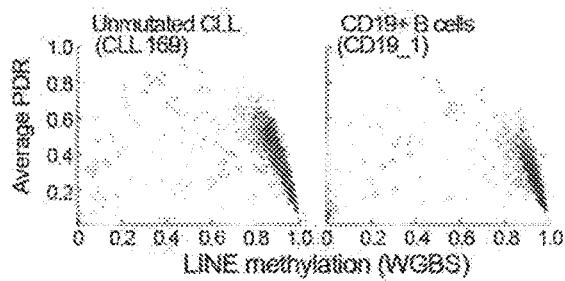

Similar to promoters, methylation of ~1900 LINE repeat elements also displayed a similar relationship between methylation and PDR (FIG. 10C). A comparable distribution was observed for other genomic features (FIG. 9E), and with RRBS data (FIG. 9F). This pattern was also found in promoter CpGs of tumor suppressor genes implicated in lymphoproliferation, such as WT1 (Menke et al., 2002) and DAPK1 (Raval et al., 2007) (FIG. 9G).

Figure 10D:
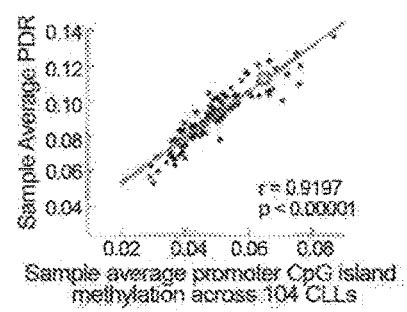
Figure 10E:
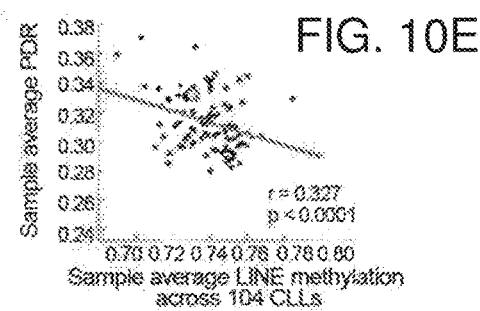

Altogether, these data support the hypothesis that the most commonly described cancer-related methylation alterations (Baylin and Jones, 2011), increased methylation of CGIs and decreased methylation in repeat regions, are largely generated through a seemingly stochastic process. Indeed, across the 104 CLLs, sample average promoter CGI PDR was highly correlated with an increase in sample average promoter CGI methylation (Pearson correlation coefficient r=0.90, p=1.01×10$^{-38}$, FIG. 10D). When this analysis was repeated with genes grouped based on their average methylation level across the samples, this strong correlation was positive for genes with methylation <0.5 and negative for genes with methylation >0.5 as expected from the aforedescribed distribution in FIG. 10B (FIG. 9H). Overall, a key implication of this analysis is that a change in CGI methylation in CLL does not arise from alteration in a relatively small proportion of cells with uniformly methylated alleles but rather from a larger proportion of cells with randomly scattered methylation. Applicants likewise observed sample average LINE repeat elements PDR to be correlated with a decrease in methylation (r=−0.32, p=6.99×10$^{-4}$, FIG. 10E).

Figure 10F:
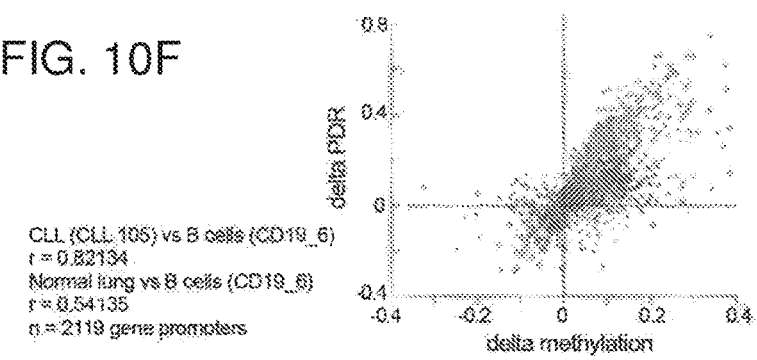
Figure 10G:
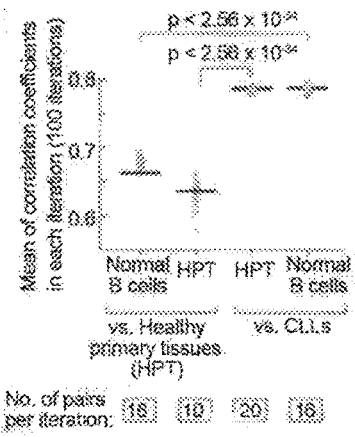

These data reveal that DNA methylation changes in this cancer predominately arise from a disordered change in methylation, resulting in a strong correlation between difference in PDR (ΔPDR) and difference in methylation (ΔMeth). Since previous reports have indicated that a large degree of methylation disorder occurs during normal differentiation (Landan et al., 2012), Applicants sought to compare the correlation between ΔPDR and ΔMeth amongst pairs of cancer and normal samples, to the correlation between pairs of healthy human tissues. Indeed, the correlation coefficient between ΔPDR and ΔMeth was significantly higher when CLL samples were paired to either normal B cells or to other healthy primary tissue samples, compared to the pairing of healthy primary tissues against either normal B cells or other healthy tissue samples (FIG. 10F-G). Thus, methylation changes associated with the malignant process differ substantially from those that occur during changes in physiological cellular states, and show a significantly higher degree of methylation disorder.

Example 7

Increased Susceptibility to Locally Disordered Methylation in Gene-Poor Regions and Silent Genes Some regions of the genome may be more prone to stochastic variation in methylation (Pujadas and Feinberg, 2012). Applicants found three-fold higher promoter PDR in regions with the lowest gene density compared to those with highest gene density (with similar correlations to CTCF density, FIG. 11A). In addition, previously described hypomethylated blocks are regions notable for their association with the nuclear lamina, and furthermore, are enriched with genes that have high expression variability in cancer and impact critical cellular processes such as mitosis and cell cycle control (Hansen et al., 2011; Timp and Feinberg, 2013). In these regions as well, Applicants observed a significant PDR increase in CLL (FIG. 11B, FIG. 12A). Finally, in concert with these findings Applicants observed higher promoter PDR in genes with later replication time across the 104 CLL samples (FIG. 11C, r=0.35. P=1.3×10$^{-153}$), in agreement with other recent reports (Berman et al., 2012; Shipony et al., 2014). Notably, late replication time is closely associated with increased somatic mutation rate (Lawrence et al., 2013). Thus, similar genomic regions may share lower genetic and epigenetic fidelity, as we observed in a joint analysis of somatic single nucleotide variants (sSNVs) and locally disordered methylation (FIG. 11D, FIG. 12B-C).

As many features of chromatin and spatial organization may be shared between the CLL and normal B cell genomes, Applicants hypothesized that some degree of locally disordered methylation might exist in normal B cells in regions with high PDR in CLL. In fact, average PDR of individual CGI in CLL and B cell samples was highly correlated (FIG. 11E—left, r=0.83, p<2×10$^{16}$). Thus, the promoters with highest PDR in CLL already have increased PDR in normal B cells. Consistent with the notion that non-expressed genes are the most vulnerable to aberrant methylation (Meissner et al., 2008), promoter CGIs with a high PDR in both CLL and normal B cells were often found in genes not expressed in normal B cells (FIG. 11E—right).

Example 8

Disordered DNA Methylation Alters the Relationship Between Promoter Methylation and Transcription To test the impact of locally disordered methylation on CLL gene transcription, Applicants generated matching RNAseq data for 40 CLLs. Applicants then computed the odds ratio of a gene with a methylated promoter (promoter methylation >0.8 vs. promoter methylation <0.2) to be transcribed across ~8000 genes in 33 samples where sequencing coverage was sufficient to perform this analysis. Applicants found that the relationship between promoter methylation and gene transcription was markedly weakened in promoters with PDR>0.1 (mean of promoter PDR means=0.1001, FIG. 13A). These results may explain the observation that promoter methylation in CLL is not very predictive of effects on gene transcription. Indeed, the addition of the PDR information to a model that utilizes promoter methylation to predict gene transcription (evaluated for 363,846 matched values of expression and methylation from 40 patient samples) resulted in a striking increase of the model R2 from 0.11 to 0.285. In addition, promoters with significantly skewed allele specific expression had significantly higher PDR in 26 of 40 samples evaluable (at p<0.05, FIG. 13B). These data suggest that locally disordered methylation contributes to the increase transcriptional variation associated with epigenetic heterogeneity.

Example 9

Locally Disordered Methylation and Gene Expression

To examine the relationship between locally disordered DNA methylation and gene expression in more detail, Applicants analysed matched RRBS and RNA-seq profiles of 33 CLL samples (PDR and methylation calculated based on an average (±SD) of 12.1 (±4.8) CpGs per promoter). As in normal B cells, in the 33 CLL samples, PDR was inversely correlated with gene expression (r=−0.51, p<2×10$^{-16}$, FIG. 14A, FIG. 15A-B). Notably, while promoter PDR was negatively correlated with mean transcript levels, it was positively correlated with inter-sample variation in transcript levels (FIG. 14B). While it may be difficult to definitively deconvolute the positive correlation between PDR and expression variation from the strong negative correlation of mean expression and expression variation, both low gene expression and high promoter PDR levels were predictive of higher coefficient of variation of gene expression in a linear model (p<2×10$^{-16}$ for both).

Figure 14C:
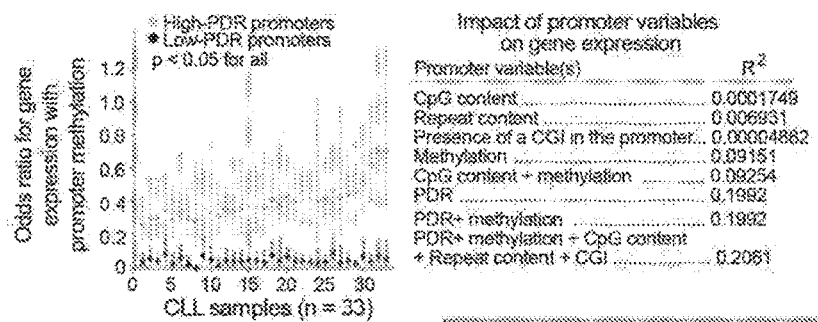
Figure 14D:
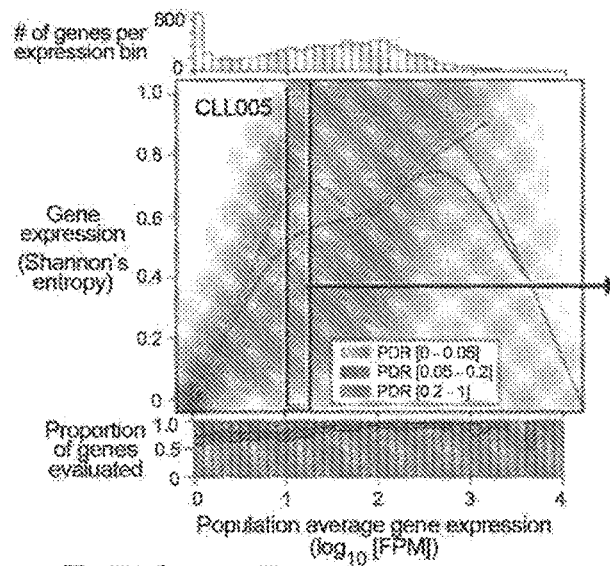
Figure 15A:
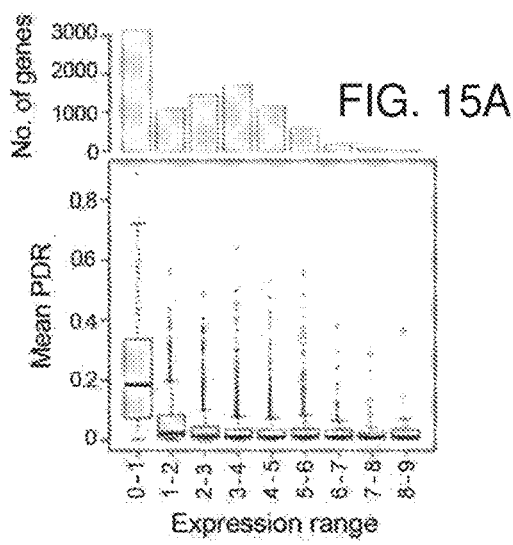
Figure 15B:
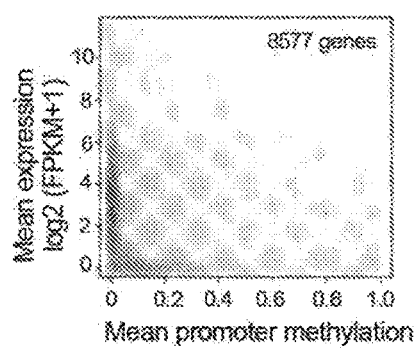
Figure 15C:
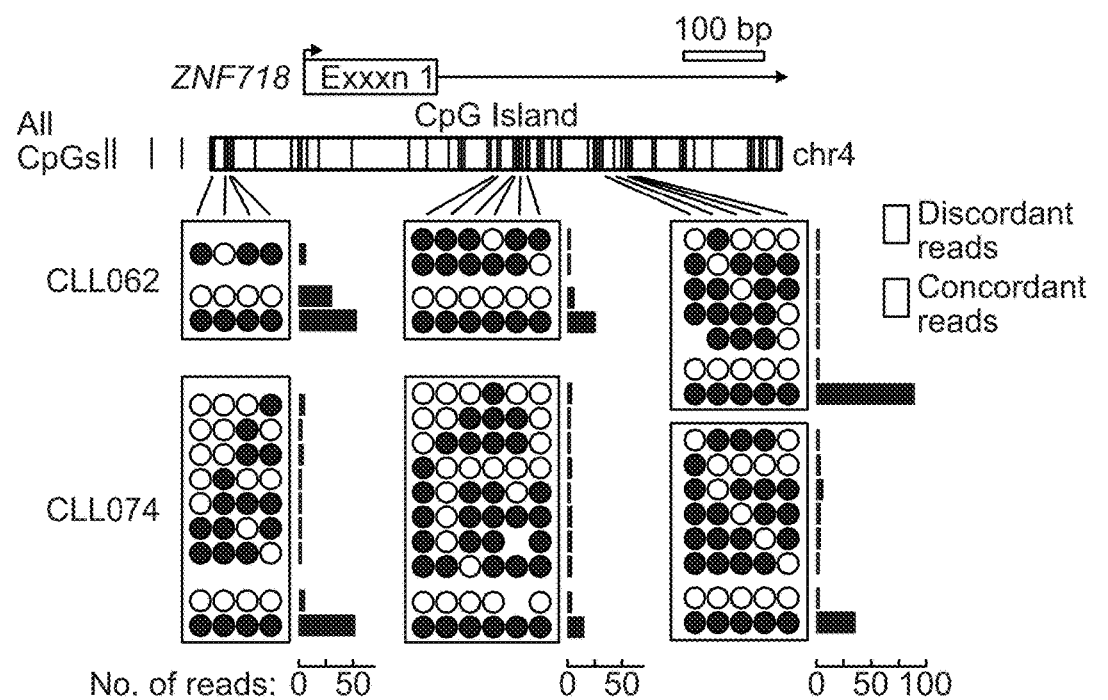
Figure 15C:
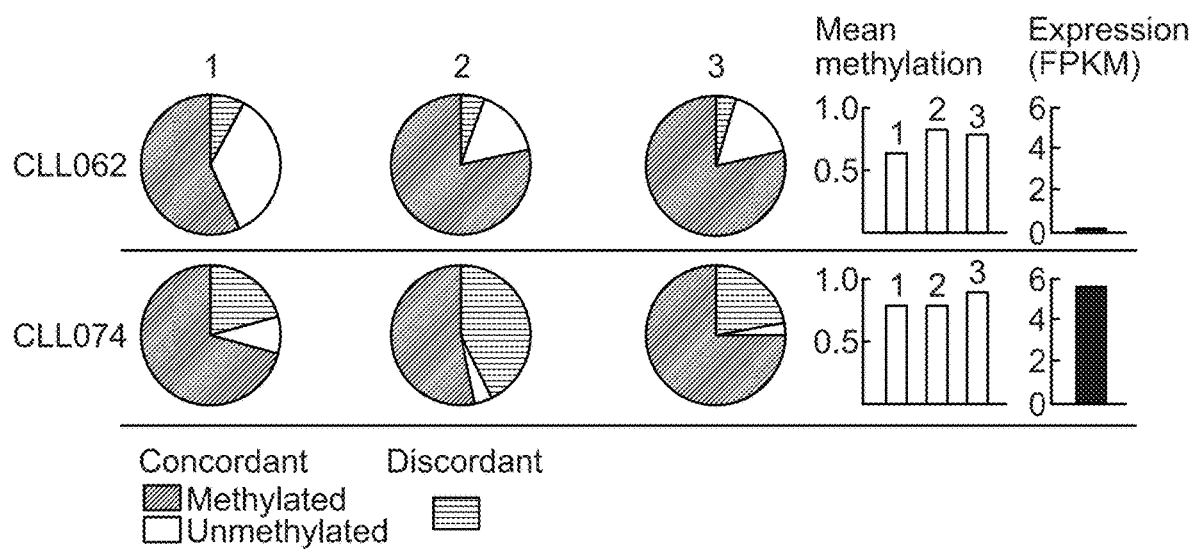

To further examine the impact of locally disordered methylation in CLL on expression levels, Applicants calculated the odds ratio of gene expression (defined as fragments per kilobase of exon per million fragments mapped (FPKM) >1) with a methylated promoter (defined as methylation >0.8, unmethylated defined as <0.2). Promoters with low PDR (i.e., lower than the mean PDR [mean (±SD) promoter PDR was 0.10 (±0.01)]) tended to preserve the expected relationship between promoter methylation and expression, and rarely generated transcripts in the presence of a methylated promoter. Across 33 CLL samples, the average odds ratio (OR) was 0.043 (range 0.036-0.050). In contrast, genes with high PDR promoters (>mean PDR) had a greater likelihood of undergoing transcription (OR 0.396 [range 0.259-0.698], Wilcoxon p=6.5×10$^{-11}$, FIG. 14C), despite comparable promoter methylation levels. As a representative example, Applicants show ZNF718 in two samples with comparable levels of promoter methylation (0.82 in CLL062, 0.87 in CLL74) but low promoter PDR (0.04) in the former, and high promoter PDR (0.24) in the latter. Consistent with the odds-ratio analysis above, Applicants observed undetectable expression in CLL062 (FPKM of 0.03) and measurable RNA expression in CLL074 (FPKM of 5.6) (FIG. 15C).

These observations demonstrate how locally disordered methylation and epigenetic heterogeneity may contribute to increased transcriptional variation. To assess the relationship between PDR and gene expression as continuous variables. Applicants utilized linear models to predict expression based on methylation information. Across the 33 samples, a univariate model that predicts expression based on average promoter methylation yielded an adjusted R2 of 0.092 while one utilizing promoter PDR yielded an average adjusted R2 of 0.202. Inclusion of additional features such as CpG and repeat content only modestly improved the predictive power of the model (average adjusted R2=0.214, Table 3). Indeed, the addition of PDR information to a model that utilizes promoter methylation to predict gene expression as a continuous variable (evaluated for 320.574 matched values of expression and methylation from 33 CLL) resulted in a significant improvement with more than doubling of the model's explanatory power (increase in adjusted R2 value from 0.0915 to 0.1992, likelihood ratio test p<1×10$^{-16}$). This held true when the model included only genes with lowly methylated or only genes with highly methylated promoters (p<1×10$^{-16}$). Even after adding additional variables such as repeat element content, the presence of a CGI in the promoter and CpG content, PDR remained the strongest predictor of expression (FIG. 14C-right).

TABLE 3

Results of models of prediction of gene expression for 33 CLL samples with matched RNAseq and RRBS: Values represent the adjusted R squared for the model.

| Sample | PDR + Meth + CpG_content + Repeat_content | Meth | PDR | Meth + PDR | Genes measured per sample |
|---|---|---|---|---|---|
| CLL146 | 0.223 | 0.087 | 0.210 | 0.210 | 6110 |
| CLL124 | 0.170 | 0.068 | 0.160 | 0.161 | 7016 |
| CLL131 | 0.168 | 0.062 | 0.155 | 0.156 | 7264 |
| CLL170 | 0.191 | 0.080 | 0.179 | 0.179 | 7636 |
| CLL097 | 0.213 | 0.073 | 0.192 | 0.193 | 8511 |
| CLL141 | 0.222 | 0.089 | 0.217 | 0.217 | 8818 |
| CLL117 | 0.285 | 0.128 | 0.276 | 0.276 | 8926 |
| CLL140 | 0.196 | 0.088 | 0.182 | 0.182 | 9005 |
| CLL096 | 0.222 | 0.093 | 0.209 | 0.209 | 9016 |
| CLL003 | 0.237 | 0.118 | 0.226 | 0.226 | 9044 |
| CLL041 | 0.231 | 0.104 | 0.220 | 0.220 | 9045 |
| CLL074 | 0.217 | 0.086 | 0.208 | 0.208 | 9566 |
| CLL120 | 0.215 | 0.099 | 0.203 | 0.203 | 9871 |
| CLL138 | 0.268 | 0.133 | 0.255 | 0.256 | 9914 |
| CLL129 | 0.221 | 0.093 | 0.206 | 0.206 | 9976 |
| CLL068 | 0.248 | 0.112 | 0.235 | 0.235 | 10029 |
| CLL038 | 0.117 | 0.038 | 0.100 | 0.101 | 10058 |
| CLL062 | 0.163 | 0.066 | 0.143 | 0.143 | 10141 |
| CLL105 | 0.226 | 0.074 | 0.211 | 0.211 | 10311 |
| CLL119 | 0.239 | 0.128 | 0.232 | 0.232 | 10351 |
| CLL100 | 0.230 | 0.115 | 0.221 | 0.221 | 10387 |
| CLL153 | 0.256 | 0.132 | 0.247 | 0.248 | 10426 |
| CLL069 | 0.205 | 0.082 | 0.196 | 0.196 | 10600 |
| CLL123 | 0.189 | 0.069 | 0.182 | 0.182 | 10655 |
| CLL067 | 0.242 | 0.116 | 0.230 | 0.230 | 10684 |
| CLL057 | 0.237 | 0.110 | 0.227 | 0.228 | 10745 |
| CLL128 | 0.171 | 0.068 | 0.158 | 0.158 | 10750 |
| CLL054 | 0.208 | 0.083 | 0.198 | 0.198 | 10755 |
| CLL152 | 0.219 | 0.096 | 0.210 | 0.210 | 10828 |
| CLL007 | 0.210 | 0.101 | 0.199 | 0.199 | 10883 |
| CLL126 | 0.203 | 0.075 | 0.181 | 0.181 | 11051 |
| CLL005 | 0.218 | 0.111 | 0.202 | 0.203 | 11064 |
| CLL049 | 0.193 | 0.086 | 0.180 | 0.180 | 11138 |

Example 10

Figure 14F:
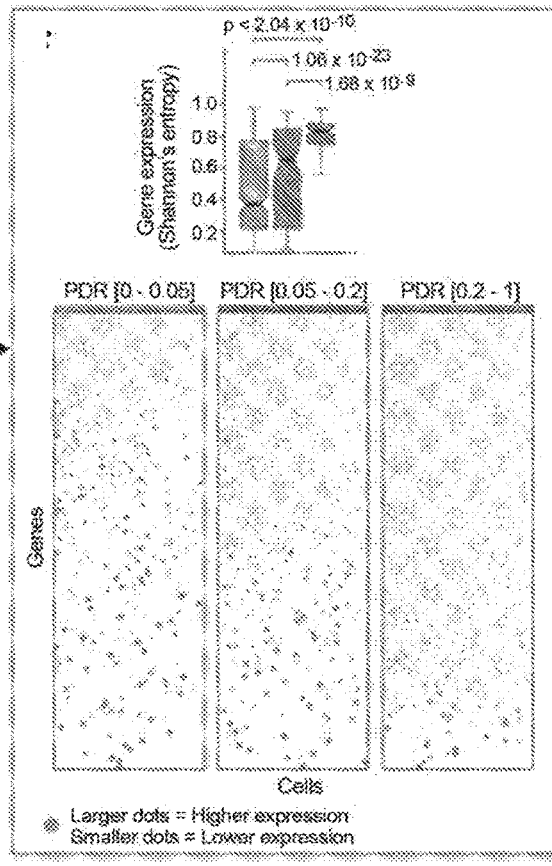
Figure 14E:
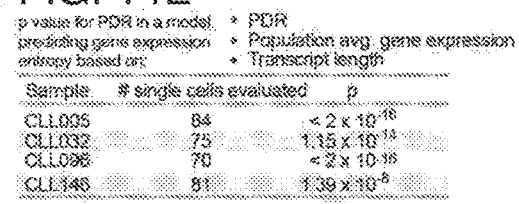
Figures 15D, 15E:
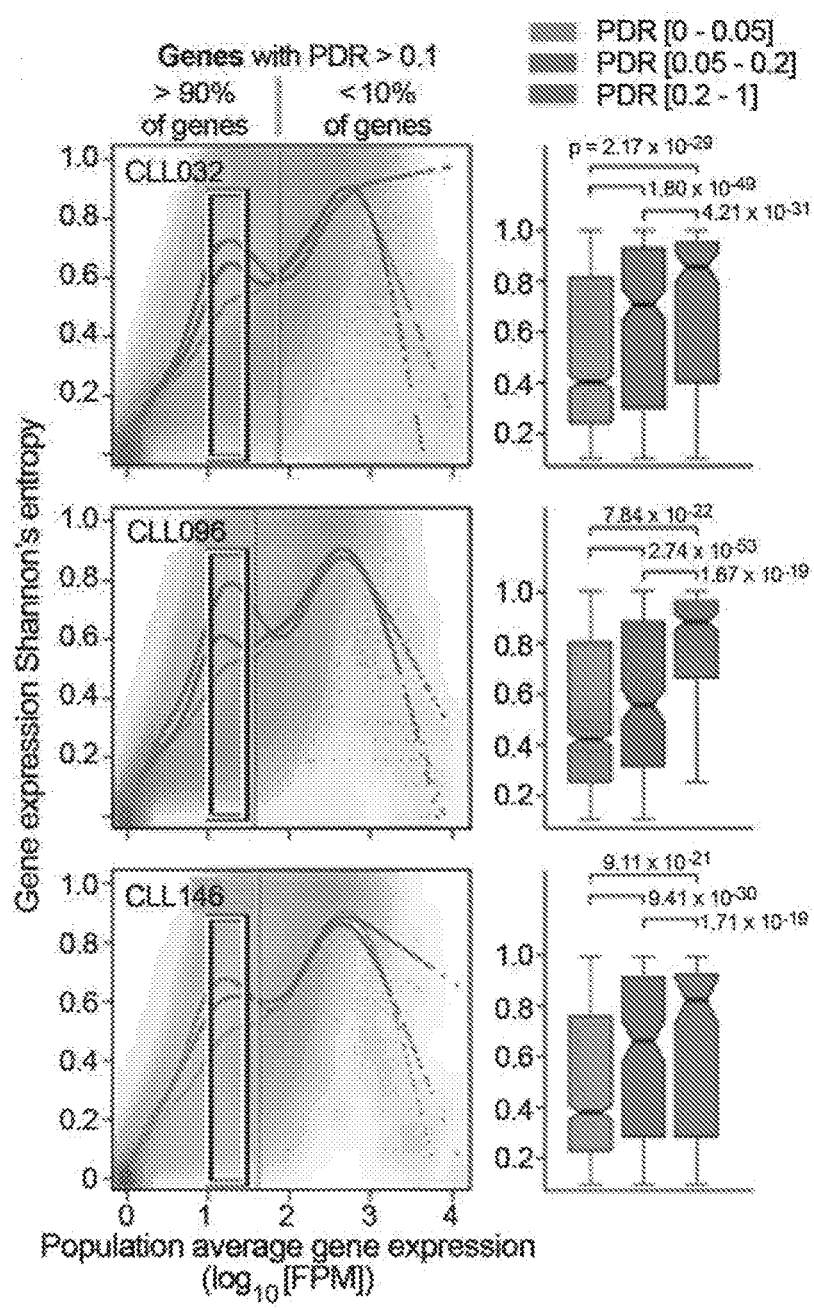

Single Cell Gene Expression Patterns of Genes with Disordered Promoter Methylation Applicants next isolated 96 individual cells from four CD19+CD5+ purified CLL samples and generated single-cell full-length transcriptomes using SMART-seq (75-84 cells analyzed per sample after excluding cells with <1×10$^4$ aligned reads). Promoter PDR was associated with significantly higher intra-tumoral expression information entropy in all 4 samples (p<1.4×10$^{-8}$, FIG. 14D-E, FIG. 15D), in a model that included transcript length as well as population average gene expression (see Methods), which is the variable associated most closely with technical noise in single cell transcriptome analyses (Shalek et al., 2014). These results remained significant even after the addition of promoter methylation to the model (FIG. 15E). As expression information entropy may be affected by variation in sampling of lowly expressed transcripts, Applicants compared the single cell expression patterns of genes with low or high promoter methylation disorder, but with similar population average expression levels (FIG. 14F). Applicants observed that high promoter PDR genes tend to be expressed in larger numbers of cells at lower expression magnitude, whereas low promoter PDR genes tend to be expressed in smaller numbers of cells at higher expression magnitude. Thus, promoter methylation disorder correlates with an intermediate transcriptional state that interferes with both complete silencing and high-level expression.

Example 11

Epigenetic Heterogeneity Contributes to Clonal Evolution

Increased epigenetic disorder is expected to result in a more plastic evolutionary landscape that facilitates the emergence of fitness-enhancing genetic and epigenetic alterations. The footprint of selection may be inferred across samples by assessing significantly differentially expressed genes, as genes that are recurrently differentially expressed across many samples are likely selected. Applicants identified 447 down-regulated genes (FDR, Q<0.01) and found that their promoter PDR was higher compared with 1770 genes that were not significantly down-regulated (Q>0.2, FIG. 16A). Further, Applicants defined a gene set (n=1357)

with promoters exhibiting high PDR (mean promoter PDR>0.1). This set was enriched for genes shown to be differentially methylated across various malignancies, for TP53 targets and for gene sets up-regulated in stem cells (FWER Q<0.1, compared to genes with PDR<0.1, FIG. 16B). The 'increased PDR' gene set included genes important for stem-like properties (e.g., lin28, and SOX2) and genes that have well-defined roles in CLL biology (e.g., DAPK1, and TERT). Finally, CLL with a higher number of subclonal mutations also had higher PDR, while no association was seen with the number of clonal mutations (FIG. 16C-D). Together, these findings suggest that locally disordered methylation creates a rich substrate for CLL evolution by stochastic variation amenable to positive selection.

To probe the relationship between genetic and epigenetic evolution, Applicants performed RRBS at two time points for 13 CLLs with characterized patterns of genetic evolution (median time between time points 3.4 yrs.; 4 unevolved, 9 evolved). The PDR increase between time points was higher in evolved vs. unevolved CLLs (P=0.029). In addition, Applicants identified 329 genes with promoters that were demethylated over time (greater than 10% decrease, Q<0.1), and observed a significant enrichment for the same stem cell related gene-sets that were described herein (Q<1e−10). Genes with promoters significantly hypermethylated over time (n:=159) were enriched for genes methylated in lymphoma. In evolved CLLs, specific promoters revealed changes over time in methylation proportions corresponding to increases in subclone size inferred from the genetic analysis. For example, an increase in size of a subclone harboring an SF3B1 somatic mutation was observed in conjunction with progressive hypomethylation, in a similar proportion of cells, of the TERT promoter, a critical gene for CLL proliferation.

Example 12

Locally Disordered Methylation Impacts Stem Cell Genes and May Facilitate Leukemic Evolution Increased epigenetic 'noise' would be expected to generate a more plastic evolutionary landscape that facilitates the emergence of fitness-enhancing genetic and epigenetic alterations. To explore the potential relationship between locally disordered methylation and selection. Applicants identified differentially methylated regions (DMRs) in promoters and CGIs, since the presence of recurrent epigenetic alterations might signal the presence of evolutionary convergence. In fact, these DMRs were associated with significantly higher PDR, suggestive of positive selection operating against a backdrop of stochastic epigenetic heterogeneity (FIG. 17A).

Furthermore, a gene-set enrichment analysis of genes with consistently high promoter PDR across CLL samples compared with genes with consistently low promoter PDR, revealed enrichment in TP53 targets (Perez et al., 2007), in genes differentially methylated across various malignancies (Acevedo et al., 2008: Sato et al., 2003) and in gene-sets associated with stem cell biology (Lim et al., 2010; Wong et al., 2008) (BH-FDR Q<0.1; FIG. 18A, FIG. 17B, Table 4). Finally, regions that are specifically hypomethylated in human embryonic stem cells compared with a diverse collection of differentiated cells (Ziller et al., 2013), also showed decreased methylation and increased PDR in CLL compared to normal B cells, suggestive of a drift towards a more stem-like state (FIG. 18B). Collectively, these findings suggest that locally disordered methylation creates a rich substrate for CLL evolution by stochastic variation amenable to positive selection and by increasing the number of cells that carry the potential to propagate new genotypes to progeny populations. Indeed, CLLs with a higher number of subclonal mutations also exhibit higher PDR (p=0.002, FIG. 18C).

To directly observe the relationship between genetic and epigenetic evolution, Applicants studied RRBS data from 14 longitudinally sampled CLL patients with characterized patterns of genetic evolution (median time between samples 3.45 yrs; 9 CLLs with and 5 without evidence of genetic evolution, Table 5). CLLs that underwent genetic clonal evolution also had increased average promoter PDR over time (paired t-test, p=0.037. FIG. 18D), which may indicate a higher PDR in the subclone that expanded over time. In addition, genes with promoters that were demethylated over time, were significantly enriched for the same aforementioned stem cell-related gene-sets (Boquest et al., 2005; Jaatinen et al., 2006; Lim et al., 2010; Wong et al., 2008) (FIG. 18E, Table 6). Importantly, the correlation coefficient between ΔPDR and ΔMeth was markedly lower for gene promoters that were significantly demethylated or hypermethylated over time (r=0.0937 and r=0.0987, respectively), compared with the correlation coefficient for gene promoters without a significant change in methylation (r=0.4163; 144, 161 promoters across 14 CLLs). These results suggest that gene promoters with significant changes in methylation over time were enriched with genes that underwent ordered methylation change, as expected from positive selection.

TABLE 4

Gene set enrichments of genes with promoters with consistently high PDR across 104 CLL samples (top 30 enrichments shown).

| Gene Set Name | $Q_{high}$ | $Q_{highvslow}$1 |
|---|---|---|
| ZWANG_TRANSIENTLY_UP_BY_2ND_EGF_PULSE_ONLY | 5.55E−52 | 2.89E−28 |
| YOSHIMURA_MAPK8_TARGETS_UP | 1.73E−43 | 5.92E−11 |
| ACEVEDO_METHYLATED_IN_LIVER_CANCER_DN | 4.91E−22 | 3.32E−10 |
| LIM_MAMMARY_STEM_CELL_UP | 5.42E−38 | 3.32E−10 |
| SATO_SILENCED_BY_METHYLATION_IN_PANCREATIC_CANCER_1 | 1.98E−28 | 2.00E−09 |
| MCBRYAN_PUBERTAL_BREAST_4_5WK_UP | 4.44E−25 | 2.23E−08 |
| DURAND_STROMA_MAX_UP | 1.11E−25 | 2.23E−08 |
| LIU_PROSTATE_CANCER_DN | 3.43E−27 | 2.25E−07 |
| ONDER_CDH1_TARGETS_2_UP | 8.01E−21 | 1.78E−06 |
| SCHUETZ_BREAST_CANCER_DUCTAL_INVASIVE_UP | 5.67E−16 | 5.10E−06 |
| WU_CELL_MIGRATION | 1.44E−13 | 6.49E−05 |
| SMID_BREAST_CANCER_RELAPSE_IN_BONE_DN | 2.06E−14 | 9.04E−05 |
| MIKKELSEN_ES_ICP_WITH_H3K4ME3 | 1.47E−06 | 9.04E−05 |
| SERVITJA_ISLET_HNF1A_TARGETS_UP | 2.34E−13 | 1.19E−04 |

TABLE 4-continued

Gene set enrichments of genes with promoters with consistently high PDR across 104 CLL samples (top 30 enrichments shown).

| Gene Set Name | $Q_{high}$ | $Q_{highvslow}$I |
|---|---|---|
| WONG_ADULT_TISSUE_STEM_MODULE | 1.52E−36 | 1.28E−04 |
| ACEVEDO_LIVER_CANCER_WITH_H3K27ME3_DN | 5.36E−12 | 1.65E−04 |
| MIYAGAWA_TARGETS_OF_EWSR1_ETS_FUSIONS_DN | 1.17E−16 | 1.67E−04 |
| SMID_BREAST_CANCER_LUMINAL_B_DN | 1.50E−12 | 1.71E−04 |
| RIGGI_EWING_SARCOMA_PROGENITOR_UP | 3.68E−23 | 2.14E−04 |
| SCHAEFFER_PROSTATE_DEVELOPMENT_48HR_DN | 3.02E−23 | 2.55E−04 |
| MARTORIATI_MDM4_TARGETS_NEUROEPITHELIUM_DN | 9.08E−15 | 2.73E−04 |
| VART_KSHV_INFECTION_ANGIOGENIC_MARKERS_UP | 4.12E−11 | 2.73E−04 |
| SCHAEFFER_PROSTATE_DEVELOPMENT_48HR_UP | 1.90E−22 | 2.93E−04 |
| KATSANOU_ELAVL1_TARGETS_UP | 1.37E−09 | 3.65E−04 |
| MOHANKUMAR_TLX1_TARGETS_DN | 4.84E−11 | 3.79E−04 |
| PEREZ_TP63_TARGETS | 4.83E−25 | 6.73E−04 |
| BRUINS_UVC_RESPONSE_VIA_TP53_GROUP_A | 6.89E−26 | 6.73E−04 |
| GOZGIT_ESR1_TARGETS_DN | 1.42E−25 | 7.30E−04 |
| YAUCH_HEDGEHOG_SIGNALING_PARACRINE_UP | 6.46E−10 | 1.16E−03 |
| YAUCH_HEDGEHOG_SIGNALING_PARACRINE_DN | 2.31E−09 | 1.33E−03 |

TABLE 5

Clinical characteristics of 14 patients for whom longitudinal samples were studied.

| CLL IDs | Age | Therapy Prior to timepoint 1 | Therapy Between timepoints 1 & 2 | IGHV mutation status | Genetic evolution | ZAP70 status | FISH Cytogenetics | Years between samples |
|---|---|---|---|---|---|---|---|---|
| CLL018 | 71 | None | None | Y | N | − | del(13q) | 2.4 |
| CLL020 | 54 | None | None | Y | N | + | del(13q) | 2.5 |
| CLL019 | 52 | None | None | Y | Y | − | del(13q) | 3.2 |
| CLL030 | 54 | None | None | Y | N | + | del(13q) | 3.5 |
| CLL011 | 41 | None | FCR | N | Y | + | del(13q) | 5 |
| CLL088 | 60 | None | FCR, Alem + R | N | Y | − | tri12 | 4.5 |
| CLL169 | 69 | None | FR | Y | Y | + | del(13q) | 4.7 |
| CLL167 | 56 | None | FR | Y | Y | − | del(13q), tri12 | 2.7 |
| CLL016 | 59 | None | FR | N | Y | + | del(13q) | 3.4 |
| CLL001 | 58 | None | FR | N | Y | + | del(11q, 13q) | 3.5 |
| CLL006 | 67 | FC, Chloram | Alem + R, FR, exp. | N | Y | − | del(13q), del(11q) | 4.6 |
| CLL014 | 65 | R | FR | Y | N | − | del(13q) | 2.9 |
| CLL066 | 70 | FR, Chloram | R-CVP | Y | N | − | del(13q) | 3.5 |
| CLL040 | 60 | FCR | FCR, Alem + R | N | Y | + | del(13q), del(11q) | 3 |

Abbreviations:
Y—Yes,
N—No,
Mut.—Mutated,
FISH—Fluorescence In Situ Hybridization,
F—Fludarabine,
C—Cyclophosphamide,
R—Rituximab,
V—Vincristine,
Chloram—Chlorambucil,
Alem—Alemtuzumab;
Rev—Revlimid;
exp—experimental

TABLE 6

Gene set enrichments of genes with significant promoter methylation changes
over time (top 30 enrichments for demethylation and methylation are shown).

| Gene Set Name | $Q_{high}$ | $Q_{high}$ vs. genes with no change | Methylation change |
|---|---|---|---|
| MEISSNER_BRAIN_HCP_WITH_H3K4ME3_AND_H3K27ME3 | 1.82E-17 | 3.42E-22 | decrease |
| BENPORATH_SUZ12_TARGETS | 3.76E-15 | 9.10E-21 | decrease |
| BENPORATH_ES_WITH_H3K27ME3 | 4.89E-14 | 4.70E-19 | decrease |
| PEREZ_TP53_TARGETS | 2.45E-11 | 3.96E-17 | decrease |
| ACEVEDO_METHYLATED_IN_LIVER_CANCER_DN | 3.16E-08 | 4.60E-17 | decrease |
| BENPORATH_EED_TARGETS | 4.47E-12 | 7.05E-17 | decrease |
| DODD_NASOPHARYNGEAL_CARCINOMA_UP | 5.63E-08 | 2.73E-16 | decrease |
| MIKKELSEN_MCV6_HCP_WITH_H3K27ME3 | 6.78E-12 | 1.06E-14 | decrease |
| SMID_BREAST_CANCER_BASAL_DN | 3.88E-09 | 3.35E-14 | decrease |
| MEISSNER_NPC_HCP_WITH_H3K4ME2_AND_H3K27ME3 | 6.78E-12 | 4.87E-14 | decrease |
| MIKKELSEN_MEF_HCP_WITH_H3K27ME3 | 7.35E-11 | 5.53E-14 | decrease |
| ZWANG_TRANSIENTLY_UP_BY_2ND_EGF_PULSE_ONLY | 9.93E-05 | 2.06E-13 | decrease |
| JAATINEN_HEMATOPOIETIC_STEM_CELL_UP | 6.96E-10 | 2.83E-13 | decrease |
| WONG_ADULT_TISSUE_STEM_MODULE | 6.82E-09 | 2.89E-13 | decrease |
| BENPORATH_PRC2_TARGETS | 6.96E-10 | 6.13E-13 | decrease |
| MEISSNER_NPC_HCP_WITH_H3K4ME2 | 3.91E-10 | 1.28E-12 | decrease |
| LIM_MAMMARY_STEM_CELL_UP | 5.58E-09 | 2.10E-12 | decrease |
| MIKKELSEN_NPC_HCP_WITH_H3K27ME3 | 6.18E-10 | 4.62E-12 | decrease |
| GOZGIT_ESR1_TARGETS_DN | 1.56E-06 | 1.56E-11 | decrease |
| ONDER_CDH1_TARGETS_2_UP | 1.99E-08 | 2.55E-11 | decrease |
| CUI_TCF21_TARGETS_2_DN | 1.62E-07 | 6.88E-11 | decrease |
| MEISSNER_BRAIN_HCP_WITH_H3K27ME3 | 3.98E-08 | 1.52E-09 | decrease |
| ZWANG_TRANSIENTLY_UP_BY_1ST__EGF_PULSE_ONLY | 1.70E-03 | 1.91E-09 | decrease |
| DACOSTA__UV_RESPONSE_VIA_ERCC3_DN | 3.23E-06 | 8.12E-09 | decrease |
| CHYLA_CBFA2T3_TARGETS_UP | 3.83E-05 | 2.48E-08 | decrease |
| CHEN_METABOLIC_SYNDROM_NETWORK | 5.55E-04 | 3.21E-08 | decrease |
| LEE_BMP2_TARGETS_UP | 5.39E-05 | 5.16E-08 | decrease |
| MEISSNER_NPC_HCP_WITH_H3_UNMETHYLATED | 7.13E-06 | 6.43E-08 | decrease |
| LIU_PROSTATE_CANCER_DN | 5.55E-05 | 7.34E-08 | decrease |
| GOBERT_OLIGODENDROCYTE_DIFFERENTIATION_DN | 9.93E-05 | 1.08E-07 | decrease |
| MEISSNER_BRAIN_HCP_WITH_H3K4ME3_AND_H3K27ME3 | 1.82E-17 | 3.42E-22 | decrease |
| BENPORATH_SUZ12_TARGETS | 1.49E-19 | 2.99E-25 | increase |
| BENPORATH_ES_WITH_H3K27ME3 | 2.27E-18 | 2.05E-23 | increase |
| MEISSNER_BRAIN_HCP_WITH_H3K4ME3_AND_H3K27ME3 | 4.03E-18 | 6.63E-22 | increase |
| BENPORATH_EED_TARGETS | 3.55E-15 | 1.21E-19 | increase |
| MIKKELSEN_MCV6_HCP_WITH_H3K27ME3 | 5.84E-14 | 2.80E-16 | increase |
| DODD_NASOPHARYNGEAL_CARCINOMA_UP | 6.53E-08 | 1.40E-15 | increase |
| BENPORATH_PRC2_TARGETS | 1.72E-11 | 3.77E-14 | increase |
| MEISSNER_NPC_HCP_WITH_H3K4ME2 | 7.06E-12 | 5.84E-14 | increase |
| MIKKELSEN_MEF_HCP_WITH_H3K27ME3 | 2.32E-11 | 6.76E-14 | increase |
| MEISSNER_NPC_HCP_WITH_H3K4ME2_AND_H3K27ME3 | 4.49E-10 | 2.21E-11 | increase |
| ZWANG_TRANSIENTLY_UP_BY_2ND_EGF_PULSE_ONLY | 7.57E-04 | 7.91E-11 | increase |
| MARTENS_TRETINOIN_RESPONSE_UP | 1.48E-05 | 1.04E-10 | increase |
| GOZGIT_ESR1_TARGETS_DN | 3.29E-06 | 6.73E-10 | increase |
| SCHAEFFER_PROSTATE_DEVELOPMENT_48HR_UP | 9.59E-07 | 7.99E-10 | increase |
| MEISSNER_NPC_HCP_WITH_H3_UNMETHYLATED | 9.09E-08 | 8.06E-10 | increase |
| LEE_BMP2_TARGETS_UP | 1.01E-06 | 8.06E-10 | increase |
| CHEMNITZ_RESPONSE_TO_PROSTAGLANDIN_E2_DN | 1.71E-06 | 6.84E-09 | increase |
| ZWANG_TRANSIENTLY_UP_BY_1ST_EGF_PULSE_ONLY | 2.06E-03 | 8.66E-09 | increase |
| MEISSNER_BRAIN_HCP_WITH_H3K27ME3 | 1.84E-07 | 1.31E-08 | increase |
| BLALOCK_ALZHEIMERS_DISEASE_UP | 1.40E-04 | 2.97E-08 | increase |
| MIKKELSEN_NPC_HCP_WITH_H3K27ME3 | 1.01E-06 | 6.16E-08 | increase |
| SMID_BREAST_CANCER_BASAL_UP | 8.09E-05 | 7.55E-08 | increase |
| GRAESSMANN_APOPTOSIS_BY_DOXORUBICIN_UP | 7.07E-05 | 1.05E-07 | increase |
| DAWSON_METHYLATED_IN_LYMPHOMA_TCL1 | 9.59E-07 | 1.68E-07 | increase |
| WONG_ENDMETRIUM_CANCER_DN | 1.16E-05 | 2.55E-07 | increase |
| BRUINS_UVC_RESPONSE_VIA_TP53_GROUP_A | 5.02E-04 | 2.68E-07 | increase |
| GINESTIER_BREAST_CANCER_ZNF217_AMPLIFIED_DN | 1.48E-05 | 3.12E-07 | increase |
| CREIGHTON_ENDOCRINE_THERAPY_RESISTANCE_5 | 3.55E-05 | 3.62E-07 | increase |
| MARTINEZ_TP53_TARGETS_DN | 1.91E-04 | 9.25E-07 | increase |
| BENPORATH_SUZ12_TARGETS | 1.49E-19 | 2.99E-25 | increase |
| BENPORATH_ES_WITH_H3K27ME3 | 2.27E-18 | 2.05E-23 | increase |

Example 13

Locally Disordered Methylation Impacts Clinical Outcome

The presented data support a model in which locally disordered DNA methylation facilitates tumor evolution through increased genetic and epigenetic plasticity. Thus, Applicants hypothesized that increased PDR would be associated with a shorter remission time after treatment, which was previously linked with clonal evolution (Landau et al., 2013).

Applicants therefore examined failure-free survival after treatment (FFS, failure defined as retreatment or death) in 49 patients included in the cohort that were treated after tumor sampling for RRBS. A higher mean sample promoter PDR (>mean for cohort) was significantly associated with shorter FFS (median FFS of 16.5 vs. 44 months, hazard ratio=2.5 [95% CI: 1.1-5.7], p=0.028, FIG. 19A; 52% and 65% of patients, respectively, were treated with fludarabine based immunochemotherapy, p=0.39). A regression model including established CLL risk indicators (IGHV unmutated status, del(17p) and del(11q)) showed an adjusted hazard ratio of 2.81 (95% CI 1.05-7.53, p=0.039, FIG. 19B) for high promoter PDR. Similar results were obtained after inclusion of additional variables in the model including mutation burden and average promoter methylation (Table 7). Samples with higher promoter PDR were also more likely to have a subclonal driver mutation as previously defined (Landau et al., 2013) (p=0.01). When the presence of a subclonal driver was added to the regression model, the increased risk associated with the elevated PDR was no longer preserved (FIG. 19B). These results support the notion that epigenetic 'noise' may function primarily as a facilitating feature, allowing the emergence of subclonal drivers, which then contribute to the adverse clinical outcome A further extension of this model proposes that locally disorder methylation enhances the evolutionary capacity of CLL by optimizing the process of genetic diversification. This framework would necessitate coincidence of a novel somatic mutation with an epigenetic state permissive to the propagation of the new genotype to a progeny population. In cellular populations with a preserved epigenetic landscape (FIG. 20—top), the proportion of cells capable of actively participating in the evolutionary process is predicted to be small. On the other hand, in a more malleable epigenetic landscape (FIG. 20—bottom) as is expected with a high level of locally disordered methylation, a greater proportion of cells can give birth to new subclones. This process would accelerate genetic evolution, provide a greater adaptive capacity for the cancer population and result in adverse clinical outcome with therapy, as was saw in the CLL cohort (FIG. 20).

Example 14

Figure 4I:
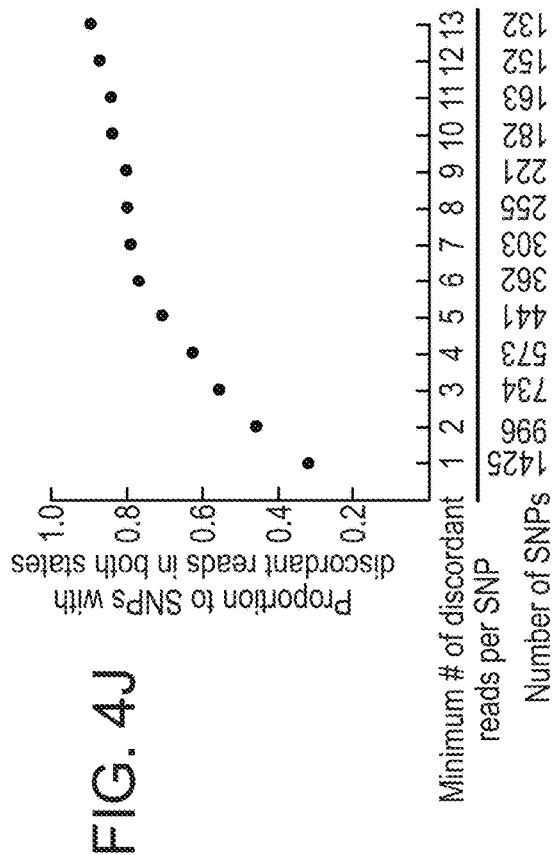
Figure 4J:
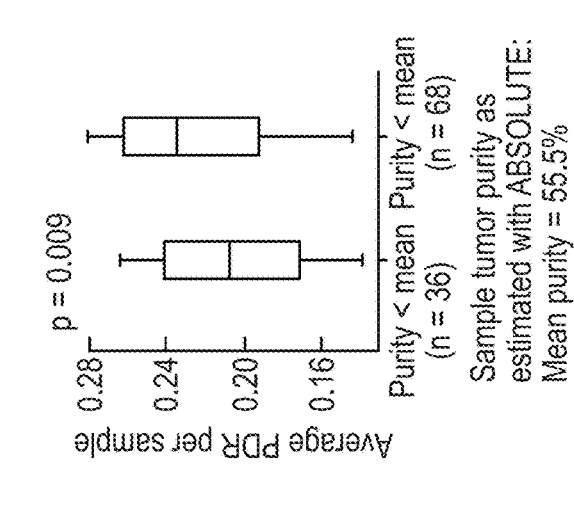
Figure 4K:
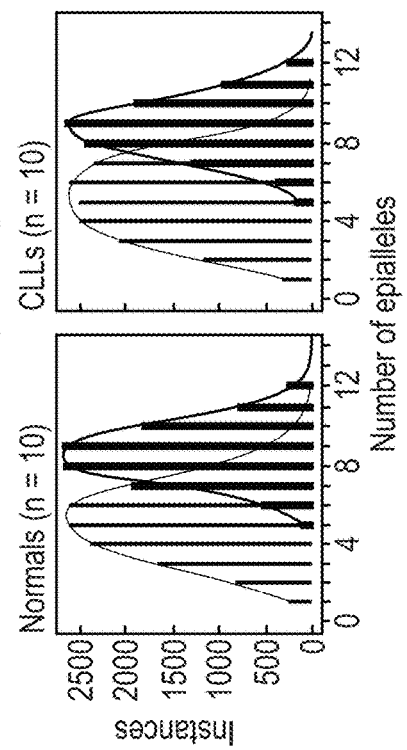

Excluding Alternative Explanations for High PDR Other than Locally Disordered Methylation Applicants considered several possible alternative explanations to these findings. First, the contaminating non-malignant cell fraction of samples may contribute to the PDR, even though the overall purity of the CLL samples was consistently high (90.2% median purity). However, when Applicants compared samples with purity above and below the overall average (86.6%), PDR was higher in the former (mean±SEM, 0.2259±0.0047 vs. 0.2062±0.0066, t-test p=0.009), indicating that indeed the malignant cells in the samples contribute to the high PDR (FIG. 4I). Second, Applicants considered the possibility that elevated PDR may affect only one allele in the sample as part of allele-specific methylation (ASM). To test this, Applicants identified germline SNPs that did not involve CpGs across 53 randomly selected CLL samples in the cohort. Of these germline SNPs, 4.486 had equivalent coverage of both genotypes in the RRBS reads (ratio of 0.4-0.6 in variant reads/total reads). At these sites, discordant reads were found to contain both alternative genotypes in an increasing proportion of SNPs in association with an increased total number of discordant reads per locus (FIG. 4J), converging towards 1. This result demonstrates that locally disordered methylation likely affects both parental alleles. Furthermore, even within a given genotype different discordancy patterns were seen (FIG. 4K), revealing that high PDR results indeed from locally disordered methylation and not simply from allele-specific methylation patterns. In this context, it is important to note that X/Y chromosomes were excluded from the entire analysis.

In addition to the germline variants, Applicants carried out a similar analysis with regards to somatic single nucleotide mutations, by integrating WGS and WGBS data for CLL007 and CLL169. After excluding C>T mutations, and limiting the analysis to regions with >4 CpGs per read on average (to ensure accurate estimation of PDR) and to mutations with >20× coverage in the WGS (to ensure accurately distinguishing clonal vs. subclonal events),

TABLE 7

Stepwise regression model for prediction of clinical outcome.

|  | Unadjusted HR [95% CI] | Stepwise selection Final model (without subclonal driver) HR [95% CI] | Stepwise selection Final model (including subclonal driver as candidate) HR [95% CI] |
|---|---|---|---|
| Promoter PDR: cutpoint at the Mean >0.1033 vs. ≤0.1033 | 2.51 [1.10-5.17] p = 0.029 | 3.48 [1.37-8.86] p = 0.009 | |
| IGVH Mutated vs. Unmutated | 0.29 [0.11-0.77] p = 0.013 | 0.16 [0.05-0.47] p = 0.0009 | 0.20 [0.07-0.58] p = 0.003 |
| Presence of del11q | 1.26 [0.55-2.86] p = 0.58 | | |
| Presence of del17p | 3.46 [1.39-8.62] p = 0.008 | 2.51 [0.84-7.51] p = 0.10 | 3.24 [0.99-10.54] p = 0.051 |
| Presence of a subclonal driver | 4.80 [1.79-12.92] p = 0.002 | NA | 6.54 [2.16-19.86] p = 0.0009 |
| Promoter methylation: cutpoint at mean >0.0735 vs. ≤0.0735 | 1.81 [0.83-3.99] p = 0.14 | | |
| Mutation number: cutpoint at mean >18.8 vs. ≤18.8 | 1.89 [0.85-4.23] p = 0.012 | 2.57 [1.04-6.35] p = 0.040 | 3.42 [1.39-8.39] p = 0.007 |

Applicants identified 52 and 66 high confidence mutations for analysis, respectively (91% and 79% of these mutations were either intronic or intergenic mutations in CLL007 and CLL169, respectively). The correlation between the average methylation values of the clonally mutated alleles and the matching germline alleles was high (CLL169–number of clonal mutations evaluated=30, r=0.96, p=1.9×10$^{-17}$, CLL007–number of clonal mutations evaluated=10, r=0.94, p=3.6×10$^{-5}$). Similarly, the correlation between the PDR of the clonally mutated alleles and the matched germline alleles was also high (CLL169: r=0.72, p=5.6×10$^{-7}$; CLL007: r=0.65, p=0.04). While the correlation of average methylation values remained high between the mutated alleles and the matched germline alleles for subclonal mutations (CLL169–number of subclonal mutations evaluated=36, r=0.47, p=0.008, CLL007–number of subclonal mutations evaluated=42, r=0.81, p=5.3×10$^{-11}$), the correlation between the PDR values of the two alleles was lower (r=0.09 and 0.45, p=0.5 and p=0.002, respectively), with a trend towards higher PDR in the mutated subclonal allele (20.5% and 34.6% increase in PDR in mutated alleles, for CLL169 and CLL007, respectively, with p=0.2 and 0.048). Collectively, these data show that disordered methylation involved both the mutant and germline alleles, with a trend towards higher PDR in subclonally mutated alleles.

Figure 4L:
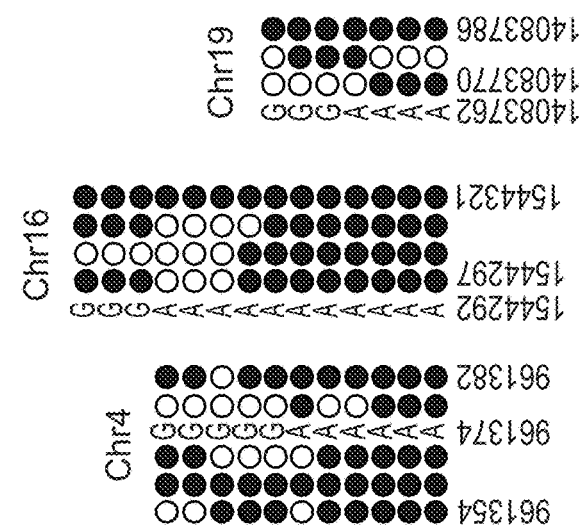

Moreover, if high PDR results from ASM, then it would be expected to find predominately 1 or 2 consistent patterns of discordancy, across all reads covered for a particular locus. However, a histogram of the number of distinct discordancy pattern in loci that have a significant number of discordant reads (10-20) across ten randomly selected CLL samples, shows a normal distribution centered at 5 discordant patterns, consistent with a model of stochastic disorder rather than ASM (FIG. 4L). This latter finding also confirms that most of the PDR does not result from reads that cover an ordered transition point from one methylation state to another, which is also expected to yield 1 recurrent discordancy pattern.

Another potential explanation for increased PDR could be related to methQTL (Gibbs et al., 2010). This is unlikely to account for the genome-wide pervasive process described for the following reasons: i) this effect is expected to be of importance in a tumor with a high mutation load. However, CLL is a malignancy with one of the lowest mutational loads, 1000-2000 mutations per genome (Wang et al., 2011). Extrapolating from the study by Gibbs et al., which evaluated ~1.5M germline SNPs and only found association with 4-5% of CpGs, the mutational load in CLL at best will only affect 0.005% of CpGs. This is expected to have a small effect in comparison to the pervasive disorder in methylation patterns (e.g., in CLL169 WGBS, 73.39% of CpGs have PDR>0.1), ii) Cancer cell lines, which harbor 1-3 orders of magnitude more somatic mutations than primary CLLs, harbor marginally higher rates of PDR, iii) Finally, the PDR pattern would more likely result from methQTLs of subclonal mutations, as clonal mutations would behave largely like germline SNPs and therefore are unlikely to result in increase in PDR in cancer vs. normal tissue, given their number in the CLL genome. To assess for the confounding effect of methQTL on PDR, which may be related to subclonal mutations, Applicants compared the correlation to PDR between clonal mutations and subclonal mutations and found that the distance from clonal mutations shows a stronger negative correlation to PDR, compared to the distance from subclonal mutations (FIG. 12B-C). Although methQTL may have long-range effects, at least a third supposedly act in cis (defined in Gibbs et al., as <1 MB). These results, therefore, are not consistent with a significant impact of methQTL.

Finally, technical artifacts were also considered as a potential cause of locally disordered methylation. Incomplete bisulfite conversion is an unlikely explanation for these findings as bisulfite conversion rates were high in both CLL and normal B cell samples (average of 99.66% and 99.72%, respectively) as measured by the rate of unmethylated cytosines in a non-CpG context (Bock et al., 2005). Furthermore, incomplete conversion is expected to decrease PDR preferentially in highly methylated region, however, Applicants observed an increase in PDR in CLLs in regions with both low and high methylation.

Figure 4O:
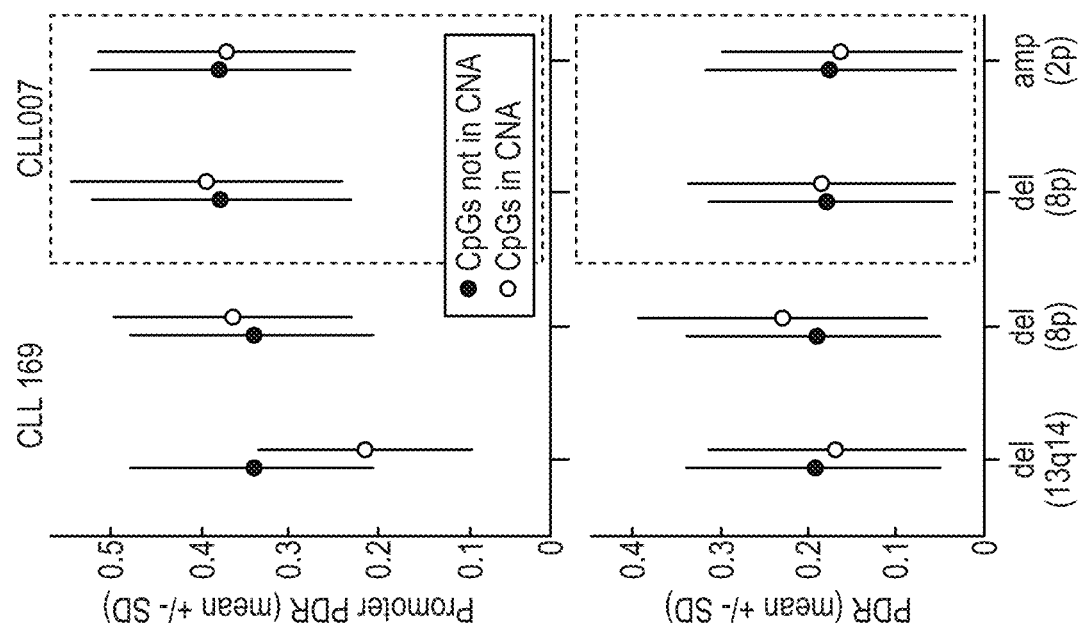
Figure 4M:
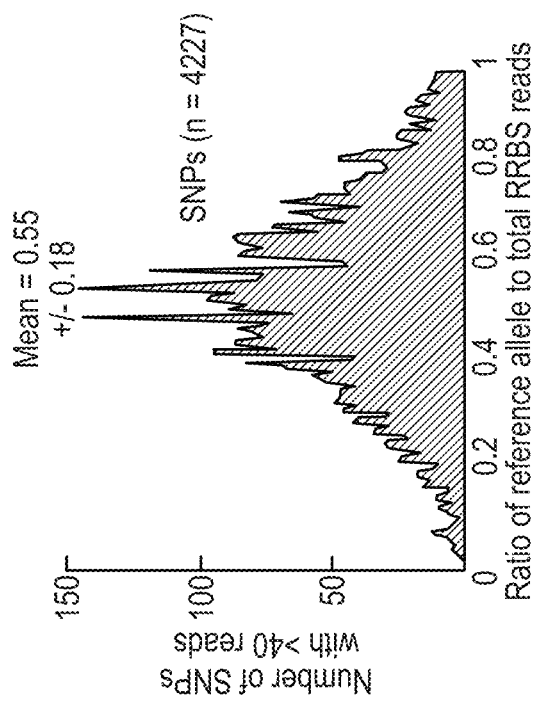
Figure 4N:
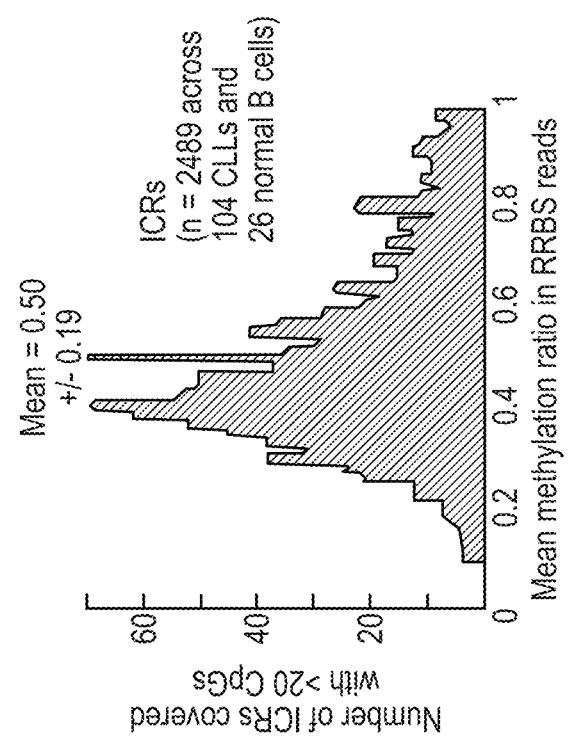

PCR amplification biases in the RRBS procedure are not likely to contribute significantly to this result. First, Applicants have no reason to expect differential impact on CLL samples and normal B cells. Second, the consistency of the finding in WGBS where duplicate reads were discarded makes this technical bias an unlikely source for locally disordered methylation. Indeed the Pearson's correlation of PDR in promoter CpGs covered by both RRBS and WGBS at >30× was high (CLL169; r=0.856, CLL007; r=0.855, and Normal_IGD_3; r=0.737). Finally, given that there is no reason to expect duplicate reads to affect concordant reads less than discordant reads, duplicate reads are expected to decrease PDR, as the overall number of concordant reads is higher than discordant reads (87.1±2% of RRBS reads evaluated are concordant, evaluated in randomly selected 5 samples (CLL003, CLL005, CLL006_TP1, CLL001_TP1 and CLL001_TP2). To quantify PCR amplification biases, Applicants measured the ratio of reads for each of the heterozygous SNP and found a similar representation of both parental alleles (FIG. 4M). In addition, measured methylation values for germline Imprinted Control Regions (ICRs) (Woodfine et al., 2011) and found that these loci approximated 50% methylation, as expected (FIG. 4N).

Finally, although CLL genomes are mostly diploid (Brown et al., 2012), and therefore the analysis is not expected to be significantly impacted by somatic copy number variations (sCNV), Applicants examined the PDR in regions of sCNV in WGBS of CLL007 and CLL169. Altogether in these tumors, 4 sCNVs were detected (using SNP array analysis as described previously (Landau et al., 2013)). As shown in FIG. 4O, both the overall PDR and the promoter PDR do not differ substantially in the sCNVs compared to the remainder of the genome.

Methods

Sample Acquisition.

Heparinized blood samples were obtained from patients and healthy adult volunteers enrolled on clinical research protocols at the Dana-Farber/Harvard Cancer Center (DF/HCC), approved by the DF/HCC Human Subjects Protection Committee. The diagnosis of CLL according to WHO criteria was confirmed in all cases by flow cytometry, or by lymph node or bone marrow biopsy. Peripheral blood mononuclear cells (PBMC) from normal donors and patients were isolated by Ficoll/Hypaque density gradient centrifugation. Mononuclear cells were cryopreserved with FBS/10% DMSO and stored in vapor-phase liquid nitrogen until the time of analysis. The patients included in the cohort represent the broad clinical spectrum of CLL (Table 1). Informed consent on DFCI IRB-approved protocols for genomic sequencing of patients' samples was obtained prior to the initiation of sequencing studies.

Genomic DNA from CLL samples, normal B cell samples and cancer cell line samples were used to produce RRBS libraries. These were generated by digesting genomic DNA with MspI to enrich for CpG-rich fragments, and then were ligated to barcoded TruSeq adapters (Illumina) to allow immediate subsequent pooling. This was followed by bisulfite conversion and PCR, as previously described (Boylec et al., 2012). Libraries were sequenced and 29mers were aligned to the hg19 genome using MAQ version 0.6.6 (Li et al., 2008). Reads were further filtered if: i) The read did not align to an autosome, ii) The read failed platform/vendor quality checks (samtools flag 0x200), and/or iii) the read did not align to an MspI cut site. The methylation state of each CpG was determined by comparing bisulfite-treated reads aligning to that CpG with the genomic reference sequence. The methylation level was computed by dividing the number of observed methylated cytosines (which did not undergo bisulfite conversion) by the total number of reads aligned to that CpG (FIG. 3E). In addition, the number of CpG measurements on each read was noted. In order to identify locations in the genome where concordant methylation (in either methylated or unmethylated states) occurs, Applicants devised a measure called the Proportion of Discordant Reads (PDR). This measure can be computed for a specific genomic location or for the entire genome. After reads are aligned to the reference genome, the methylation state of each CpG on a read is determined. If all the CpGs on a specific read are methylated, or all of the CpGs on a read are unmethylated, the read is classified as concordant; otherwise it is classified as discordant. At each CpG, the PDR is equal to the number of discordant reads that cover that location divided by the total number of reads that cover that location (FIG. 3E). The PDR across the entire genome or for a specified genomic region is given by averaging the values of individual CpGs, as calculated for all CpGs within the region of interest with read depth greater than 10 reads and that are covered by reads that contain at least 4 CpGs. It is important to note that PDR and variances were also calculated with means weighted by depth of coverage of a particular CpG with consistently similar results. For example, overall variance weighted by the number of read depth per CpG shows similar difference in variance of 0.0696 [0.0679-0.0714] for CLL samples, vs. 0.0437 [0.0399-0.0475] for normal B cell samples ($p=2.61 \times 10^{-13}$). Weighted average of PDR for CLL samples was 0.2476 [0.2431-0.2520] vs. 0.1402 [0.1275-0.1528] for normal B cell samples ($p=1.06 \times 10^{-14}$). The CLL and normal B cell RRBS raw data are deposited in dbGaP (phs000435.v2.p1), and processed data format files containing PDR and methylation values for each CpG evaluated in the CLL and normal B cell samples are deposited in GEO (GSE58889). RRBS of primary diverse human tissue samples were previously reported (roadmapepigenomics.org). Reads were realigned and methylation was determined using identical protocols to the rest of the samples.

Whole Genome Bisulfite Sequencing (WGBS).

Genomic DNA was fragmented to 100-500 bp fragments using a Covaris S2 sonicator (Woburn, MA). DNA fragments were cleaned-up, end-repaired, A-tailed and ligated with methylated paired-end adapters (from ATDBio, Southampton, UK). Libraries were sequenced and WGBS reads were aligned using BSMAP version 2.7 (Xi and Li, 2009) to the hg9/GRCh37 reference assembly. Subsequently, CpG methylation calls were made using custom software, excluding duplicate, low-quality reads, as well as reads with more than 10% mismatches. Applicants note that as previously reported (Kulis et al., 2012), non-CpG methylation levels were minimal (0.08% in both CLL samples). Only CpGs covered by >10 reads were considered for further analysis. A methylation-calling pipeline was implemented in Perl and determines CpG methylation state by observing bisulfite conversion at read locations aligned to a CpG in the reference genome. Previously published WGBS data for 2 CLL samples and 3 normal B cell samples (Kulis et al., 2012) were downloaded with permission from the European Genome-Phenome Archive. The raw sequencing reads were processed in identical fashion to the in-house produced WGBS libraries. Additional processing steps for WGBS reads included trimming by 4 bp to ensure high data quality, and filtering out reads that: i) did not align to an autosome, ii) failed platform/vendor quality checks (samtools flag 0x200), iii) had poor alignment score (samtools flag 0x2), iv) had poor alignment of the read mate (samtools flag 0x8), v) aligned to the same location as another read (read duplicate), or vi) contained nucleotides at a CpG location that could not have been produced by bisulfite conversion. The determination of the concordant vs. discordant classification was performed in identical fashion as with RRBS reads. The CLL and normal B cell WGBS data are deposited in dbGaP (phs000435.v2.p1), and processed data format files containing PDR and methylation values for each CpG evaluated in the sample are deposited in GEO (GSE58889).

RNA-sequencing of CLL and normal B cell samples was performed as previously described (Landau et al., 2013). For single cell RNAseq, the C1 Single-Cell Auto Prep System (Fluidigm, San Francisco, Calif.) was used to perform SMARTer® (Clontech, Mountain View, Calif.) whole transcriptome amplification (WTA), on up to 96 individual cells per sample from 4 primary CLL patient samples. WTA products were then converted to Illumina sequencing libraries using Nextera XT® (Illumina, San Diego, Calif.) (Ramskold et al., 2012).

Statistical analysis was performed with MATLAB® (MathWorks, Natick, Mass.). R version 2.15.2 and SAS version 9.2 (SAS Institute, Cary, N.C.). Categorical variables were compared using the Fisher Exact test, and continuous variables were compared using the Student's t-test, Wilcoxon rank sum test, or Kruskal-Wallis test as appropriate. Linear modeling for expression as a predicted variable, based on methylation and PDR was performed using built in R linear model function. FFS (failure-free survival from first treatment after sampling) was defined as the time to the $2^{nd}$ treatment or death from the $1^{st}$ treatment following sampling, was calculated only for those patients who had a $1^{st}$ treatment after the sample and was censored at the date of last contact for those who had only one treatment after the sample, and estimated using the method of Kaplan and Meier. The difference between groups was assessed using the log-rank test. Unadjusted and adjusted Cox modeling was performed to assess the impact of established CLL high-risk predictors and the presence of a subclonal driver. Models were adjusted for known prognostic factors including the presence of a 17p deletion, the presence of a 11q deletion and IGHV mutational status. Cytogenetic abnormalities were primarily assessed by FISH; if FISH was unavailable, genomic data were used. For unknown IGHV mutational status an indicator was included in adjusted modeling and was not found to be significant. Similarly, unadjusted and adjusted Cox modeling was performed to assess the impact of mutational burden and average promoter methylation in addition to established CLL prognostic factors. Given the large number of potential variables, a stepwise selection procedure was used to determine a final multivariable model considering all factors listed above. All p-values are two-sided and considered significant at the 0.05 level unless otherwise noted. The CLL and normal B cell sequencing data were deposited in dbGaP (phs000435.v2.p1), and the processed data deposited in GEO (GSE58889).

Established CLL Prognostic Factor Analysis.

Immunoglobulin heavy-chain variable (IGHV) homology (unmutated was defined as greater than or equal to 98% homology to the closest germline match) and ZAP-70 expression (high risk defined as >20% positive) were determined (Rassenti et al., 2008). Cytogenetics were evaluated by FISH for the most common CLL abnormalities (del(13q), trisomy 12, del(17q), del(17p), all probes from Vysis, Des Plaines, IL, performed at the Brigham and Women's Hospital Cytogentics Laboratory, Boston MA). Samples were scored positive for a chromosomal aberration based on consensus cytogenetic scoring (Smoley et al., 2010).

Genomic DNA was extracted from CLL cells or normal B cell populations utilizing the ROCHE DNA Isolation Kit (Roche Applied Science, Indianapolis, Ind.). Control $CD19^+$ B cell samples were isolated from buffy coats of healthy adult volunteers using a two-step enrichment procedure. B cells were first enriched using the RosetteSep® Human B cell Enrichment System (StemCell Technologies Inc., Vancouver, British Columbia, Canada) and then further purified by immunomagnetic bead selection ($CD19^+$ beads, Miltenyi Biotec, Cambridge, Mass.). From these purified $CD19^+$ cells, naive B cells ($CD19^+CD27^-IgD^+$) and memory B cells ($CD19^+CD27^+IgD^-$) were isolated by flow cytometric sorting (FACSAria II, BD Biosciences) using CD27-PC5 (Beckman Coulter, Brea, Calif.) and IgD-CY7 (Biolegend, San Diego, Calif.) antibodies. Standard protocols for DNA quality control for genomic studies were applied, as recently described (Berger et al., 2011; Chapman et al., 2011 Landau et al., 2013).

Reanalysis of Whole-Exome DNA Sequencing (WES) Data from CLL Samples.

Applicants re-analyzed WES from 104 of 160 previously reported CLLs and their matched germline samples (Landau et al., 2013), deposited in dbGaP (phs000435.v2.p1). Details of whole-exome library construction and analysis have been detailed elsewhere (Fisher et al., 2011; Landau et al., 2013). Briefly, output from Illumina software (Illumina, San Diego, CA) was processed by the "Picard" data processing pipeline to yield BAM files containing aligned reads with well-calibrated quality scores (Chapman et al., 2011; DePristo et al., 2011). Somatic alterations were identified using a set of tools within the "Firehose" pipeline, developed at the Broad Institute (www.broadinstitute.org/cancer/cga) (Berger et al., 2011; Chapman et al., 2011). Somatic single nucleotide variations (sSNVs) were detected using MuTect (Cibulskis et al., 2013). Applicants used the ABSOLUTE algorithm to calculate the purity, ploidy, and absolute DNA copy-numbers of each sample (Carter et al., 2012) and clonal/sub-clonal status of each alteration inferred using a probabilistic approach (Escobar and West, 1995; Landau et al., 2013). Applicants note that the spectrum of mutations in these samples was consistent with prior publications (Quesada et al., 2012), with C>T transitions constituting the most frequent sSNVs (average of 41.8±15% of all sSNV across all 104 CLL WES analyzed in this study). There was no significant correlation between the proportion per sample of any specific subtype of sSNV and PDR ($-0.1<r<0.1$, $p>0.3$).

Library construction was performed using 1-3 micrograms of native DNA from primary tumor (peripheral blood) and germline (saliva) samples. The DNA was sheared to a range of 101-700 bp using the Covaris E210 Instrument and was then phosphorylated and adenylated according to the Illumina protocol. Adaptor ligated purification was done by preparatory gel electrophoresis, and size was selected by excision of two bands (500-520 bp and 520-540 bp, respectively), yielding two libraries per sample with average of 380 bp and 400 bp, respectively. The libraries were then sequenced with the Illumina GA-II or Illumina HiSeq sequencer with 76 or 101 bp reads, achieving an average of ~30x coverage depth. The resulting data were analyzed with the current Illumina pipeline, which generates data files (BAM files) that contain the reads and quality parameters. Sequencing data are available in the dbGaP database (ncbi.nlm.nih.gov/gap) under accession number phs000435.v2.p1. Somatic single nucleotide variations (sSNVs) were detected using MuTect (Cibulskis et al., 2013). Replication times were adopted from Chen et al. (Chen et al., 2010). S50 values (for a defined genome region, S50 corresponds to the fraction of the S phase at which 50% of the sequence reads that map in this region were obtained) were rescaled to vary from 100 (early) to 1000 (late) as previously described (Lawrence et al., 2013). Although replication times reported by Chen et al., were not measured directly in CLL cells or B cells, previous studies have shown that replication time is fairly consistent across different cell types (Kamani et al., 2007). Furthermore, Chen and colleagues confirmed a high correlation with previously measured replication time in other cell types including human lymphocytes.

5 μg of total RNA was poly-A selected using oligo-dT beads to extract the desired mRNA, and used to construct dUTP libraries as previously described (Landau et al., 2013). Samples were pooled and sequenced using either 76 or 101 bp paired end reads. RNAseq BAMs were aligned to the hg19 genome using the TopHat suite. FPKM values were generated with the Cufflinks suite (cufflinks.cbcb.umd.edu/). These data are deposited in dbGaP (phs000435.v2.p1).

Methylation Array Analysis.

Data for previously published 450K methylation arrays (Kulis et al., 2012) were downloaded with permission from the European Genome-Phenome Archive. Data from the 450k Human Methylation Array were analyzed by GenomeStudio (Illumina) and R using the lumi package available through Bioconductor.

Four primary cryopreserved peripheral blood CLL samples were thawed and stained with anti-CD19 FITC and anti-CD5 PE antibodies (Beckman Coulter, Indianapolis. Ind.). 7-AAD (Invitrogen, Grand Island, N.Y.) was added before FACS sorting as a viability control. Live CD19+ $CD5^+$ tumor cells were preliminarily sorted into a collection tube. Subsequently, the bulk cell concentration was adjusted to 250 cell/μl and applied to the C1 Single-Cell Auto Prep System for single cell capture with a 5-10 micron chip (Fluidigm, San Francisco, Calif.). The capture rate was measured at >80%. Following capture, whole transcriptome amplification (WTA) was immediately performed using the C1 Single-Cell Auto Prep System with the SMARTer Kit (Clontech, Mountain View. Calif.) on up to 96 individual cells. The C1 WTA products were then converted to Illumina sequencing libraries using Nextera® XT (Illumina). RNA-Seq was performed on a MiSeq® instrument (Illumina).

Analysis of Single-Cell RNA-Seq Data.

Paired-ended reads were aligned against UCSC hg19 human annotation (Mar. 6, 2013 version) using Tophat 2.0.10 (Kim et al., 2013), and read counts for each gene were determined using HTSeq 0.5.4 (Anders et al., 2014). A subset of cells with more than 10,000 total reads across all genes was selected for further analysis (73-87% of cells). To determine population average gene expression (performed separately for each of the 4 primary CLL samples), the read counts observed in each cell were normalized by the effective library size, determined by edgeR (Robinson et al., 2010) 'calcNormFactors' method.

than 10%. Well-covered regions with at least 5 CpGs in at least 80% of the samples were used for the analysis, as previously described (Bock et al., 2011).

Summary statistics of methylation across DMRs between CLL and normal B cells.

| | Mean methylation | | Standard deviation | | |
|---|---|---|---|---|---|
| DMR category | CLL | Normal B cells | CLL | Normal B cells | Number of elements |
| Promoters hypermethylated in IGHV mutated CLL | 3.06E−01 | 1.71E−01 | 1.51E−01 | 1.40E−01 | 213 |
| Promoters hypomethylated in IGHV mutated CLL | 4.95E−01 | 6.40E−01 | 2.11E−01 | 2.02E−01 | 28 |
| CGIs hypomethylated in IGHV mutated CLL t | 4.01E−01 | 5.54E−01 | 3.08E−01 | 2.97E−01 | 41 |
| CGIs hypermethylated in IGHV mutated CLL | 3.27E−01 | 1.87E−01 | 1.61E−01 | 1.51E−01 | 558 |
| CGIs hypomethylated in IGHV unmutated CLL | 4.70E−01 | 6.69E−01 | 3.15E−01 | 2.81 E−01 | 115 |
| CGIs hypermethylated in IGHV unmutated CLL | 2.84E−01 | 1.24E−01 | 1.63E−01 | 1.55E−01 | 817 |
| Promoters hypomethylated in IGHV unmutated CLL | 5.57E−01 | 7.11E−01 | 2.55E−0 I | 2.56E−01 | 145 |
| Promoters hypermethylated in IGHV unmutated CLL | 2.59E−01 | 1.02E−01 | 1.53E−01 | 1.42E−01 | 332 |

To test for significance of association of PDR with expression heterogeneity, first the fraction of positive cells (fpc) was calculated per gene (a cell is defined as positive if >0 reads aligned to the gene). Subsequently, Shannon's information entropy (ent) was calculated ent=[−1×(fpc×log 2(fpc)+(1−fpc)×log 2(1−fpc)]. The association with PDR was tested using generalized additive models (implemented by gam R package). The following types of models were tested:

ent~$s$(population average expression)+PDR+transcript length ent~$s$(population average expression)+PDR+transcript length+methylation where s( ) indicates local regression. The population average expression values were entered into the models on $\log_{10}$ scale (adding 1).

Promoters were defined as 1 Kb upstream and 1 Kb downstream of hg19 Refgene gene transcription start sites (TSSs). The set of CpG Islands (CGIs) were defined using biologically-verified CGs (Illingworth et al., 2010). Enhancer regions were defined as the union of the 'Distal Regulatory Modules' class from all cell types as previously identified (Ramskold et al., 2012). CTCF binding sites were annotated based on published CTCF binding ChIP-seq experiments using 27 healthy donor transformed B cells ChIP-seq experiments (Wang et al., 2012). Applicants curated a list of CTCF binding sites based on sites that were detected in at least 75% of these B cell samples, and then calculated the CTCF binding site per megabase across the human genome. The location of repeat elements was identified based on the RepBase database version 18.09 for hg19 (girinst.org/servr/archive/RepBase18.09/). Hypomethylated regions in embryonic stem cells were defined as previously described (Ziller et al., 2013), and the analysis was limited to regions with at least 20 CpGs. Differentially-methylated regions (DMRs) were called using a two-sample t-test with significance of p<0.01 and in which the difference between the weighted average region methylation levels was greater Modeling Locally Disordered Methylation.

In order to describe the expected PDR for a given set of reads covering the same set of CpGs, Applicants developed a model to describe the likelihood of finding a certain number of discordant reads, given a methylation value for the set of reads. The input parameters for the model were the number of CpGs covered by the reads, the average methylation value of the covered CpGs, and the number of reads covering the CpGs. Applicants modeled the methylation state of each CpG on each read as an independent Bernoulli trial, with the probability of getting a methylated CpG being set to the overall empirical methylation average. The probability of seeing a specified number of discordant reads was then unity minus the probability of observing a specified number of concordant reads (a probability derived directly from the independent Bernoulli trials for each CpG).

Using this model, Applicants were able to predict the maximum likelihood for PDR for a set of reads covering a certain number of CpGs, with a certain methylation value. In addition to finding the maximum likelihood PDR, Applicants were able to assign a P-value for the probability of finding a specified number of discordant reads, given the number of CpGs covered by the reads, the average methylation value, and the total number of reads. Applicants plotted the 99% confidence interval using this model in FIG. 10A.

Germline variants were detected using the UnifiedGenotyper in the Genome Analysis Toolkit (broadinstitute.org/gatk/), using default options, followed by the filtering of SNPs using Variant Quality Score Recalibration, and hard-filtering of indels (DePristo et al., 2011; McKenna et al., 2010). Germline variants were annotated using SeatleSeq137 (snp.gs.washington.edu/SeattleSeqAnnotation137/).

Gene Set Enrichment Analysis.

Gene set enrichment analysis was limited to the C2 gene set collection (Subramanian et al., 2005). To assess gene set enrichments in genes that exhibit consistently elevated PDR (greater than mean promoter PDR of 0.1 in >75% of 104 CLL samples) a Fisher's exact test was used to measure the enrichment of these genes in each gene-set, followed by a Benjamini-Hochberg FDR procedure. Similarly, to compare enrichments between the set of genes with high promoter PDR and low promoter PDR (less than mean promoter PDR of 0.1 in >75% of 104 CLL samples), a Fisher's exact test was used, followed by a Benjamini-Hochberg FDR procedure. This latter procedure was done to avoid potential biases related to the CpG content of different promoters as previously described. By comparing enrichments of two gene sets both covered by RRBS, these biases are likely to have minimal impact. A similar procedure was undertaken for gene set enrichment analysis of genes with significant change in methylation in the longitudinal samples (Q<0.1). By comparing these gene-sets with genes that did not have a significant change in methylation (Q>0.2), Applicants were able to assess the gene set enrichment while limiting the impact of biases related to CpG content of different gene promoters.

REFERENCES

Acevedo, L. G., Bieda, M., Green, R., and Farnham, P. J. (2008). Analysis of the mechanisms mediating tumor-specific changes in gene expression in human liver tumors. Cancer Res. 68, 2641-2651.

Akiyama, Y., Watkins, N., Suzuki, H., Jair, K. W., van Engeland, M., Esteller, M., Sakai, H., Ren, C. Y., Yuasa, Y., Herman, J. G., et al. (2003). GATA-4 and GATA-5 transcription factor genes and potential downstream anti-tumor target genes are epigenetically silenced in colorectal and gastric cancer. Mol Cell Biol. 23, 8429-8439.

Anders, S., Pyl, P. T., and Iuber, W. (2014). HTSeq—A Python framework to work with high-throughput sequencing data. bioRxiv.

Balazsi, G., van Oudenaarden, A., and Collins, J. J. (2011). Cellular decision making and biological noise: from microbes to mammals. Cell. 144, 910-925.

Baylin, S. B. (2005). DNA methylation and gene silencing in cancer. Nat Clin Pract Oncol. 2 Suppl 1, S4-11.

Baylin, S. B., and Jones, P. A. (2011). A decade of exploring the cancer epigenome—biological and translational implications. Nat Rev Cancer. 11, 726-734.

Berger, M. F., Lawrence, M. S., Demichelis, F., Drier, Y., Cibulskis, K., Sivachenko, A. Y., Sboner, A., Esgueva, R., Pflueger, D., Sougnez, C., et al. (2011). The genomic complexity of primary human prostate cancer. Nature. 470, 214-220.

Berman, B. P., Weisenberger, D. J., Aman, J. F., Hinoue, T., Ramjan, Z., Liu, Y., Noushmehr, H., Lange, C. P., van Dijk, C. M., Tollenaar, R. A., et al. (2012). Regions of focal DNA hypermethylation and long-range hypomethylation in colorectal cancer coincide with nuclear lamina-associated domains. Nat Genet. 44, 40-46.

Bird, A. (2002). DNA methylation patterns and epigenetic memory. Genes Dev. 16, 6-21.

Bock, C., Kiskinis, E., Verstappen, G., Gu, H., Boulting, G., Smith, Z. D., Ziller, M., Croft, G. F., Amoroso, M. W., Oakley, D. H., et al. (2011). Reference Maps of human ES and iPS cell variation enable high-throughput characterization of pluripotent cell lines. Cell. 144, 439-452.

Bock, C., Reither, S., Mikeska, T., Paulsen, M., Walter, J., and Lengauer, T. (2005). BiQ Analyzer: visualization and quality control for DNA methylation data from bisulfite sequencing. Bioinformatics. 21, 4067-4068.

Boquest, A. C., Shahdadfar, A., Fronsdal, K., Sigurjonsson, O., Tunheim, S. H., Collas, P., and Brinchmann, J. E. (2005). Isolation and transcription profiling of purified uncultured human stromal stem cells: alteration of gene expression after in vitro cell culture. Mol Biol Cell. 16, 1131-1141.

Boyle, P., Clement, K., Gu, H., Smith, Z. D., Ziller, M., Fostel, J. L., Holmes, L., Meldrim, J., Kelley, F., Gnirke, A., et al. (2012). Gel-free multiplexed reduced representation bisulfite sequencing for large-scale DNA methylation profiling. Genome Biol. 13, R92.

Brown, J. R., Hanna, M., Tesar, B., Werner, L., Pochet, N., Asara, J. M., Wang, Y. E., Dal Cin, P., Fernandes, S. M., Thompson, C., et al. (2012). Integrative genomic analysis implicates gain of PIK3CA at 3q26 and MYC at 8q24 in chronic lymphocytic leukemia. Clin Cancer Res. 18, 3791-3802.

Cahill, N., Bergh, A. C., Kanduri, M., Goransson-Kultima, H., Mansouri, L., Isaksson, A., Ryan, F., Smedby, K. E., Juliusson, G., Sundstrom, C., et al. (2013). 450K-array analysis of chronic lymphocytic leukemia cells reveals global DNA methylation to be relatively stable over time and similar in resting and proliferative compartments. Leukemia. 27, 150-158.

Carter, S. L., Cibulskis, K., Helman, E., McKenna, A., Shen, H., Zack, T., Laird, P. W., Onofrio, R. C., Winckler. W., Weir, B. A., et al. (2012). Absolute quantification of somatic DNA alterations in human cancer. Nat Biotechnol. 30, 413-421.

Chapman, M. A., Lawrence, M. S., Keats, J. J., Cibulskis, K., Sougnez, C., Schinzel, A. C., Harview, C. L., Brunet, J. P., Ahmann, G. J., Adli, M., et al. (2011). Initial genome sequencing and analysis of multiple myeloma. Nature. 471, 467-472.

Chen, C. L., Rappailles, A., Duquenne, L., Huvet, M., Guilbaud, G., Farinelli, L., Audit, B., d'Aubenton-Carafa, Y., Arneodo, A., Hyrien, O., et al. (2010). Impact of replication timing on non-CpG and CpG substitution rates in mammalian genomes. Genome Res. 20, 447-457.

Chim, C., Pang, R., and Liang, R. (2008). Epigenetic dysregulation of the Wnt signalling pathway in chronic lymphocytic leukaemia. J Clin Pathol. 61, 1214-1219.

Cibulskis, K., Lawrence, M. S., Carter, S. L., Sivachenko, A., Jaffe, D., Sougnez, C., Gabriel, S., Meyerson, M., Lander, E. S., and Getz, G. (2013). Sensitive detection of somatic point mutations in impure and heterogeneous cancer samples. Nat Biotechnol. 31, 213-219.

De, S., Shaknovich, R., Riester, M., Elemento, O., Geng, H., Kormaksson, M., Jiang, Y., Woolcock, B., Johnson, N., Polo, J. M., et al. (2013). Aberration in DNA methylation in B-cell lymphomas has a complex origin and increases with disease severity. PLoS Genet. 9, e1003137.

DePristo, M. A., Banks, E., Poplin, R., Garimella, K. V., Maguire, J. R., Hartl, C., Philippakis, A. A., del Angel, G., Rivas, M. A., Hanna, M., et al. (2011). A framework for variation discovery and genotyping using next-generation DNA sequencing data. Nat Genet. 43, 491-498.

Eckhardt, F., Lewin, J., Cortese, R., Rakyan, V. K., Attwood, J., Burger, M., Burton, J., Cox, T. V., Davies, R., Down, T. A., et al. (2006). DNA methylation profiling of human chromosomes 6, 20 and 22. Nat Genet. 38, 1378-1385.

Ehrlich, M. (2009). DNA hypomethylation in cancer cells. Epigenomics. 1, 239-259.

Escobar, M., and West, M. (1995). Bayesian density estimation and inference using mixtures. Journal of the American Statistical Association. 90, 577-588.

Fisher, S., Barry, A., Abreu, J., Minic, B., Nolan, J., Delorey, T. M., Young, G., Fennell, T. J., Allen, A., Ambrogio, L., et al. (2011). A scalable, fully automated process for construction of sequence-ready human exome targeted capture libraries. Genome Biol. 12, R1.

Gibbs, J. R., van der Brug, M. P., Hernandez, D. G., Traynor, B. J., Nalls, M. A., Lai, S. L., Arepalli, S., Dillman, A., Rafferty, I. P., Troncoso, J., et al. (2010). Abundant quantitative trait loci exist for DNA methylation and gene expression in human brain. PLoS genetics. 6, e1000952.

Hanahan, D., and Weinberg, R. A. (2011). Hallmarks of cancer: the next generation. Cell. 144, 646-674.

Hansen, K. D., Timp, W., Bravo, I. C., Sabunciyan, S., Langmead, B., McDonald, O. G., Wen, B., Wu, H., Liu, Y., Diep, D., et al. (2011). Increased methylation variation in epigenetic domains across cancer types. Nat Genet. 43, 768-775.

Harris, R. A., Wang, T., Coarfa, C., Nagarajan, R. P., Hong, C., Downey, S. L., Johnson, B. E., Fouse, S. D., Delaney, A., Zhao, Y., et al. (2010). Comparison of sequencing-based methods to profile DNA methylation and identification of monoallelic epigenetic modifications. Nat Biotechnol. 28, 1097-1105.

Illingworth, R. S., Gruenewald-Schneider, U., Webb, S., Kerr, A. R., James, K. D., Turner, D. J., Smith, C., Harrison, D. J., Andrews, R., and Bird, A. P. (2010). Orphan CpG islands identify numerous conserved promoters in the mammalian genome. PLoS Genet. 6, e1001134.

Inokuchi, K., Miyake, K., Takahashi, H., Dan, K., and Nomura, T. (1996). DCC protein expression in hematopoietic cell populations and its relation to leukemogenesis. J Clin Invest. 97, 852-857.

Jaatinen, T., Hemmoranta, H., Hautaniemi, S., Niemi, J., Nicorici, D., Laine, J., Yli-Harja, O., and Partanen, J. (2006). Global gene expression profile of human cord blood-derived CD133+ cells. Stem Cells. 24, 631-641.

Jantus Lewintre, E., Reinoso Martin, C., Montaner, D., Marin, M., José Terol, M., Farras, R., Benet, I., Calvete, J., Dopazo, J., and Garcia-Conde, J. (2009). Analysis of chronic lymphotic leukemia transcriptomic profile: differences between molecular subgroups. Leuk Lymphoma. 50, 68-79.

Jones, P. A. (2012). Functions of DNA methylation: islands, start sites, gene bodies and beyond. Nat Rev Genet. 13, 484-492.

Jones, P. A., and Baylin, S. B. (2007). The epigenomics of cancer. Cell. 128, 683-692.

Karnani, N., Taylor, C., Malhotra, A., and Dutta, A. (2007). Pan-S replication patterns and chromosomal domains defined by genome-tiling arrays of ENCODE genomic areas. Genome research. 17, 865-876.

Kim, D., Pertea, G., Trapnell, C., Pimentel, H., Kelley, R., and Salzberg, S. L. (2013). TopHat2: accurate alignment of transcriptomes in the presence of insertions, deletions and gene fusions. Genome biology. 14, R36.

Kim, J., Woo, A. J., Chu, J., Snow, J. W., Fujiwara, Y., Kim, C. G., Cantor, A. B., and Orkin, S. H. (2010). A Myc network accounts for similarities between embryonic stem and cancer cell transcription programs. Cell. 143, 313-324.

Kreso, A., O'Brien, C. A., van Galen, P., Gan, O. I., Notta, F., Brown, A. M., Ng, K., Ma, J., Wienholds, E., Dunant, C., et al. (2013). Variable clonal repopulation dynamics influence chemotherapy response in colorectal cancer. Science. 339, 543-548.

Kulis, M., Heath, S., Bibikova, M., Queiros, A. C., Navarro, A., Clot, G., Martinez-Trillos, A., Castellano, G., Brun-Heath, I., Pinyol, M., et al. (2012). Epigenomic analysis detects widespread gene-body DNA hypomethylation in chronic lymphocytic leukemia. Nat Genet. 44, 1236-1242.

Landan, G., Cohen, N. M., Mukamel, Z., Bar, A., Molchadsky, A., Brosh, R., Horn-Saban, S., Zalcenstein, D. A., Goldfinger, N., Zundelevich, A., et al. (2012). Epigenetic polymorphism and the stochastic formation of differentially methylated regions in normal and cancerous tissues. Nat Genet. 44, 1207-1214.

Landau, D. A., Carter, S. L., Getz, G., and Wu, C. J. (2014). Clonal evolution in hematological malignancies and therapeutic implications. Leukemia. 28, 34-43.

Landau, D. A., Carter, S. L., Stojanov, P., McKenna, A., Stevenson, K., Lawrence, M. S., Sougnez, C., Stewart, C., Sivachenko, A., Wang, L., et al. (2013). Evolution and impact of subclonal mutations in chronic lymphocytic leukemia. Cell. 152, 714-726.

Lawrence, M. S., Stojanov, P., Polak, P., Kryukov, G. V., Cibulskis, K., Sivachenko, A., Carter, S. L., Stewart, C., Mermcl, C. H., Roberts, S. A., et al. (2013). Mutational heterogeneity in cancer and the search for new cancer-associated genes. Nature. 499, 214-218.

Ley, T. J., Ding, L., Walter, M. J., McLellan, M. D., Lamprecht, T., Larson, D. E., Kandoth, C., Payton, J. E., Baty, J., Welch, J., et al. (2010). DNMT3A mutations in acute myeloid leukemia. N Engl J Med. 363, 2424-2433.

Li, H., Ruan, J., and Durbin, R. (2008). Mapping short DNA sequencing reads and calling variants using mapping quality scores. Genome Res. 18, 1851-1858.

Lim, E., Wu, D., Pal, B., Bouras, T., Asselin-Labat, M. L., Vaillant, F., Yagita, H., Lindeman, G. J., Smyth, G. K., and Visvader, J. E. (2010). Transcriptome analyses of mouse and human mammary cell subpopulations reveal multiple conserved genes and pathways. Breast Cancer Res. 12, R21.

Maegawa, S., Gough, S. M., Watanabe-Okochi, N., Lu, Y., Zhang, N., Castoro, R. J., Estecio, M. R., Jelinek, J., Liang, S., Kitamura, T., et al. (2014). Age-related epigenetic drift in the pathogenesis of MDS and AML. Genome Res. 24, 580-591.

McKenna, A., Hanna, M., Banks, E., Sivachenko, A., Cibulskis, K., Kernytsky, A., Garimella, K., Altshuler, D., Gabriel, S., Daly, M., et al. (2010). The Genome Analysis Toolkit: a MapReduce framework for analyzing next-generation DNA sequencing data. Genome Res. 20, 1297-1303.

Meissner, A., Mikkelsen, T. S., Gu, H., Wernig, M., Hanna, J., Sivachenko, A., Zhang, X., Bernstein, B. E., Nusbaum, C., Jaffe, D. B., et al. (2008). Genome-scale DNA methylation maps of pluripotent and differentiated cells. Nature. 454, 766-770.

Menke, A. L., Clarke, A. R., Leitch, A., Ijpenberg, A., Williamson, K. A., Spraggon, L., Harrison, D. J., and Hastie, N. D. (2002). Genetic interactions between the Wilms' tumor I gene and the p53 gene. Cancer Res. 62, 6615-6620.

Morison, I. M., Ramsay, J. P., and Spencer, H. G. (2005). A census of mammalian imprinting. Trends Genet. 21, 457-465.

Ohnishi, K., Semi, K., Yamamoto, T., Shimizu, M., Tanaka, A., Mitsunaga, K., Okita, K., Osafunc, K., Arioka, Y., Macda, T., et al. (2014). Premature Termination of Reprogramming In Vivo Leads to Cancer Development through Altered Epigenetic Regulation. Cell. 156, 663-677.

Pei, L., Choi, J. H., Liu, J., Lee, E. J., McCarthy, B., Wilson, J. M., Speir, E., Awan, F., Tae, H., Arthur, G., et al. (2012).

Genome-wide DNA methylation analysis reveals novel epigenetic changes in chronic lymphocytic leukemia. Epigenetics. 7, 567-578.

Perez. C. A., Ott, J., Mays, D. J., and Pietenpol, J. A. (2007). p63 consensus DNA-binding site: identification, analysis and application into a p63MH algorithm. Oncogene. 26, 7363-7370.

Pujadas, E., and Feinberg, A. P. (2012). Regulated noise in the epigenetic landscape of development and disease. Cell. 148, 1123-1131.

Quesada, V., Conde, L., Villamor, N., Ordonez, G. R., Jares, P., Bassaganyas, L., Ramsay, A. J., Bea, S., Pinyol, M., Martinez-Trillos, A., et al. (2012). Exome sequencing identifies recurrent mutations of the splicing factor SF3B1 gene in chronic lymphocytic leukemia. Nat Genet. 44, 47-52.

Ramskold, D., Luo, S., Wang, Y. C., Li, R., Deng, Q., Faridani, O. R., Daniels, G. A., Khrebtukova, I., Loring, J. F., Laurent, L. C., et al. (2012). Full-length mRNA-Seq from single-cell levels of RNA and individual circulating tumor cells. Nat Biotechnol. 30, 777-782.

Rassenti, L., Jain, S., Keating, M., Wierda, W., Grever, M., Byrd, J., Kay, N., Brown, J., Gribben, J., Neuberg, D., et al. (2008). Relative value of ZAP-70, CD38, and immunoglobulin mutation status in predicting aggressive disease in chronic lymphocytic leukemia. Blood. 112, 1923-1930.

Raval, A., Tanner, S., Byrd, J., Angerman, E., Perko, J., Chen, S., Hackanson, B., Grever, M., Lucas, D., Matkovic, J., et al. (2007). Downregulation of death-associated protein kinase 1 (DAPK1) in chronic lymphocytic leukemia. Cell. 129, 879-890.

Robinson, M. D., McCarthy, D. J., and Smyth, G. K. (2010). edgeR: a Bioconductor package for differential expression analysis of digital gene expression data. Bioinformatics. 26, 139-140.

Rossi, D., Rasi, S., Spina, V., Bruscaggin, A., Monti, S., Ciardullo, C., Deambrogi, C., Khiabanian, H., Serra, R., Bertoni, F., et al. (2013). Integrated mutational and cytogenetic analysis identifies new prognostic subgroups in chronic lymphocytic leukemia. Blood. 121, 1403-1412.

Sato, N., Fukushima, N., Maitra, A., Matsubayashi, H., Yeo, C. J., Cameron, J. L., Hruban, R. H., and Goggins, M. (2003). Discovery of novel targets for aberrant methylation in pancreatic carcinoma using high-throughput microarrays. Cancer Res. 63, 3735-3742.

Shalek, A. K., Satija, R., Shuga, J., Trombetta, J. J., Gennert, D., Lu, D., Chen, P., Gertner, R. S., Gaublomme, J. T., Yosef, N., et al. (2014). Single-cell RNA-seq reveals dynamic paracrine control of cellular variation. Nature. 510, 363-369.

Shannon, C. E. (1948). A Mathematical Theory of Communication. Bell System Technical Journal. 27, 379-423.

Shipony, Z., Mukamel, Z., Cohen, N. M., Landan, G., Chomsky, E., Zeliger, S. R., Fried, Y. C., Ainbinder, E., Friedman, N., and Tanay, A. (2014). Dynamic and static maintenance of epigenetic memory in pluripotent and somatic cells. Nature. 513, 115-119.

Siegmund, K. D., Marjoram, P., Woo, Y. J., Tavare, S., and Shibata, D. (2009). Inferring clonal expansion and cancer stem cell dynamics from DNA methylation patterns in colorectal cancers. Proc Natl Acad Sci USA. 106, 4828-4833.

Smoley, S. A., Van Dyke, D. L., Kay, N. E., Heerema, N. A., Dell' Aquila, M. L., Dal Cin, P., Koduru, P., Aviram, A., Rassenti, L., Byrd, J. C., et al. (2010). Standardization of fluorescence in situ hybridization studies on chronic lymphocytic leukemia (CLL) blood and marrow cells by the CLL Research Consortium. Cancer Genet Cytogenet. 203, 141-148.

Spencer, S. L., Gaudet, S., Albeck, J. G., Burke, J. M., and Sorger, P. K. (2009). Non-genetic origins of cell-to-cell variability in TRAIL-induced apoptosis. Nature. 459, 428-432.

Subramanian, A., Tamayo, P., Mootha, V., Mukherjee, S., Ebert, B., Gillette, M., Paulovich, A., Pomeroy, S., Golub, T., Lander, E., et al. (2005). Gene set enrichment analysis: a knowledge-based approach for interpreting genome-wide expression profiles. Proc Natl Acad Sci USA. 102, 15545-15550.

Timp, W., and Feinberg, A. P. (2013). Cancer as a dysregulated epigenome allowing cellular growth advantage at the expense of the host. Nat Rev Cancer. 13, 497-510.

Ushijima, T., Watanabe, N., Okochi, E., Kaneda, A., Sugimura, T., and Miyamoto, K. (2003). Fidelity of the methylation pattern and its variation in the genome. Genome research. 13, 868-874.

Wang, H., Maurano, M. T., Qu, H., Varley, K. E., Gertz, J., Pauli, F., Lee, K., Canfield, T., Weaver, M., Sandstrom, R., et al. (2012). Widespread plasticity in CTCF occupancy linked to DNA methylation. Genome Res. 22, 1680-1688.

Wang, L., Lawrence, M. S., Wan, Y., Stojanov, P., Sougnez, C., Stevenson, K., Werner, L., Sivachenko, A., DeLuca, D. S., Zhang, L., et al. (2011). SF3B1 and other novel cancer genes in chronic lymphocytic leukemia. N Engl J Med. 365, 2497-2506.

Widschwendter, M., Fiegl, H., Egle, D., Mueller-Holzner, E., Spizzo, G., Marth, C., Weisenberger, D. J., Campan, M., Young, J., Jacobs, I., et al. (2007). Epigenetic stem cell signature in cancer. Nat Genet. 39, 157-158.

Woodfine, K., Huddleston, J. E., and Murrell, A. (2011). Quantitative analysis of DNA methylation at all human imprinted regions reveals preservation of epigenetic stability in adult somatic tissue. Epigenetics & chromatin. 4, 1.

Wong, D. J., Liu, H., Ridky, T. W., Cassarino, D., Segal, E., and Chang, H. Y. (2008). Module map of stem cell genes guides creation of epithelial cancer stem cells. Cell Stem Cell. 2, 333-344.

Xi, Y., and Li, W. (2009). BSMAP: whole genome bisulfite sequence MAPping program. BMC Bioinformatics. 10, 232.

Yuille, M., Condie, A., Stone, E., Wilsher, J., Bradshaw, P., Brooks, L., and Catovsky, D. (2001). TCL1 is activated by chromosomal rearrangement or by hypomethylation. Genes Chromosomes Cancer. 30, 336-341.

Ziller, M. J., Gu, H., Muller, F., Donaghey, J., Tsai, L. T., Kohlbacher, O., De Jager, P. L., Rosen, E. D., Bennett, D. A., Bernstin, B. E., et al. (2013). Charting a dynamic DNA methylation landscape of the human genome. Nature. 500, 477-481.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed:

1. A method of treating cancer in a subject comprising calculating a proportion of discordant reads (PDR) in a tumor sample from the subject comprising:

detecting DNA methylation status by massive parallel sequencing with bisulfite conversion; whole-genome bisulfite sequencing; reduced representation bisulfite sequencing; microarray, or a genome-wide microarray at one or more regions of neighboring CpG sites in a plurality of cells in the tumor sample;

comparing the DNA methylation status in multiple regions of neighboring CpG sites along a sequence of CpG sites in DNA of the plurality of cells; and determining a relative number of cells in the tumor sample having inconsistent DNA methylation status across the sequence of CpG sites as compared to the total number of cells in the tumor sample or a number of cells in the tumor sample having consistent DNA methylation status across the sequence of CpG sites thereby calculating the PDR in the tumor sample, determining the PDR in the tumor sample to be less than or equal to 0.15, and administering to the subject an antitumor agent.

2. The method according to claim 1, wherein DNA methylation is detected by microarray or wherein a PDR greater than 0.15 indicates that the subject is more likely to (1) develop resistance to an antitumor agent; (2) relapse after treatment with an antitumor agent; (3) develop a metastatic tumor; or (4) any combination of the above.

3. The method according to claim 1, wherein the method further comprises performing a second PDR calculation on a second tumor sample from the subject comprising:

detecting DNA methylation status by massive parallel sequencing with bisulfite conversion; whole-genome bisulfite sequencing; reduced representation bisulfite sequencing; microarray, or a genome-wide microarray at one or more regions of neighboring CpG sites in a plurality of cells in the second tumor sample;

comparing the DNA methylation status in multiple regions of neighboring CpG sites along a sequence of CpG sites in DNA of the plurality of cells; and determining a relative number of cells in the second tumor sample having inconsistent DNA methylation status across the sequence of CpG sites as compared to the total number of cells in the second tumor sample or a number of cells in the second tumor sample having consistent DNA methylation status across the sequence of CpG sites thereby calculating the PDR in the second tumor sample.

4. The method according to claim 3, wherein the method further comprises the step of comparing the PDR from the first tumor sample to the PDR from the second tumor sample, wherein the first and second tumor samples are from different tumors.

5. The method according to claim 3, wherein the first and second tumor samples are obtained from the same tumor at different times.

6. The method according to claim 5, wherein the subject is treated with an antitumor agent between obtaining the first tumor sample and obtaining the second tumor sample.

7. The method of claim 6, wherein the method further comprises stopping or changing the treatment with the antitumor agent if the PDR from the second tumor sample is greater than the PDR from the first tumor sample, or continuing the treatment with the antitumor agent if the PDR from the second tumor sample is the same as or less than the PDR from the first tumor sample.

8. The method of claim 1, wherein the method further comprises, calculating a second PDR from a tumor sample obtained from the same tumor in the subject; and comparing the second PDR to the first PDR;

wherein the antitumor agent is administered after obtaining the first tumor sample and before obtaining the second tumor sample, and wherein treatment with the antitumor agent is stopped or changed if the second PDR, is different than the first PDR.

9. The method according to claim 8, wherein the subject is treated with the antitumor agent for 3 months, 6 months, 9 months or 12 months before obtaining the second tumor sample.

10. The method according to claim 1, wherein the neighboring CpG sites comprise a collection of CpG sites:

(1) along one or more sequences in DNA, and/or (2) at genomic loci of one or more genes.

* * * * *

UNITED STATES PATENT AND TRADEMARK OFFICE
CERTIFICATE OF CORRECTION

PATENT NO. : 11,834,718 B2  
APPLICATION NO. : 17/017045  
DATED : December 5, 2023  
INVENTOR(S) : Mark Kendell Clement et al.

Page 1 of 1

It is certified that error appears in the above-identified patent and that said Letters Patent is hereby corrected as shown below:

In the Specification

At Column 1, Line number 32, before the heading, FIELD OF INVENTION, please insert:
--GOVERNMENT FUNDING STATEMENT
This invention was made with government support under Grant Nos. DA036898 and ES017155 awarded by the National Institutes of Health. The government has certain rights in the invention.--

Signed and Sealed this  
Seventh Day of January, 2025

Derrick Brent  
*Acting Director of the United States Patent and Trademark Office*